US 11,427,619 B2

(12) United States Patent
Strugnell et al.

(10) Patent No.: US 11,427,619 B2
(45) Date of Patent: Aug. 30, 2022

(54) METHODS OF OPTIMIZING NUCLEOTIDE SEQUENCES ENCODING ENGINEERED INFLUENZA PROTEINS

(71) Applicant: SANOFI PASTEUR INC., Swiftwater, PA (US)

(72) Inventors: Tod Dwayne Strugnell, Charlestown, MA (US); Guadalupe Cortes-Garcia, Brookline, MA (US); Tim Alefantis, Springbrook Township, PA (US)

(73) Assignee: SANOFI PASTEUR INC., Swiftwater, PA (US)

( * ) Notice: Subject to any disclaimer, the term of this patent is extended or adjusted under 35 U.S.C. 154(b) by 46 days.

(21) Appl. No.: 17/147,137

(22) Filed: Jan. 12, 2021

(65) Prior Publication Data

US 2021/0130416 A1    May 6, 2021

Related U.S. Application Data

(62) Division of application No. 15/580,192, filed as application No. PCT/US2016/036740 on Jun. 9, 2016, now Pat. No. 10,927,151.

(Continued)

(51) Int. Cl.
*C07K 14/11* (2006.01)
*C07K 14/005* (2006.01)
(Continued)

(52) U.S. Cl.
CPC ............ *C07K 14/11* (2013.01); *C07K 14/005* (2013.01); *C07K 16/10* (2013.01); *G01N 33/569* (2013.01);
(Continued)

(58) Field of Classification Search
None
See application file for complete search history.

(56) References Cited

U.S. PATENT DOCUMENTS 10,059,925 B2 *   8/2018   Kawaoka ................. C12N 7/00
2005/0003349 A1   1/2005   Kawaoka
(Continued)

FOREIGN PATENT DOCUMENTS

WO   2010/101663 A2   9/2010
WO   2013/122827 A1   8/2013
WO   2016/196846 A3   12/2016

OTHER PUBLICATIONS

Giles et al. (Vaccine, 2011, p. 3042-3054).*
(Continued)

*Primary Examiner* — Agnieszka Boesen
(74) *Attorney, Agent, or Firm* — MH2 Technology Law Group, LLP

(57) ABSTRACT

The disclosure provides methods for generating an optimized nucleotide sequence encoding an engineered influenza structural protein and the optimized nucleotide sequences obtained therefrom. The optimized nucleotide sequences can be used in a reverse genetics system to facilitate the rescue of infectious influenza virus containing the engineered structural proteins and/or enhance viral titers. Also provided are methods of preparing an influenza vaccine composition using the optimized nucleotide sequences, as well as methods of inducing an immune response using the influenza vaccine composition.

18 Claims, 4 Drawing Sheets

Specification includes a Sequence Listing.

Related U.S. Application Data

(60) Provisional application No. 62/172,949, filed on Jun. 9, 2015.

(51) Int. Cl.
  G01N 33/569 (2006.01)
  C07K 16/10 (2006.01)

(52) U.S. Cl.
  CPC .............. *C12N 2760/16122* (2013.01); *C12N 2760/16134* (2013.01); *C12N 2760/16222* (2013.01); *C12N 2760/16234* (2013.01); *C12N 2800/22* (2013.01)

(56) References Cited

U.S. PATENT DOCUMENTS

| | | | |
|---|---|---|---|
| 2008/0050401 A1 | 2/2008 | De Wit et al. | |
| 2008/0118530 A1 | 5/2008 | Kew et al. | |
| 2011/0262481 A1 | 10/2011 | Muster et al. | |
| 2013/0183342 A1 | 7/2013 | Ross et al. | |
| 2014/0127248 A1 | 5/2014 | Ross et al. | |
| 2014/0147459 A1* | 5/2014 | Ross .................. | A61K 39/12 435/325 |
| 2015/0017196 A1* | 1/2015 | Ross .................. | A61P 31/16 435/325 |
| 2015/0044247 A1 | 2/2015 | Ross et al. | |

OTHER PUBLICATIONS

Carter et al. (Journal of Virology, 2016, p. 4720-4734).*

International Search Report and Written Opinion dated Oct. 24, 2016 from International Application No. PCT/US2016/036740, pp. 1-10.

Supplementary European Search Report and European Search Report dated Dec. 13, 2018 for European Patent Application No. 16808307.9, 10 pages.

Gomila et al., "Improving influenza virus backbones by including terminal regions of MDCK-adapted strains on hemagglutinin and neuraminidase gene segments", Vaccine, Aug. 20, 2013, vol. 31, No. 42, pp. 4736-4743.

Plotkin et al., "Codon bias and frequency-dependent selection on the hemagglutinin epitopes of influenza A virus", PNAS, Jun. 10, 2003, vol. 100, No. 12, pp. 7152-7157.

Wong et al., "Codon usage bias and the evolution of influenza A viruses. Codon Usage Biases of Influenza Virus", BMC Evolutionary Biology, Aug. 19, 2010, vol. 10, No. 1, p. 253, 14 pages.

Baker et al., "Downregulating viral gene expression: codon usage bias manipulation for the generation of novel influenza A virus vaccines", Future Virology, Jun. 1, 2015, vol. 10, No. 6, pp. 715-730.

Singapore Search Report and Written Opinion dated Jan. 18, 2019 from Singaporean Patent Application No. 11201709910P (Authorized Officer, Wan Yen Lee), 13 pages.

Milian et al., "Current and Emerging Cell Culture Manufacturing Technologies for Influenza Vaccines", BioMed Research International, Mar. 1, 2015, vol. 2015, 11 pages.

Giles et al., "A con1putationally optimized broadly reactive antigen (COBRA) based H5N1 VLP vaccine elicits broadly reactive antibodies in mice and ferrets", Vaccine, 2011, vol. 29, pp. 3043-3054.

Carter et al., "Design and Characterization of a Computationally Optimized Broadly Reactive Hemagglutinin Vaccine for H1N1 Influenza Viruses", Journal of Virology, 2016, vol. 90, No. 9, pp. 4720-4734.

* cited by examiner

```
MEARLLVLLCAFA...
```

1. Reverse Translation

2. Obtain Closely-Matched WT Influenza Nucleotide Sequence

```
ATGGAAGCAAGACTACTGGT            ATGAAAGTAAAACTACTGG
```

3a. Exchange Codons with WT Strain if Amino Acids Match

```
ATGGAAGCAAAACTACTGG
```

3b. Replace Codons Using Influenza Codon Usage Preferences if Amino Acids Differ

```
ATGGACGCCAAACTACTGG
```

4. Optionally Incorporate 5' and 3' Non-Coding Regions from WT or Previously Rescued Virus Flanking NCR 5. Optionally Exchange 5' or 3' Termini (e.g., Signal Peptide, Transmembrane and/or Cytoplasmic Domains) from WT or Previously Rescued Viral Sequence Termini Swapped

FIG. 1

| Strain | Subtype | Amino Acid Sequence |
|---|---|---|
| A/PUERTO RICO/8/4 | H1 | Q--ILAIYSTVASSLVLLVSLGAISFWMCSN |
| A/JAPAN/305/57 | H2 | Q--ILAIYATVAGSLSLAIMMAGISFWMCSN |
| A/TURKEY/ONTARIO/7732/66 | H5 | Q--ILSIYSTVASSLALAIMVAGLSFWMCSN |
| A/SHEARWATER/AUSTRALIA/72 | H6 | Q--ILAIYSTVSSSLVLVGLIIAVGLWMCSN |
| A/TURKEY/ONTARIO/6118/68 | H8 | K--ILSIYSTVAASLCLAILIAGGLILGMQN |
| A/TURKEY/WISCONSIN/1/66 | H9 | K--ILTIYSTVASSLVLAMGFAAFLFWAMSN |
| A/DUCK/ENGLAND/1/56 | H11 | K--ILSIYSCIASSLVLAALIMGFMFWACSN |
| A/DUCK/ALBERTA/60/76 | H12 | K--ILSIYSSVASSLVLLLMIIGGFIFGCQN |
| A/GULL/MARYLAND/704/77 | H13 | K--ALSIYSCIASSVVLVGLIISFIMWACSS |
| A/HONG KONG/1968 (X:31) | H3 | (183)KDWILWISFAISCFLLCVVLL-GFIMWACQR(212)<br>c-label f-label |
| A/MEMPHIS/1/71 | H3 | KDWILWISFAISCFLLCVVLL-GFIMWACQR |
| A/VICTORIA/3/75 | H3 | KDWILWISFAISCFLLCVVLL-GFIMWACQK |
| A/UDORN/307/72 | H3 | KDWILWISFAISCFLLCVVLL-GFIMTACQK |
| A/EQUINE/ALGIERS/72 | H3 | KDWILWISFAISCFLICVVLL-GFIMWACQK |
| A/DUCK/CZECHOSLOVAKIA/56 | H4 | KDIILWISFSISCFLLVALLL-AFILWACQN |
| A/FPV/ROSTOCK/34 | H7 | KDVILWFSFGASCFLLLAIAV-GLV-FICVK |
| A/CHICKEN/GERMANY/N/49 | H10 | KDIILWFSFGASCFVLLAAVM-GLV-FFCLK |
| A/MALLARD/ASTRAKHAN/244/82 | H14 | KDIILWISFSMSCFVFVALIL-GFVLWACQN |

FIG. 4

SEQUENCE LISTING

```
<160> NUMBER OF SEQ ID NOS: 106

<210> SEQ ID NO 1
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Glu Lys Ile Val Leu Leu Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asp Phe Asn
                100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Asn His Glu Ala Ser
    130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
                180                 185                 190

Gly Ile His His Pro Asn Asp Ala Ala Glu Gln Thr Lys Leu Tyr Gln
            195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240
```

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
            565

<210> SEQ ID NO 2
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
                35                  40                  45

Leu Glu Lys Thr His Asn Gly Lys Leu Cys Asp Leu Asp Gly Val Lys
 50                  55                  60

Pro Leu Ile Leu Arg Asp Cys Ser Val Ala Gly Trp Leu Leu Gly Asn
 65                  70                  75                  80

Pro Met Cys Asp Glu Phe Ile Asn Val Pro Glu Trp Ser Tyr Ile Val
                 85                  90                  95

Glu Lys Ala Asn Pro Ala Asn Asp Leu Cys Tyr Pro Gly Asn Phe Asn
                100                 105                 110

Asp Tyr Glu Glu Leu Lys His Leu Leu Ser Arg Ile Asn His Phe Glu
                115                 120                 125

Lys Ile Gln Ile Ile Pro Lys Ser Ser Trp Ser Asp His Glu Ala Ser
130                 135                 140

Ser Gly Val Ser Ser Ala Cys Pro Tyr Gln Gly Lys Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
                180                 185                 190

Gly Ile His His Pro Asn Asp Ala Ala Glu Gln Thr Arg Leu Tyr Gln
                195                 200                 205

Asn Pro Thr Thr Tyr Ile Ser Val Gly Thr Ser Thr Leu Asn Gln Arg
210                 215                 220

Leu Val Pro Lys Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Met Lys Ser Glu Leu Glu Tyr Gly
                275                 280                 285

Asn Cys Asn Thr Lys Cys Gln Thr Pro Met Gly Ala Ile Asn Ser Ser
                290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Arg Lys Arg Gly Leu Phe Gly Ala Ile Ala
                340                 345                 350

Gly Phe Ile Glu Gly Gly Trp Gln Gly Met Val Asp Gly Trp Tyr Gly
                355                 360                 365

Tyr His His Ser Asn Glu Gln Gly Ser Gly Tyr Ala Ala Asp Lys Glu
                370                 375                 380

Ser Thr Gln Lys Ala Ile Asp Gly Val Thr Asn Lys Val Asn Ser Ile
385                 390                 395                 400

Ile Asp Lys Met Asn Thr Gln Phe Glu Ala Val Gly Arg Glu Phe Asn
                405                 410                 415

Asn Leu Glu Arg Arg Ile Glu Asn Leu Asn Lys Lys Met Glu Asp Gly
                420                 425                 430

Phe Leu Asp Val Trp Thr Tyr Asn Ala Glu Leu Leu Val Leu Met Glu
                435                 440                 445

-continued

```
Asn Glu Arg Thr Leu Asp Phe His Asp Ser Asn Val Lys Asn Leu Tyr
    450                 455                 460

Asp Lys Val Arg Leu Gln Leu Arg Asp Asn Ala Lys Glu Leu Gly Asn
465                 470                 475                 480

Gly Cys Phe Glu Phe Tyr His Lys Cys Asp Asn Glu Cys Met Glu Ser
                485                 490                 495

Val Arg Asn Gly Thr Tyr Asp Tyr Pro Gln Tyr Ser Glu Glu Ala Arg
                500                 505                 510

Leu Lys Arg Glu Glu Ile Ser Gly Val Lys Leu Glu Ser Ile Gly Thr
                515                 520                 525

Tyr Gln Ile Leu Ser Ile Tyr Ser Thr Val Ala Ser Ser Leu Ala Leu
    530                 535                 540

Ala Ile Met Val Ala Gly Leu Ser Leu Trp Met Cys Ser Asn Gly Ser
545                 550                 555                 560

Leu Gln Cys Arg Ile Cys Ile
                565

<210> SEQ ID NO 3
<211> LENGTH: 568
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
                35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Ala Asn Asp Leu Cys Tyr Pro Gly Asn Phe Asn
                100                 105                 110

Asp Tyr Glu Glu Leu Lys His Leu Leu Ser Arg Ile Asn His Phe Glu
            115                 120                 125

Lys Ile Gln Ile Ile Pro Lys Ser Ser Trp Ser Asp His Glu Ala Ser
    130                 135                 140

Ser Gly Val Ser Ser Ala Cys Pro Tyr Gln Gly Ser Pro Ser Phe Phe
145                 150                 155                 160

Arg Asn Val Val Trp Leu Ile Lys Lys Asn Asn Thr Tyr Pro Thr Ile
                165                 170                 175

Lys Arg Ser Tyr Asn Asn Thr Asn Gln Glu Asp Leu Leu Val Leu Trp
                180                 185                 190

Gly Ile His His Pro Asn Asp Ala Ala Glu Gln Thr Arg Leu Tyr Gln
            195                 200                 205

Asn Pro Thr Thr Tyr Ile Ser Val Gly Thr Ser Thr Leu Asn Gln Arg
    210                 215                 220

Leu Val Pro Lys Ile Ala Thr Arg Ser Lys Val Asn Gly Gln Ser Gly
225                 230                 235                 240
```

```
Arg Met Glu Phe Phe Trp Thr Ile Leu Lys Pro Asn Asp Ala Ile Asn
            245                 250                 255

Phe Glu Ser Asn Gly Asn Phe Ile Ala Pro Glu Tyr Ala Tyr Lys Ile
        260                 265                 270

Val Lys Lys Gly Asp Ser Ala Ile Met Lys Ser Glu Leu Glu Tyr Gly
    275                 280                 285

Asn Cys Asn Thr Lys Cys Gln Thr Pro Ile Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Val Ala Gly Leu Ser Leu Trp Met Cys Ser Asn Gly
545                 550                 555                 560

Ser Leu Gln Cys Arg Ile Cys Ile
                565

<210> SEQ ID NO 4
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Lys Ala Arg Leu Leu Val Leu Leu Cys Ala Leu Ala Ala Thr Asp
1               5                   10                  15

Ala Asp Thr Ile Cys Ile Gly Tyr His Ala Asn Asn Ser Thr Asp Thr
```

```
            20                  25                  30
Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
 50                  55                  60

Ala Pro Leu Gln Leu Lys Cys Asn Ile Ala Gly Trp Leu Leu Gly
 65                  70                  75                  80

Asn Pro Glu Cys Glu Ser Leu Leu Ser Ala Arg Ser Trp Ser Tyr Ile
                     85                  90                  95

Val Glu Thr Pro Asn Ser Glu Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
        130                 135                 140

Thr Thr Lys Gly Val Thr Ala Ala Cys Ser His Ala Gly Lys Ser Ser
145                 150                 155                 160

Phe Tyr Arg Asn Leu Leu Trp Leu Thr Lys Lys Gly Gly Ser Tyr Pro
                165                 170                 175

Lys Leu Ser Lys Ser Tyr Val Asn Asn Lys Gly Lys Glu Val Leu Val
                180                 185                 190

Leu Trp Gly Val His His Pro Ser Thr Ser Thr Asp Gln Gln Ser Leu
            195                 200                 205

Tyr Gln Asn Glu Asn Ala Tyr Val Ser Val Val Ser Ser Asn Tyr Asn
        210                 215                 220

Arg Arg Phe Thr Pro Glu Ile Ala Glu Arg Pro Lys Val Arg Gly Gln
225                 230                 235                 240

Ala Gly Arg Met Asn Tyr Tyr Trp Thr Leu Leu Glu Pro Gly Asp Thr
                245                 250                 255

Ile Ile Phe Glu Ala Thr Gly Asn Leu Ile Ala Pro Trp Tyr Ala Phe
                260                 265                 270

Ala Leu Ser Arg Gly Ser Gly Ser Gly Ile Ile Thr Ser Asn Ala Ser
            275                 280                 285

Met His Glu Cys Asn Thr Lys Cys Gln Thr Pro Gln Gly Ala Ile Asn
        290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
        370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415

Leu Glu Lys Arg Met Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
            435                 440                 445
```

Glu Arg Thr Leu Asp Phe His Asp Ser Asn Val Lys Asn Leu Tyr Glu
            450                 455                 460

Lys Val Lys Ser Gln Leu Arg Asn Asn Ala Lys Glu Ile Gly Asn Gly
465                 470                 475                 480

Cys Phe Glu Phe Tyr His Lys Cys Asp Asn Glu Cys Met Glu Ser Val
            485                 490                 495

Lys Asn Gly Thr Tyr Asp Tyr Pro Lys Tyr Ser Glu Ser Lys Leu
            500                 505                 510

Asn Arg Glu Lys Ile Asp Gly Val Lys Leu Glu Ser Met Gly Val Tyr
            515                 520                 525

Gln Ile Leu Ala Ile Tyr Ser Thr Val Ala Ser Ser Leu Val Leu Leu
            530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 5
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Leu Leu Lys Gly Ile
            50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
            85                  90                  95

Val Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
            165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
            195                 200                 205

His Thr Glu Asn Ala Tyr Val Ser Val Val Ser Ser His Tyr Ser Arg
            210                 215                 220

Lys Phe Thr Pro Glu Ile Ala Lys Arg Pro Lys Val Arg Asp Gln Glu 225                 230                 235                 240
Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
                260                 265                 270

Leu Ser Arg Gly Phe Gly Ser Gly Ile Ile Thr Ser Asn Ala Pro Met
                275                 280                 285

Asp Glu Cys Asp Ala Lys Cys Gln Thr Pro Gln Gly Ala Ile Asn Ser
                290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
                355                 360                 365

His Gln Asn Glu Gln Gly Ser Gly Tyr Ala Ala Asp Gln Lys Ser Thr
                370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
                435                 440                 445

Arg Thr Leu Asp Phe His Asp Ser Asn Val Lys Asn Leu Tyr Glu Lys
                450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
                515                 520                 525

Ile Leu Ala Ile Tyr Ser Thr Val Ala Ser Ser Leu Val Leu Leu Val
                530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 6
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Ser Leu Phe Ser Lys Glu Ser Trp Ser Tyr Ile
            85                  90                  95

Ala Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
            130                 135                 140

Val Thr Lys Gly Val Thr Ala Ser Cys Ser His Asn Gly Lys Ser Ser
145                 150                 155                 160

Phe Tyr Arg Asn Leu Leu Trp Leu Thr Glu Lys Asn Gly Leu Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
            195                 200                 205

Tyr His Thr Glu Asn Ala Tyr Val Ser Val Val Ser Ser His Tyr Ser
            210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
            275                 280                 285

Met Asp Glu Cys Asp Ala Lys Cys Gln Thr Pro Gln Gly Ala Ile Asn
            290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
            325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
            370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
            405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn

```
            435                 440                 445
Glu Arg Thr Leu Asp Phe His Asp Ser Asn Val Lys Asn Leu Tyr Glu
450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                    485                 490                 495

Lys Asn Gly Thr Tyr Asp Tyr Pro Lys Tyr Ser Glu Glu Ser Lys Leu
                500                 505                 510

Asn Arg Glu Lys Ile Asp Gly Val Lys Leu Glu Ser Met Gly Val Tyr
            515                 520                 525

Gln Ile Leu Ala Ile Tyr Ser Thr Val Ala Ser Ser Leu Val Leu Leu
530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 7
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Ile Leu Gly
65                  70                  75                  80

Asn Pro Glu Cys Glu Ser Leu Leu Ser Lys Arg Ser Trp Ser Tyr Ile
                85                  90                  95

Val Glu Thr Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Thr Lys Gly Val Thr Ala Ala Cys Ser His Ala Gly Lys Ser Ser
145                 150                 155                 160

Phe Tyr Arg Asn Leu Leu Trp Leu Thr Lys Lys Asn Gly Ser Tyr Pro
                165                 170                 175

Asn Leu Ser Lys Ser Tyr Val Asn Asn Lys Gly Lys Glu Val Leu Val
            180                 185                 190

Leu Trp Gly Val His His Pro Ser Asn Ile Glu Asp Gln Gln Ser Leu
        195                 200                 205

Tyr Gln Asn Glu Asn Ala Tyr Val Ser Val Val Ser Ser Asn Tyr Asn
    210                 215                 220
```

```
Arg Arg Phe Thr Pro Glu Ile Ala Lys Arg Pro Lys Val Arg Asp Gln
225                 230                 235                 240

Glu Gly Arg Met Asn Tyr Tyr Trp Thr Leu Leu Glu Pro Gly Asp Thr
            245                 250                 255

Ile Ile Phe Glu Ala Asn Gly Asn Leu Ile Ala Pro Trp Tyr Ala Phe
        260                 265                 270

Ala Leu Ser Arg Gly Phe Gly Ser Gly Ile Ile Thr Ser Asn Ala Ser
    275                 280                 285

Met His Glu Cys Asp Thr Lys Cys Gln Thr Pro Gln Gly Ala Ile Asn
290                 295                 300

Ser Ser Leu Pro Phe Gln Asn Ile His Pro Val Thr Ile Gly Glu Cys
305                 310                 315                 320

Pro Lys Tyr Val Arg Ser Thr Lys Leu Arg Met Val Thr Gly Leu Arg
            325                 330                 335

Asn Ile Pro Ser Ile Gln Ser Arg Gly Leu Phe Gly Ala Ile Ala Gly
        340                 345                 350

Phe Ile Glu Gly Gly Trp Thr Gly Met Ile Asp Gly Trp Tyr Gly Tyr
    355                 360                 365

His His Gln Asn Glu Gln Gly Ser Gly Tyr Ala Ala Asp Gln Lys Ser
370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Asn
            405                 410                 415

Leu Glu Lys Arg Met Glu Asn Leu Asn Lys Lys Val Asp Asp Gly Phe
        420                 425                 430

Leu Asp Ile Trp Thr Tyr Asn Ala Glu Leu Leu Val Leu Leu Glu Asn
    435                 440                 445

Glu Arg Thr Leu Asp Phe His Asp Ser Asn Val Lys Asn Leu Tyr Glu
450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
            485                 490                 495

Lys Asn Gly Thr Tyr Asp Tyr Pro Lys Tyr Ser Glu Glu Ser Lys Leu
        500                 505                 510

Asn Arg Glu Lys Ile Asp Gly Val Lys Leu Glu Ser Met Gly Val Tyr
    515                 520                 525

Gln Ile Leu Ala Ile Tyr Ser Thr Val Ala Ser Ser Leu Val Leu Leu
530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 8
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Ala Lys Leu Leu Val Leu Leu Cys Ala Phe Thr Ala Thr Tyr
1               5                   10                  15
```

```
Ala Asp Thr Ile Cys Ile Gly Tyr His Ala Asn Asn Ser Thr Asp Thr
             20                  25                  30

Val Asp Thr Val Leu Glu Lys Asn Val Thr Val Thr His Ser Val Asn
         35                  40                  45

Leu Leu Glu Asp Ser His Asn Gly Lys Leu Cys Arg Leu Lys Gly Ile
 50                  55                  60

Ala Pro Leu Gln Leu Gly Asn Cys Ser Ile Ala Gly Trp Ile Leu Gly
 65                  70                  75                  80

Asn Pro Glu Cys Glu Ser Leu Phe Ser Lys Glu Ser Trp Ser Tyr Ile
                 85                  90                  95

Val Glu Thr Pro Asn Ser Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
    130                 135                 140

Val Thr Lys Gly Val Thr Ala Ser Cys Ser His Asn Gly Lys Ser Ser
145                 150                 155                 160

Phe Tyr Arg Asn Leu Leu Trp Leu Thr Glu Lys Asn Gly Ser Tyr Pro
                165                 170                 175

Asn Leu Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205

Tyr His Thr Glu Asn Ala Tyr Val Ser Val Val Ser Ser His Tyr Ser
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430
```

```
Leu Asp Ile Trp Thr Tyr Asn Ala Glu Leu Leu Val Leu Glu Asn
        435                 440                 445

Glu Arg Thr Leu Asp Phe His Asp Ser Asn Val Lys Asn Leu Tyr Glu
450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 9
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Ser Val Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Thr Ala Ser Cys Ser His Ala Gly Lys Ser Ser Phe
145                 150                 155                 160

Tyr Arg Asn Leu Leu Trp Leu Thr Gly Lys Asn Gly Ser Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Ser Asn Ile Gly Asp Gln Gln Thr Leu Tyr
        195                 200                 205

Gln Thr Glu Asn Ala Tyr Val Ser Val Val Ser Ser Arg Tyr Ser Arg
    210                 215                 220
```

Arg Phe Thr Pro Glu Ile Ala Lys Arg Pro Lys Val Arg Asp Gln Glu
225                 230                 235                 240

Gly Arg Met Asn Tyr Tyr Trp Thr Leu Val Glu Pro Gly Asp Thr Ile
            245                 250                 255

Ile Phe Glu Ala Asn Gly Asn Leu Ile Ala Pro Trp Tyr Ala Phe Ala
        260                 265                 270

Leu Ser Arg Gly Phe Gly Ser Gly Ile Ile Thr Ser Asn Ala Pro Val
    275                 280                 285

His Asp Cys Asn Thr Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 10
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Ala Lys Leu Leu Val Leu Leu Cys Thr Phe Thr Ala Thr Tyr

-continued

```
  1               5                   10                  15
Ala Asp Thr Ile Cys Ile Gly Tyr His Ala Asn Asn Ser Thr Asp Thr
                 20                  25                  30

Val Asp Thr Val Leu Glu Lys Asn Val Thr Val Thr His Ser Val Asn
                 35                  40                  45

Leu Leu Glu Asp Ser His Asn Gly Lys Leu Cys Leu Leu Lys Gly Ile
 50                  55                  60

Ala Pro Leu Gln Leu Gly Asn Cys Ser Val Ala Gly Trp Ile Leu Gly
 65                  70                  75                  80

Asn Pro Glu Cys Glu Leu Leu Ser Thr Lys Ser Ser Trp Ser Tyr Ile
                 85                  90                  95

Val Glu Thr Pro Asn Pro Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
                115                 120                 125

Glu Arg Phe Glu Ile Phe Pro Lys Glu Ser Ser Trp Pro Asn His Asp
                130                 135                 140

Val Thr Gly Val Ser Ala Ser Cys Ser His Asn Gly Ala Ser Ser Phe
145                 150                 155                 160

Tyr Arg Asn Leu Leu Trp Leu Thr Lys Lys Asn Asn Leu Tyr Pro Asn
                165                 170                 175

Leu Ser Lys Ser Tyr Ala Asn Asn Lys Gly Lys Glu Val Leu Val Leu
                180                 185                 190

Trp Gly Val His His Pro Ser Thr Ile Ala Asp Gln Gln Thr Leu Tyr
                195                 200                 205

His Thr Glu Asn Ala Tyr Val Ser Val Val Ser Ser His Tyr Ser Arg
                210                 215                 220

Arg Phe Thr Pro Glu Ile Ala Ile Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
                260                 265                 270

Leu Ser Arg Gly Phe Gly Ser Gly Ile Ile Thr Ser Asn Ala Pro Met
                275                 280                 285

Asp Glu Cys Asn Thr Thr Cys Gln Thr Pro Gln Gly Ala Ile Asn Ser
                290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
                355                 360                 365

His Gln Asn Glu Gln Gly Ser Gly Tyr Ala Ala Asp Leu Lys Ser Thr
                370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
                420                 425                 430
```

```
Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565
```

<210> SEQ ID NO 11
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Ser Val Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Pro Asp Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
130                 135                 140

Ser Asn Gly Val Thr Ala Ser Cys Pro His Ala Gly Ala Lys Ser Phe
145                 150                 155                 160

Tyr Arg Asn Leu Leu Trp Leu Val Lys Lys Gly Asn Ser Tyr Pro Lys
                165                 170                 175

Leu Ser Lys Ser Tyr Ile Asn Asp Lys Gly Lys Glu Val Leu Val Leu
            180                 185                 190

Trp Gly Val His His Pro Ser Thr Ser Ala Asp Gln Gln Ser Leu Tyr
        195                 200                 205

Gln Asn Ala Asn Ala Tyr Val Ser Val Val Thr Ser Arg Tyr Ser Arg
```

210                 215                 220
Arg Phe Thr Pro Glu Ile Ala Ile Arg Pro Lys Val Arg Asp Gln Glu
225                 230                 235                 240

Gly Arg Met Asn Tyr Tyr Trp Thr Leu Val Glu Pro Gly Asp Thr Ile
                245                 250                 255

Ile Phe Glu Ala Thr Gly Asn Leu Ile Ala Pro Trp Tyr Ala Phe Ala
            260                 265                 270

Leu Ser Arg Gly Phe Gly Ser Gly Ile Ile Thr Ser Asp Thr Pro Val
        275                 280                 285

His Asp Cys Asn Thr Thr Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 12
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Phe Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu

Asp Ile Trp Thr Tyr Asn Ala Glu Leu Leu Val Leu Leu Glu Asn Glu
            420                 425                 430
                435                 440                 445

Arg Thr Leu Asp Phe His Asp Ser Asn Val Lys Asn Leu Tyr Glu Lys
            450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
                515                 520                 525

Ile Leu Ala Ile Tyr Ser Thr Val Ala Ser Ser Leu Val Leu Leu Val
                530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 13
<211> LENGTH: 565
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Ile Leu Glu Asp Ser His Asn Gly Lys Leu Cys Leu Leu Lys Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
130                 135                 140

Val Thr Gly Val Ser Ala Ser Cys Pro His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Lys Thr Leu Tyr
            195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Ala Thr Gly Leu Arg Asn
                325                 330                 335

Ile Gln Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 14
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

-continued

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
                35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Asn Ser Glu Asn Gly Thr Cys Tyr Pro Gly Asp Phe
                100                 105                 110

Ile Asp Tyr Glu Glu Leu Arg Glu Gln Leu Ser Ser Val Ser Ser Phe
                115                 120                 125

Glu Arg Phe Glu Ile Phe Pro Lys Glu Ser Ser Trp Pro Asn His Thr
                130                 135                 140

Val Thr Lys Gly Val Thr Ala Ala Cys Ser His Ala Gly Lys Ser Ser
145                 150                 155                 160

Phe Tyr Lys Asn Leu Ile Trp Leu Thr Gly Lys Asn Gly Ser Tyr Pro
                165                 170                 175

Asn Leu Ser Lys Ser Tyr Val Asn Asn Lys Glu Lys Glu Val Leu Val
                180                 185                 190

Leu Trp Gly Ile His His Pro Ser Asn Ile Gly Asp Gln Gln Thr Leu
                195                 200                 205

Tyr Gln Thr Glu Asp Thr Tyr Val Phe Val Gly Ser Ser Arg Tyr Ser
210                 215                 220

Lys Lys Phe Lys Pro Glu Ile Ala Lys Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Asn Gly Asn Leu Val Val Pro Arg Tyr Ala Phe
                260                 265                 270

Ala Met Glu Arg Asn Ala Gly Ser Gly Ile Ile Ile Ser Asn Ala Pro
                275                 280                 285

Val His Asp Cys Asn Thr Lys Cys Gln Thr Pro Lys Gly Ala Ile Asn
                290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
                355                 360                 365

His His Gln Asn Glu Gln Gly Ser Gly Tyr Ala Ala Asp Gln Lys Ser
                370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415
```

```
Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
            485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 15
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Leu Leu Arg Gly Val
    50                  55                  60

Ala Pro Leu His Leu Gly Asn Cys Asn Ile Ala Gly Trp Ile Leu Gly
65                  70                  75                  80

Asn Pro Glu Cys Glu Leu Leu Ser Thr Lys Ser Ser Trp Ser Tyr Ile
            85                  90                  95

Val Glu Thr Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asp
    130                 135                 140

Val Thr Lys Gly Val Ser Ala Ala Cys Ser His Asn Gly Ala Ser Ser
145                 150                 155                 160

Phe Tyr Lys Asn Leu Ile Trp Leu Thr Lys Lys Asn Asn Leu Tyr Pro
            165                 170                 175

Asn Leu Ser Lys Ser Tyr Ala Asn Asn Lys Gly Lys Glu Val Leu Val
            180                 185                 190

Leu Trp Gly Ile His His Pro Ser Thr Ile Ala Asp Gln Gln Thr Leu
        195                 200                 205
```

```
Tyr His Thr Glu Asp Thr Tyr Val Phe Val Gly Ser Ser His Tyr Ser
210                 215                 220

Lys Lys Phe Lys Pro Glu Ile Ala Ile Arg Pro Lys Val Arg Asp Gln
225                 230                 235                 240

Glu Gly Arg Ile Asn Tyr Tyr Trp Thr Leu Leu Glu Pro Gly Asp Lys
                245                 250                 255

Ile Thr Phe Glu Ala Asn Gly Asn Leu Val Val Pro Arg Tyr Ala Phe
                260                 265                 270

Ala Met Glu Arg Asn Ala Gly Ser Gly Ile Ile Ile Ser Asn Ala Pro
            275                 280                 285

Met Asp Glu Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Val Thr Gly Leu Arg
                325                 330                 335

Asn Ile Pro Ser Ile Gln Ser Arg Gly Leu Phe Gly Ala Ile Ala Gly
                340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
    370                 375                 380

Thr Gln Asn Ala Ile Asn Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
                420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Glu Cys Met Glu Ser Val
                485                 490                 495

Lys Asn Gly Thr Tyr Asp Tyr Pro Lys Tyr Ser Glu Glu Ala Lys Leu
                500                 505                 510

Asn Arg Glu Glu Ile Asp Gly Val Lys Leu Glu Ser Thr Arg Ile Tyr
            515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565
```

<210> SEQ ID NO 16
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 16

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
    195                 200                 205

Tyr Gln Asn Ala Asp Thr Tyr Val Phe Val Gly Thr Ser Arg Tyr Ser
    210                 215                 220

Lys Lys Phe Lys Pro Glu Ile Ala Ile Arg Pro Lys Val Arg Asp Gln
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
            260                 265                 270

Ala Met Glu Arg Asn Ala Gly Ser Gly Ile Ile Ile Ser Asp Thr Pro
            275                 280                 285

Val His Asp Cys Asn Thr Thr Cys Gln Thr Pro Lys Gly Ala Ile Asn
    290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
    370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415
```

```
Leu Glu Lys Arg Ile Glu Asn Leu Asn Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
            485                 490                 495

Lys Asn Gly Thr Tyr Asp Tyr Pro Lys Tyr Ser Glu Glu Ala Lys Leu
        500                 505                 510

Asn Arg Glu Glu Ile Asp Gly Val Lys Leu Glu Ser Thr Arg Ile Tyr
    515                 520                 525

Gln Ile Leu Ala Ile Tyr Ser Thr Val Ala Ser Ser Leu Val Leu Val
530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 17
<211> LENGTH: 566
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Lys His Asn Gly Lys Leu Cys Leu Leu Arg Gly Val
    50                  55                  60

Ala Pro Leu His Leu Gly Asn Cys Asn Ile Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Ser Ala Ala Cys Ser His Asn Gly Lys Ser Ser
145                 150                 155                 160

Phe Tyr Lys Asn Leu Ile Trp Leu Thr Gly Lys Asn Gly Leu Tyr Pro
                165                 170                 175

Asn Leu Ser Lys Ser Tyr Ala Asn Asn Lys Glu Lys Glu Val Leu Val
            180                 185                 190

Leu Trp Gly Ile His His Pro Pro Asn Ile Gly Asp Gln Arg Ala Leu
```

```
              195                 200                 205
Tyr His Thr Glu Asp Thr Tyr Val Phe Val Gly Ser Ser His Tyr Ser
210                 215                 220
Lys Lys Phe Lys Pro Glu Ile Ala Lys Arg Pro Lys Val Arg Asp Gln
225                 230                 235                 240
Glu Gly Arg Ile Asn Tyr Tyr Trp Thr Leu Glu Pro Gly Asp Lys
            245                 250                 255
Ile Thr Phe Glu Ala Asn Gly Asn Leu Val Val Pro Arg Tyr Ala Phe
            260                 265                 270
Ala Met Glu Arg Asn Ala Gly Ser Gly Ile Ile Ile Ser Asn Ala Pro
    275                 280                 285
Met Asp Lys Cys Asp Ala Lys Cys Gln Thr Pro Lys Gly Ala Ile Asn
    290                 295                 300
Thr Ser Leu Pro Phe Gln Asn Ile His Pro Ile Thr Ile Gly Lys Cys
305                 310                 315                 320
Pro Lys Tyr Val Lys Ser Thr Lys Leu Arg Leu Val Thr Gly Leu Arg
                325                 330                 335
Asn Ile Pro Phe Ile Gln Ser Arg Gly Leu Phe Gly Ala Ile Ala Gly
            340                 345                 350
Phe Ile Glu Gly Gly Trp Thr Gly Met Val Asp Gly Trp Tyr Gly Tyr
            355                 360                 365
His His Gln Asn Glu Gln Gly Ser Gly Tyr Ala Ala Asp Gln Lys Ser
    370                 375                 380
Thr Gln Asn Ala Ile Asn Glu Ile Thr Asn Lys Val Asn Ser Val Ile
385                 390                 395                 400
Glu Lys Met Asn Thr Gln Phe Thr Ala Val Gly Lys Glu Phe Asn His
                405                 410                 415
Leu Glu Lys Arg Ile Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
            435                 440                 445
Glu Arg Thr Leu Asp Tyr His Asp Ser Asn Val Lys Asn Leu Tyr Glu
    450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asp Glu Cys Met Glu Ser Val
                485                 490                 495
Lys Asn Gly Thr Tyr Asp Tyr Pro Lys Tyr Ser Glu Glu Ala Lys Leu
            500                 505                 510
Asn Arg Glu Glu Ile Asp Gly Val Lys Leu Glu Ser Thr Arg Ile Tyr
            515                 520                 525
Gln Ile Leu Ala Ile Tyr Ser Thr Val Ala Ser Ser Leu Val Leu Val
    530                 535                 540
Val Ser Leu Gly Ala Ile Ser Phe Trp Met Cys Ser Asn Gly Ser Leu
545                 550                 555                 560
Gln Cys Arg Ile Cys Ile
                565
```

<210> SEQ ID NO 18
<211> LENGTH: 566
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 18

| | | | | | | | | | | | | | | |
|---|---|---|---|---|---|---|---|---|---|---|---|---|---|---|
|Met|Lys|Ala|Ile|Leu|Val|Val|Leu|Leu|Tyr|Thr|Phe|Ala|Thr|Ala|Asn|
|1| | | |5| | | | |10| | | | |15|

| | | | | | | | | | | | | | | |
|---|---|---|---|---|---|---|---|---|---|---|---|---|---|---|
|Ala|Asp|Thr|Leu|Cys|Ile|Gly|Tyr|His|Ala|Asn|Asn|Ser|Thr|Asp|Thr|
| | | |20| | | | |25| | | | |30| | |

| | | | | | | | | | | | | | | |
|---|---|---|---|---|---|---|---|---|---|---|---|---|---|---|
|Val|Asp|Thr|Val|Leu|Glu|Lys|Asn|Val|Thr|Val|Thr|His|Ser|Val|Asn|
| | | |35| | | | |40| | | | |45| | |

| | | | | | | | | | | | | | | |
|---|---|---|---|---|---|---|---|---|---|---|---|---|---|---|
|Ile|Leu|Glu|Asp|Lys|His|Asn|Gly|Lys|Leu|Cys|Leu|Leu|Arg|Gly|Val|
|50| | | | |55| | | | |60| | | | | |

| | | | | | | | | | | | | | | |
|---|---|---|---|---|---|---|---|---|---|---|---|---|---|---|
|Ala|Pro|Leu|His|Leu|Gly|Asn|Cys|Asn|Ile|Ala|Gly|Trp|Ile|Leu|Gly|
|65| | | | |70| | | | |75| | | | |80|

| | | | | | | | | | | | | | | |
|---|---|---|---|---|---|---|---|---|---|---|---|---|---|---|
|Asn|Pro|Glu|Cys|Glu|Leu|Leu|Ile|Ser|Lys|Glu|Ser|Trp|Ser|Tyr|Ile|
| | | | |85| | | | |90| | | | |95| |

| | | | | | | | | | | | | | | |
|---|---|---|---|---|---|---|---|---|---|---|---|---|---|---|
|Val|Glu|Lys|Pro|Asn|Ser|Glu|Asn|Gly|Thr|Cys|Tyr|Pro|Gly|Asp|Phe|
| | | |100| | | | |105| | | | |110| | |

| | | | | | | | | | | | | | | |
|---|---|---|---|---|---|---|---|---|---|---|---|---|---|---|
|Ile|Asp|Tyr|Glu|Glu|Leu|Arg|Glu|Gln|Leu|Ser|Ser|Val|Ser|Ser|Phe|
| | | |115| | | | |120| | | | |125| | |

| | | | | | | | | | | | | | | |
|---|---|---|---|---|---|---|---|---|---|---|---|---|---|---|
|Glu|Arg|Phe|Glu|Ile|Phe|Pro|Lys|Glu|Ser|Ser|Trp|Pro|Asn|His|Thr|
| |130| | | | |135| | | | |140| | | | |

| | | | | | | | | | | | | | | |
|---|---|---|---|---|---|---|---|---|---|---|---|---|---|---|
|Val|Thr|Lys|Gly|Val|Ser|Ala|Ala|Cys|Pro|His|Asn|Gly|Glu|Ser|Ser|
|145| | | | |150| | | | |155| | | | |160|

| | | | | | | | | | | | | | | |
|---|---|---|---|---|---|---|---|---|---|---|---|---|---|---|
|Phe|Tyr|Lys|Asn|Leu|Ile|Trp|Leu|Thr|Gly|Lys|Asn|Gly|Leu|Tyr|Pro|
| | | | |165| | | | |170| | | | |175| |

| | | | | | | | | | | | | | | |
|---|---|---|---|---|---|---|---|---|---|---|---|---|---|---|
|Asn|Leu|Ser|Lys|Ser|Tyr|Ala|Asn|Asn|Lys|Glu|Lys|Glu|Val|Leu|Val|
| | | |180| | | | |185| | | | |190| | |

| | | | | | | | | | | | | | | |
|---|---|---|---|---|---|---|---|---|---|---|---|---|---|---|
|Leu|Trp|Gly|Ile|His|His|Pro|Pro|Asn|Ile|Gly|Asp|Gln|Lys|Thr|Leu|
| | |195| | | | |200| | | | |205| | | |

| | | | | | | | | | | | | | | |
|---|---|---|---|---|---|---|---|---|---|---|---|---|---|---|
|Tyr|His|Thr|Glu|Asp|Thr|Tyr|Val|Phe|Val|Gly|Ser|Ser|His|Tyr|Ser|
| | |210| | | | |215| | | | |220| | | |

| | | | | | | | | | | | | | | |
|---|---|---|---|---|---|---|---|---|---|---|---|---|---|---|
|Lys|Lys|Phe|Lys|Pro|Glu|Ile|Ala|Lys|Arg|Pro|Lys|Val|Arg|Asp|Gln|
|225| | | | |230| | | | |235| | | | |240|

| | | | | | | | | | | | | | | |
|---|---|---|---|---|---|---|---|---|---|---|---|---|---|---|
|Glu|Gly|Arg|Ile|Asn|Tyr|Tyr|Trp|Thr|Leu|Leu|Glu|Pro|Gly|Asp|Lys|
| | | |245| | | | |250| | | | |255| | |

| | | | | | | | | | | | | | | |
|---|---|---|---|---|---|---|---|---|---|---|---|---|---|---|
|Ile|Thr|Phe|Glu|Ala|Asn|Gly|Asn|Leu|Val|Val|Pro|Arg|Tyr|Ala|Phe|
| | | |260| | | | |265| | | | |270| | |

| | | | | | | | | | | | | | | |
|---|---|---|---|---|---|---|---|---|---|---|---|---|---|---|
|Ala|Met|Glu|Arg|Asn|Ala|Gly|Ser|Gly|Ile|Ile|Ile|Ser|Asn|Ala|Pro|
| | | |275| | | | |280| | | | |285| | |

| | | | | | | | | | | | | | | |
|---|---|---|---|---|---|---|---|---|---|---|---|---|---|---|
|Met|Asp|Lys|Cys|Asp|Ala|Lys|Cys|Gln|Thr|Pro|Lys|Gly|Ala|Ile|Asn|
| |290| | | | |295| | | | |300| | | | |

| | | | | | | | | | | | | | | |
|---|---|---|---|---|---|---|---|---|---|---|---|---|---|---|
|Thr|Ser|Leu|Pro|Phe|Gln|Asn|Ile|His|Pro|Ile|Thr|Ile|Gly|Lys|Cys|
|305| | | | |310| | | | |315| | | | |320|

| | | | | | | | | | | | | | | |
|---|---|---|---|---|---|---|---|---|---|---|---|---|---|---|
|Pro|Lys|Tyr|Val|Lys|Ser|Thr|Lys|Leu|Arg|Leu|Ala|Thr|Gly|Leu|Arg|
| | | |325| | | | |330| | | | |335| | |

| | | | | | | | | | | | | | | |
|---|---|---|---|---|---|---|---|---|---|---|---|---|---|---|
|Asn|Ile|Gln|Ser|Ile|Gln|Ser|Arg|Gly|Leu|Phe|Gly|Ala|Ile|Ala|Gly|
| | | |340| | | | |345| | | | |350| | |

| | | | | | | | | | | | | | | |
|---|---|---|---|---|---|---|---|---|---|---|---|---|---|---|
|Phe|Ile|Glu|Gly|Gly|Trp|Thr|Gly|Met|Val|Asp|Gly|Trp|Tyr|Gly|Tyr|
| | | |355| | | | |360| | | | |365| | |

| | | | | | | | | | | | | | | |
|---|---|---|---|---|---|---|---|---|---|---|---|---|---|---|
|His|His|Gln|Asn|Glu|Gln|Gly|Ser|Gly|Tyr|Ala|Ala|Asp|Leu|Lys|Ser|
| | |370| | | | |375| | | | |380| | | |

| | | | | | | | | | | | | | | |
|---|---|---|---|---|---|---|---|---|---|---|---|---|---|---|
|Thr|Gln|Asn|Ala|Ile|Asn|Glu|Ile|Thr|Asn|Lys|Val|Asn|Ser|Val|Ile|
|385| | | | |390| | | | |395| | | | |400|

| | | | | | | | | | | | | | | |
|---|---|---|---|---|---|---|---|---|---|---|---|---|---|---|
|Glu|Lys|Met|Asn|Thr|Gln|Phe|Thr|Ala|Val|Gly|Lys|Glu|Phe|Asn|His|

```
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Glu Arg Thr Leu Asp Tyr His Asp Ser Asn Val Lys Asn Leu Tyr Glu
    450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 19
<211> LENGTH: 4
<212> TYPE: PRT
<213> ORGANISM: Influenza A virus

<400> SEQUENCE: 19

Asp Thr Ile Cys
1

<210> SEQ ID NO 20
<211> LENGTH: 4
<212> TYPE: PRT
<213> ORGANISM: Influenza A virus

<400> SEQUENCE: 20

Asp Thr Leu Cys
1

<210> SEQ ID NO 21
<211> LENGTH: 4
<212> TYPE: PRT
<213> ORGANISM: Influenza A virus

<400> SEQUENCE: 21

Gln Lys Leu Pro
1

<210> SEQ ID NO 22
<211> LENGTH: 4
<212> TYPE: PRT
<213> ORGANISM: Influenza A virus

<400> SEQUENCE: 22

Gln Asp Leu Pro
1

<210> SEQ ID NO 23
<211> LENGTH: 83

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agcaaaagca ggggaaaata aaacaacca aaatgaaggc aaacctactg gtcctgttat      60
gtgcacttgc agctgcagat gca                                            83

<210> SEQ ID NO 24
<211> LENGTH: 159
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
cagattctgg cgatctactc aactgtcgcc agttcactgg tgcttttggt ctccctgggg    60
gcaatcagtt tctggatgtg ttctaatgga tctttgcagt gcagaatatg catctgagat   120
tagaatttca gagatatgag gaaaaacacc cttgtttct                          159

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
atgaaagtaa aactactggt cctgttatgt acatttacag ctacatatgc               50

<210> SEQ ID NO 26
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atggaagcaa gactactagt cctgttatgt gcatttgcag ctacaaatgc agacacaata    60
tgtataggct accatgcg                                                  78

<210> SEQ ID NO 27
<211> LENGTH: 210
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atgaaagcaa aactactagt tctgttatgt gcatttacag ctacatatgc agacacaata    60
tgtataggct accatgcgaa caactcaacc gacactgttg acacagtact gaaaagaac    120 gtgacagtga cacactctgt caacctactt gaggacagtc acaacggaaa actatgtcga   180
ctaaaaggaa tagccccact acaattgggt                                    210

<210> SEQ ID NO 28
<211> LENGTH: 333
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
aagaacaatg ccaaagaaat aggaaacggg tgttttgaat tctaccacaa gtgtaacaat    60
gaatgcatgg aaagtgtgaa aaatggaact tatgactatc caaaatattc cgaggaatca   120
aagttaaaca gggaaaaaat tgatggagtg aaattggaat caatgggagt ctatcagatt   180
ctggcgatct actcaactgt cgccagttca ctggtgcttt tggtctccct ggggggcaatc   240 agcttctgga tgtgttctaa tgggtctttg cagtgtagaa tatgcatctg agattagaat   300
ttcagagata tgaggaaaaa cacccttgtt tct                                333

<210> SEQ ID NO 29
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
agcaaaagca ggggaaaata aaacaacca aatgaaggc aaacctactg gtcctgttat    60
gtgcacttgc agctgcagat gc                                             82

<210> SEQ ID NO 30
<211> LENGTH: 160
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
acagattctg gcgatctact caactgtcgc cagttcactg gtgcttttgg tctccctggg    60
ggcaatcagt ttctggatgt gttctaatgg atctttgcag tgcagaatat gcatctgaga   120 ttagaattc agagatatga ggaaaaacac ccttgtttct                          160

<210> SEQ ID NO 31
<211> LENGTH: 174
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
atgaaagcaa aactactagt tctgttatgt gcatttacag ctacatatgc agacacaata    60
tgtataggct accatgcgaa caactcaacc gacactgttg acacagtact tgaaaagaac   120
gtgacagtga cacactctgt caacctactt gaggacagtc acaacggaaa acta         174

<210> SEQ ID NO 32
<211> LENGTH: 258
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
gtgaaaaatg gaacttatga ctatccaaaa tattccgagg aatcaaagtt aaacagggaa      60
aaaattgatg gagtgaaatt ggaatcaatg ggagtctatc agattctggc gatctactca    120
actgtcgcca gttcactggt gcttttggtc tccctggggg caatcagctt ctggatgtgt    180
tctaatgggt ctttgcagtg tagaaatatgc atctgagatt agaatttcag agatatgagg    240
aaaaacaccc ttgtttct                                                    258
```

```
<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Met Glu Ala Arg Leu Leu Val Leu Leu Cys Ala Phe Ala
1               5                   10
```

```
<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
atggaagcaa gactactggt                                                  20
```

```
<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
atgaaagtaa aactactggt                                                  20
```

```
<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
atggaagcaa aactactggt                                                  20
```

```
<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atggacgcca aactactggt                                                  20
```

```
<210> SEQ ID NO 38
```

```
<211> LENGTH: 566
<212> TYPE: PRT
<213> ORGANISM: Influenza A virus
<220> FEATURE:
<221> NAME/KEY: MOD_RES
<222> LOCATION: (18)..(59)
<223> OTHER INFORMATION: Any amino acid
<220> FEATURE:
<221> NAME/KEY: MOD_RES
<222> LOCATION: (61)..(82)
<223> OTHER INFORMATION: Any amino acid
<220> FEATURE:
<221> NAME/KEY: MOD_RES
<222> LOCATION: (84)..(85)
<223> OTHER INFORMATION: Any amino acid
<220> FEATURE:
<221> NAME/KEY: MOD_RES
<222> LOCATION: (87)..(87)
<223> OTHER INFORMATION: Any amino acid
<220> FEATURE:
<221> NAME/KEY: MOD_RES
<222> LOCATION: (89)..(96)
<223> OTHER INFORMATION: Any amino acid
<220> FEATURE:
<221> NAME/KEY: MOD_RES
<222> LOCATION: (98)..(110)
<223> OTHER INFORMATION: Any amino acid
<220> FEATURE:
<221> NAME/KEY: MOD_RES
<222> LOCATION: (112)..(149)
<223> OTHER INFORMATION: Any amino acid
<220> FEATURE:
<221> NAME/KEY: MOD_RES
<222> LOCATION: (152)..(157)
<223> OTHER INFORMATION: Any amino acid
<220> FEATURE:
<221> NAME/KEY: MOD_RES
<222> LOCATION: (159)..(169)
<223> OTHER INFORMATION: Any amino acid
<220> FEATURE:
<221> NAME/KEY: MOD_RES
<222> LOCATION: (171)..(177)
<223> OTHER INFORMATION: Any amino acid
<220> FEATURE:
<221> NAME/KEY: MOD_RES
<222> LOCATION: (179)..(182)
<223> OTHER INFORMATION: Any amino acid
<220> FEATURE:
<221> NAME/KEY: MOD_RES
<222> LOCATION: (184)..(199)
<223> OTHER INFORMATION: Any amino acid
<220> FEATURE:
<221> NAME/KEY: MOD_RES
<222> LOCATION: (201)..(207)
<223> OTHER INFORMATION: Any amino acid
<220> FEATURE:
<221> NAME/KEY: MOD_RES
<222> LOCATION: (209)..(225)
<223> OTHER INFORMATION: Any amino acid
<220> FEATURE:
<221> NAME/KEY: MOD_RES
<222> LOCATION: (227)..(268)
<223> OTHER INFORMATION: Any amino acid
<220> FEATURE:
<221> NAME/KEY: MOD_RES
<222> LOCATION: (270)..(283)
<223> OTHER INFORMATION: Any amino acid
<220> FEATURE:
<221> NAME/KEY: MOD_RES
<222> LOCATION: (285)..(287)
<223> OTHER INFORMATION: Any amino acid
<220> FEATURE:
<221> NAME/KEY: MOD_RES
<222> LOCATION: (289)..(326)
<223> OTHER INFORMATION: Any amino acid
<220> FEATURE:
<221> NAME/KEY: MOD_RES
<222> LOCATION: (328)..(361)
<223> OTHER INFORMATION: Any amino acid
```

```
<220> FEATURE:
<221> NAME/KEY: MOD_RES
<222> LOCATION: (363)..(448)
<223> OTHER INFORMATION: Any amino acid
<220> FEATURE:
<221> NAME/KEY: MOD_RES
<222> LOCATION: (450)..(514)
<223> OTHER INFORMATION: Any amino acid
<220> FEATURE:
<221> NAME/KEY: MOD_RES
<222> LOCATION: (516)..(528)
<223> OTHER INFORMATION: Any amino acid

<400> SEQUENCE: 38

Met Lys Ala Lys Leu Leu Val Leu Leu Cys Ala Phe Thr Ala Thr Tyr
1               5                   10                  15

Ala Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Arg Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Lys Xaa Xaa Ser Xaa Phe Xaa Xaa Xaa Xaa Xaa Xaa Xaa Xaa
                85                  90                  95

Ala Xaa Xaa Xaa Xaa Xaa Xaa Xaa Xaa Xaa Xaa Xaa Xaa Tyr Xaa Xaa
                100                 105                 110

Xaa Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Thr Thr Xaa Xaa Xaa Xaa Xaa Xaa Lys Xaa Xaa
    145                 150                 155                 160

Xaa Xaa Xaa Xaa Xaa Xaa Xaa Xaa Lys Xaa Xaa Xaa Xaa Xaa Xaa Xaa
                165                 170                 175

Xaa Val Xaa Xaa Xaa Xaa Val Xaa Xaa Xaa Xaa Xaa Xaa Xaa Xaa Xaa
                180                 185                 190

Xaa Xaa Xaa Xaa Xaa Xaa Ser Xaa Xaa Xaa Xaa Xaa Xaa Xaa Xaa Ile
            195                 200                 205

Xaa Xaa Xaa Xaa Xaa Xaa Xaa Xaa Xaa Xaa Xaa Xaa Xaa Xaa Xaa Xaa
        210                 215                 220

Xaa Arg Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Trp Xaa Xaa Xaa Xaa Xaa
                260                 265                 270

Xaa Xaa Xaa Xaa Xaa Xaa Xaa Xaa Xaa Thr Xaa Xaa Xaa Ser Xaa Xaa
            275                 280                 285

Xaa Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Thr Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa
```

```
                    340                 345                 350
Xaa Xaa Xaa Xaa Xaa Xaa Xaa Xaa Ile Xaa Xaa Xaa Xaa Xaa Xaa
                355                 360                 365

Xaa Xaa Xaa Xaa Xaa Xaa Xaa Xaa Xaa Xaa Xaa Xaa Xaa Xaa Xaa
            370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa
        435                 440                 445

Gly Xaa Xaa Xaa Xaa Xaa Xaa Xaa Xaa Xaa Xaa Xaa Xaa Xaa Xaa
            450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa
            500                 505                 510

Xaa Xaa Gly Xaa Xaa Xaa Xaa Xaa Xaa Xaa Xaa Xaa Xaa Xaa Xaa
        515                 520                 525

Gln Ile Leu Ala Ile Tyr Ser Thr Val Ala Ser Ser Leu Val Leu Leu
            530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 39
<211> LENGTH: 565
<212> TYPE: PRT
<213> ORGANISM: Influenza A virus
<220> FEATURE:
<221> NAME/KEY: MOD_RES
<222> LOCATION: (18)..(110)
<223> OTHER INFORMATION: Any amino acid
<220> FEATURE:
<221> NAME/KEY: MOD_RES
<222> LOCATION: (112)..(156)
<223> OTHER INFORMATION: Any amino acid
<220> FEATURE:
<221> NAME/KEY: MOD_RES
<222> LOCATION: (158)..(181)
<223> OTHER INFORMATION: Any amino acid
<220> FEATURE:
<221> NAME/KEY: MOD_RES
<222> LOCATION: (183)..(202)
<223> OTHER INFORMATION: Any amino acid
<220> FEATURE:
<221> NAME/KEY: MOD_RES
<222> LOCATION: (204)..(224)
<223> OTHER INFORMATION: Any amino acid
<220> FEATURE:
<221> NAME/KEY: MOD_RES
<222> LOCATION: (226)..(267)
<223> OTHER INFORMATION: Any amino acid
<220> FEATURE:
<221> NAME/KEY: MOD_RES
<222> LOCATION: (269)..(282)
<223> OTHER INFORMATION: Any amino acid
<220> FEATURE:
<221> NAME/KEY: MOD_RES
```

<222> LOCATION: (284)..(527)
<223> OTHER INFORMATION: Any amino acid

<400> SEQUENCE: 39

```
Met Lys Ala Lys Leu Leu Val Leu Leu Cys Thr Phe Thr Ala Thr Tyr
1               5                   10                  15

Ala Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Tyr Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Lys Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Val Xaa Xaa Xaa Xaa Xaa Xaa Xaa Xaa Xaa Xaa Xaa
            180                 185                 190

Xaa Xaa Xaa Xaa Xaa Xaa Xaa Xaa Asn Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
210                 215                 220

Arg Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Trp Xaa Xaa Xaa Xaa Xaa
            260                 265                 270

Xaa Xaa Xaa Xaa Xaa Xaa Xaa Xaa Xaa Thr Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
370                 375                 380

Xaa Xaa Xaa Xaa Xaa Xaa Xaa Xaa Xaa Xaa Xaa Xaa Xaa Xaa Xaa Xaa
385                 390                 395                 400
```

```
Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa
                420                 425                 430

Xaa Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Gln
        515                 520                 525

Ile Leu Ala Ile Tyr Ser Thr Val Ala Ser Ser Leu Val Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 40
<211> LENGTH: 565
<212> TYPE: PRT
<213> ORGANISM: Influenza A virus
<220> FEATURE:
<221> NAME/KEY: MOD_RES
<222> LOCATION: (18)..(89)
<223> OTHER INFORMATION: Any amino acid
<220> FEATURE:
<221> NAME/KEY: MOD_RES
<222> LOCATION: (91)..(98)
<223> OTHER INFORMATION: Any amino acid
<220> FEATURE:
<221> NAME/KEY: MOD_RES
<222> LOCATION: (100)..(110)
<223> OTHER INFORMATION: Any amino acid
<220> FEATURE:
<221> NAME/KEY: MOD_RES
<222> LOCATION: (112)..(144)
<223> OTHER INFORMATION: Any amino acid
<220> FEATURE:
<221> NAME/KEY: MOD_RES
<222> LOCATION: (146)..(156)
<223> OTHER INFORMATION: Any amino acid
<220> FEATURE:
<221> NAME/KEY: MOD_RES
<222> LOCATION: (158)..(161)
<223> OTHER INFORMATION: Any amino acid
<220> FEATURE:
<221> NAME/KEY: MOD_RES
<222> LOCATION: (163)..(181)
<223> OTHER INFORMATION: Any amino acid
<220> FEATURE:
<221> NAME/KEY: MOD_RES
<222> LOCATION: (183)..(238)
<223> OTHER INFORMATION: Any amino acid
<220> FEATURE:
<221> NAME/KEY: MOD_RES
<222> LOCATION: (240)..(282)
<223> OTHER INFORMATION: Any amino acid
<220> FEATURE:
<221> NAME/KEY: MOD_RES
<222> LOCATION: (284)..(431)
<223> OTHER INFORMATION: Any amino acid
```

```
<220> FEATURE:
<221> NAME/KEY: MOD_RES
<222> LOCATION: (433)..(488)
<223> OTHER INFORMATION: Any amino acid
<220> FEATURE:
<221> NAME/KEY: MOD_RES
<222> LOCATION: (490)..(527)
<223> OTHER INFORMATION: Any amino acid

<400> SEQUENCE: 40
```

| Met | Lys | Val | Lys | Leu | Leu | Val | Leu | Leu | Cys | Thr | Phe | Thr | Ala | Thr | Tyr |
|---|---|---|---|---|---|---|---|---|---|---|---|---|---|---|---|
| 1 | | | | 5 | | | | | 10 | | | | | 15 | |

| Ala | Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|---|
| | | | | 20 | | | | | 25 | | | | | 30 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 35 | | | | | 40 | | | | | 45 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| 50 | | | | | 55 | | | | | 60 | | | | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| 65 | | | | | 70 | | | | | 75 | | | | 80 |

| Xaa | Xaa | Xaa | Xaa | Xaa | Xaa | Xaa | Xaa | Arg | Xaa | Xaa | Xaa | Xaa | Xaa | Xaa |
|---|---|---|---|---|---|---|---|---|---|---|---|---|---|---|
| | | | | 85 | | | | | 90 | | | | | 95 |

| Xaa | Xaa | Lys | Xaa | Xaa | Xaa | Xaa | Xaa | Xaa | Xaa | Xaa | Xaa | Xaa | His | Xaa |
|---|---|---|---|---|---|---|---|---|---|---|---|---|---|---|
| | | | 100 | | | | | 105 | | | | | 110 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | 115 | | | | | 120 | | | | | 125 | | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| 130 | | | | | 135 | | | | | 140 | | | | |

| Thr | Xaa | Xaa | Xaa | Xaa | Xaa | Xaa | Xaa | Xaa | Xaa | Xaa | Glu | Xaa | Xaa | Xaa |
|---|---|---|---|---|---|---|---|---|---|---|---|---|---|---|
| 145 | | | | | 150 | | | | | 155 | | | | 160 |

| Xaa | Lys | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | | 165 | | | | | 170 | | | | | 175 |

| Xaa | Xaa | Xaa | Xaa | Xaa | Ala | Xaa | Xaa | Xaa | Xaa | Xaa | Xaa | Xaa | Xaa | Xaa |
|---|---|---|---|---|---|---|---|---|---|---|---|---|---|---|
| | | | | 180 | | | | | 185 | | | | | 190 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | 195 | | | | | 200 | | | | | 205 | | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| 210 | | | | | 215 | | | | | 220 | | | | |

| Xaa | Xaa | Xaa | Xaa | Xaa | Xaa | Xaa | Xaa | Xaa | Xaa | Xaa | Xaa | Arg | Xaa |
|---|---|---|---|---|---|---|---|---|---|---|---|---|---|
| 225 | | | | | 230 | | | | | 235 | | | 240 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | | 245 | | | | | 250 | | | | | 255 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | | 260 | | | | | 265 | | | | | 270 |

| Xaa | Xaa | Xaa | Xaa | Xaa | Xaa | Xaa | Xaa | Asn | Xaa | Xaa | Xaa | Xaa | Xaa |
|---|---|---|---|---|---|---|---|---|---|---|---|---|---|
| | | 275 | | | | | 280 | | | | | 285 | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| 290 | | | | | 295 | | | | | 300 | | | | |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| 305 | | | | | 310 | | | | | 315 | | | | 320 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | | 325 | | | | | 330 | | | | | 335 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | | 340 | | | | | 345 | | | | | 350 |

| Xaa | Xaa | Xaa | Xaa | Xaa | Xaa | Xaa | Xaa | Xaa | Xaa | Xaa | Xaa | Xaa | Xaa | Xaa |
|---|---|---|---|---|---|---|---|---|---|---|---|---|---|---|
| | | | 355 | | | | | 360 | | | | | 365 | |

```
Xaa Xaa Xaa Xaa Xaa Xaa Xaa Xaa Xaa Xaa Xaa Xaa Xaa Xaa Xaa
        370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
        405                 410                 415

Xaa Xaa Xaa Xaa Xaa Xaa Xaa Xaa Xaa Xaa Xaa Xaa Xaa Xaa Ile
            420                 425                 430

Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Asp Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
        500                 505                 510

Xaa Xaa Xaa Xaa Xaa Xaa Xaa Xaa Xaa Xaa Xaa Xaa Xaa Xaa Gln
        515                 520                 525

Ile Leu Ala Ile Tyr Ser Thr Val Ala Ser Ser Arg Val Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 41
<211> LENGTH: 565
<212> TYPE: PRT
<213> ORGANISM: Influenza A virus
<220> FEATURE:
<221> NAME/KEY: MOD_RES
<222> LOCATION: (18)..(51)
<223> OTHER INFORMATION: Any amino acid
<220> FEATURE:
<221> NAME/KEY: MOD_RES
<222> LOCATION: (53)..(98)
<223> OTHER INFORMATION: Any amino acid
<220> FEATURE:
<221> NAME/KEY: MOD_RES
<222> LOCATION: (100)..(110)
<223> OTHER INFORMATION: Any amino acid
<220> FEATURE:
<221> NAME/KEY: MOD_RES
<222> LOCATION: (112)..(156)
<223> OTHER INFORMATION: Any amino acid
<220> FEATURE:
<221> NAME/KEY: MOD_RES
<222> LOCATION: (158)..(181)
<223> OTHER INFORMATION: Any amino acid
<220> FEATURE:
<221> NAME/KEY: MOD_RES
<222> LOCATION: (183)..(202)
<223> OTHER INFORMATION: Any amino acid
<220> FEATURE:
<221> NAME/KEY: MOD_RES
<222> LOCATION: (204)..(204)
<223> OTHER INFORMATION: Any amino acid
<220> FEATURE:
<221> NAME/KEY: MOD_RES
<222> LOCATION: (206)..(282)
<223> OTHER INFORMATION: Any amino acid
<220> FEATURE:
<221> NAME/KEY: MOD_RES
```

-continued

```
<222> LOCATION: (284)..(289)
<223> OTHER INFORMATION: Any amino acid
<220> FEATURE:
<221> NAME/KEY: MOD_RES
<222> LOCATION: (291)..(431)
<223> OTHER INFORMATION: Any amino acid
<220> FEATURE:
<221> NAME/KEY: MOD_RES
<222> LOCATION: (433)..(488)
<223> OTHER INFORMATION: Any amino acid
<220> FEATURE:
<221> NAME/KEY: MOD_RES
<222> LOCATION: (490)..(527)
<223> OTHER INFORMATION: Any amino acid

<400> SEQUENCE: 41

Met Lys Val Lys Leu Leu Val Leu Leu Cys Thr Phe Thr Ala Thr Tyr
1               5                   10                  15

Ala Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Asn Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Lys Xaa Xaa Xaa Xaa Xaa Xaa Xaa Xaa Xaa Xaa His Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Glu Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Ala Xaa Xaa Xaa Xaa Xaa Xaa Xaa Xaa Xaa Xaa
            180                 185                 190

Xaa Xaa Xaa Xaa Xaa Xaa Xaa Xaa Asn Xaa Lys Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Asn Xaa Xaa Xaa Xaa Xaa Xaa Xaa
        275                 280                 285

Xaa Lys Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa Xaa
                325                 330                 335
```

```
Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Ile
        420                 425                 430

Xaa Xaa Xaa Xaa Xaa Xaa Xaa Xaa Xaa Xaa Xaa Xaa Xaa Xaa
    435                 440                 445

Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Asp Xaa Xaa Xaa Xaa Xaa
            485                 490                 495

Xaa Xaa Xaa Xaa Xaa Xaa Xaa Xaa Xaa Xaa Xaa Xaa Xaa Xaa
        500                 505                 510

Xaa Xaa Xaa Xaa Xaa Xaa Xaa Xaa Xaa Xaa Xaa Xaa Xaa Gln
    515                 520                 525

Ile Leu Ala Ile Tyr Ser Thr Val Ala Ser Ser Leu Val Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 42
<211> LENGTH: 566
<212> TYPE: PRT
<213> ORGANISM: Influenza A virus
<220> FEATURE:
<221> NAME/KEY: MOD_RES
<222> LOCATION: (18)..(19)
<223> OTHER INFORMATION: Any amino acid
<220> FEATURE:
<221> NAME/KEY: MOD_RES
<222> LOCATION: (21)..(52)
<223> OTHER INFORMATION: Any amino acid
<220> FEATURE:
<221> NAME/KEY: MOD_RES
<222> LOCATION: (54)..(59)
<223> OTHER INFORMATION: Any amino acid
<220> FEATURE:
<221> NAME/KEY: MOD_RES
<222> LOCATION: (61)..(61)
<223> OTHER INFORMATION: Any amino acid
<220> FEATURE:
<221> NAME/KEY: MOD_RES
<222> LOCATION: (63)..(63)
<223> OTHER INFORMATION: Any amino acid
<220> FEATURE:
<221> NAME/KEY: MOD_RES
<222> LOCATION: (65)..(67)
<223> OTHER INFORMATION: Any amino acid
<220> FEATURE:
<221> NAME/KEY: MOD_RES
<222> LOCATION: (69)..(70)
<223> OTHER INFORMATION: Any amino acid
```

-continued

```
<220> FEATURE:
<221> NAME/KEY: MOD_RES
<222> LOCATION: (72)..(72)
<223> OTHER INFORMATION: Any amino acid
<220> FEATURE:
<221> NAME/KEY: MOD_RES
<222> LOCATION: (75)..(85)
<223> OTHER INFORMATION: Any amino acid
<220> FEATURE:
<221> NAME/KEY: MOD_RES
<222> LOCATION: (87)..(87)
<223> OTHER INFORMATION: Any amino acid
<220> FEATURE:
<221> NAME/KEY: MOD_RES
<222> LOCATION: (92)..(100)
<223> OTHER INFORMATION: Any amino acid
<220> FEATURE:
<221> NAME/KEY: MOD_RES
<222> LOCATION: (104)..(110)
<223> OTHER INFORMATION: Any amino acid
<220> FEATURE:
<221> NAME/KEY: MOD_RES
<222> LOCATION: (112)..(112)
<223> OTHER INFORMATION: Any amino acid
<220> FEATURE:
<221> NAME/KEY: MOD_RES
<222> LOCATION: (114)..(136)
<223> OTHER INFORMATION: Any amino acid
<220> FEATURE:
<221> NAME/KEY: MOD_RES
<222> LOCATION: (138)..(143)
<223> OTHER INFORMATION: Any amino acid
<220> FEATURE:
<221> NAME/KEY: MOD_RES
<222> LOCATION: (147)..(149)
<223> OTHER INFORMATION: Any amino acid
<220> FEATURE:
<221> NAME/KEY: MOD_RES
<222> LOCATION: (151)..(151)
<223> OTHER INFORMATION: Any amino acid
<220> FEATURE:
<221> NAME/KEY: MOD_RES
<222> LOCATION: (153)..(153)
<223> OTHER INFORMATION: Any amino acid
<220> FEATURE:
<221> NAME/KEY: MOD_RES
<222> LOCATION: (155)..(155)
<223> OTHER INFORMATION: Any amino acid
<220> FEATURE:
<221> NAME/KEY: MOD_RES
<222> LOCATION: (157)..(157)
<223> OTHER INFORMATION: Any amino acid
<220> FEATURE:
<221> NAME/KEY: MOD_RES
<222> LOCATION: (160)..(162)
<223> OTHER INFORMATION: Any amino acid
<220> FEATURE:
<221> NAME/KEY: MOD_RES
<222> LOCATION: (164)..(165)
<223> OTHER INFORMATION: Any amino acid
<220> FEATURE:
<221> NAME/KEY: MOD_RES
<222> LOCATION: (167)..(168)
<223> OTHER INFORMATION: Any amino acid
<220> FEATURE:
<221> NAME/KEY: MOD_RES
<222> LOCATION: (171)..(171)
<223> OTHER INFORMATION: Any amino acid
<220> FEATURE:
<221> NAME/KEY: MOD_RES
<222> LOCATION: (175)..(176)
<223> OTHER INFORMATION: Any amino acid
<220> FEATURE:
<221> NAME/KEY: MOD_RES
<222> LOCATION: (178)..(182)
<223> OTHER INFORMATION: Any amino acid
<220> FEATURE:
<221> NAME/KEY: MOD_RES
<222> LOCATION: (184)..(184)
```

```
<223> OTHER INFORMATION: Any amino acid
<220> FEATURE:
<221> NAME/KEY: MOD_RES
<222> LOCATION: (186)..(186)
<223> OTHER INFORMATION: Any amino acid
<220> FEATURE:
<221> NAME/KEY: MOD_RES
<222> LOCATION: (188)..(195)
<223> OTHER INFORMATION: Any amino acid
<220> FEATURE:
<221> NAME/KEY: MOD_RES
<222> LOCATION: (197)..(199)
<223> OTHER INFORMATION: Any amino acid
<220> FEATURE:
<221> NAME/KEY: MOD_RES
<222> LOCATION: (204)..(205)
<223> OTHER INFORMATION: Any amino acid
<220> FEATURE:
<221> NAME/KEY: MOD_RES
<222> LOCATION: (208)..(209)
<223> OTHER INFORMATION: Any amino acid
<220> FEATURE:
<221> NAME/KEY: MOD_RES
<222> LOCATION: (214)..(216)
<223> OTHER INFORMATION: Any amino acid
<220> FEATURE:
<221> NAME/KEY: MOD_RES
<222> LOCATION: (218)..(218)
<223> OTHER INFORMATION: Any amino acid
<220> FEATURE:
<221> NAME/KEY: MOD_RES
<222> LOCATION: (220)..(221)
<223> OTHER INFORMATION: Any amino acid
<220> FEATURE:
<221> NAME/KEY: MOD_RES
<222> LOCATION: (223)..(224)
<223> OTHER INFORMATION: Any amino acid
<220> FEATURE:
<221> NAME/KEY: MOD_RES
<222> LOCATION: (226)..(227)
<223> OTHER INFORMATION: Any amino acid
<220> FEATURE:
<221> NAME/KEY: MOD_RES
<222> LOCATION: (229)..(232)
<223> OTHER INFORMATION: Any amino acid
<220> FEATURE:
<221> NAME/KEY: MOD_RES
<222> LOCATION: (234)..(239)
<223> OTHER INFORMATION: Any amino acid
<220> FEATURE:
<221> NAME/KEY: MOD_RES
<222> LOCATION: (241)..(243)
<223> OTHER INFORMATION: Any amino acid
<220> FEATURE:
<221> NAME/KEY: MOD_RES
<222> LOCATION: (245)..(250)
<223> OTHER INFORMATION: Any amino acid
<220> FEATURE:
<221> NAME/KEY: MOD_RES
<222> LOCATION: (252)..(255)
<223> OTHER INFORMATION: Any amino acid
<220> FEATURE:
<221> NAME/KEY: MOD_RES
<222> LOCATION: (257)..(257)
<223> OTHER INFORMATION: Any amino acid
<220> FEATURE:
<221> NAME/KEY: MOD_RES
<222> LOCATION: (259)..(261)
<223> OTHER INFORMATION: Any amino acid
<220> FEATURE:
<221> NAME/KEY: MOD_RES
<222> LOCATION: (263)..(265)
<223> OTHER INFORMATION: Any amino acid
<220> FEATURE:
<221> NAME/KEY: MOD_RES
<222> LOCATION: (268)..(273)
<223> OTHER INFORMATION: Any amino acid
<220> FEATURE:
<221> NAME/KEY: MOD_RES
```

```
<222> LOCATION: (276)..(276)
<223> OTHER INFORMATION: Any amino acid
<220> FEATURE:
<221> NAME/KEY: MOD_RES
<222> LOCATION: (279)..(283)
<223> OTHER INFORMATION: Any amino acid
<220> FEATURE:
<221> NAME/KEY: MOD_RES
<222> LOCATION: (285)..(285)
<223> OTHER INFORMATION: Any amino acid
<220> FEATURE:
<221> NAME/KEY: MOD_RES
<222> LOCATION: (288)..(288)
<223> OTHER INFORMATION: Any amino acid
<220> FEATURE:
<221> NAME/KEY: MOD_RES
<222> LOCATION: (292)..(292)
<223> OTHER INFORMATION: Any amino acid
<220> FEATURE:
<221> NAME/KEY: MOD_RES
<222> LOCATION: (296)..(299)
<223> OTHER INFORMATION: Any amino acid
<220> FEATURE:
<221> NAME/KEY: MOD_RES
<222> LOCATION: (301)..(304)
<223> OTHER INFORMATION: Any amino acid
<220> FEATURE:
<221> NAME/KEY: MOD_RES
<222> LOCATION: (306)..(311)
<223> OTHER INFORMATION: Any amino acid
<220> FEATURE:
<221> NAME/KEY: MOD_RES
<222> LOCATION: (313)..(314)
<223> OTHER INFORMATION: Any amino acid
<220> FEATURE:
<221> NAME/KEY: MOD_RES
<222> LOCATION: (316)..(318)
<223> OTHER INFORMATION: Any amino acid
<220> FEATURE:
<221> NAME/KEY: MOD_RES
<222> LOCATION: (320)..(324)
<223> OTHER INFORMATION: Any amino acid
<220> FEATURE:
<221> NAME/KEY: MOD_RES
<222> LOCATION: (326)..(326)
<223> OTHER INFORMATION: Any amino acid
<220> FEATURE:
<221> NAME/KEY: MOD_RES
<222> LOCATION: (328)..(330)
<223> OTHER INFORMATION: Any amino acid
<220> FEATURE:
<221> NAME/KEY: MOD_RES
<222> LOCATION: (333)..(381)
<223> OTHER INFORMATION: Any amino acid
<220> FEATURE:
<221> NAME/KEY: MOD_RES
<222> LOCATION: (383)..(389)
<223> OTHER INFORMATION: Any amino acid
<220> FEATURE:
<221> NAME/KEY: MOD_RES
<222> LOCATION: (392)..(415)
<223> OTHER INFORMATION: Any amino acid
<220> FEATURE:
<221> NAME/KEY: MOD_RES
<222> LOCATION: (417)..(418)
<223> OTHER INFORMATION: Any amino acid
<220> FEATURE:
<221> NAME/KEY: MOD_RES
<222> LOCATION: (420)..(420)
<223> OTHER INFORMATION: Any amino acid
<220> FEATURE:
<221> NAME/KEY: MOD_RES
<222> LOCATION: (422)..(453)
<223> OTHER INFORMATION: Any amino acid
<220> FEATURE:
<221> NAME/KEY: MOD_RES
<222> LOCATION: (455)..(466)
<223> OTHER INFORMATION: Any amino acid
<220> FEATURE:
```

```
<221> NAME/KEY: MOD_RES
<222> LOCATION: (468)..(488)
<223> OTHER INFORMATION: Any amino acid
<220> FEATURE:
<221> NAME/KEY: MOD_RES
<222> LOCATION: (490)..(490)
<223> OTHER INFORMATION: Any amino acid
<220> FEATURE:
<221> NAME/KEY: MOD_RES
<222> LOCATION: (492)..(509)
<223> OTHER INFORMATION: Any amino acid
<220> FEATURE:
<221> NAME/KEY: MOD_RES
<222> LOCATION: (511)..(515)
<223> OTHER INFORMATION: Any amino acid
<220> FEATURE:
<221> NAME/KEY: MOD_RES
<222> LOCATION: (517)..(524)
<223> OTHER INFORMATION: Any amino acid
<220> FEATURE:
<221> NAME/KEY: MOD_RES
<222> LOCATION: (528)..(528)
<223> OTHER INFORMATION: Any amino acid

<400> SEQUENCE: 42

Met Lys Ala Ile Leu Val Val Leu Leu Tyr Thr Phe Ala Thr Ala Asn
1               5                   10                  15

Ala Xaa Xaa Leu Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Lys Xaa Xaa Xaa Xaa Xaa Xaa Lys Xaa Arg Xaa Val
    50                  55                  60

Xaa Xaa Xaa His Xaa Xaa Lys Xaa Asn Ile Xaa Xaa Xaa Xaa Xaa Xaa
65                  70                  75                  80

Xaa Xaa Xaa Xaa Xaa Ser Xaa Ser Thr Ala Ser Xaa Xaa Xaa Xaa Xaa
                85                  90                  95

Xaa Xaa Xaa Xaa Ser Ser Asp Xaa Xaa Xaa Xaa Xaa Xaa Xaa Asp Xaa
            100                 105                 110

Ile Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Thr Xaa Xaa Xaa Xaa Xaa Xaa Xaa Asp
    130                 135                 140

Ser Asn Xaa Xaa Xaa Thr Xaa Ala Xaa Pro Xaa Ala Xaa Ala Lys Xaa
145                 150                 155                 160

Xaa Xaa Lys Xaa Xaa Ile Xaa Xaa Val Lys Xaa Gly Asn Ser Xaa Xaa
                165                 170                 175

Lys Xaa Xaa Xaa Xaa Xaa Ile Xaa Asp Xaa Gly Xaa Xaa Xaa Xaa Xaa
            180                 185                 190

Xaa Xaa Xaa Ile Xaa Xaa Xaa Ser Thr Ser Ala Xaa Xaa Gln Ser Xaa
        195                 200                 205

Xaa Gln Asn Ala Asp Xaa Xaa Xaa Phe Xaa Gly Xaa Xaa Arg Xaa Xaa
    210                 215                 220

Lys Xaa Xaa Lys Xaa Xaa Xaa Xaa Ile Xaa Xaa Xaa Xaa Xaa Xaa Arg
225                 230                 235                 240

Xaa Xaa Xaa Met Xaa Xaa Xaa Xaa Xaa Xaa Val Xaa Xaa Xaa Xaa Lys
                245                 250                 255

Xaa Thr Xaa Xaa Xaa Thr Xaa Xaa Xaa Xaa Val Val Xaa Xaa Xaa Xaa
            260                 265                 270

Xaa Met Glu Xaa Asn Ala Xaa Xaa Xaa Xaa Xaa Ile Xaa Asp Thr Xaa
        275                 280                 285
```

```
Val His Asp Xaa Asn Thr Thr Xaa Xaa Xaa Xaa Lys Xaa Xaa Xaa Xaa
290                 295                 300

Thr Xaa Xaa Xaa Xaa Xaa Xaa Ile Xaa Xaa Ile Xaa Xaa Xaa Lys Xaa
305                 310                 315                 320

Xaa Xaa Xaa Xaa Lys Xaa Thr Xaa Xaa Leu Ala Xaa Xaa Xaa Xaa
            325                 330                 335

Xaa Xaa Xaa Xaa Xaa Xaa Xaa Xaa Xaa Xaa Xaa Xaa Xaa Xaa Xaa
        340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Leu Xaa Xaa
        370                 375                 380

Xaa Xaa Xaa Xaa Xaa Asp Glu Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa His
                405                 410                 415

Xaa Xaa Lys Xaa Ile Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa
        435                 440                 445

Xaa Xaa Xaa Xaa Xaa Tyr Xaa Xaa Xaa Xaa Xaa Xaa Xaa Xaa
450                 455                 460

Xaa Xaa Arg Xaa Xaa Xaa Xaa Xaa Xaa Xaa Xaa Xaa Xaa Xaa
465                 470                 475                 480

Xaa Xaa Xaa Xaa Xaa Xaa Xaa Asp Xaa Thr Xaa Xaa Xaa Xaa
                485                 490                 495

Xaa Xaa Xaa Xaa Xaa Xaa Xaa Xaa Xaa Xaa Xaa Ala Xaa Xaa
            500                 505                 510

Xaa Xaa Xaa Glu Xaa Xaa Xaa Xaa Xaa Xaa Xaa Thr Arg Ile Xaa
            515                 520                 525

Gln Ile Leu Ala Ile Tyr Ser Thr Val Ala Ser Ser Leu Val Leu Val
530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 43
<211> LENGTH: 566
<212> TYPE: PRT
<213> ORGANISM: Influenza A virus
<220> FEATURE:
<221> NAME/KEY: MOD_RES
<222> LOCATION: (17)..(65)
<223> OTHER INFORMATION: Any amino acid
<220> FEATURE:
<221> NAME/KEY: MOD_RES
<222> LOCATION: (67)..(137)
<223> OTHER INFORMATION: Any amino acid
<220> FEATURE:
<221> NAME/KEY: MOD_RES
<222> LOCATION: (139)..(153)
<223> OTHER INFORMATION: Any amino acid
<220> FEATURE:
<221> NAME/KEY: MOD_RES
<222> LOCATION: (155)..(155)
<223> OTHER INFORMATION: Any amino acid
<220> FEATURE:
<221> NAME/KEY: MOD_RES
<222> LOCATION: (157)..(171)
```

```
<223> OTHER INFORMATION: Any amino acid
<220> FEATURE:
<221> NAME/KEY: MOD_RES
<222> LOCATION: (173)..(173)
<223> OTHER INFORMATION: Any amino acid
<220> FEATURE:
<221> NAME/KEY: MOD_RES
<222> LOCATION: (175)..(188)
<223> OTHER INFORMATION: Any amino acid
<220> FEATURE:
<221> NAME/KEY: MOD_RES
<222> LOCATION: (190)..(201)
<223> OTHER INFORMATION: Any amino acid
<220> FEATURE:
<221> NAME/KEY: MOD_RES
<222> LOCATION: (203)..(204)
<223> OTHER INFORMATION: Any amino acid
<220> FEATURE:
<221> NAME/KEY: MOD_RES
<222> LOCATION: (206)..(376)
<223> OTHER INFORMATION: Any amino acid
<220> FEATURE:
<221> NAME/KEY: MOD_RES
<222> LOCATION: (378)..(390)
<223> OTHER INFORMATION: Any amino acid
<220> FEATURE:
<221> NAME/KEY: MOD_RES
<222> LOCATION: (392)..(419)
<223> OTHER INFORMATION: Any amino acid
<220> FEATURE:
<221> NAME/KEY: MOD_RES
<222> LOCATION: (421)..(465)
<223> OTHER INFORMATION: Any amino acid
<220> FEATURE:
<221> NAME/KEY: MOD_RES
<222> LOCATION: (467)..(527)
<223> OTHER INFORMATION: Any amino acid

<400> SEQUENCE: 43

Met Lys Thr Ile Ile Ala Leu Ser Tyr Ile Leu Cys Leu Val Phe Ala
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Gly Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Asp Xaa Xaa Xaa Xaa Xaa
130                 135                 140

Xaa Xaa Xaa Xaa Xaa Xaa Xaa Xaa Ser Xaa Lys Xaa Xaa Xaa Xaa
            145                 150                 155                 160

Xaa Xaa Xaa Xaa Xaa Xaa Xaa Xaa Xaa Xaa Gln Xaa Lys Xaa Xaa
        165                 170                 175

Xaa Xaa Xaa Xaa Xaa Xaa Xaa Xaa Xaa Xaa Xaa Lys Xaa Xaa Xaa
    180                 185                 190

Xaa Xaa Xaa Xaa Xaa Xaa Xaa Xaa Val Xaa Xaa Asn Xaa Xaa Xaa
195                 200                 205
```

Xaa Xaa Xaa Xaa Xaa Xaa Xaa Xaa Xaa Xaa Xaa Xaa Xaa Xaa Xaa
    210                 215                 220
Xaa Xaa Xaa Xaa Xaa Xaa Xaa Xaa Xaa Xaa Xaa Xaa Xaa Xaa Xaa
225                 230                 235                 240
Xaa Xaa Xaa Xaa Xaa Xaa Xaa Xaa Xaa Xaa Xaa Xaa Xaa Xaa Xaa
                245                 250                 255
Xaa Xaa Xaa Xaa Xaa Xaa Xaa Xaa Xaa Xaa Xaa Xaa Xaa Xaa Xaa
    260                 265                 270
Xaa Xaa Xaa Xaa Xaa Xaa Xaa Xaa Xaa Xaa Xaa Xaa Xaa Xaa Xaa
            275                 280                 285
Xaa Xaa Xaa Xaa Xaa Xaa Xaa Xaa Xaa Xaa Xaa Xaa Xaa Xaa Xaa
    290                 295                 300
Xaa Xaa Xaa Xaa Xaa Xaa Xaa Xaa Xaa Xaa Xaa Xaa Xaa Xaa Xaa
305                 310                 315                 320
Xaa Xaa Xaa Xaa Xaa Xaa Xaa Xaa Xaa Xaa Xaa Xaa Xaa Xaa Xaa
                325                 330                 335
Xaa Xaa Xaa Xaa Xaa Xaa Xaa Xaa Xaa Xaa Xaa Xaa Xaa Xaa Xaa
    340                 345                 350
Xaa Xaa Xaa Xaa Xaa Xaa Xaa Xaa Xaa Xaa Xaa Xaa Xaa Xaa Xaa
            355                 360                 365
Xaa Xaa Xaa Xaa Xaa Xaa Xaa Ile Xaa Xaa Xaa Xaa Xaa Xaa Xaa
    370                 375                 380
Xaa Xaa Xaa Xaa Xaa Asn Xaa Xaa Xaa Xaa Xaa Xaa Xaa Xaa Xaa
385                 390                 395                 400
Xaa Xaa Xaa Xaa Xaa Xaa Xaa Xaa Xaa Xaa Xaa Xaa Xaa Xaa Xaa
                405                 410                 415
Xaa Xaa Xaa Arg Xaa Xaa Xaa Xaa Xaa Xaa Xaa Xaa Xaa Xaa Xaa
    420                 425                 430
Xaa Xaa Xaa Xaa Xaa Xaa Xaa Xaa Xaa Xaa Xaa Xaa Xaa Xaa Xaa
            435                 440                 445
Xaa Xaa Xaa Xaa Xaa Xaa Xaa Xaa Xaa Xaa Xaa Xaa Xaa Xaa Xaa
    450                 455                 460
Xaa Arg Xaa Xaa Xaa Xaa Xaa Xaa Xaa Xaa Xaa Xaa Xaa Xaa Xaa
465                 470                 475                 480
Xaa Xaa Xaa Xaa Xaa Xaa Xaa Xaa Xaa Xaa Xaa Xaa Xaa Xaa Xaa
                485                 490                 495
Xaa Xaa Xaa Xaa Xaa Xaa Xaa Xaa Xaa Xaa Xaa Xaa Xaa Xaa Xaa
    500                 505                 510
Xaa Xaa Xaa Xaa Xaa Xaa Xaa Xaa Xaa Xaa Xaa Xaa Xaa Xaa Lys
            515                 520                 525
Asp Trp Ile Leu Trp Ile Ser Phe Ala Ile Ser Cys Phe Leu Cys
    530                 535                 540
Val Ala Leu Leu Gly Phe Ile Met Trp Ala Cys Gln Lys Gly Asn Ile
545                 550                 555                 560
Arg Cys Asn Ile Cys Ile
            565

<210> SEQ ID NO 44
<211> LENGTH: 566
<212> TYPE: PRT
<213> ORGANISM: Influenza A virus
<220> FEATURE:
<221> NAME/KEY: MOD_RES
<222> LOCATION: (17)..(60)
<223> OTHER INFORMATION: Any amino acid
<220> FEATURE:

-continued

```
<221> NAME/KEY: MOD_RES
<222> LOCATION: (62)..(63)
<223> OTHER INFORMATION: Any amino acid
<220> FEATURE:
<221> NAME/KEY: MOD_RES
<222> LOCATION: (65)..(201)
<223> OTHER INFORMATION: Any amino acid
<220> FEATURE:
<221> NAME/KEY: MOD_RES
<222> LOCATION: (203)..(213)
<223> OTHER INFORMATION: Any amino acid
<220> FEATURE:
<221> NAME/KEY: MOD_RES
<222> LOCATION: (215)..(227)
<223> OTHER INFORMATION: Any amino acid
<220> FEATURE:
<221> NAME/KEY: MOD_RES
<222> LOCATION: (229)..(327)
<223> OTHER INFORMATION: Any amino acid
<220> FEATURE:
<221> NAME/KEY: MOD_RES
<222> LOCATION: (329)..(527)
<223> OTHER INFORMATION: Any amino acid

<400> SEQUENCE: 44

Met Lys Thr Ile Ile Ala Leu Ser His Ile Leu Cys Leu Val Phe Ala
 1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Asn Xaa Xaa Ile
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Gly Xaa Xaa Xaa Xaa Xaa Xaa
        195                 200                 205

Xaa Xaa Xaa Xaa Xaa Ser Xaa Xaa Xaa Xaa Xaa Xaa Xaa Xaa
        210                 215                 220

Xaa Xaa Xaa Ala Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Xaa Xaa Xaa Xaa Xaa Xaa Xaa Xaa
        275                 280                 285
```

Xaa Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Ser Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa
        340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
        370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
        405                 410                 415

Xaa Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
        485                 490                 495

Xaa Xaa Xaa Xaa Xaa Xaa Xaa Xaa Xaa Xaa Xaa Xaa Xaa Xaa Xaa
        500                 505                 510

Xaa Xaa Xaa Xaa Xaa Xaa Xaa Xaa Xaa Xaa Xaa Xaa Xaa Xaa Lys
        515                 520                 525

Asp Trp Ile Leu Trp Ile Ser Phe Ala Ile Ser Cys Phe Leu Leu Cys
        530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 45
<211> LENGTH: 566
<212> TYPE: PRT
<213> ORGANISM: Influenza A virus
<220> FEATURE:
<221> NAME/KEY: MOD_RES
<222> LOCATION: (17)..(48)
<223> OTHER INFORMATION: Any amino acid
<220> FEATURE:
<221> NAME/KEY: MOD_RES
<222> LOCATION: (50)..(60)
<223> OTHER INFORMATION: Any amino acid
<220> FEATURE:
<221> NAME/KEY: MOD_RES
<222> LOCATION: (62)..(63)
<223> OTHER INFORMATION: Any amino acid
<220> FEATURE:
<221> NAME/KEY: MOD_RES
<222> LOCATION: (65)..(143)
<223> OTHER INFORMATION: Any amino acid
<220> FEATURE:
<221> NAME/KEY: MOD_RES
<222> LOCATION: (145)..(201)

<223> OTHER INFORMATION: Any amino acid
<220> FEATURE:
<221> NAME/KEY: MOD_RES
<222> LOCATION: (203)..(213)
<223> OTHER INFORMATION: Any amino acid
<220> FEATURE:
<221> NAME/KEY: MOD_RES
<222> LOCATION: (215)..(227)
<223> OTHER INFORMATION: Any amino acid
<220> FEATURE:
<221> NAME/KEY: MOD_RES
<222> LOCATION: (229)..(234)
<223> OTHER INFORMATION: Any amino acid
<220> FEATURE:
<221> NAME/KEY: MOD_RES
<222> LOCATION: (236)..(293)
<223> OTHER INFORMATION: Any amino acid
<220> FEATURE:
<221> NAME/KEY: MOD_RES
<222> LOCATION: (295)..(327)
<223> OTHER INFORMATION: Any amino acid
<220> FEATURE:
<221> NAME/KEY: MOD_RES
<222> LOCATION: (329)..(527)
<223> OTHER INFORMATION: Any amino acid

<400> SEQUENCE: 45

Met Lys Thr Ile Ile Ala Leu Ser Tyr Ile Leu Cys Leu Val Phe Ala
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Arg Xaa Xaa Xaa Xaa Xaa Xaa Xaa Xaa Xaa Asn Xaa Xaa Ile
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa Asn
130                 135                 140

Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Val Xaa Xaa Xaa Xaa Xaa Xaa
            195                 200                 205

Xaa Xaa Xaa Xaa Xaa Pro Xaa Xaa Xaa Xaa Xaa Xaa Xaa Xaa Xaa
            210                 215                 220

Xaa Xaa Xaa Ala Xaa Xaa Xaa Xaa Xaa Xaa Phe Xaa Xaa Xaa Xaa
225                 230                 235                 240

Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa
            260                 265                 270

-continued

Xaa Xaa Xaa Xaa Xaa Xaa Xaa Xaa Xaa Xaa Xaa Xaa Xaa Xaa Xaa
            275                 280                 285

Xaa Xaa Xaa Xaa Xaa Lys Xaa Xaa Xaa Xaa Xaa Xaa Xaa Xaa Xaa
        290                 295                 300

Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Ser Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa
            340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
    370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
                405                 410                 415

Xaa Xaa Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa
    450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
                485                 490                 495

Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Lys
        515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 46
<211> LENGTH: 566
<212> TYPE: PRT
<213> ORGANISM: Influenza A virus
<220> FEATURE:
<221> NAME/KEY: MOD_RES
<222> LOCATION: (17)..(77)
<223> OTHER INFORMATION: Any amino acid
<220> FEATURE:
<221> NAME/KEY: MOD_RES
<222> LOCATION: (79)..(159)
<223> OTHER INFORMATION: Any amino acid
<220> FEATURE:
<221> NAME/KEY: MOD_RES
<222> LOCATION: (161)..(198)
<223> OTHER INFORMATION: Any amino acid
<220> FEATURE:
<221> NAME/KEY: MOD_RES
<222> LOCATION: (200)..(201)
<223> OTHER INFORMATION: Any amino acid
<220> FEATURE:

```
<221> NAME/KEY: MOD_RES
<222> LOCATION: (203)..(229)
<223> OTHER INFORMATION: Any amino acid
<220> FEATURE:
<221> NAME/KEY: MOD_RES
<222> LOCATION: (231)..(238)
<223> OTHER INFORMATION: Any amino acid
<220> FEATURE:
<221> NAME/KEY: MOD_RES
<222> LOCATION: (240)..(527)
<223> OTHER INFORMATION: Any amino acid

<400> SEQUENCE: 46

Met Lys Thr Ile Ile Ala Leu Ser Tyr Ile Leu Cys Leu Val Phe Ala
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Lys Xaa Xaa
65              70                  75                  80

Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa
    115                 120                 125

Xaa Xaa Xaa Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Lys
145                 150                 155                 160

Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa
            180                 185                 190

Xaa Xaa Xaa Xaa Xaa Leu Xaa Xaa Gly Xaa Xaa Xaa Xaa Xaa
        195                 200                 205

Xaa Xaa Xaa Xaa Xaa Xaa Xaa Xaa Xaa Xaa Xaa Xaa Xaa Xaa
    210                 215                 220

Xaa Xaa Xaa Xaa Xaa Ser Xaa Xaa Xaa Xaa Xaa Xaa Xaa Val Xaa
225                 230                 235                 240

Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
                325                 330                 335

Xaa Xaa Xaa Xaa Xaa Xaa Xaa Xaa Xaa Xaa Xaa Xaa Xaa Xaa Xaa
            340                 345                 350
```

```
Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
        370                 375                 380

Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Xaa Lys
        515                 520                 525

Asp Trp Ile Leu Trp Ile Ser Phe Ala Ile Ser Cys Phe Leu Cys
        530                 535                 540

Val Ala Leu Leu Gly Phe Ile Met Trp Ala Cys Gln Lys Gly Asn
545                 550                 555                 560

Arg Cys Asn Ile Cys Ile
            565

<210> SEQ ID NO 47
<211> LENGTH: 566
<212> TYPE: PRT
<213> ORGANISM: Influenza A virus
<220> FEATURE:
<221> NAME/KEY: MOD_RES
<222> LOCATION: (17)..(17)
<223> OTHER INFORMATION: Any amino acid
<220> FEATURE:
<221> NAME/KEY: MOD_RES
<222> LOCATION: (19)..(40)
<223> OTHER INFORMATION: Any amino acid
<220> FEATURE:
<221> NAME/KEY: MOD_RES
<222> LOCATION: (42)..(46)
<223> OTHER INFORMATION: Any amino acid
<220> FEATURE:
<221> NAME/KEY: MOD_RES
<222> LOCATION: (48)..(65)
<223> OTHER INFORMATION: Any amino acid
<220> FEATURE:
<221> NAME/KEY: MOD_RES
<222> LOCATION: (67)..(68)
<223> OTHER INFORMATION: Any amino acid
<220> FEATURE:
<221> NAME/KEY: MOD_RES
<222> LOCATION: (71)..(72)
<223> OTHER INFORMATION: Any amino acid
<220> FEATURE:
<221> NAME/KEY: MOD_RES
<222> LOCATION: (74)..(77)
<223> OTHER INFORMATION: Any amino acid
<220> FEATURE:
<221> NAME/KEY: MOD_RES
<222> LOCATION: (80)..(90)
```

```
<223> OTHER INFORMATION: Any amino acid
<220> FEATURE:
<221> NAME/KEY: MOD_RES
<222> LOCATION: (92)..(93)
<223> OTHER INFORMATION: Any amino acid
<220> FEATURE:
<221> NAME/KEY: MOD_RES
<222> LOCATION: (95)..(97)
<223> OTHER INFORMATION: Any amino acid
<220> FEATURE:
<221> NAME/KEY: MOD_RES
<222> LOCATION: (100)..(109)
<223> OTHER INFORMATION: Any amino acid
<220> FEATURE:
<221> NAME/KEY: MOD_RES
<222> LOCATION: (111)..(136)
<223> OTHER INFORMATION: Any amino acid
<220> FEATURE:
<221> NAME/KEY: MOD_RES
<222> LOCATION: (139)..(139)
<223> OTHER INFORMATION: Any amino acid
<220> FEATURE:
<221> NAME/KEY: MOD_RES
<222> LOCATION: (141)..(141)
<223> OTHER INFORMATION: Any amino acid
<220> FEATURE:
<221> NAME/KEY: MOD_RES
<222> LOCATION: (143)..(150)
<223> OTHER INFORMATION: Any amino acid
<220> FEATURE:
<221> NAME/KEY: MOD_RES
<222> LOCATION: (152)..(152)
<223> OTHER INFORMATION: Any amino acid
<220> FEATURE:
<221> NAME/KEY: MOD_RES
<222> LOCATION: (154)..(155)
<223> OTHER INFORMATION: Any amino acid
<220> FEATURE:
<221> NAME/KEY: MOD_RES
<222> LOCATION: (157)..(157)
<223> OTHER INFORMATION: Any amino acid
<220> FEATURE:
<221> NAME/KEY: MOD_RES
<222> LOCATION: (163)..(171)
<223> OTHER INFORMATION: Any amino acid
<220> FEATURE:
<221> NAME/KEY: MOD_RES
<222> LOCATION: (177)..(178)
<223> OTHER INFORMATION: Any amino acid
<220> FEATURE:
<221> NAME/KEY: MOD_RES
<222> LOCATION: (180)..(187)
<223> OTHER INFORMATION: Any amino acid
<220> FEATURE:
<221> NAME/KEY: MOD_RES
<222> LOCATION: (190)..(201)
<223> OTHER INFORMATION: Any amino acid
<220> FEATURE:
<221> NAME/KEY: MOD_RES
<222> LOCATION: (203)..(203)
<223> OTHER INFORMATION: Any amino acid
<220> FEATURE:
<221> NAME/KEY: MOD_RES
<222> LOCATION: (207)..(207)
<223> OTHER INFORMATION: Any amino acid
<220> FEATURE:
<221> NAME/KEY: MOD_RES
<222> LOCATION: (210)..(211)
<223> OTHER INFORMATION: Any amino acid
<220> FEATURE:
<221> NAME/KEY: MOD_RES
<222> LOCATION: (213)..(217)
<223> OTHER INFORMATION: Any amino acid
<220> FEATURE:
<221> NAME/KEY: MOD_RES
<222> LOCATION: (219)..(222)
<223> OTHER INFORMATION: Any amino acid
<220> FEATURE:
<221> NAME/KEY: MOD_RES
```

```
<222> LOCATION: (224)..(228)
<223> OTHER INFORMATION: Any amino acid
<220> FEATURE:
<221> NAME/KEY: MOD_RES
<222> LOCATION: (230)..(237)
<223> OTHER INFORMATION: Any amino acid
<220> FEATURE:
<221> NAME/KEY: MOD_RES
<222> LOCATION: (240)..(240)
<223> OTHER INFORMATION: Any amino acid
<220> FEATURE:
<221> NAME/KEY: MOD_RES
<222> LOCATION: (244)..(257)
<223> OTHER INFORMATION: Any amino acid
<220> FEATURE:
<221> NAME/KEY: MOD_RES
<222> LOCATION: (259)..(259)
<223> OTHER INFORMATION: Any amino acid
<220> FEATURE:
<221> NAME/KEY: MOD_RES
<222> LOCATION: (261)..(263)
<223> OTHER INFORMATION: Any amino acid
<220> FEATURE:
<221> NAME/KEY: MOD_RES
<222> LOCATION: (265)..(275)
<223> OTHER INFORMATION: Any amino acid
<220> FEATURE:
<221> NAME/KEY: MOD_RES
<222> LOCATION: (277)..(277)
<223> OTHER INFORMATION: Any amino acid
<220> FEATURE:
<221> NAME/KEY: MOD_RES
<222> LOCATION: (279)..(290)
<223> OTHER INFORMATION: Any amino acid
<220> FEATURE:
<221> NAME/KEY: MOD_RES
<222> LOCATION: (293)..(293)
<223> OTHER INFORMATION: Any amino acid
<220> FEATURE:
<221> NAME/KEY: MOD_RES
<222> LOCATION: (295)..(314)
<223> OTHER INFORMATION: Any amino acid
<220> FEATURE:
<221> NAME/KEY: MOD_RES
<222> LOCATION: (316)..(322)
<223> OTHER INFORMATION: Any amino acid
<220> FEATURE:
<221> NAME/KEY: MOD_RES
<222> LOCATION: (324)..(346)
<223> OTHER INFORMATION: Any amino acid
<220> FEATURE:
<221> NAME/KEY: MOD_RES
<222> LOCATION: (348)..(362)
<223> OTHER INFORMATION: Any amino acid
<220> FEATURE:
<221> NAME/KEY: MOD_RES
<222> LOCATION: (364)..(376)
<223> OTHER INFORMATION: Any amino acid
<220> FEATURE:
<221> NAME/KEY: MOD_RES
<222> LOCATION: (378)..(399)
<223> OTHER INFORMATION: Any amino acid
<220> FEATURE:
<221> NAME/KEY: MOD_RES
<222> LOCATION: (401)..(401)
<223> OTHER INFORMATION: Any amino acid
<220> FEATURE:
<221> NAME/KEY: MOD_RES
<222> LOCATION: (403)..(467)
<223> OTHER INFORMATION: Any amino acid
<220> FEATURE:
<221> NAME/KEY: MOD_RES
<222> LOCATION: (470)..(494)
<223> OTHER INFORMATION: Any amino acid
<220> FEATURE:
<221> NAME/KEY: MOD_RES
<222> LOCATION: (496)..(527)
<223> OTHER INFORMATION: Any amino acid
```

-continued

```
<400> SEQUENCE: 47

Met Lys Thr Ile Ile Ala Leu Ser Tyr Ile Phe Cys Leu Ala Leu Gly
1               5                   10                  15

Xaa Asp Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Leu Xaa Xaa Xaa Xaa Xaa Xaa Asp Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Lys Xaa Xaa Asn Asn Xaa Xaa Arg Xaa Xaa Xaa Xaa Ile Asp Xaa
65                  70                  75                  80

Xaa Xaa Xaa Xaa Xaa Xaa Xaa Xaa Xaa His Xaa Xaa Val Xaa Xaa
                85                  90                  95

Xaa Glu Thr Xaa Xaa Xaa Xaa Xaa Xaa Xaa Xaa Xaa Phe Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Ile Thr Xaa Gly Xaa Thr Xaa Xaa
    130                 135                 140

Xaa Xaa Xaa Xaa Xaa Xaa Gly Xaa Asn Xaa Xaa Lys Xaa Gly Pro Gly
145                 150                 155                 160

Ser Gly Xaa Xaa Xaa Xaa Xaa Xaa Xaa Xaa Lys Ser Gly Ser Thr
                165                 170                 175

Xaa Xaa Val Xaa Xaa Xaa Xaa Xaa Xaa Xaa Asp Asn Xaa Xaa Xaa
            180                 185                 190

Xaa Xaa Xaa Xaa Xaa Xaa Xaa Xaa Ser Xaa Asn Gln Glu Xaa Thr
        195                 200                 205

Ser Xaa Xaa Val Xaa Xaa Xaa Xaa Xaa Val Xaa Xaa Xaa Xaa Arg Xaa
    210                 215                 220

Xaa Xaa Xaa Xaa Ile Xaa Xaa Xaa Xaa Xaa Xaa Xaa Xaa Trp Val Xaa
225                 230                 235                 240

Gly Leu Ser Xaa Xaa Xaa Xaa Xaa Xaa Xaa Xaa Xaa Xaa Xaa Xaa
            245                 250                 255

Xaa Val Xaa Val Xaa Xaa Xaa Asn Xaa Xaa Xaa Xaa Xaa Xaa Xaa
        260                 265                 270

Xaa Xaa Xaa Met Xaa Thr Xaa Xaa Xaa Xaa Xaa Xaa Xaa Xaa Xaa
            275                 280                 285

Xaa Xaa Asp Thr Xaa Ile Xaa Xaa Xaa Xaa Xaa Xaa Xaa Xaa Xaa
        290                 295                 300

Xaa Xaa Xaa Xaa Xaa Xaa Xaa Xaa Xaa Lys Xaa Xaa Xaa Xaa Xaa
305                 310                 315                 320

Xaa Xaa Lys Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Leu Xaa Xaa Xaa Xaa Xaa
        340                 345                 350

Xaa Xaa Xaa Xaa Xaa Xaa Xaa Xaa Ile Xaa Xaa Xaa Xaa Xaa
    355                 360                 365

Xaa Xaa Xaa Xaa Xaa Xaa Xaa Thr Xaa Xaa Xaa Xaa Xaa Xaa
        370                 375                 380

Xaa Xaa Xaa Xaa Xaa Xaa Xaa Xaa Xaa Xaa Xaa Xaa Xaa Xaa Val
385                 390                 395                 400

Xaa Glu Xaa Xaa Xaa Xaa Xaa Xaa Xaa Xaa Xaa Xaa Xaa Xaa Xaa
            405                 410                 415
```

```
Xaa Xaa Xaa Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa
            435                 440                 445

Xaa Xaa Xaa Xaa Xaa Xaa Xaa Xaa Xaa Xaa Xaa Xaa Xaa
            450                 455                 460

Xaa Xaa Xaa Arg Arg Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Glu Xaa
            485                 490                 495

Xaa Xaa Xaa Xaa Xaa Xaa Xaa Xaa Xaa Xaa Xaa Xaa Xaa
            500                 505                 510

Xaa Xaa Xaa Xaa Xaa Xaa Xaa Xaa Xaa Xaa Xaa Xaa Xaa Lys
            515                 520                 525

Asp Trp Ile Leu Trp Ile Ser Phe Ala Ile Ser Cys Phe Leu Leu Cys
            530                 535                 540

Val Val Leu Leu Gly Phe Ile Met Trp Ala Cys Gln Arg Gly Asn Ile
545                 550                 555                 560

Arg Cys Asn Ile Cys Ile
                565

<210> SEQ ID NO 48
<211> LENGTH: 29
<212> TYPE: PRT
<213> ORGANISM: Influenza A virus

<400> SEQUENCE: 48

Gln Ile Leu Ala Ile Tyr Ser Thr Val Ala Ser Ser Leu Val Leu Leu
1               5                   10                  15

Val Ser Leu Gly Ala Ile Ser Phe Trp Met Cys Ser Asn
            20                  25

<210> SEQ ID NO 49
<211> LENGTH: 29
<212> TYPE: PRT
<213> ORGANISM: Influenza A virus

<400> SEQUENCE: 49

Gln Ile Leu Ala Ile Tyr Ala Thr Val Ala Gly Ser Leu Ser Leu Ala
1               5                   10                  15

Ile Met Met Ala Gly Ile Ser Phe Trp Met Cys Ser Asn
            20                  25

<210> SEQ ID NO 50
<211> LENGTH: 29
<212> TYPE: PRT
<213> ORGANISM: Influenza A virus

<400> SEQUENCE: 50

Gln Ile Leu Ser Ile Tyr Ser Thr Val Ala Ser Ser Leu Ala Leu Ala
1               5                   10                  15

Ile Met Val Ala Gly Leu Ser Phe Trp Met Cys Ser Asn
            20                  25

<210> SEQ ID NO 51
<211> LENGTH: 29
<212> TYPE: PRT
<213> ORGANISM: Influenza A virus
```

```
<400> SEQUENCE: 51

Gln Ile Leu Ala Ile Tyr Ser Thr Val Ser Ser Ser Leu Val Leu Val
1               5                   10                  15

Gly Leu Ile Ile Ala Val Gly Leu Trp Met Cys Ser Asn
            20                  25

<210> SEQ ID NO 52
<211> LENGTH: 29
<212> TYPE: PRT
<213> ORGANISM: Influenza A virus

<400> SEQUENCE: 52

Lys Ile Leu Ser Ile Tyr Ser Thr Val Ala Ala Ser Leu Cys Leu Ala
1               5                   10                  15

Ile Leu Ile Ala Gly Gly Leu Ile Leu Gly Met Gln Asn
            20                  25

<210> SEQ ID NO 53
<211> LENGTH: 29
<212> TYPE: PRT
<213> ORGANISM: Influenza A virus

<400> SEQUENCE: 53

Lys Ile Leu Thr Ile Tyr Ser Thr Val Ala Ser Ser Leu Val Leu Ala
1               5                   10                  15

Met Gly Phe Ala Ala Phe Leu Phe Trp Ala Asn Ser Asn
            20                  25

<210> SEQ ID NO 54
<211> LENGTH: 29
<212> TYPE: PRT
<213> ORGANISM: Influenza A virus

<400> SEQUENCE: 54

Lys Ile Leu Ser Ile Tyr Ser Cys Ile Ala Ser Ser Leu Val Leu Ala
1               5                   10                  15

Ala Leu Ile Met Gly Phe Met Phe Trp Ala Cys Ser Asn
            20                  25

<210> SEQ ID NO 55
<211> LENGTH: 29
<212> TYPE: PRT
<213> ORGANISM: Influenza A virus

<400> SEQUENCE: 55

Lys Ile Leu Ser Ile Tyr Ser Ser Val Ala Ser Ser Leu Val Leu Leu
1               5                   10                  15

Leu Met Ile Ile Gly Gly Phe Ile Phe Gly Cys Gln Asn
            20                  25

<210> SEQ ID NO 56
<211> LENGTH: 29
<212> TYPE: PRT
<213> ORGANISM: Influenza A virus

<400> SEQUENCE: 56

Lys Ala Leu Ser Ile Tyr Ser Cys Ile Ala Ser Ser Val Val Leu Val
1               5                   10                  15

Gly Leu Ile Leu Ser Phe Ile Met Trp Ala Cys Ser Ser
            20                  25
```

<210> SEQ ID NO 57
<211> LENGTH: 30
<212> TYPE: PRT
<213> ORGANISM: Influenza A virus

<400> SEQUENCE: 57

Lys Asp Trp Ile Leu Trp Ile Ser Phe Ala Ile Ser Cys Phe Leu Leu
1               5                   10                  15

Cys Val Val Leu Leu Gly Phe Ile Met Trp Ala Cys Gln Arg
            20                  25                  30

<210> SEQ ID NO 58
<211> LENGTH: 30
<212> TYPE: PRT
<213> ORGANISM: Influenza A virus

<400> SEQUENCE: 58

Lys Asp Trp Ile Leu Trp Ile Ser Phe Ala Ile Ser Cys Phe Leu Leu
1               5                   10                  15

Cys Val Val Leu Leu Gly Phe Ile Met Trp Ala Cys Gln Lys
            20                  25                  30

<210> SEQ ID NO 59
<211> LENGTH: 30
<212> TYPE: PRT
<213> ORGANISM: Influenza A virus

<400> SEQUENCE: 59

Lys Asp Trp Ile Leu Trp Ile Ser Phe Ala Ile Ser Cys Phe Leu Leu
1               5                   10                  15

Cys Val Val Leu Leu Gly Phe Ile Met Trp Ala Cys Gln Lys
            20                  25                  30

<210> SEQ ID NO 60
<211> LENGTH: 30
<212> TYPE: PRT
<213> ORGANISM: Influenza A virus

<400> SEQUENCE: 60

Lys Asp Trp Ile Leu Trp Ile Ser Phe Ala Ile Ser Cys Phe Leu Ile
1               5                   10                  15

Cys Val Val Leu Leu Gly Phe Ile Met Trp Ala Cys Gln Lys
            20                  25                  30

<210> SEQ ID NO 61
<211> LENGTH: 30
<212> TYPE: PRT
<213> ORGANISM: Influenza A virus

<400> SEQUENCE: 61

Lys Asp Ile Ile Leu Trp Ile Ser Phe Ser Ile Ser Cys Phe Leu Leu
1               5                   10                  15

Val Ala Leu Leu Leu Ala Phe Ile Leu Trp Ala Cys Gln Asn
            20                  25                  30

<210> SEQ ID NO 62
<211> LENGTH: 29
<212> TYPE: PRT
<213> ORGANISM: Influenza A virus

<400> SEQUENCE: 62

Lys Asp Val Ile Leu Trp Phe Ser Phe Gly Ala Ser Cys Phe Leu Leu
1               5                   10                  15

```
Leu Ala Ile Ala Val Gly Leu Val Phe Ile Cys Val Lys
            20                  25

<210> SEQ ID NO 63
<211> LENGTH: 29
<212> TYPE: PRT
<213> ORGANISM: Influenza A virus

<400> SEQUENCE: 63

Lys Asp Ile Ile Leu Trp Phe Ser Phe Gly Ala Ser Cys Phe Val Leu
1               5                   10                  15

Leu Ala Ala Val Met Gly Leu Val Phe Phe Cys Leu Lys
            20                  25

<210> SEQ ID NO 64
<211> LENGTH: 30
<212> TYPE: PRT
<213> ORGANISM: Influenza A virus

<400> SEQUENCE: 64

Lys Asp Ile Ile Leu Trp Ile Ser Phe Ser Met Ser Cys Phe Val Phe
1               5                   10                  15

Val Ala Leu Ile Leu Gly Phe Val Leu Trp Ala Cys Gln Asn
            20                  25                  30

<210> SEQ ID NO 65
<211> LENGTH: 566
<212> TYPE: PRT
<213> ORGANISM: Influenza A virus

<400> SEQUENCE: 65

Met Lys Ala Lys Leu Leu Val Leu Leu Cys Ala Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
    50                  55                  60

Ala Pro Leu Gln Leu Gly Asn Cys Ser Val Ala Gly Trp Ile Leu Gly
65                  70                  75                  80

Asn Pro Lys Cys Glu Ser Leu Phe Ser Lys Glu Ser Trp Ser Tyr Ile
                85                  90                  95

Ala Glu Thr Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Lys Gly Val Thr Thr Ser Cys Ser His Asn Gly Lys Ser Ser
145                 150                 155                 160

Phe Tyr Arg Asn Leu Leu Trp Leu Thr Lys Lys Asn Gly Leu Tyr Pro
                165                 170                 175

Asn Val Ser Lys Ser Tyr Val Asn Asn Lys Glu Lys Glu Val Leu Val
            180                 185                 190

Leu Trp Gly Val His His Pro Ser Asn Ile Gly Asp Gln Arg Ala Ile
        195                 200                 205
```

Tyr His Thr Glu Asn Ala Tyr Val Ser Val Val Ser Ser His Tyr Ser
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Ser
        275                 280                 285

Met Asp Glu Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320

Pro Lys Tyr Val Arg Ser Thr Lys Leu Arg Met Val Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Ile Asp Gly Trp Tyr Gly Tyr
        355                 360                 365

His His Gln Asn Glu Gln Gly Ser Gly Tyr Ala Ala Asp Gln Lys Ser
    370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
        435                 440                 445

Gly Arg Thr Leu Asp Phe His Asp Ser Asn Val Lys Asn Leu Tyr Glu
    450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asn Glu Cys Met Glu Ser Val
                485                 490                 495

Lys Asn Gly Thr Tyr Asp Tyr Pro Lys Tyr Ser Glu Glu Ser Lys Leu
            500                 505                 510

Asn Arg Gly Lys Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 66
<211> LENGTH: 565
<212> TYPE: PRT
<213> ORGANISM: Influenza A virus

<400> SEQUENCE: 66

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
             20                  25                  30

Val Asp Thr Val Leu Glu Lys Asn Val Thr Val Thr His Ser Val Asn
         35                  40                  45

Leu Leu Glu Asp Ser His Asn Gly Lys Leu Cys Leu Leu Lys Gly Ile
 50                  55                  60

Ala Pro Leu Gln Leu Gly Asn Cys Ser Val Ala Gly Trp Ile Leu Gly
 65                  70                  75                  80

Asn Pro Glu Cys Glu Leu Leu Ile Ser Lys Glu Ser Trp Ser Tyr Ile
             85                  90                  95

Val Glu Thr Pro Asn Pro Glu Asn Gly Thr Cys Tyr Pro Gly Tyr Phe
             100                 105                 110

Ala Asp Tyr Glu Glu Leu Arg Glu Gln Leu Ser Ser Val Ser Ser Phe
             115                 120                 125

Glu Arg Phe Glu Ile Phe Pro Lys Glu Ser Ser Trp Pro Asn His Thr
             130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Val Asn Asn Lys Glu Lys Glu Val Leu Val Leu
            180                 185                 190

Trp Gly Val His His Pro Pro Asn Ile Gly Asn Gln Arg Ala Leu Tyr
            195                 200                 205

His Thr Glu Asn Ala Tyr Val Ser Val Val Ser Ser His Tyr Ser Arg
            210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
            275                 280                 285

Asp Glu Cys Asp Ala Lys Cys Gln Thr Pro Gln Gly Ala Ile Asn Ser
            290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

-continued

```
Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 67
<211> LENGTH: 565
<212> TYPE: PRT
<213> ORGANISM: Influenza A virus

<400> SEQUENCE: 67

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Arg Glu Ser Trp Ser Tyr Ile
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Thr Thr Gly Val Ser Ala Ser Cys Ser His Asn Gly Glu Ser Ser Phe
145                 150                 155                 160

Tyr Lys Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Arg Glu
225                 230                 235                 240
```

```
Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Glu Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Arg Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 68
<211> LENGTH: 565
<212> TYPE: PRT
<213> ORGANISM: Influenza A virus

<400> SEQUENCE: 68

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
```

```
                35                  40                  45
Leu Leu Glu Asn Ser His Asn Gly Lys Leu Cys Leu Lys Gly Ile
         50                  55                  60
Ala Pro Leu Gln Leu Gly Asn Cys Ser Val Ala Gly Trp Ile Leu Gly
 65                  70                  75                  80
Asn Pro Glu Cys Glu Leu Leu Ile Ser Lys Glu Ser Trp Ser Tyr Ile
                 85                  90                  95
Val Glu Lys Pro Asn Pro Glu Asn Gly Thr Cys Tyr Pro Gly His Phe
            100                 105                 110
Ala Asp Tyr Glu Glu Leu Arg Glu Gln Leu Ser Ser Val Ser Ser Phe
            115                 120                 125
Glu Arg Phe Glu Ile Phe Pro Lys Glu Ser Ser Trp Pro Asn His Thr
            130                 135                 140
Val Thr Gly Val Ser Ala Ser Cys Ser His Asn Gly Glu Ser Ser Phe
145                 150                 155                 160
Tyr Arg Asn Leu Leu Trp Leu Thr Gly Lys Asn Gly Leu Tyr Pro Asn
                165                 170                 175
Leu Ser Lys Ser Tyr Ala Asn Asn Lys Glu Lys Glu Val Leu Val Leu
            180                 185                 190
Trp Gly Val His His Pro Pro Asn Ile Gly Asn Gln Lys Ala Leu Tyr
            195                 200                 205
His Thr Glu Asn Ala Tyr Val Ser Val Val Ser Ser His Tyr Ser Arg
            210                 215                 220
Lys Phe Thr Pro Glu Ile Ala Lys Arg Pro Lys Val Arg Asp Gln Glu
225                 230                 235                 240
Gly Arg Ile Asn Tyr Tyr Trp Thr Leu Leu Glu Pro Gly Asp Thr Ile
                245                 250                 255
Ile Phe Glu Ala Asn Gly Asn Leu Ile Ala Pro Arg Tyr Ala Phe Ala
            260                 265                 270
Leu Ser Arg Gly Phe Gly Ser Gly Ile Ile Asn Ser Asn Ala Pro Met
            275                 280                 285
Asp Lys Cys Asp Ala Lys Cys Gln Thr Pro Gln Gly Ala Ile Asn Ser
            290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Ser Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
            355                 360                 365
His Gln Asn Glu Gln Gly Ser Gly Tyr Ala Ala Asp Gln Lys Ser Thr
            370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Ile
            420                 425                 430
Asp Ile Trp Thr Tyr Asn Ala Glu Leu Leu Val Leu Leu Glu Asn Glu
            435                 440                 445
Arg Thr Leu Asp Phe His Asp Ser Asn Val Lys Asn Leu Tyr Glu Lys
450                 455                 460
```

```
Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 69
<211> LENGTH: 566
<212> TYPE: PRT
<213> ORGANISM: Influenza A virus

<400> SEQUENCE: 69

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Thr Ser Ser Trp Pro Asn His Asp
130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
            195                 200                 205

Tyr Gln Asn Ala Asp Ala Tyr Val Phe Val Gly Ser Ser Arg Tyr Ser
210                 215                 220

Lys Lys Phe Lys Pro Glu Ile Ala Ile Arg Pro Lys Val Arg Asp Arg
225                 230                 235                 240

Glu Gly Arg Met Asn Tyr Tyr Trp Thr Leu Val Glu Pro Gly Asp Lys
                245                 250                 255

Ile Thr Phe Glu Ala Thr Gly Asn Leu Val Val Pro Arg Tyr Ala Phe
```

```
                260                 265                 270
Ala Met Glu Arg Asn Ala Gly Ser Gly Ile Ile Ile Ser Asp Thr Pro
                275                 280                 285

Val His Asp Cys Asn Thr Thr Cys Gln Thr Pro Lys Gly Ala Ile Asn
            290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
                325                 330                 335

Asn Ile Pro Ser Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Leu Lys Ser
        370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
                405                 410                 415

Leu Glu Lys Arg Ile Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Tyr His Asp Ser Asn Val Lys Asn Leu Tyr Glu
        450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
                485                 490                 495

Lys Asn Gly Thr Tyr Asp Tyr Pro Lys Tyr Ser Glu Glu Ala Lys Leu
            500                 505                 510

Asn Arg Glu Glu Ile Asp Gly Val Lys Leu Glu Ser Thr Arg Ile Tyr
        515                 520                 525

Gln Ile Leu Ala Ile Tyr Ser Thr Val Ala Ser Ser Leu Val Leu Val
        530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 70
<211> LENGTH: 566
<212> TYPE: PRT
<213> ORGANISM: Influenza A virus

<400> SEQUENCE: 70

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60
```

```
Gly Gly Ile Cys Asp Ser Pro His Gln Ile Leu Asp Gly Glu Asn Cys
 65                  70                  75                  80

Thr Leu Ile Asp Ala Leu Leu Gly Asp Pro Gln Cys Asp Gly Phe Gln
                 85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
            115                 120                 125

Ala Ser Ser Gly Thr Leu Glu Phe Asn Asp Glu Ser Phe Asn Trp Thr
130                 135                 140

Gly Val Thr Gln Asn Gly Thr Ser Ser Cys Lys Arg Arg Ser Asn
145                 150                 155                 160

Asn Ser Phe Phe Ser Arg Leu Asn Trp Leu Thr Gln Leu Lys Phe Lys
                165                 170                 175

Tyr Pro Ala Leu Asn Val Thr Met Pro Asn Asn Glu Lys Phe Asp Lys
            180                 185                 190

Leu Tyr Ile Trp Gly Val His His Pro Val Thr Asp Asn Asp Gln Ile
            195                 200                 205

Phe Leu Tyr Ala Gln Ala Ser Gly Arg Ile Thr Val Ser Thr Lys Arg
210                 215                 220

Ser Gln Gln Thr Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
            275                 280                 285

Pro Ile Gly Lys Cys Asn Ser Glu Cys Ile Thr Pro Asn Gly Ser Ile
290                 295                 300

Pro Asn Asp Lys Pro Phe Gln Asn Val Asn Arg Ile Thr Tyr Gly Ala
305                 310                 315                 320

Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
            340                 345                 350

Gly Phe Ile Glu Asn Gly Trp Glu Gly Met Val Asp Gly Trp Tyr Gly
            355                 360                 365

Phe Arg His Gln Asn Ser Glu Gly Ile Gly Gln Ala Ala Asp Leu Lys
370                 375                 380

Ser Thr Gln Ala Ala Ile Asn Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
            420                 425                 430

Lys Ile Asp Leu Trp Ser Tyr Asn Ala Glu Leu Leu Val Ala Leu Glu
            435                 440                 445

Asn Gln His Thr Ile Asp Leu Thr Asp Ser Glu Met Asn Lys Leu Phe
            450                 455                 460

Glu Arg Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
```

```
                     485                 490                 495
Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
        530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 71
<211> LENGTH: 566
<212> TYPE: PRT
<213> ORGANISM: Influenza A virus

<400> SEQUENCE: 71

Met Lys Thr Ile Ile Ala Leu Ser His Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Asn Ser Ser Ile
    50                  55                  60

Gly Glu Ile Cys Asp Ser Pro His Gln Ile Leu Asp Gly Glu Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Asn
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ser Ser Gly Arg Ile Thr Val Ser Thr Lys Arg
    210                 215                 220

Ser Gln Gln Ala Val Ile Pro Asn Ile Gly Ser Arg Pro Arg Ile Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285
```

```
Pro Ile Gly Lys Cys Asn Ser Glu Cys Ile Thr Pro Asn Gly Ser Ile
    290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Ser Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
        355                 360                 365
Phe Arg His Gln Asn Ser Glu Gly Arg Gly Gln Ala Ala Asp Leu Lys
370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
        435                 440                 445
Asn Gln His Thr Ile Asp Leu Thr Asp Ser Glu Met Asn Lys Leu Phe
450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
Asn Asn Arg Phe Gln Ile Lys Gly Val Glu Leu Lys Ser Gly Tyr Lys
        515                 520                 525
Asp Trp Ile Leu Trp Ile Ser Phe Ala Ile Ser Cys Phe Leu Leu Cys
530                 535                 540
Val Ala Leu Leu Gly Phe Ile Met Trp Ala Cys Gln Lys Gly Asn Ile
545                 550                 555                 560
Arg Cys Asn Ile Cys Ile
                565

<210> SEQ ID NO 72
<211> LENGTH: 566
<212> TYPE: PRT
<213> ORGANISM: Influenza A virus

<400> SEQUENCE: 72

Met Lys Thr Ile Ile Ala Leu Ser Tyr Ile Leu Cys Leu Val Phe Ala
1               5                   10                  15
Gln Lys Leu Pro Gly Asn Asp Asn Ser Thr Ala Thr Leu Cys Leu Gly
            20                  25                  30
His His Ala Val Pro Asn Gly Thr Ile Val Lys Thr Ile Thr Asn Asp
        35                  40                  45
Arg Ile Glu Val Thr Asn Ala Thr Glu Leu Val Gln Asn Ser Ser Ile
    50                  55                  60
Gly Glu Ile Cys Asp Ser Pro His Gln Ile Leu Asp Gly Glu Asn Cys
65                  70                  75                  80
Thr Leu Ile Asp Ala Leu Leu Gly Asp Pro Gln Cys Asp Gly Phe Gln
                85                  90                  95
```

```
Asn Lys Lys Trp Asp Leu Phe Val Glu Arg Ser Lys Ala Tyr Ser Asn
            100                 105                 110
Cys Tyr Pro Tyr Asp Val Pro Asp Tyr Ala Ser Leu Arg Ser Leu Val
            115                 120                 125
Ala Ser Ser Gly Thr Leu Glu Phe Asn Asn Glu Ser Phe Asn Trp Asn
130                 135                 140
Gly Val Thr Gln Asn Gly Thr Ser Ser Ala Cys Ile Arg Arg Ser Asn
145                 150                 155                 160
Asn Ser Phe Phe Ser Arg Leu Asn Trp Leu Thr His Leu Asn Phe Lys
                165                 170                 175
Tyr Pro Ala Leu Asn Val Thr Met Pro Asn Asn Glu Gln Phe Asp Lys
            180                 185                 190
Leu Tyr Ile Trp Gly Val His His Pro Val Thr Asp Lys Asp Gln Ile
            195                 200                 205
Phe Leu Tyr Ala Gln Pro Ser Gly Arg Ile Thr Val Ser Thr Lys Arg
            210                 215                 220
Ser Gln Gln Ala Val Ile Pro Asn Ile Gly Phe Arg Pro Arg Ile Arg
225                 230                 235                 240
Asn Ile Pro Ser Arg Ile Ser Ile Tyr Trp Thr Ile Val Lys Pro Gly
                245                 250                 255
Asp Ile Leu Leu Ile Asn Ser Thr Gly Asn Leu Ile Ala Pro Arg Gly
            260                 265                 270
Tyr Phe Lys Ile Arg Ser Gly Lys Ser Ser Ile Met Arg Ser Asp Ala
            275                 280                 285
Pro Ile Gly Lys Cys Lys Ser Glu Cys Ile Thr Pro Asn Gly Ser Ile
            290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Ser Thr Leu Lys Leu Ala Thr Gly Met
                325                 330                 335
Arg Asn Val Pro Glu Lys Gln Thr Arg Gly Ile Phe Gly Ala Ile Ala
            340                 345                 350
Gly Phe Ile Glu Asn Gly Trp Glu Gly Met Val Asp Gly Trp Tyr Gly
            355                 360                 365
Phe Arg His Gln Asn Ser Glu Gly Arg Gly Gln Ala Ala Asp Leu Lys
            370                 375                 380
Ser Thr Gln Ala Ala Ile Asp Gln Ile Asn Gly Lys Leu Asn Arg Leu
385                 390                 395                 400
Ile Gly Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
            420                 425                 430
Lys Ile Asp Leu Trp Ser Tyr Asn Ala Glu Leu Leu Val Ala Leu Glu
            435                 440                 445
Asn Gln His Thr Ile Asp Leu Thr Asp Ser Glu Met Asn Lys Leu Phe
            450                 455                 460
Glu Lys Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                485                 490                 495
Ile Arg Asn Gly Thr Tyr Asp His Asp Val Tyr Arg Asp Glu Ala Leu
            500                 505                 510
```

```
Asn Asn Arg Phe Gln Ile Lys Gly Val Glu Leu Lys Ser Gly Tyr Lys
            515                 520                 525

Asp Trp Ile Leu Trp Ile Ser Phe Ala Ile Ser Cys Phe Leu Leu Cys
530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 73
<211> LENGTH: 566
<212> TYPE: PRT
<213> ORGANISM: Influenza A virus

<400> SEQUENCE: 73

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Pro Asn Gly Thr Ile Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Glu Ile Cys Asp Ser Pro His Gln Ile Leu Asp Gly Lys Asn Cys
65                  70                  75                  80

Thr Leu Ile Asp Ala Leu Leu Gly Asp Pro Gln Cys Asp Gly Phe Gln
                85                  90                  95

Asn Lys Lys Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Thr Gln Asn Gly Thr Ser Ser Ala Cys Ile Arg Arg Ser Lys
145                 150                 155                 160

Asn Ser Phe Phe Ser Arg Leu Asn Trp Leu Thr His Leu Asn Phe Lys
                165                 170                 175

Tyr Pro Ala Leu Asn Val Thr Met Pro Asn Asn Glu Gln Phe Asp Lys
            180                 185                 190

Leu Tyr Ile Trp Gly Val His His Pro Gly Thr Asp Lys Asp Gln Ile
        195                 200                 205

Phe Leu Tyr Ala Gln Ala Ser Gly Arg Ile Thr Val Ser Thr Lys Arg
    210                 215                 220

Ser Gln Gln Thr Val Ser Pro Asn Ile Gly Ser Arg Pro Arg Val Arg
225                 230                 235                 240

Asn Ile Pro Ser Arg Ile Ser Ile Tyr Trp Thr Ile Val Lys Pro Gly
                245                 250                 255

Asp Ile Leu Leu Ile Asn Ser Thr Gly Asn Leu Ile Ala Pro Arg Gly
            260                 265                 270

Tyr Phe Lys Ile Arg Ser Gly Lys Ser Ser Ile Met Arg Ser Asp Ala
        275                 280                 285

Pro Ile Gly Lys Cys Asn Ser Glu Cys Ile Thr Pro Asn Gly Ser Ile
    290                 295                 300

Pro Asn Asp Lys Pro Phe Gln Asn Val Asn Arg Ile Thr Tyr Gly Ala
305                 310                 315                 320
```

```
Cys Pro Arg Tyr Val Lys Gln Asn Thr Leu Lys Leu Ala Thr Gly Met
                325                 330                 335

Arg Asn Val Pro Glu Lys Gln Thr Arg Gly Ile Phe Gly Ala Ile Ala
                340                 345                 350

Gly Phe Ile Glu Asn Gly Trp Glu Gly Met Val Asp Gly Trp Tyr Gly
                355                 360                 365

Phe Arg His Gln Asn Ser Glu Gly Arg Gly Gln Ala Ala Asp Leu Lys
                370                 375                 380

Ser Thr Gln Ala Ala Ile Asp Gln Ile Asn Gly Lys Leu Asn Arg Leu
385                 390                 395                 400

Ile Gly Lys Thr Asn Glu Lys Phe His Gln Ile Glu Lys Glu Phe Ser
                405                 410                 415

Glu Val Glu Gly Arg Ile Gln Asp Leu Glu Lys Tyr Val Glu Asp Thr
                420                 425                 430

Lys Ile Asp Leu Trp Ser Tyr Asn Ala Glu Leu Leu Val Ala Leu Glu
                435                 440                 445

Asn Gln His Thr Ile Asp Leu Thr Asp Ser Glu Met Asn Lys Leu Phe
                450                 455                 460

Glu Lys Thr Lys Lys Gln Leu Arg Glu Asn Ala Glu Asp Met Gly Asn
465                 470                 475                 480

Gly Cys Phe Lys Ile Tyr His Lys Cys Asp Asn Ala Cys Ile Gly Ser
                485                 490                 495

Ile Arg Asn Gly Thr Tyr Asp His Asp Val Tyr Arg Asp Glu Ala Leu
                500                 505                 510

Asn Asn Arg Phe Gln Ile Lys Gly Val Glu Leu Lys Ser Gly Tyr Lys
                515                 520                 525

Asp Trp Ile Leu Trp Ile Ser Phe Ala Ile Ser Cys Phe Leu Leu Cys
                530                 535                 540

Val Ala Leu Leu Gly Phe Ile Met Trp Ala Cys Gln Lys Gly Asn Ile
545                 550                 555                 560

Arg Cys Asn Ile Cys Ile
                565

<210> SEQ ID NO 74
<211> LENGTH: 566
<212> TYPE: PRT
<213> ORGANISM: Influenza A virus

<400> SEQUENCE: 74

Met Lys Thr Ile Ile Ala Leu Ser Tyr Ile Phe Cys Leu Ala Leu Gly
1               5                   10                  15

Gln Asp Leu Pro Gly Asn Asp Asn Ser Thr Ala Thr Leu Cys Leu Gly
                20                  25                  30

His His Ala Val Pro Asn Gly Thr Leu Val Lys Thr Ile Thr Asp Asp
            35                  40                  45

Gln Ile Glu Val Thr Asn Ala Thr Glu Leu Val Gln Ser Ser Ser Thr
        50                  55                  60

Gly Lys Ile Cys Asn Asn Pro His Arg Ile Leu Asp Gly Ile Asp Cys
65                  70                  75                  80

Thr Leu Ile Asp Ala Leu Leu Gly Asp Pro His Cys Asp Val Phe Gln
                85                  90                  95

Asn Glu Thr Trp Asp Leu Phe Val Glu Arg Ser Lys Ala Phe Ser Asn
                100                 105                 110

Cys Tyr Pro Tyr Asp Val Pro Asp Tyr Ala Ser Leu Arg Ser Leu Val
```

-continued

```
            115                 120                 125
Ala Ser Ser Gly Thr Leu Glu Phe Ile Thr Glu Gly Phe Thr Trp Thr
130                 135                 140
Gly Val Thr Gln Asn Gly Gly Ser Asn Ala Cys Lys Arg Gly Pro Gly
145                 150                 155                 160
Ser Gly Phe Phe Ser Arg Leu Asn Trp Leu Thr Lys Ser Gly Ser Thr
                165                 170                 175
Tyr Pro Val Leu Asn Val Thr Met Pro Asn Asn Asp Asn Phe Asp Lys
                180                 185                 190
Leu Tyr Ile Trp Gly Val His His Pro Ser Thr Asn Gln Glu Gln Thr
            195                 200                 205
Ser Leu Tyr Val Gln Ala Ser Gly Arg Val Thr Val Ser Thr Arg Arg
210                 215                 220
Ser Gln Gln Thr Ile Ile Pro Asn Ile Gly Ser Arg Pro Trp Val Arg
225                 230                 235                 240
Gly Leu Ser Ser Arg Ile Ser Ile Tyr Trp Thr Ile Val Lys Pro Gly
                245                 250                 255
Asp Val Leu Val Ile Asn Ser Asn Gly Asn Leu Ile Ala Pro Arg Gly
                260                 265                 270
Tyr Phe Lys Met Arg Thr Gly Lys Ser Ser Ile Met Arg Ser Asp Ala
            275                 280                 285
Pro Ile Asp Thr Cys Ile Ser Glu Cys Ile Thr Pro Asn Gly Ser Ile
290                 295                 300
Pro Asn Asp Lys Pro Phe Gln Asn Val Asn Lys Ile Thr Tyr Gly Ala
305                 310                 315                 320
Cys Pro Lys Tyr Val Lys Gln Asn Thr Leu Lys Leu Ala Thr Gly Met
                325                 330                 335
Arg Asn Val Pro Glu Lys Gln Thr Arg Gly Leu Phe Gly Ala Ile Ala
                340                 345                 350
Gly Phe Ile Glu Asn Gly Trp Glu Gly Met Ile Asp Gly Trp Tyr Gly
            355                 360                 365
Phe Arg His Gln Asn Ser Glu Gly Thr Gly Gln Ala Ala Asp Leu Lys
370                 375                 380
Ser Thr Gln Ala Ala Ile Asp Gln Ile Asn Gly Lys Leu Asn Arg Val
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Lys Tyr Val Glu Asp Thr
                420                 425                 430
Lys Ile Asp Leu Trp Ser Tyr Asn Ala Glu Leu Leu Val Ala Leu Glu
            435                 440                 445
Asn Gln His Thr Ile Asp Leu Thr Asp Ser Glu Met Asn Lys Leu Phe
450                 455                 460
Glu Lys Thr Arg Arg Gln Leu Arg Glu Asn Ala Glu Asp Met Gly Asn
465                 470                 475                 480
Gly Cys Phe Lys Ile Tyr His Lys Cys Asp Asn Ala Cys Ile Glu Ser
                485                 490                 495
Ile Arg Asn Gly Thr Tyr Asp His Asp Val Tyr Arg Asp Glu Ala Leu
                500                 505                 510
Asn Asn Arg Phe Gln Ile Lys Gly Val Glu Leu Lys Ser Gly Tyr Lys
            515                 520                 525
Asp Trp Ile Leu Trp Ile Ser Phe Ala Ile Ser Cys Phe Leu Leu Cys
530                 535                 540
```

-continued

```
Val Val Leu Gly Phe Ile Met Trp Ala Cys Gln Arg Gly Asn Ile
545                 550                 555                 560

Arg Cys Asn Ile Cys Ile
                565

<210> SEQ ID NO 75
<211> LENGTH: 585
<212> TYPE: PRT
<213> ORGANISM: Influenza B virus

<400> SEQUENCE: 75

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Lys Gly Thr Glu Thr
        50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Arg Val
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Pro Asn Leu Leu Arg Gly
            115                 120                 125

Tyr Glu His Ile Arg Leu Ser Thr Gln Asn Val Ile Asn Ala Glu Asn
        130                 135                 140

Ala Pro Gly Gly Pro Tyr Lys Ile Gly Thr Ser Gly Ser Cys Pro Asn
145                 150                 155                 160

Ala Thr Asn Lys Ser Gly Phe Phe Ala Thr Met Ala Trp Ala Val Pro
                165                 170                 175

Lys Asn Asp Asn Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
            195                 200                 205

His Ser Asp Asn Lys Thr Gln Met Lys Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Pro Gly Lys
                260                 265                 270

Thr Gly Thr Ile Val Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
```

```
            340                 345                 350
Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 76
<211> LENGTH: 585
<212> TYPE: PRT
<213> ORGANISM: Influenza B virus

<400> SEQUENCE: 76

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Lys Ile Pro Ser Ala Lys Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125
```

-continued

```
Tyr Glu His Ile Arg Leu Ser Thr Gln Asn Val Ile Asp Ala Glu Asn
        130                 135                 140

Ala Pro Gly Gly Pro Tyr Lys Ile Gly Thr Ser Gly Ser Cys Pro Asn
145                 150                 155                 160

Ala Thr Asn Lys Ser Gly Phe Phe Ala Thr Met Ala Trp Ala Val Pro
                165                 170                 175

Lys Asn Asp Asn Asn Lys Thr Ala Thr Asn Pro Leu Thr Ile Glu Val
                180                 185                 190

Pro Tyr Ile Cys Thr Glu Gly Glu Asp Gln Ile Thr Val Trp Gly Phe
                195                 200                 205

His Ser Asp Asn Lys Thr Gln Met Lys Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asp Gln Thr Glu Asp Gly Gly Leu Pro
                245                 250                 255

Gln Ser Gly Arg Ile Val Val Asp Tyr Met Val Gln Lys Pro Gly Lys
                260                 265                 270

Thr Gly Thr Ile Val Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Val Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Ile Lys Asn Leu Gln Arg Leu Ser Gly Ala Met
                420                 425                 430

Asp Glu Leu His Asn Glu Ile Leu Glu Leu Asp Glu Lys Val Asp Asp
            435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
                500                 505                 510

Arg Ile Ala Ala Gly Thr Phe Asp Ala Gly Glu Phe Ser Leu Pro Thr
            515                 520                 525

Phe Asp Ser Leu Asn Ile Thr Ala Ala Ser Leu Asn Asp Asp Gly Leu
    530                 535                 540

Asp Asn His Thr Ile Leu Leu Tyr Tyr Ser Thr Ala Ala Ser Ser Leu
```

```
            545                 550                 555                 560
        Ala Val Thr Leu Met Ile Ala Ile Phe Val Val Tyr Met Val Ser Arg
                            565                 570                 575

Asp Asn Val Ser Cys Ser Ile Cys Leu
                            580                 585

<210> SEQ ID NO 77
<211> LENGTH: 585
<212> TYPE: PRT
<213> ORGANISM: Influenza B virus

<400> SEQUENCE: 77

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Ser Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Lys Cys Pro Asn Cys Thr Asp Leu Asp Val
65                  70                  75                  80

Ala Leu Gly Arg Pro Met Cys Thr Gly Thr Ile Pro Ser Ala Lys Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Ala Thr Asn Lys Ile Gly Phe Phe Ala Thr Met Ala Trp Ala Val Pro
                165                 170                 175

Lys Asn Asp Asn Asn Lys Thr Ala Thr Asn Pro Leu Thr Ile Glu Val
            180                 185                 190

Pro Tyr Ile Cys Ala Glu Gly Glu Asp Gln Ile Thr Val Trp Gly Phe
        195                 200                 205

His Ser Asp Asp Lys Thr Gln Met Lys Lys Leu Tyr Gly Asp Ser Lys
    210                 215                 220

Pro Gln Lys Phe Thr Ser Ser Ala Asn Gly Val Thr Thr His Tyr Val
225                 230                 235                 240

Ser Gln Ile Gly Asp Phe Pro Asn Gln Thr Glu Asp Gly Gly Leu Pro
                245                 250                 255

Gln Ser Gly Arg Ile Val Val Asp Tyr Met Val Gln Lys Pro Gly Lys
            260                 265                 270

Thr Gly Thr Ile Thr Tyr Gln Arg Gly Ile Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335
```

```
Pro Ile Trp Val Lys Thr Pro Leu Lys Leu Ala Asn Gly Thr Lys Tyr
                340                 345                 350

Arg Pro Pro Thr Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asn
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 78
<211> LENGTH: 585
<212> TYPE: PRT
<213> ORGANISM: Influenza B virus

<400> SEQUENCE: 78

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser Tyr Phe Ala Asn Leu Lys Gly Thr Glu Thr
    50                  55                  60

Arg Gly Lys Leu Cys Pro Asn Cys Leu Asn Cys Thr Asp Leu Asp Val
65                  70                  75                  80

Ala Leu Gly Arg Pro Lys Cys Val Gly Lys Ile Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125
```

```
Tyr Glu His Ile Arg Leu Ser Thr Gln Asn Val Ile Asp Ala Glu Arg
            130                 135                 140

Ala Pro Gly Gly Pro Tyr Arg Leu Gly Thr Ser Gly Ser Cys Pro Asn
145                 150                 155                 160

Ala Thr Ser Lys Ser Gly Phe Phe Ala Thr Met Ala Trp Ala Val Pro
                165                 170                 175

Lys Asp Asp Asn Asn Lys Thr Ala Thr Asn Pro Leu Thr Val Glu Val
                180                 185                 190

Pro Tyr Ile Cys Thr Glu Gly Glu Asp Gln Ile Thr Val Trp Gly Phe
            195                 200                 205

His Ser Asp Asn Lys Thr Gln Met Lys Asn Leu Tyr Gly Asp Ser Asn
    210                 215                 220

Pro Gln Lys Phe Thr Ser Ser Ala Asn Gly Val Thr Thr His Tyr Val
225                 230                 235                 240

Ser Gln Ile Gly Gly Phe Pro Asp Gln Thr Glu Asp Gly Gly Leu Pro
                245                 250                 255

Gln Ser Gly Arg Ile Val Val Asp Tyr Met Val Gln Lys Pro Gly Lys
            260                 265                 270

Thr Gly Thr Ile Val Tyr Gln Arg Gly Val Leu Leu Pro Gln Lys Val
            275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Val Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Ile Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Asp Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asn Ala Gly Glu Phe Ser Leu Pro Thr
        515                 520                 525

Phe Asp Ser Leu Asn Ile Thr Ala Ala Ser Leu Asn Asp Asp Gly Leu
530                 535                 540
```

```
Asp Asn His Thr Ile Leu Leu Tyr Tyr Ser Thr Ala Ala Ser Ser Leu
545                 550                 555                 560

Ala Val Thr Leu Met Ile Ala Ile Phe Ile Val Tyr Met Val Ser Arg
            565                 570                 575

Asp Asn Val Ser Cys Ser Ile Cys Leu
            580                 585

<210> SEQ ID NO 79
<211> LENGTH: 585
<212> TYPE: PRT
<213> ORGANISM: Influenza B virus

<400> SEQUENCE: 79

Met Lys Ala Ile Ile Val Leu Leu Met Val Val Thr Ser Asn Ala Asp
1               5                   10                  15

Arg Ile Cys Thr Gly Ile Thr Ser Ser Lys Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser His Phe Ala Asn Leu Arg Gly Thr Lys Thr
        50                  55                  60

Arg Gly Lys Leu Cys Pro Asp Cys Leu Asn Cys Thr Asp Leu Asp Val
65                  70                  75                  80

Ala Leu Gly Arg Pro Lys Cys Val Gly Asn Thr Pro Ser Ala Lys Ala
                85                  90                  95

Ser Ile Leu His Glu Val Arg Pro Val Thr Ser Gly Cys Phe Pro Ile
                100                 105                 110

Met His Asp Arg Thr Lys Ile Arg Gln Leu Ala Asn Leu Leu Arg Gly
            115                 120                 125

Tyr Glu His Ile Arg Leu Ser Asn Tyr Asn Val Ile Asp Ala Glu Lys
        130                 135                 140

Ala Pro Gly Gly Pro Tyr Arg Leu Gly Thr Ser Arg Ser Cys Pro Asn
145                 150                 155                 160

Val Thr Ser Arg Ser Gly Phe Phe Ala Thr Met Ala Trp Ala Val Pro
                165                 170                 175

Lys Asp Asp Ser Asn Lys Asn Ala Thr Asn Pro Leu Thr Val Glu Val
                180                 185                 190

Pro Tyr Ile Cys Thr Glu Gly Glu Asp Gln Ile Thr Val Trp Gly Phe
                195                 200                 205

His Ser Asp Asn Lys Thr Gln Met Val Asn Leu Tyr Gly Asp Ser Asn
        210                 215                 220

Pro Gln Lys Phe Thr Ser Ser Ala Asn Gly Val Thr Thr His Tyr Val
225                 230                 235                 240

Ser Gln Ile Gly Asp Phe Pro Asn Gln Thr Glu Asp Gly Gly Leu Pro
                245                 250                 255

Gln Ser Gly Arg Ile Val Val Asp Tyr Met Met Gln Lys Ser Gly Lys
                260                 265                 270

Thr Gly Thr Ile Thr Tyr Gln Arg Gly Val Leu Leu Pro Gln Lys Val
            275                 280                 285

Trp Cys Ala Ser Gly Arg Ser Lys Val Ile Lys Gly Thr Leu Pro Leu
            290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335
```

```
Pro Ile Trp Val Lys Thr Pro Leu Lys Leu Ala Asn Gly Thr Lys Tyr
            340                 345                 350

Arg P

-continued

```
            115                 120                 125
Tyr Glu Asn Ile Arg Leu Ser Thr His Asn Val Ile Asn Ala Glu Arg
    130                 135                 140

Ala Pro Gly Gly Pro Tyr Ile Ile Gly Thr Ser Gly Ser Cys Pro Asn
145                 150                 155                 160

Ala Thr Asn Lys Asn Gly Phe Phe Ala Thr Met Ala Trp Ala Val Pro
                165                 170                 175

Lys Asp Asp Asn Asn Lys Thr Ala Thr Asn Pro Leu Thr Val Glu Val
                180                 185                 190

Pro Tyr Ile Cys Thr Glu Gly Glu Asp Gln Ile Thr Val Trp Gly Phe
            195                 200                 205

His Ser Asp Asn Lys Thr Gln Met Lys Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asp Gln Thr Glu Asp Gly Gly Leu Pro
                245                 250                 255

Gln Ser Gly Arg Ile Val Val Asp Tyr Met Val Gln Lys Ser Gly Lys
            260                 265                 270

Thr Gly Thr Ile Thr Tyr Gln Arg Gly Val Leu Leu Pro Gln Lys Val
        275                 280                 285

Trp Cys Ala Ser Gly Arg Ser Lys Val Ile Lys Gly Ser Leu Pro Leu
    290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
            340                 345                 350

Arg Pro Pro Ala Lys Leu Leu Lys Glu Arg Gly Phe Phe Gly Ala Ile
        355                 360                 365

Ala Gly Phe Leu Glu Gly Gly Trp Glu Gly Met Ile Ala Gly Trp His
    370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
    450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Asp Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asn Ala Gly Glu Phe Ser Leu Pro Thr
        515                 520                 525

Phe Asp Ser Leu Asn Ile Thr Ala Ala Ser Leu Asn Asp Asp Gly Leu
    530                 535                 540
```

```
Asp Asn His Thr Ile Leu Leu Tyr Tyr Ser Thr Ala Ala Ser Ser Leu
545                 550                 555                 560

Ala Val Thr Leu Met Ile Ala Ile Phe Ile Val Tyr Met Val Ser Arg
                565                 570                 575

Asp Asn Val Ser Cys Ser Ile Cys Leu
                580                 585

<210> SEQ ID NO 81
<211> LENGTH: 565
<212> TYPE: PRT
<213> ORGANISM: Influenza virus

<400> SEQUENCE: 81

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
                35                  40                  45

Ile Leu Glu Asp Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
                100                 105                 110

Ala Asp Tyr Glu Glu Leu Arg Glu Gln Leu Ser Ser Val Ser Ser Phe
                115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
                180                 185                 190

Trp Gly Val His His Pro Pro Asn Ile Gly Asp Gln Arg Ala Leu Tyr
                195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
                260                 265                 270

Leu Ser Arg Gly Phe Gly Ser Gly Ile Ile Thr Ser Asn Ala Pro Met
                275                 280                 285

Asp Lys Cys Asp Ala Lys Cys Gln Thr Pro Gln Gly Ala Ile Asn Ser
                290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
```

```
            325                 330                 335
Ile Pro Phe Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
            355                 360                 365
His Gln Asn Glu Gln Gly Ser Gly Tyr Ala Ala Asp Gln Lys Ser Thr
            370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Leu
                420                 425                 430
Asp Ile Trp Thr Tyr Asn Ala Glu Leu Leu Val Leu Leu Glu Asn Glu
                435                 440                 445
Arg Thr Leu Asp Phe His Asp Ser Asn Val Lys Asn Leu Tyr Glu Lys
                450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asp Glu Cys Met Glu Ser Val Lys
                485                 490                 495
Asn Gly Thr Tyr Asp Tyr Pro Lys Tyr Ser Glu Glu Ser Lys Leu Asn
                500                 505                 510
Arg Glu Lys Ile Asp Gly Val Lys Leu Glu Ser Met Gly Val Tyr Gln
                515                 520                 525
Ile Leu Ala Ile Tyr Ser Thr Val Ala Ser Ser Leu Val Leu Leu Val
                530                 535                 540
Ser Leu Gly Ala Ile Ser Phe Trp Met Cys Ser Asn Gly Ser Leu Gln
545                 550                 555                 560
Cys Arg Ile Cys Ile
                565

<210> SEQ ID NO 82
<211> LENGTH: 565
<212> TYPE: PRT
<213> ORGANISM: Influenza virus

<400> SEQUENCE: 82

Met Lys Ala Lys Leu Leu Val Leu Leu Cys Thr Phe Thr Ala Thr Tyr
1               5                   10                  15
Ala Asp Thr Ile Cys Ile Gly Tyr His Ala Asn Asn Ser Thr Asp Thr
                20                  25                  30
Val Asp Thr Val Leu Glu Lys Asn Val Thr Val Thr His Ser Val Asn
            35                  40                  45
Leu Leu Glu Asp Ser His Asn Gly Lys Leu Cys Lys Leu Lys Gly Ile
        50                  55                  60
Ala Pro Leu Gln Leu Gly Asn Cys Ser Val Ala Gly Trp Ile Leu Gly
65                  70                  75                  80
Asn Pro Glu Cys Glu Leu Leu Ile Ser Lys Glu Ser Trp Ser Tyr Ile
                85                  90                  95
Val Glu Lys Pro Asn Pro Glu Asn Gly Thr Cys Tyr Pro Gly Tyr Phe
                100                 105                 110
Ala Asp Tyr Glu Glu Leu Arg Glu Gln Leu Ser Ser Val Ser Ser Phe
            115                 120                 125
```

-continued

```
Glu Arg Phe Glu Ile Phe Pro Lys Glu Ser Ser Trp Pro Asn His Thr
        130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asp Thr Pro Val
        275                 280                 285

His Asp Cys Asn Thr Thr Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
```

-continued

```
                545                 550                 555                 560

Cys Arg Ile Cys Ile
                565

<210> SEQ ID NO 83
<211> LENGTH: 565
<212> TYPE: PRT
<213> ORGANISM: Influenza virus

<400> SEQUENCE: 83

Met Lys Ala Lys Leu Leu Val Leu Leu Cys Thr Phe Thr Ala Thr Tyr
1               5                   10                  15

Ala Asp Thr Leu Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Lys His Asn Gly Lys Leu Cys Lys Leu Arg Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Ser Ser His Tyr Ser Arg
        210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Ala Gly Ser Gly Ile Ile Ser Asp Thr Pro Val
        275                 280                 285

His Asp Cys Asn Thr Thr Cys Gln Thr Pro Lys Gly Ala Ile Asn Thr
        290                 295                 300

Ser Leu Pro Phe Gln Asn Ile His Pro Ile Thr Ile Gly Lys Cys Pro
305                 310                 315                 320

Lys Tyr Val Lys Ser Thr Lys Leu Arg Leu Ala Thr Gly Leu Arg Asn
                325                 330                 335

Ile Pro Ser Ile Gln Ser Arg Gly Leu Phe Gly Ala Ile Ala Gly Phe
            340                 345                 350
```

```
Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Glu Ile Thr Asn Lys Val Asn Ser Val Ile Glu
385                 390                 395                 400

Lys Met Asn Thr Gln Phe Thr Ala Val Gly Lys Glu Phe Asn His Leu
                405                 410                 415

Glu Lys Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Tyr His Asp Ser Asn Val Lys Asn Leu Tyr Glu Lys
    450                 455                 460

Val Arg Ser Gln Leu Lys Asn Asn Ala Lys Glu Ile Gly Asn Gly Cys
465                 470                 475                 480

Phe Glu Phe Tyr His Lys Cys Asp Asn Thr Cys Met Glu Ser Val Lys
                485                 490                 495

Asn Gly Thr Tyr Asp Tyr Pro Lys Tyr Ser Glu Glu Ala Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Val Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 84
<211> LENGTH: 565
<212> TYPE: PRT
<213> ORGANISM: Influenza virus

<400> SEQUENCE: 84

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160
```

```
Tyr Arg Asn Leu Leu Trp Leu Thr Gly Lys Asn Gly Leu Tyr Pro Asn
            165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
            195                 200                 205

His Thr Glu Asn Ala Tyr Val Ser Val Val Ser Ser His Tyr Ser Arg
            210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
            245                 250                 255

Ile Phe Glu Ala Asn Gly Asn Leu Ile Ala Pro Trp Tyr Ala Phe Ala
            260                 265                 270

Leu Ser Arg Gly Ser Gly Ser Gly Ile Ile Thr Ser Asp Ala Pro Val
            275                 280                 285

His Asp Cys Asn Thr Lys Cys Gln Thr Pro His Gly Ala Ile Asn Ser
            290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Ala Thr Gly Leu Arg Asn
            325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
            405                 410                 415

Glu Arg Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Arg Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asp Ala Cys Met Glu Ser Val Arg
            485                 490                 495

Asn Gly Thr Tyr Asp Tyr Pro Lys Tyr Ser Glu Glu Ser Lys Leu Asn
            500                 505                 510

Arg Glu Glu Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565
```

<210> SEQ ID NO 85
<211> LENGTH: 565
<212> TYPE: PRT
<213> ORGANISM: Influenza virus

<400> SEQUENCE: 85

```
Met Lys Ala Lys Leu Leu Val Leu Leu Cys Thr Phe Thr Ala Thr Tyr
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Arg His Asn Gly Lys Leu Cys Lys Leu Gly Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Ser Gly Ser Gly Ile Ile Ile Ser Asp Ala Pro Val
        275                 280                 285

His Asp Cys Asn Thr Lys Cys Gln Thr Pro Lys Gly Ala Ile Asn Thr
290                 295                 300

Ser Leu Pro Phe Gln Asn Ile His Pro Val Thr Ile Gly Glu Cys Pro
305                 310                 315                 320

Lys Tyr Val Lys Ser Thr Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Arg Ser Thr
370                 375                 380
```

-continued

```
Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn His Leu
            405                 410                 415

Glu Lys Arg Ile Glu Asn Leu Asn Lys Lys Val Asp Asp Gly Phe Leu
        420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
    450                 455                 460

Val Arg Ser Gln Leu Arg Asn Asn Ala Lys Glu Ile Gly Asn Gly Cys
465                 470                 475                 480

Phe Glu Phe Tyr His Lys Cys Asp Asp Thr Cys Met Glu Ser Val Lys
            485                 490                 495

Asn Gly Thr Tyr Asp Tyr Pro Lys Tyr Ser Glu Glu Ser Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 86
<211> LENGTH: 565
<212> TYPE: PRT
<213> ORGANISM: Influenza virus

<400> SEQUENCE: 86

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Ser Val Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Pro Asp Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
```

```
                180             185             190
Trp Gly Val His His Pro Asn Ile Gly Asp Gln Arg Ala Leu Tyr
            195             200             205
His Thr Glu Asn Ala Tyr Val Ser Val Ser Ser His Tyr Ser Arg
            210             215             220
Arg Phe Thr Pro Glu Ile Ala Lys Arg Pro Lys Val Arg Asp Gln Glu
225             230             235             240
Gly Arg Ile Asn Tyr Tyr Trp Thr Leu Leu Glu Pro Gly Asp Thr Ile
            245             250             255
Ile Phe Glu Ala Asn Gly Asn Leu Ile Ala Pro Trp Tyr Ala Phe Ala
            260             265             270
Leu Ser Arg Gly Phe Gly Ser Gly Ile Ile Thr Ser Asp Thr Pro Val
            275             280             285
His Asp Cys Asn Thr Thr Cys Gln Thr Pro Gln Gly Ala Ile Asn Ser
            290             295             300
Ser Leu Pro Phe Gln Asn Val His Pro Val Thr Ile Gly Glu Cys Pro
305             310             315             320
Lys Tyr Val Arg Ser Ala Lys Leu Arg Met Ala Thr Gly Leu Arg Asn
            325             330             335
Ile Pro Ser Ile Gln Ser Arg Gly Leu Phe Gly Ala Ile Ala Gly Phe
            340             345             350
Ile Glu Gly Gly Trp Thr Gly Met Val Asp Gly Trp Tyr Gly Tyr His
            355             360             365
His Gln Asn Glu Gln Gly Ser Gly Tyr Ala Ala Asp Leu Lys Ser Thr
            370             375             380
Gln Asn Ala Ile Asp Gly Ile Thr Asn Lys Val Asn Ser Val Ile Glu
385             390             395             400
Lys Met Asn Thr Gln Phe Thr Ala Val Gly Lys Glu Phe Asn Lys Leu
            405             410             415
Glu Arg Arg Met Glu Asn Leu Asn Lys Lys Val Asp Asp Gly Phe Leu
            420             425             430
Asp Ile Trp Thr Tyr Asn Ala Glu Leu Leu Val Leu Leu Glu Asn Glu
            435             440             445
Arg Thr Leu Asp Phe His Asp Ser Asn Val Lys Asn Leu Tyr Glu Lys
            450             455             460
Val Lys Ser Gln Leu Lys Asn Asn Ala Lys Glu Ile Gly Asn Gly Cys
465             470             475             480
Phe Glu Phe Tyr His Lys Cys Asn Asn Thr Cys Met Glu Ser Val Lys
            485             490             495
Asn Gly Thr Tyr Asp Tyr Pro Lys Tyr Ser Glu Glu Ser Lys Leu Asn
            500             505             510
Arg Glu Lys Ile Asp Gly Val Lys Leu Glu Ser Met Gly Val Tyr Gln
            515             520             525
Ile Leu Ala Ile Tyr Ser Thr Val Ala Ser Ser Leu Val Leu Leu Val
            530             535             540
Ser Leu Gly Ala Ile Ser Phe Trp Met Cys Ser Asn Gly Ser Leu Gln
545             550             555             560
Cys Arg Ile Cys Ile
            565

<210> SEQ ID NO 87
<211> LENGTH: 565
<212> TYPE: PRT
<213> ORGANISM: Influenza virus
```

<400> SEQUENCE: 87

```
Met Lys Ala Lys Leu Leu Val Leu Leu Cys Thr Phe Thr Ala Thr Tyr
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Ala Gly Ser Gly Ile Ile Ser Asp Thr Pro Val
        275                 280                 285

His Asp Cys Asn Thr Thr Cys Gln Thr Pro Lys Gly Ala Ile Asn Thr
290                 295                 300

Ser Leu Pro Phe Gln Asn Ile His Pro Ile Thr Ile Gly Lys Cys Pro
305                 310                 315                 320

Lys Tyr Val Lys Ser Thr Lys Leu Arg Leu Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
370                 375                 380

Gln Asn Ala Ile Asp Glu Ile Thr Asn Lys Val Asn Ser Val Ile Glu
385                 390                 395                 400

Lys Met Asn Thr Gln Phe Thr Ala Val Gly Lys Glu Phe Asn His Leu
```

-continued

```
                405                 410                 415
Glu Lys Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Tyr His Asp Ser Asn Val Lys Asn Leu Tyr Glu Lys
    450                 455                 460

Val Arg Ser Gln Leu Lys Asn Asn Ala Lys Glu Ile Gly Asn Gly Cys
465                 470                 475                 480

Phe Glu Phe Tyr His Lys Cys Asp Asn Thr Cys Met Glu Ser Val Lys
                485                 490                 495

Asn Gly Thr Tyr Asp Tyr Pro Lys Tyr Ser Glu Glu Ala Lys Leu Asn
            500                 505                 510

Arg Glu Glu Ile Asp Gly Val Lys Leu Glu Ser Thr Arg Ile Tyr Gln
        515                 520                 525

Ile Leu Ala Ile Tyr Ser Thr Val Ala Ser Ser Leu Val Leu Val Val
    530                 535                 540

Ser Leu Gly Ala Ile Ser Phe Trp Met Cys Ser Asn Gly Ser Leu Gln
545                 550                 555                 560

Cys Arg Ile Cys Ile
            565
```

<210> SEQ ID NO 88
<211> LENGTH: 565
<212> TYPE: PRT
<213> ORGANISM: Influenza virus

<400> SEQUENCE: 88

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Lys Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205
```

```
His Thr Glu Asn Ala Tyr Val Ser Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Ser Gly Ser Gly Ile Ile Thr Ser Asp Ala Pro Val
        275                 280                 285

His Asp Cys Asn Thr Lys Cys Gln Thr Pro His Gly Ala Ile Asn Ser
    290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
                405                 410                 415

Glu Arg Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Arg Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asp Ala Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Glu Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 89
<211> LENGTH: 565
<212> TYPE: PRT
<213> ORGANISM: Influenza virus

<400> SEQUENCE: 89

Met Lys Ala Lys Leu Leu Val Leu Leu Cys Thr Phe Thr Ala Thr Tyr
1               5                   10                  15
```

```
Ala Asp Thr Leu Cys Ile Gly Tyr His Ala Asn Asn Ser Thr Asp Thr
         20                  25                  30

Val Asp Thr Val Leu Glu Lys Asn Val Thr Val Thr His Ser Val Asn
         35                  40                  45

Leu Leu Glu Asp Arg His Asn Gly Lys Leu Cys Lys Leu Gly Gly Ile
 50                  55                  60

Ala Pro Leu His Leu Gly Lys Cys Asn Ile Ala Gly Trp Leu Leu Gly
 65                  70                  75                  80

Asn Pro Glu Cys Glu Leu Leu Leu Thr Val Ser Ser Trp Ser Tyr Ile
             85                  90                  95

Val Glu Thr Ser Asn Ser Asp Asn Gly Thr Cys Tyr Pro Gly Asp Phe
         100                 105                 110

Ile Asn Tyr Glu Glu Leu Arg Glu Gln Leu Ser Ser Val Ser Ser Phe
         115                 120                 125

Glu Arg Phe Glu Ile Phe Pro Lys Glu Ser Ser Trp Pro Asn His Thr
 130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                 165                 170                 175

Leu Ser Lys Ser Tyr Ala Asn Asn Lys Glu Lys Glu Val Leu Val Leu
             180                 185                 190

Trp Gly Val His His Pro Pro Asn Ile Gly Asp Gln Arg Ala Leu Tyr
                 195                 200                 205

His Thr Glu Asn Ala Tyr Val Ser Val Val Ser Ser His Tyr Ser Arg
         210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                 245                 250                 255

Ile Phe Glu Ala Asn Gly Asn Leu Ile Ala Pro Trp Tyr Ala Phe Ala
                 260                 265                 270

Leu Ser Arg Gly Ser Gly Ser Gly Ile Ile Ser Asp Ala Pro Val
             275                 280                 285

His Asp Cys Asn Thr Lys Cys Gln Thr Pro Lys Gly Ala Ile Asn Thr
         290                 295                 300

Ser Leu Pro Phe Gln Asn Ile His Pro Val Thr Ile Gly Glu Cys Pro
305                 310                 315                 320

Lys Tyr Val Lys Ser Thr Lys Leu Arg Met Ala Thr Gly Leu Arg Asn
                 325                 330                 335

Ile Pro Ser Ile Gln Ser Arg Gly Leu Phe Gly Ala Ile Ala Gly Phe
             340                 345                 350

Ile Glu Gly Gly Trp Thr Gly Met Ile Asp Gly Trp Tyr Gly Tyr His
             355                 360                 365

His Gln Asn Glu Gln Gly Ser Gly Tyr Ala Ala Asp Gln Arg Ser Thr
         370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn His Leu
                 405                 410                 415

Glu Lys Arg Ile Glu Asn Leu Asn Lys Lys Val Asp Asp Gly Phe Leu
             420                 425                 430
```

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Arg Ser Gln Leu Arg Asn Asn Ala Lys Glu Ile Gly Asn Gly Cys
465                 470                 475                 480

Phe Glu Phe Tyr His Lys Cys Asp Asp Thr Cys Met Glu Ser Val Lys
            485                 490                 495

Asn Gly Thr Tyr Asp Tyr Pro Lys Tyr Ser Glu Glu Ser Lys Leu Asn
                500                 505                 510

Arg Glu Glu Ile Asp Gly Val Lys Leu Glu Ser Thr Arg Ile Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 90
<211> LENGTH: 565
<212> TYPE: PRT
<213> ORGANISM: Influenza virus

<400> SEQUENCE: 90

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Lys Leu Lys Gly Ile
        50                  55                  60

Ala Pro Leu Gln Leu Gly Lys Cys Ser Val Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Ser Ser Pro Asp Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

```
Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asp Thr Pro Val
        275                 280                 285

His Asp Cys Asn Thr Thr Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asn Thr Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 91
<211> LENGTH: 565
<212> TYPE: PRT
<213> ORGANISM: Influenza virus

<400> SEQUENCE: 91

Met Lys Ala Lys Leu Leu Val Leu Leu Cys Thr Phe Thr Ala Thr Tyr
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
```

```
                35                  40                  45
Leu Leu Glu Asp Lys His Asn Gly Lys Leu Cys Lys Leu Arg Gly Val
 50                  55                  60

Ala Pro Leu His Leu Gly Lys Cys Asn Ile Ala Gly Trp Ile Leu Gly
 65                  70                  75                  80

Asn Pro Glu Cys Glu Ser Leu Ser Thr Ala Ser Ser Trp Ser Tyr Ile
                 85                  90                  95

Val Glu Thr Pro Ser Ser Asp Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Thr
        130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Met Glu Arg Asn Ala Gly Ser Gly Ile Ile Ser Asp Thr Pro Val
        275                 280                 285

His Asp Cys Asn Thr Thr Cys Gln Thr Pro Lys Gly Ala Ile Asn Thr
290                 295                 300

Ser Leu Pro Phe Gln Asn Ile His Pro Ile Thr Ile Gly Lys Cys Pro
305                 310                 315                 320

Lys Tyr Val Lys Ser Thr Lys Leu Arg Leu Ala Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Leu Lys Ser Thr
        370                 375                 380

Gln Asn Ala Ile Asp Glu Ile Thr Asn Lys Val Asn Ser Val Ile Glu
385                 390                 395                 400

Lys Met Asn Thr Gln Phe Thr Ala Val Gly Lys Glu Phe Asn His Leu
                405                 410                 415

Glu Lys Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Tyr His Asp Ser Asn Val Lys Asn Leu Tyr Glu Lys
450                 455                 460
```

```
Val Arg Ser Gln Leu Lys Asn Asn Ala Lys Glu Ile Gly Asn Gly Cys
465                 470                 475                 480

Phe Glu Phe Tyr His Lys Cys Asp Asn Thr Cys Met Glu Ser Val Lys
                485                 490                 495

Asn Gly Thr Tyr Asp Tyr Pro Lys Tyr Ser Glu Glu Ala Lys Leu Asn
            500                 505                 510

Arg Glu Glu Ile Asp Gly Val Lys Leu Glu Ser Thr Arg Ile Tyr Gln
            515                 520                 525

Ile Leu Ala Ile Tyr Ser Thr Val Ala Ser Ser Leu Val Leu Val Val
        530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 92
<211> LENGTH: 565
<212> TYPE: PRT
<213> ORGANISM: Influenza virus

<400> SEQUENCE: 92

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Lys Leu Lys Gly Ile
        50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Lys Phe Glu Ile Phe Pro Lys Glu Ser Ser Trp Pro Asn His Thr
        130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
```

```
                260                 265                 270
Leu Asn Arg Gly Ser Gly Ser Gly Ile Ile Thr Ser Asp Ala Pro Val
            275                 280                 285

His Asp Cys Asn Thr Lys Cys Gln Thr Pro His Gly Ala Ile Asn Ser
            290                 295                 300

Ser Leu Pro Phe Gln Asn Ile His Pro Val Thr Ile Gly Glu Cys Pro
305                 310                 315                 320

Lys Tyr Val Arg Ser Thr Lys Leu Arg Met Ala Thr Gly Leu Arg Asn
            325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn Asn Leu
            405                 410                 415

Glu Arg Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Arg Asn Leu Tyr Glu Lys
            450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Ala Cys Met Glu Ser Val Arg
            485                 490                 495

Asn Gly Thr Tyr Asp Tyr Pro Lys Tyr Ser Glu Glu Ser Lys Leu Asn
            500                 505                 510

Arg Glu Glu Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 93
<211> LENGTH: 565
<212> TYPE: PRT
<213> ORGANISM: Influenza virus

<400> SEQUENCE: 93

Met Lys Ala Lys Leu Leu Val Leu Leu Cys Thr Phe Thr Ala Thr Tyr
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Arg His Asn Gly Lys Leu Cys Lys Leu Gly Gly Ile
    50                  55                  60
```

```
Ala Pro Leu His Leu Gly Lys Cys Asn Ile Ala Gly Trp Leu Leu Gly
 65                  70                  75                  80

Asn Pro Glu Cys Glu Leu Leu Thr Val Ser Ser Trp Ser Tyr Ile
             85                  90                  95

Val Glu Thr Ser Asn Ser Asp Asn Gly Thr Cys Tyr Pro Gly Asp Phe
            100                 105                 110

Ile Asn Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
            165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
            195                 200                 205

His Thr Glu Asn Ala Tyr Val Ser Val Val Ser Ser His Tyr Ser Arg
        210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
            245                 250                 255

Ile Phe Glu Ala Asn Gly Asn Leu Ile Ala Pro Arg Tyr Ala Phe Ala
            260                 265                 270

Met Asn Arg Gly Ser Gly Ser Gly Ile Ile Ile Ser Asp Ala Pro Val
            275                 280                 285

His Asp Cys Asn Thr Lys Cys Gln Thr Pro Lys Gly Ala Ile Asn Thr
        290                 295                 300

Ser Leu Pro Phe Gln Asn Ile His Pro Val Thr Ile Gly Glu Cys Pro
305                 310                 315                 320

Lys Tyr Val Lys Ser Thr Lys Leu Arg Met Ala Thr Gly Leu Arg Asn
            325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Arg Ser Thr
    370                 375                 380

Gln Asn Ala Ile Asp Gly Ile Thr Asn Lys Val Asn Ser Val Ile Glu
385                 390                 395                 400

Lys Met Asn Thr Gln Phe Thr Ala Val Gly Lys Glu Phe Asn His Leu
            405                 410                 415

Glu Lys Arg Ile Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
        450                 455                 460

Val Arg Ser Gln Leu Arg Asn Asn Ala Lys Glu Ile Gly Asn Gly Cys
465                 470                 475                 480

Phe Glu Phe Tyr His Lys Cys Asp Asp Thr Cys Met Glu Ser Val Lys
```

```
                     485                 490                 495
Asn Gly Thr Tyr Asp Tyr Pro Lys Tyr Ser Glu Glu Ser Lys Leu Asn
                 500                 505                 510

Arg Glu Glu Ile Asp Gly Val Lys Leu Glu Ser Thr Arg Ile Tyr Gln
            515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 94
<211> LENGTH: 565
<212> TYPE: PRT
<213> ORGANISM: Influenza virus

<400> SEQUENCE: 94

Met Lys Ala Lys Leu Leu Val Leu Leu Cys Thr Phe Thr Ala Thr Tyr
 1               5                  10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asp
    130                 135                 140

Ser Asn Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Lys
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285
```

```
Asp Lys Cys Asp Ala Lys Cys Gln Thr Pro Gln Gly Ala Ile Asn Ser
    290                 295                 300
Ser Leu Pro Phe Gln Asn Val His Pro Val Thr Ile Gly Glu Cys Pro
305                 310                 315                 320
Lys Tyr Val Arg Ser Ala Lys Leu Arg Met Val Thr Gly Leu Arg Asn
                325                 330                 335
Ile Pro Phe Ile Gln Ser Arg Gly Leu Phe Gly Ala Ile Ala Gly Phe
            340                 345                 350
Ile Glu Gly Gly Trp Thr Gly Met Val Asp Gly Trp Tyr Gly Tyr His
        355                 360                 365
His Gln Asn Glu Gln Gly Ser Gly Tyr Ala Ala Asp Gln Lys Ser Thr
370                 375                 380
Gln Asn Ala Ile Asn Gly Ile Thr Asn Lys Val Asn Ser Val Ile Glu
385                 390                 395                 400
Lys Met Asn Thr Gln Phe Thr Ala Val Gly Lys Glu Phe Asn Lys Leu
                405                 410                 415
Glu Arg Arg Met Glu Asn Leu Asn Lys Lys Val Asp Asp Gly Phe Leu
            420                 425                 430
Asp Ile Trp Thr Tyr Asn Ala Glu Leu Leu Val Leu Leu Glu Asn Glu
        435                 440                 445
Arg Thr Leu Asp Phe His Asp Ser Asn Val Lys Asn Leu Tyr Glu Lys
450                 455                 460
Val Lys Ser Gln Leu Lys Asn Asn Ala Lys Glu Ile Gly Asn Gly Cys
465                 470                 475                 480
Phe Glu Phe Tyr His Lys Cys Asn Asp Glu Cys Met Glu Ser Val Lys
                485                 490                 495
Asn Gly Thr Tyr Asp Tyr Pro Lys Tyr Ser Glu Glu Ser Lys Leu Asn
            500                 505                 510
Arg Glu Lys Ile Asp Gly Val Lys Leu Glu Ser Met Gly Val Tyr Gln
        515                 520                 525
Ile Leu Ala Ile Tyr Ser Thr Val Ala Ser Ser Leu Val Leu Leu Val
530                 535                 540
Ser Leu Gly Ala Ile Ser Phe Trp Met Cys Ser Asn Gly Ser Leu Gln
545                 550                 555                 560
Cys Arg Ile Cys Ile
                565

<210> SEQ ID NO 95
<211> LENGTH: 566
<212> TYPE: PRT
<213> ORGANISM: Influenza virus

<400> SEQUENCE: 95

Met Lys Ala Lys Leu Leu Val Leu Leu Cys Thr Phe Thr Ala Thr Tyr
1               5                   10                  15
Ala Asp Thr Ile Cys Ile Gly Tyr His Ala Asn Asn Ser Thr Asp Thr
            20                  25                  30
Val Asp Thr Val Leu Glu Lys Asn Val Thr Val Thr His Ser Val Asn
        35                  40                  45
Ile Leu Glu Asp Ser His Asn Gly Lys Leu Cys Leu Leu Lys Gly Ile
    50                  55                  60
Ala Pro Leu Gln Leu Gly Asn Cys Ser Val Ala Gly Trp Ile Leu Gly
65                  70                  75                  80
Asn Pro Glu Cys Glu Leu Leu Ile Ser Lys Glu Ser Trp Ser Tyr Ile
                85                  90                  95
```

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asp
            130                 135                 140

Ser Asn Lys Gly Val Ser Ala Ser Cys Ser His Asn Gly Lys Ser Ser
145                 150                 155                 160

Phe Tyr Arg Asn Leu Leu Trp Leu Thr Gly Lys Asn Gly Leu Tyr Pro
                165                 170                 175

Lys Leu Ser Lys Ser Tyr Ala Asn Asn Lys Glu Lys Glu Val Leu Val
            180                 185                 190

Leu Trp Gly Val His His Pro Pro Asn Ile Gly Asp Gln Arg Ala Leu
            195                 200                 205

Tyr His Thr Glu Asn Ala Tyr Val Ser Val Val Ser Ser His Tyr Ser
            210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Pro
            275                 280                 285

Met Asp Lys Cys Asp Ala Lys Cys Gln Thr Pro Gln Gly Ala Ile Asn
            290                 295                 300

Ser Ser Leu Pro Phe Gln Asn Val His Pro Val Thr Ile Gly Glu Cys
305                 310                 315                 320

Pro Lys Tyr Val Arg Ser Ala Lys Leu Arg Met Val Thr Gly Leu Arg
                325                 330                 335

Asn Ile Pro Phe Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Gln Lys Ser
            370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
                405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Phe His Asp Ser Asn Val Lys Asn Leu Tyr Glu
            450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asp Glu Cys Met Glu Ser Val
                485                 490                 495

Lys Asn Gly Thr Tyr Asp Tyr Pro Lys Tyr Ser Glu Glu Ser Lys Leu
            500                 505                 510

```
Asn Arg Glu Lys Ile Asp Gly Val Lys Leu Glu Ser Met Gly Val Tyr
            515                 520                 525

Gln Ile Leu Ala Ile Tyr Ser Thr Val Ala Ser Ser Leu Val Leu Leu
        530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 96
<211> LENGTH: 566
<212> TYPE: PRT
<213> ORGANISM: Influenza virus

<400> SEQUENCE: 96

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Glu
    130                 135                 140

Thr Thr Lys Gly Val Ser Ala Ser Cys Ser His Asn Gly Lys Ser Ser
145                 150                 155                 160

Phe Tyr Arg Asn Leu Leu Trp Leu Thr Gly Lys Asn Gly Leu Tyr Pro
                165                 170                 175

Lys Leu Ser Lys Ser Tyr Ala Asn Asn Lys Glu Lys Glu Val Leu Val
            180                 185                 190

Leu Trp Gly Val His His Pro Pro Asn Ile Gly Asp Gln Arg Ala Leu
        195                 200                 205

Tyr His Thr Glu Asn Ala Tyr Val Ser Val Ser Ser His Tyr Ser
    210                 215                 220

Arg Arg Phe Thr Pro Glu Ile Ala Lys Arg Pro Lys Val Arg Asp Gln
225                 230                 235                 240

Glu Gly Arg Ile Asn Tyr Tyr Trp Thr Leu Leu Glu Pro Gly Asp Thr
                245                 250                 255

Ile Ile Phe Glu Ala Asn Gly Asn Leu Ile Ala Pro Trp Tyr Ala Phe
            260                 265                 270

Ala Leu Ser Arg Gly Phe Gly Ser Gly Ile Ile Thr Ser Asn Ala Pro
        275                 280                 285

Met Asp Lys Cys Asp Ala Lys Cys Gln Thr Pro Gln Gly Ala Ile Asn
    290                 295                 300

Ser Ser Leu Pro Phe Gln Asn Val His Pro Val Thr Ile Gly Glu Cys
305                 310                 315                 320
```

Pro Lys Tyr Val Arg Ser Ala Lys Leu Arg Met Val Thr Gly Leu Arg
            325                 330                 335

Asn Ile Pro Phe Ile Gln Ser Arg Gly Leu Phe Gly Ala Ile Ala Gly
            340                 345                 350

Phe Ile Glu Gly Gly Trp Thr Gly Met Val Asp Gly Trp Tyr Gly Tyr
            355                 360                 365

His His Gln Asn Glu Gln Gly Ser Gly Tyr Ala Ala Asp Gln Lys Ser
            370                 375                 380

Thr Gln Asn Ala Ile Asn Gly Ile Thr Asn Lys Val Asn Ser Val Ile
385                 390                 395                 400

Glu Lys Met Asn Thr Gln Phe Thr Ala Val Gly Lys Glu Phe Asn Lys
            405                 410                 415

Leu Glu Arg Arg Met Glu Asn Leu Asn Lys Lys Val Asp Asp Gly Phe
            420                 425                 430

Leu Asp Ile Trp Thr Tyr Asn Ala Glu Leu Leu Val Leu Leu Glu Asn
            435                 440                 445

Glu Arg Thr Leu Asp Phe His Asp Ser Asn Val Lys Asn Leu Tyr Glu
            450                 455                 460

Lys Val Lys Ser Gln Leu Lys Asn Asn Ala Lys Glu Ile Gly Asn Gly
465                 470                 475                 480

Cys Phe Glu Phe Tyr His Lys Cys Asn Asp Glu Cys Met Glu Ser Val
            485                 490                 495

Lys Asn Gly Thr Tyr Asp Tyr Pro Lys Tyr Ser Glu Glu Ser Lys Leu
            500                 505                 510

Asn Arg Glu Lys Ile Asp Gly Val Lys Leu Glu Ser Met Gly Val Tyr
            515                 520                 525

Gln Ile Leu Ala Ile Tyr Ser Thr Val Ala Ser Ser Leu Val Leu Leu
            530                 535                 540

Val Ser Leu Gly Ala Ile Ser Phe Trp Met Cys Ser Asn Gly Ser Leu
545                 550                 555                 560

Gln Cys Arg Ile Cys Ile
            565

<210> SEQ ID NO 97
<211> LENGTH: 565
<212> TYPE: PRT
<213> ORGANISM: Influenza virus

<400> SEQUENCE: 97

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
            35                  40                  45

Ile Leu Glu Asp Ser His Asn Gly Lys Leu Cys Leu Leu Lys Gly Ile
            50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
            85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe

-continued

```
              115                 120                 125
Glu Arg Phe Glu Ile Phe Pro Lys Thr Ser Ser Trp Pro Asn His Thr
130                 135                 140

Val Thr Gly Val Ser Ala Ser Cys Pro His Ala Gly Ala Lys Ser Phe
145                 150                 155                 160

Tyr Arg Asn Leu Leu Trp Leu Thr Gly Lys Asn Gly Leu Tyr Pro Asn
                    165                 170                 175

Leu Ser Lys Ser Tyr Ala Asn Asn Lys Glu Lys Glu Val Leu Val Leu
                180                 185                 190

Trp Gly Val His His Pro Pro Asn Ile Gly Asp Gln Arg Ala Leu Tyr
            195                 200                 205

Gln Asn Ala Asp Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                    245                 250                 255

Ile Phe Glu Ala Thr Gly Asn Leu Ile Ala Pro Trp Tyr Ala Phe Ala
                260                 265                 270

Leu Ser Arg Gly Phe Gly Ser Gly Ile Ile Thr Ser Asn Ala Pro Met
            275                 280                 285

Asp Lys Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                    325                 330                 335

Ile Pro Phe Ile Gln Ser Arg Gly Leu Phe Gly Ala Ile Ala Gly Phe
                340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                    405                 410                 415

Glu Arg Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                    485                 490                 495

Asn Gly Thr Tyr Asp Tyr Pro Lys Tyr Ser Glu Glu Ser Lys Leu Asn
                500                 505                 510

Arg Glu Lys Ile Asp Gly Val Lys Leu Glu Ser Met Gly Val Tyr Gln
            515                 520                 525

Ile Leu Ala Ile Tyr Ser Thr Val Ala Ser Ser Leu Val Leu Leu Val
530                 535                 540
```

```
Ser Leu Gly Ala Ile Ser Phe Trp Met Cys Ser Asn Gly Ser Leu Gln
545                 550                 555                 560

Cys Arg Ile Cys Ile
            565
```

<210> SEQ ID NO 98
<211> LENGTH: 565
<212> TYPE: PRT
<213> ORGANISM: Influenza virus

<400> SEQUENCE: 98

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Ile Leu Glu Asp Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Pro His Ala Gly Ala Lys Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

His Thr Glu Asn Ala Tyr Val Ser Val Val Ser Ser His Tyr Ser Arg
    210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Phe Ile Gln Ser Arg Gly Leu Phe Gly Ala Ile Ala Gly Phe
```

```
            340                 345                 350
Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 99
<211> LENGTH: 565
<212> TYPE: PRT
<213> ORGANISM: Influenza virus

<400> SEQUENCE: 99

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Ile Leu Glu Asp Ser His Asn Gly Lys Leu Cys Leu Leu Lys Gly Ile
        50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140
```

```
Val Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

Gln Asn Ala Asp Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
                260                 265                 270

Leu Ser Arg Gly Phe Gly Ser Gly Ile Ile Thr Ser Asn Ala Pro Met
            275                 280                 285

Asp Lys Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Phe Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
            355                 360                 365

His Gln Asn Glu Gln Gly Ser Gly Tyr Ala Ala Asp Gln Lys Ser Thr
370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
            530                 535                 540

Ser Leu Gly Ala Ile Ser Phe Trp Met Cys Ser Asn Gly Ser Leu Gln
545                 550                 555                 560

Cys Arg Ile Cys Ile
```

```
<210> SEQ ID NO 100
<211> LENGTH: 565
<212> TYPE: PRT
<213> ORGANISM: Influenza virus

<400> SEQUENCE: 100
```

| | | | | | | | | | | | | | | |
|---|---|---|---|---|---|---|---|---|---|---|---|---|---|---|
| Met | Lys | Ala | Lys | Leu | Leu | Val | Leu | Leu | Cys | Thr | Phe | Thr | Ala | Thr | Tyr |
| 1 | | | | 5 | | | | | 10 | | | | | 15 | |
| Ala | Asp | Thr | Ile | Cys | Ile | Gly | Tyr | His | Ala | Asn | Asn | Ser | Thr | Asp | Thr |
| | | | 20 | | | | | 25 | | | | | 30 | | |
| Val | Asp | Thr | Val | Leu | Glu | Lys | Asn | Val | Thr | Val | Thr | His | Ser | Val | Asn |
| | | 35 | | | | | 40 | | | | | 45 | | | |
| Ile | Le

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 101
<211> LENGTH: 565
<212> TYPE: PRT
<213> ORGANISM: Influenza virus

<400> SEQUENCE: 101

Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
130                 135                 140

Thr Thr Gly Val Ser Ala Ser Cys Pro His Ala Gly Ala Lys Ser Phe
145                 150                 155                 160

Tyr Arg Asn Leu Leu Trp Leu Thr Gly Lys Asn Gly Leu Tyr Pro Lys
                165                 170                 175

```
Leu Ser Lys Ser Tyr Ala Asn Asn Lys Glu Lys Glu Val Leu Val Leu
            180                 185                 190

Trp Gly Val His His Pro Asn Ile Gly Asp Gln Arg Ala Leu Tyr
        195                 200                 205

His Thr Glu Asn Ala Tyr Val Ser Val Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Lys Cys Asp Ala Lys Cys Gln Thr Pro Gln Gly Ala Ile Asn Ser
        290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Phe Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
        370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
        450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
        530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 102
<211> LENGTH: 565
```

<212> TYPE: PRT
<213> ORGANISM: Influenza virus

<400> SEQUENCE: 102

```
Met Lys Ala Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Ile Leu Glu Asp Ser His Asn Gly Lys Leu Cys Leu Leu Lys Gly Ile
50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
                85                  90                  95

Val Glu Lys Pro Asn Pro Glu Asn Gly Thr Cys Tyr Pro Gly Tyr Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
130                 135                 140

Thr Thr Gly Val Ser Ala Ser Cys Ser His Asn Gly Lys Ser Ser Phe
145                 150                 155                 160

Tyr Arg Asn Leu Leu Trp Leu Thr Gly Lys Asn Gly Leu Tyr Pro Lys
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asp Gln Arg Ala Leu Tyr
        195                 200                 205

Gln Asn Ala Asp Ala Tyr Val Ser Val Ser Ser His Tyr Ser Arg
210                 215                 220

Arg Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Trp Tyr Ala Phe Ala
            260                 265                 270

Leu Ser Arg Gly Phe Gly Ser Gly Ile Ile Thr Ser Asn Ala Pro Met
        275                 280                 285

Asp Lys Cys Asp Ala Lys Cys Gln Thr Pro Gln Gly Ala Ile Asn Ser
290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Phe Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
370                 375                 380

Gln Asn Ala Ile Asn Gly Ile Thr Asn Lys Val Asn Ser Val Ile Glu
385                 390                 395                 400
```

```
Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510

Arg Glu Lys Ile Asp Gly Val Lys Leu Glu Ser Met Gly Val Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 103
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
agcagaagca gagcattttc taatatccac aaaatg                              36

<210> SEQ ID NO 104
<211> LENGTH: 97
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
taaggaaaat taagccctgt attttccttt attgtagtgc ttgtttgctt gttatcatta   60
caaagaaacg ttattgaaaa atgctcttgt tactact                            97

<210> SEQ ID NO 105
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
atgaaggcaa taattgtact actcatggta gtaacatcca atgcagatcg aatctgcact   60
gggataacat cgtca                                                    75

<210> SEQ ID NO 106
```

```
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
gcaggagaat tttctctccc cacctttgat tcactgaata ttactgctgc atctttaaat       60
gacgatggat tggataatca tactatactg ctttactact caactgctgc ctccagtttg      120
gctgtaacac tgatgatagc tatctttgtt gtttatatgg tctccagaga caatgtttct      180
tgctccatct gtctataa                                                    198
```

METHODS OF OPTIMIZING NUCLEOTIDE SEQUENCES ENCODING ENGINEERED INFLUENZA PROTEINS

CROSS REFERENCE TO RELATED APPLICATIONS

This application is a divisional of U.S. application Ser. No. 15/580,192 (Allowed), filed 6 Dec. 2017, which is a U.S. National Stage application of PCT/US2016/036740 filed 9 Jun. 2016, which claims the benefit of, and relies on the filing date of, U.S. provisional patent application 62/172,949, filed 9 Jun. 2015, the entire disclosure of which is incorporated herein by reference.

SEQUENCE LISTING

The instant application contains a Sequence Listing which has been submitted electronically in ASCII format and is hereby incorporated by reference in its entirety. Said ASCII copy, created on Jun. 9, 2016, is named 0171.0008-PCT_SL.txt and is 351,204 bytes in size.

BACKGROUND

Influenza has a long standing history of pandemics, epidemics, resurgences and outbreaks. Vaccines have been the most effective defense against influenza. However, the effort to design and manufacture vaccines that induce strain-specific immunity year-over-year has been difficult as influenza continues to cause significant health problems across the globe. Annual influenza epidemics are thought to result in between three and five million cases of severe illness and between 250,000 and 500,000 deaths every year around the world. Furthermore, currently marketed influenza vaccines must be updated annually based on predicted strains that will be present in human populations in the impending season.

Influenza virus is a member of Orthomyxoviridae family. There are three subtypes of influenza viruses, designated influenza A, influenza B, and influenza C. The influenza virion contains a segmented negative-sense RNA genome. In the case of Influenza A viruses, the RNA genome encodes the following proteins: hemagglutinin (HA), neuraminidase (NA), matrix (M1), proton ion-channel protein (M2), nucleoprotein (NP), polymerase basic protein 1 (PB1), polymerase basic protein 2 (PB2), polymerase acidic protein (PA), and nonstructural protein 2 (NS2). The HA, NA, M1, and M2 are membrane associated, whereas NP, PB1, PB2, PA, and NS2 are nucleocapsid associated proteins. The M1 protein is the most abundant protein in influenza particles. The HA and NA proteins are envelope glycoproteins, responsible for virus attachment and penetration of the viral particles into the cell. Specifically, HA binds the influenza virus to cells with sialic acid-containing on surface structures on their membranes.

Both HA and NA proteins are the sources of the major immunodominant epitopes for virus neutralization and protective immunity, making them important components for prophylactic influenza vaccines. The generation and recovery of influenza viruses is an important step in the evaluation of functional influenza vaccine candidates.

Reverse genetics for negative-strand RNA viruses, such as the influenza virus, has permitted genetic manipulation of viral genomes in order to generate new viruses, which can be used as live, attenuated vaccines or vectors to express heterologous proteins. Reverse genetics technology allows the generation of infectious influenza virus entirely from cloned viral cDNA (Fodor et al., 1999 J Virol, 73(11):9679-9682).

Different systems were developed based on a set of plasmids capable of inducing the expression of the eight vRNAs and at least the polymerase protein complex and the nucleoprotein (NP) required for the transcription. The polymerase protein complex and NP can also be expressed either by transfection of four additional plasmids or by the use of plasmids with bidirectional promoters that allow both vRNA and mRNA synthesis through RNA polymerase I (POL 1) and II (POL 2) (Jackson et al, 2011, J Gen Virol, 92(Pt1):1-17) respectively. The total number of plasmids transfected can vary from 16 (Neuman et al, 1999, Proc Natl Acad Sci USA, 96(16):9345-9350), or 12 (Fodor et al, 1999, J Virol, 73(11):9679-9682) to 8 (Hoffmann et al, 2002, Vaccine, 20(25-26):3165-3170), depending if the strategy is unidirectional or bidirectional, and from 3 (Neumann et al, 2005, Proc Natl Acad Sci USA, 102(46):16825-16829) to 1 (Zhang et al, 2009, J Virol, 83(18):9296-9303) if plasmid(s) encode(s) several vRNA.

Most widely used influenza vaccines comprise viruses that have been chemically or physically inactivated or live viruses that have been attenuated. Examples of such vaccines are the split influenza inactivated vaccine (IIV) or live attenuated vaccine (LAIV). Manufacturing of these vaccines typically requires the recovery and propagation of a vaccine virus in embryonated hens' eggs. However, isolates of human Influenza grow very inefficiently in eggs and isolated virus frequently need to be adapted through a process that typically involves their blind passage in eggs and their reassortment with a high-yielding laboratory virus in order to increase virus/antigen yield. Two different techniques can be used to generate reassortant Influenza virus: classical reassortment and reverse genetics. Classical reassortment of Influenza A virus involves the co-infection of eggs with the vaccine virus and a high-yielding donor virus (PR8 in most cases). The resulting reassortant progeny must undergo a process of selection in order to identify the reassortant virus with the appropriate antigenic combination and high-yielding growth phenotype. This process of selection is cumbersome and there is no guarantee that such reassortant will be obtained. In contrast to classical reassortment, reverse genetics yield a reassortant virus with a predefined combination of genes or gene constellation, and does not require further selection. Furthermore, reverse genetics can be used in the absence of a virus isolate and it is the only technique that allows the introduction of targeted gene modifications in a vaccine virus. In fact, reverse genetics has been critical in the development of Influenza H5N1 vaccine virus in which a multi-basic cleavage site had to be removed from the HA gene.

SUMMARY

Embodiments of the present invention are based on the discovery that generation of influenza vaccine virus comprising engineered Influenza proteins, which do not naturally occur, can only be achieved through reverse genetics. While most reverse genetics applications rely on PCR or RT-PCR amplification of templates from pre-existing virus, recent advances in DNA synthesis have allowed the production of viruses in the absence of a natural viral template. Wimmer et al. (2009) Nature Biotech. 27 (12):1163-1172; Wimmer et al. (2011) Annu. Rev. Microbiol. 65:583-609. In the case of influenza virus, the use of synthetic DNA and reverse genetics technology has enabled the reconstruction of the 1918 Influenza virus (Tumpey et al. (2005) Science 310:77-80.) and shows promise to accelerate the production of candidate vaccine viruses in response to a flu pandemic (Dormitzer et al. (2013) Sci Tr Med 5 (185):1-12; Verity et al. (2011) Influenza J. 101-109). Furthermore, candidate vaccine viruses could incorporate rationally engineered influenza proteins designed to be better immunogens than native antigens, such as the engineered influenza proteins disclosed in PCT/US2016/035594, WO2013/122827 and US Publication Nos. 2015/0044247, 2015/0017196, 2014/0147459, 2014/0127248, and 2013/0183342 and in U.S. Provisional Application 62/345,502 or 62/344,862, all of which are incorporated herein by reference.

One important limitation to the use of reverse genetics and synthetic DNA technologies to produce influenza viruses expressing engineered proteins is the requirement for a nucleotide sequence encoding such engineered proteins. Similarly, the inability to recover or rescue infectious influenza virus expressing engineered proteins may be due, in part, to the nucleotide sequence lacking the optimal sequences for efficient viral packaging. Influenza structural proteins (e.g., HA and NA) may also generate higher viral titers depending on their specific codon usage. Increased titer can be important for maximizing the success rate of viral rescue and for improving viral yield during vaccine manufacturing.

The present invention provides, among other things, methods of generating optimized nucleotide sequences encoding an engineered influenza structural protein. Also provided are methods of using the optimized nucleotide sequences to produce infectious influenza viruses, for example, in a reverse genetics system.

In some embodiments, the method of generating an optimized nucleotide sequence encoding an engineered influenza structural protein comprises:

a) providing an amino acid sequence of the engineered influenza structural protein;

b) reverse-translating the amino acid sequence to generate a first nucleotide sequence;

c) identifying a second nucleotide sequence that encodes an influenza structural protein that shares a high degree of sequence identity with the engineered influenza structural protein;

d) at every position where the codons in the first and second nucleotide sequences code for the same amino acid, changing codons in the first nucleotide sequence to match codons from the second nucleotide sequence; and e) at every position where the codons in the first and second nucleotide sequences code for a different amino acid, changing codons in the first nucleotide sequence to match codons that are based on structural protein-specific influenza codon usage preferences, thereby generating the optimized nucleotide sequence.

In some embodiments, the influenza structural protein that shares a high degree of sequence identity with the engineered influenza structural protein is a wild-type influenza structural protein. In some embodiments, the influenza structural protein shares the highest degree of sequence identity with the engineered influenza structural protein (i.e., is the closest match). In some embodiments, the second nucleotide sequence encodes a wild type version of the influenza structural protein and is identified from a publicly available database comprising influenza nucleotide sequences.

In some embodiments, the engineered influenza structural protein comprises an amino acid sequence selected from the group consisting of SEQ ID NO: 4, SEQ ID NO: 5, SEQ ID NO: 6, and SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO:18, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83 SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, and SEQ ID NO: 102.

In some embodiments, the method further comprises adding the 5' and 3' non-coding sequences from a high titer rescued strain (e.g., A/PuertoRico/8/34; "PR8") to the optimized nucleotide sequence. In some embodiments, the 5' non-coding sequence comprises the nucleotide sequence of SEQ ID NO: 23 and/or the 3' non-coding sequence comprises the nucleotide sequence of SEQ ID NO: 24 or wherein the 5' non-coding sequence comprises the nucleotide sequence of SEQ ID NO: 103 and/or the 3' non-coding sequence comprises the nucleotide sequence of SEQ ID NO: 104.

In some embodiments, the method further comprises exchanging the nucleotide sequence encoding the signal peptide in the optimized nucleotide sequence with a nucleotide sequence encoding the signal peptide from a high titer rescued strain (e.g., PR8). In some embodiments, the method further comprises exchanging the nucleotide sequence encoding the transmembrane domain with a nucleotide sequence encoding the transmembrane domain from a high titer rescued strain (e.g., PR8). In some embodiments, the method further comprises exchanging the nucleotide sequence encoding the cytoplasmic domain with a nucleotide sequence encoding the cytoplasmic domain from a high titer rescued strain (e.g., PR8).

In some embodiments, the amino acid sequence of the engineered influenza structural protein encoded by the optimized nucleotide sequence is the same as the amino acid sequence encoded by the first nucleotide sequence.

In some embodiments, the optimized nucleotide sequence further comprises a nucleotide sequence encoding a signal peptide, a nucleotide sequence coding for a transmembrane domain, and/or a nucleotide sequence coding for a cytoplasmic domain.

In some embodiments, the engineered influenza structural protein is an influenza type A hemagglutinin protein. In some embodiments, the hemagglutinin protein is a subtype selected from the group consisting of H1, H2, H3, H4, H5, H6, H7, H8, H9, H10, H11, H12, H13, H14, H15, H16, and H17.

In some embodiments, the structural protein-specific influenza codon usage preferences are set forth in Tables 1-10.

In some embodiments, reverse translating the amino acid sequence to generate a first nucleotide sequence comprises use of a codon usage table specific for influenza viruses.

Also provided are methods of expressing the optimized nucleotide sequence generated by the methods described herein, the method comprising:

inserting the optimized nucleotide sequence into an expression plasmid; and expressing the optimized nucleotide sequence to generate the engineered influenza structural protein.

Also provided are reverse genetics method for producing an infectious influenza virus, the method comprising:

transfecting mammalian cells with one or more expression vectors, wherein the one or more expression vectors comprise an optimized nucleotide sequence encoding an engineered influenza structural protein generated by the methods described herein and b) nucleotide sequences coding for influenza proteins from one or more donor viruses;

producing the infectious influenza virus.

In some embodiments, the one or more donor viruses are selected from the group consisting of A/Puerto Rico/8/34 (H1N1) (PR8), B/Lee/40, and B/Panama/45/90.

In some embodiments, the infectious influenza virus is an infectious reassortant influenza virus comprising the genetic material of one or more donor viruses. In some embodiments, the infectious reassortant influenza virus is chimeric.

In some embodiments, the method further comprises:
harvesting the infectious influenza virus; and
infecting eggs or mammalian cells with the harvested influenza virus.

Also provided are methods of preparing an influenza vaccine composition, the method comprising:
generating a seed virus by transfecting mammalian cells with a set of expression vectors, one or more of which comprises an optimized nucleotide sequence encoding an engineered influenza structural protein generated by the methods described herein;
harvesting the seed virus; and
producing infectious influenza virus by infecting eggs or mammalian cells with the seed virus;
harvesting the infectious influenza virus after multiplication in the eggs or mammalian cells;
purifying the harvested infectious influenza virus;
optionally inactivating the purified virus; and
mixing the purified virus with a pharmaceutically acceptable carrier.

Also provided are methods of inducing an immune response to one or more influenza polypeptides in a subject, the method comprising administering the influenza vaccine composition as described herein.

Also provided are optimized nucleotide sequence encoding an engineered influenza structural protein, wherein the optimized nucleotide sequence is obtained by the methods described herein. The foregoing and other objects, features, and advantages of the invention will become more apparent from the following detailed description, which proceeds with reference to the accompanying figures.

BRIEF DESCRIPTION OF THE DRAWING

The Drawing included herein, which is comprised of the following Figures, is for illustration purposes only not for limitation.

FIG. 1 shows a flow chart of a method of generating an optimized nucleotide sequence encoding an engineered influenza according to certain embodiments of the present invention (SEQ ID NOS 33-37, respectively, in order of appearance).

FIG. 4 shows the aligned amino acid sequences of the transmembrane region (amino acid residues 183-212) of representatives of 14 subtypes and additional subtype H3 sequences of type A influenza hemagglutinins (SEQ ID NOS 48-57 and 57-64, respectively, in order of appearance). The usual single-letter amino acid codes are used. Dashes are introduced to maximize sequence alignment. Letters in boldface refer to residues that are conserved in 50% or more of the sequences of all different subtypes, including a few conservative replacements as described in the text. Residues are numbered using the X:31 HA2 numbering system.

DEFINITIONS

Figure 2:
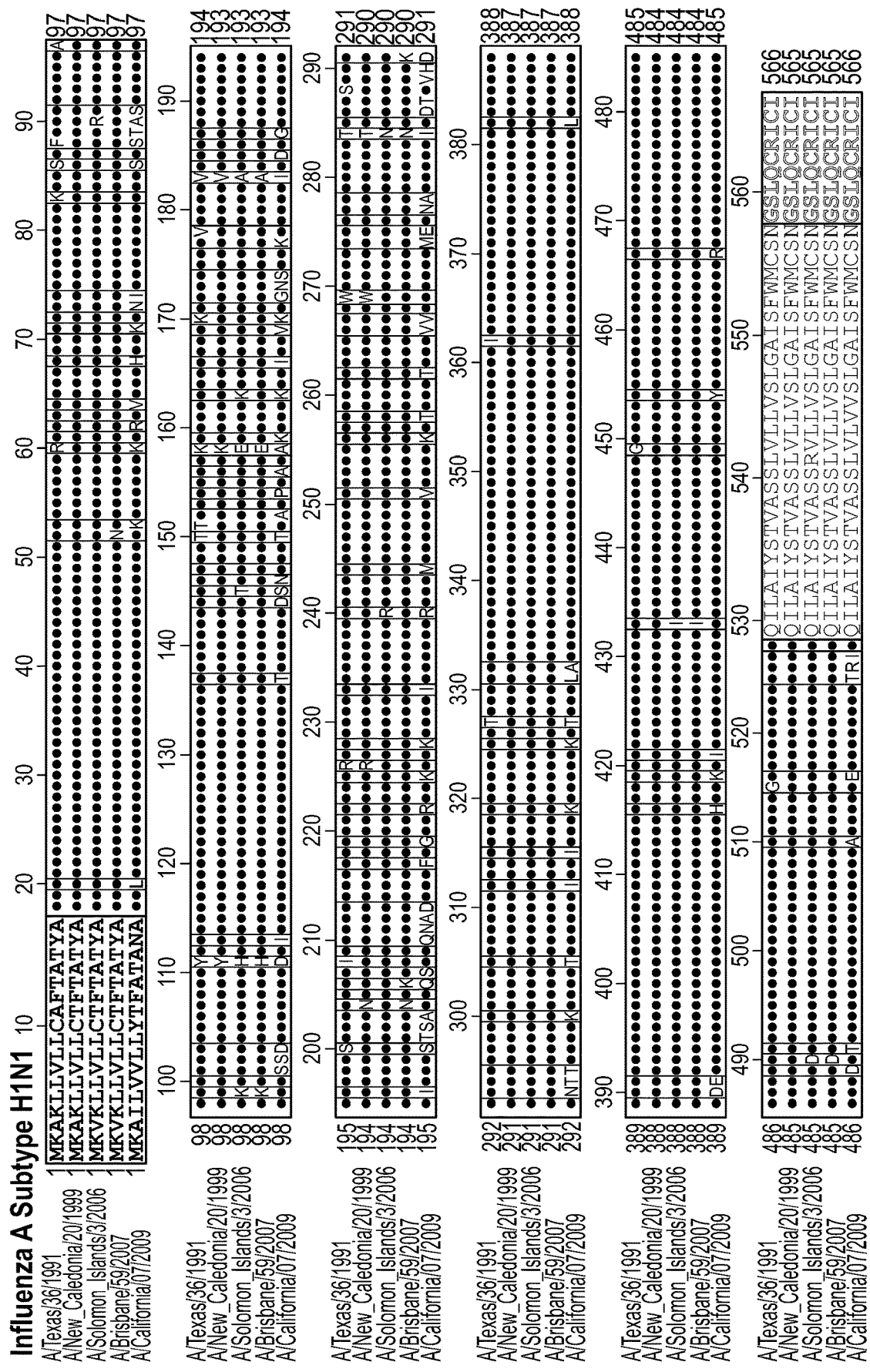
FIG. 2 shows the annotated alignment of HA protein sequences of several influenza A subtype H1N1 strains (SEQ ID NOS 38-42, respectively, in order of appearance). The full length sequences of the HA proteins of the strains exemplified in FIG. 2 are provided in the sequence listing as follows: A/Texas/36/1991 (SEQ ID NO: 65); A/New_Caledonia/20/1999 (SEQ ID NO: 66); A/Solomon_Islands/3/2006 (SEQ ID NO: 67); A/Brisbane/59/2007 (SEQ ID NO: 68); and A/California/07/2009 (SEQ ID NO: 69).

In order for the present invention to be more readily understood, certain terms are first defined below. Additional definitions for the following terms and other terms are set forth through the specification.

Adjuvant: As used herein, the term "adjuvant" refers to a substance or vehicle that non-specifically enhances the immune response to an antigen. Adjuvants can include a suspension of minerals (alum, aluminum salts, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as lipids and costimulatory molecules. Exemplary biological adjuvants include AS04 (Didierlaurent, A. M. et al, *J. Immunol.*, 2009, 183: 6186-6197), IL-2, RANTES, GM-CSF, TNF-α, IFN-γ, G-CSF, LFA-3, CD72, B7-1, B7-2, OX-40L and 41 BBL.

Administer: As used herein, "administering" a composition to a subject means to give, apply or bring the composition into contact with the subject. Administration can be accomplished by any of a number of routes, such as, for example, topical, oral, subcutaneous, intramuscular, intraperitoneal, intravenous, intrathecal and intradermal.

Antibody: As used herein, the term "antibody" refers to a polypeptide that includes canonical immunoglobulin sequence elements sufficient to confer specific binding to a particular target antigen. In some embodiments, as used herein, the term "antibody" also refers to an "antibody fragment" or "antibody fragments", which includes a portion of an intact antibody, such as, for example, the antigen-binding or variable region of an antibody. Examples of "antibody fragments" include Fab, Fab', F(ab')2, and Fv fragments; triabodies; tetrabodies; linear antibodies; single-chain antibody molecules; and CDR-containing moieties included in multi-specific antibodies formed from antibody fragments. Those skilled in the art will appreciate that the term "antibody fragment" does not imply and is not restricted to any particular mode of generation. An antibody fragment may be produced through use of any appropriate methodology, including but not limited to cleavage of an intact antibody, chemical synthesis, recombinant production, etc. As is known in the art, intact antibodies as produced in nature are approximately 150 kD tetrameric agents comprised of two identical heavy chain polypeptides (about 50 kD each) and two identical light chain polypeptides (about 25 kD each) that associate with each other into what is commonly referred to as a "Y-shaped" structure. Each heavy chain is comprised of at least four domains (each about 110 amino acids long)—an amino-terminal variable ($V_H$) domain (located at the tips of the Y structure), followed by three constant domains: $C_H1$, $C_H2$, and the carboxy-terminal $C_H3$ (located at the base of the Y's stem). A short region, known as the "switch", connects the heavy chain variable and constant regions. The "hinge" connects $C_H2$ and $C_H3$ domains to the rest of the antibody. Two disulfide bonds in this hinge region connect the two heavy chain polypeptides to one another in an intact antibody. Each light chain is comprised of two domains—an amino-terminal variable ($V_L$) domain, followed by a carboxy-terminal constant ($C_L$) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the $C_H2$ domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. Amino acid sequence comparisons among antibody polypeptide chains have defined two light chain ($\kappa$ and $\lambda$) classes, several heavy chain (e.g., $\mu$, $\gamma$, $\alpha$, $\varepsilon$, $\delta$) classes, and certain heavy chain subclasses ($\alpha1$, $\alpha2$, $\gamma1$, $\gamma2$, $\gamma3$, and $\gamma4$). Antibody classes (IgA [including IgA1, IgA2], IgD, IgE, IgG [including IgG1, IgG2, IgG3, IgG4], IgM) are defined based on the class of the utilized heavy chain sequences. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is monoclonal; in some embodiments, an antibody is polyclonal. In some embodiments, an antibody has constant region sequences that are characteristic of mouse, rabbit, primate, or human antibodies. In some embodiments, an antibody sequence elements are humanized, primatized, chimeric, etc., as is known in the art. Moreover, the term "antibody" as used herein, will be understood to encompass (unless otherwise stated or clear from context) can refer in appropriate embodiments to any of the art-known or developed constructs or formats for capturing antibody structural and functional features in alternative presentation. For example, in some embodiments, the term can refer to bi- or other multi-specific (e.g., zybodies, etc.) antibodies, Small Modular ImmunoPharmaceuticals ("SMIPs™"), single chain antibodies, camelid antibodies, and/or antibody fragments. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]).

Antigen: As used herein, the term "antigen", refers to an agent that elicits an immune response; and/or (ii) an agent that is bound by a T cell receptor (e.g., when presented by an MEW molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In some embodiments, an antigen reacts with the products of specific humoral or cellular immunity, including those induced by heterologous immunogens. In some embodiments of the disclosed compositions and methods, influenza HA H5N1 protein is an antigen.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can be assessed in any of a variety of contexts—including where interacting entities or moieties are studied in isolation or in the context of more complex systems (e.g., while covalently or otherwise associated with a carrier entity and/or in a biological system or cell).

Broadly Reactive: As used herein, "broadly reactive" means the protein sequence elicits an immune response in a subject that is sufficient to inhibit, neutralize or prevent infection of a broad range of influenza viruses (such as most or all influenza viruses within a specific subtype of, e.g., H1N1, H5N1, H3N2).

Carrier: As used herein, the term "carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

COBRA: As used herein, "COBRA," refers to a Computationally Optimized Broadly Reactive Antigen, as described in WO2013/122827 and US Publication Nos. 2015/0044247, 2015/0017196, 2014/0147459, 2014/0127248, and 2013/0183342, all of which are hereby incorporated by reference in their entirety. COBRAs are engineered HA proteins that elicit a broadly reactive immune response to influenza virus. The amino acid sequence of COBRAs are designed through a series of HA protein alignments and subsequent generation of a consensus sequence based on selected influenza isolates, and these HA amino acid sequences do not occur in natural influenza strains.

Codon-optimized: As used herein, a "codon-optimized" nucleic acid sequence refers to a nucleic acid sequence that has been altered such that translation of the nucleic acid sequence and expression of the resulting protein is improved or optimized for a particular expression system. A "codon-optimized" nucleic acid sequence preferably encodes the same protein as a non-optimized parental sequence upon which the "codon-optimized" nucleic acid sequence is based. For example, a nucleic acid sequence may be "codon-optimized" for expression in mammalian cells (e.g., CHO cells, human cells, mouse cells etc.), bacterial cells (e.g., E. coli), insect cells, yeast cells or plant cells. A nucleic acid may also be codon-optimized to permit or enhance expression of infectious influenza virus in a reverse genetics system.

Comparable: The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

Determine: Many methodologies described herein include a step of "determining". Those of ordinary skill in the art, reading the present specification, will appreciate that such "determining" can utilize any of a variety of techniques available to those skilled in the art, including for example specific techniques explicitly referred to herein. In some embodiments, a determination involves manipulation of a physical sample. In some embodiments, a determination involves consideration and/or manipulation of data or information, for example utilizing a computer or other processing unit adapted to perform a relevant analysis. In some embodiments, a determination involves receiving relevant information and/or materials from a source. In some embodiments, determining involves comparing one or more features of a sample or entity to a comparable reference.

Engineered: The term "engineered," as used herein, describes a polypeptide whose amino acid sequence has been designed by man and/or whose existence and production require action of the hand of man. For example, an engineered HA polypeptide has an amino acid sequence that differs from the amino acid sequences of HA polypeptides found in natural influenza isolates. In some embodiments, an engineered HA polypeptide has an amino acid sequence that differs from the amino acid sequence of HA polypeptides included in the NCBI database.

Epitope: As used herein, the term "epitope" includes any moiety that is specifically recognized by an immunoglobulin (e.g., antibody or receptor) binding component in whole or in part. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

Excipient: As used herein, the term "excipient" refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

Expression: The term "expression", when used in reference to a nucleic acid herein, refers to one or more of the following events: (1) production of an RNA transcript of a DNA template (e.g., by transcription); (2) processing of an RNA transcript (e.g., by splicing, editing, 5' cap formation, and/or 3' end formation); (3) translation of an RNA into a polypeptide; and/or (4) post-translational modification of a polypeptide.

Fusion protein: As used herein, the term "fusion protein" refers to a protein encoded by a nucleic acid sequence engineered from nucleic acid sequences encoding at least a portion of two different (e.g., heterologous) proteins. As persons of skill are no doubt aware, to create a fusion protein nucleic acid sequences are joined such that the resulting reading does not contain an internal stop codon. In some embodiments, fusion proteins as described herein include an influenza HA polypeptide or fragment thereof.

Hemagglutinin (HA) polypeptide: As used herein, the term "hemagglutinin polypeptide" (or "HA polypeptide") refers to a polypeptide whose amino acid sequence includes at least one characteristic sequence of HA. A wide variety of HA sequences from influenza isolates are known in the art; indeed, the National Center for Biotechnology Information (NCBI) maintains a database (available through the world wide web at ncbi.nlm.nih.gov/genomes/FLU/) that, as of the filing of the present application included at least 9796 HA sequences. Those of ordinary skill in the art, referring to this database, can readily identify sequences that are characteristic of HA polypeptides generally, and/or of particular HA polypeptides (e.g., H1, H2, H3, H4, H5, H6, H7, H8, H9, H10, H11, H12, H13, H14, H15, H16, or H17 polypeptides; or of HAs that mediate infection of particular hosts, e.g., avian, camel, canine, cat, civet, environment, equine, human, leopard, mink, mouse, seal, stone martin, swine, tiger, whale, etc.). For example, in some embodiments, an HA polypeptide includes one or more characteristic sequence elements found between about residues 97 and about 185, about 324 and about 340, about 96 and about 100, and/or about 130 and 230 of an HA protein found in a natural isolate of an influenza virus.

H1N1 HA polypeptide: An "H1N1 HA polypeptide", as that term is used herein, is an HA polypeptide whose amino acid sequence includes at least one sequence element that is characteristic of H1N1 and distinguishes H1N1 from other HA subtypes. Representative sequence elements can be determined by alignments as will be understood by those skilled in the art.

H5N1 HA polypeptide: An "H5N1 HA polypeptide", as that term is used herein, is an HA polypeptide whose amino acid sequence includes at least one sequence element that is characteristic of H5N1 and distinguishes H5N1 from other HA subtypes. Representative sequence elements can be determined by alignments as will be understood by those skilled in the art.

High titer rescued strain: A "high titer rescued strain" refers to any influenza strain that can be produced at high titers (at least $1 \times 10^6$ pfu/ml) using reverse genetics methods. High titer rescued strains are known in the art and include, but are not limited to A/PuertoRico/8/34 (PR8).

Host: The term "host" is used herein to refer to a system (e.g., a cell, organism, etc.) in which a polypeptide of interest is present. In some embodiments, a host is a system that is susceptible to infection with a particular infectious agent. In some embodiments, a host is a system that expresses a particular polypeptide of interest.

Host cell: As used herein, the phrase "host cell" refers to a cell into which exogenous DNA (recombinant or otherwise) has been introduced. For example, host cells may be used to produce the optimized influenza hemagglutinin polypeptides described herein by standard recombinant techniques. Persons of skill upon reading this disclosure will understand that such terms refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include any prokaryotic and eukaryotic cells suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells: CHO (e.g., CHO K1, DXB-11 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

Immune response: As used herein, the term "immune response" refers to a response of a cell of the immune system, such as a B cell, T cell, dendritic cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate and/or adaptive immune response. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells; e.g. by hemagglutination inhibition assays), secretion of cytokines or chemokines, inflammation, antibody production and the like.

Immunogen: As used herein, the term "immunogen" refers to a compound, composition, or substance which is capable, under appropriate conditions, of stimulating an immune response, such as the production of antibodies or a T cell response in an animal, including compositions that are injected or absorbed into an animal. As used herein, an "immunogenic composition" is an administerable composition comprising an immunogen (such as an HA polypeptide). "Immunogenic compositions" include, for example, vaccines. As used herein, "immunize" means to render a subject protected from an infectious disease, such as by vaccination.

Infectious influenza virus: By "infectious influenza virus" is meant an influenza virus which is able to replicate into a permissive cell. Methods for determining if a virus is infectious are well known by the one skilled in the art. For example, determining if a virus is infectious may be performed using the $TCID_{50}$ assay. The $TCID_{50}$ is a method to assess the amount of infectious virus in a sample (for instance an infected cell culture supernatant, or an infected allantoic fluid) by introducing incremental dilutions of the sample on permissive cells (such as MDCK or Vero cells) and determining the endpoint dilution that induces the infection of 50% of the permissive cells using the Spearman-Karber statistical method.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Influenza virus proteins: "Influenza virus proteins", as used herein, denote the PB1, PB2, PA, HA, NP, NA, M1, M2, NS1 and NS2/NEP proteins for type A influenza, PB1, PB2, PA, HA, NP, NA, NB, M1, BM2, NS1 and NS2/NEP proteins for type B influenza, or PB1, PB2, PA, HEF, NP, M1, M1 \ CM2, NS1 and NS2/NEP for type C influenza.

Influenza structural protein: As used herein, the term "influenza structural protein" refers to any protein associated with the influenza nucleocapsid, matrix and envelope, including the surface glycoproteins, hemagglutinin (HA) and neuraminidase (NA), and the matrix (M1) protein and proton ion-channel protein (M2), and functional or antigenic fragments thereof. By contrast, non-structural proteins of the influenza virus include influenza virus proteins necessary to form the ribonucleoprotein complex. By "influenza virus proteins necessary to form the ribonucleoprotein complex" is meant the proteins PA, PB1, PB2 and NP for type A, B or C influenza virus. Non-structural proteins also include NS1 and NS2.

Influenza vaccine: As used herein, the term "influenza vaccine" refers to an immunogenic composition capable of stimulating an immune response, administered for the prophylaxis, prevention, amelioration, or treatment of influenza virus infection. An influenza vaccine may include, for example, attenuated or killed influenza virus, subunit preparations thereof (i.e., split-inactivated vaccines), virus-like particles (VLPs) and/or antigenic polypeptides (e.g., the computationally optimized hemagglutinins described herein) or DNA derived from them, or any recombinant versions of such immunogenic materials. Influenza vaccines as described herein may optionally contain one or more adjuvants.

Isolated: As used herein, the term "isolated" refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

Nucleic acid: As used herein, the phrase "nucleic acid", in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

Operably linked: As used herein, the phrase "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

Outbreak: As used herein, an influenza virus "outbreak" refers to a collection of virus isolates from within a single country in a given year.

Pandemic strain: A "pandemic" influenza strain is one that has caused or has capacity to cause pandemic infection of human populations. In some embodiments, a pandemic strain has caused pandemic infection. In some embodiments, such pandemic infection involves epidemic infection across multiple territories; in some embodiments, pandemic infection involves infection across territories that are separated from one another (e.g., by mountains, bodies of water, as part of distinct continents, etc.) such that infections ordinarily do not pass between them.

Permissive cells: By "permissive cells" is meant cells that allow influenza virus to both penetrate into said cells and to achieve its full replication cycle until the production of new infectious virus. Highly permissive cells are cells where influenza viruses actively replicate and produce high amounts of infectious virus.

Pharmaceutically acceptable vehicles: As used herein, the term "pharmaceutically acceptable carrier" means any solvent, dispersing medium, charge, etc., commonly used on the formulation of pharmaceuticals and vaccines to enhance stability, sterility and deliverability of the active agent, which does not produce any secondary reaction, for example an allergic reaction, in humans. The excipient is selected on the basis of the pharmaceutical form chosen, the method and the route of administration. Appropriate excipients, and requirements in relation to pharmaceutical formulation, are described in Remington's Pharmaceutical Sciences (19th Edition, A. R. Gennaro, Ed., Mack Publishing Co., Easton, Pa. (1995)), which represents a reference work in the field. Examples of pharmaceutically acceptable excipients are water, phosphate-buffered saline solutions, 0.3% glycine solution.

Polypeptide: A "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally. In some embodiments, the term "polypeptide" is used to refer to specific functional classes of polypeptides, such as, HA polypeptides, etc. In some embodiments, a useful polypeptide may comprise or consist of a fragment of a parent polypeptide (e.g., an epitope). In some embodiments, a useful polypeptide as may comprise or consist of multiple (e.g., two, three, four, etc.) fragments (e.g., epitopes), each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide. Alternatively, in some embodiments, a useful polypeptide may comprise or consist of multiple (e.g., two, three, four, etc.) fragments (e.g., epitopes), each of which is found in different parent polypeptides than the polypeptide of interest (e.g., fragments that originate in different parent polypeptides, and/or fragments may be present in a different order in the polypeptide of interest than in the parent polypeptides), so that the polypeptide of interest is a derivative of its parent polypeptides.

Prevention: The term "prevention", as used herein, refers to prophylaxis, avoidance of disease manifestation, a delay of onset, and/or reduction in frequency and/or severity of one or more symptoms of a particular disease, disorder or condition (e.g., infection for example with influenza virus). In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition.

Pure: As used herein, an agent or entity is "pure" if it is substantially free of other components. For example, a preparation that contains more than about 90% of a particular agent or entity is typically considered to be a pure preparation. In some embodiments, an agent or entity is at least 91%, at least 92%, at least 93%, at least 94%, at least 95%, at least 96%, at least 97%, at least 98%, or at least 99% pure.

Reassortant virus: The term "reassortant virus" denotes a virus which contains genetic material that results from the combination of genetic material of at least two donor viruses. As used herein, the term may describe any influenza virus comprising parts from more than one parental strain, regardless of whether the virus is made by classic reassortant recombination or reverse genetics. When the reassortant virus is used for preparing a flu vaccine, its genetic material usually contains at least the HA and NA genes from a seasonal or pandemic virus (or an engineered version thereof) whereas the other genes (backbone genes) are from one or several other donor viruses which have been selected for their ability to grow easily on the substrate of production used for manufacturing the flu vaccine (such as the allantoic cavity of embryonated hen's eggs or a permissive cell line) and/or to be less or non-pathogenic to humans. Examples of donor viruses that contribute as "provider" of backbone genes include A/Puerto Rico/8/34 (H1N1) (A/PR/8/34), B/Lee/40 and/or B/Panama/45/90 viruses.

Receptor-Binding Site (RBS): As used herein, the term "receptor-binding site" or "RBS" comprises contiguous or non-contiguous amino acid residues of the head region of an influenza HA polypeptide, which include amino acids involved in direct binding of sialic acid on the target cell receptor proteins. Amino acid residues that make up a "receptor-binding site" or "RBS" of an influenza HA polypeptide may be described from crystal structures of HA polypeptides complexed with sialic acid analogs and identifying amino acid residues within a certain proximity to the analog or may be described in reference to an HA polypeptide sequence from a particular viral strain (e.g., A/New Caledonia/20/99 or A/California/07/2009). Thus, in some embodiments, the "receptor-binding site" or "RBS" of an engineered HA polypeptide as described herein may be determined using a reference HA polypeptide sequence. In some embodiments, the "receptor-binding site" or "RBS" of an engineered HA polypeptide as described herein may be determined using the crystal structures of HA polypeptide sequence in complex with human and avian receptor analogs (ex. LSTa, LSTc). An exemplary reference crystal structure of HA polypeptide sequence in complex with LSTc includes A/Puerto Rico/8/1934 (H1N1) pdb|1RVZ.

Recombinant: As used herein, the term "recombinant" is intended to refer to polypeptides (e.g., HA polypeptides as described herein) that are designed, engineered, prepared, expressed, created or isolated by recombinant means, such as polypeptides expressed using a recombinant expression vector transfected into a host cell, polypeptides isolated from a recombinant, combinatorial polypeptide library or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. In some embodiments, one or more such selected sequence elements results from the combination of multiple (e.g., two or more) known sequence elements that are not naturally present in the same polypeptide (e.g., two epitopes from two separate H5 HA polypeptides).

Reference: The term "reference" is often used herein to describe a standard or control agent, individual, population, sample, sequence or value against which an agent, individual, population, sample, sequence or value of interest is compared. In some embodiments, a reference agent, individual, population, sample, sequence or value is tested and/or determined substantially simultaneously with the testing or determination of the agent, individual, population, sample, sequence or value of interest. In some embodiments, a reference agent, individual, population, sample, sequence or value is a historical reference, optionally embodied in a tangible medium. Typically, as would be understood by those skilled in the art, a reference agent, individual, population, sample, sequence or value is determined or characterized under conditions comparable to those utilized to determine or characterize the agent, individual, population, sample, sequence or value of interest.

Reverse genetics: The term "reverse genetics" denotes molecular methods to produce infectious, reassortant viruses, or attenuated viruses from their complementary DNAs (cDNAs). These methods are very advantageous for producing reassortant influenza viruses by reassortment of vRNAs between different influenza viruses. The reverse genetics methods are well-known by the one skilled in the art (see, e.g., Neumann, G. and Kawaoka, Y., Virology, 2001, 287, 243-250).

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods. Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Pearson and Lipman, Proc. Natl. Acad. Sci. U.S.A. 85:2444, 1988; Higgins and Sharp, Gene 73:237-244, 1988; Higgins and Sharp, CABIOS 5:151-153, 1989; Corpet et al., Nucleic Acids Research 16:10881-10890, 1988; and Pearson and Lipman, Proc. Natl. Acad. Sci. U.S.A. 85:2444, 1988. Altschul et al., Nature Genet. 6:119-129, 1994. The NCBI Basic Local Alignment Search Tool (BLAST®) (Altschul et al., J. Mol. Biol. 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Subject: As used herein, the term "subject" means any mammal, including mice, ferrets and humans. In certain embodiments of the present invention the subject is an adult, an adolescent or an infant. In some embodiments, terms "individual" or "patient" are used and are intended to be interchangeable with "subject". Also contemplated by the present invention are the co-administration of the optimized H5N1 influenza HA proteins and/or performance of the methods to/or birds, including chickens and ducks.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Transformation: As used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

Vaccination: As used herein, the term "vaccination" refers to the administration of a composition (specifically co-administration of two or more of the three computationally optimized H5N1 HA polypeptides described herein) intended to generate an immune response, for example to a disease-causing agent such as influenza. Vaccination can be administered before, during, and/or after exposure to a disease-causing agent, and/or to the development of one or more symptoms, and in some embodiments, before, during, and/or shortly after exposure to the agent. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response. In some embodiments, vaccination includes multiple administrations, appropriately spaced in time, of a vaccinating composition.

Vector: As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Virus-like particle (VLP): As used herein, the phrase "virus-like particle" or "VLP" refers to particles that resemble a virus yet lack any viral genetic material and, therefore, are not infectious. A "virus-like particle" or "VLP" may be produced by heterologous expression in a variety of cell culture systems including mammalian cell lines, insect cell lines, yeast, and plant cells. In addition, VLPs can be purified by methods known in the art. In some embodiments, influenza VLPs as described herein comprise hemagglutinin (HA) polypeptides and neuraminidase (NA) polypeptides. In some embodiments, influenza VLPs as described herein comprises HA polypeptides, NA polypeptides and/or viral structural polypeptides (e.g., an influenza structural protein such as influenza M1). In some certain embodiments, influenza VLPs as described herein comprises HA polypeptides, NA polypeptides and/or M1 polypeptides. In some embodiments, influenza VLPs as described herein comprises HA polypeptides, NA polypeptides and/or HIV gag polypeptides. As persons of skill are aware, other viral structural proteins may be used as alternatives to those exemplified herein. Influenza VLPs can be produced by transfection of host cells (e.g., mammalian cells) with plasmids encoding HA and NA proteins, and optionally HIV gag proteins. After incubation of the transfected cells for an appropriate time to allow for protein expression (such as for approximately 72 hours), VLPs can be isolated from cell culture supernatants. In some embodiments, influenza VLPs as described herein are produced by transient transfection in mammalian cells (e.g., human cells). In some embodiments, influenza VLPs are analyzed by the use of one or more assays. To give but a few examples, influenza VLPs may be analyzed for hemagglutinin activity, dynamic light scattering and hemagglutinin content quantitation by protein staining. Other assays will be readily apparent to persons of skill upon reviewing the present disclosure.

vRNA: By "vRNA" is meant the negative-sense viral RNA of the influenza virus which is encapsulated into the ribonucleoprotein complex. When the influenza virus is of type A or B, said vRNAs are PB2, PB1, PA, HA, NP, NA, M and NS vRNAs. When the influenza virus is of type C, said vRNAs are PB1, PB2, PA, HEF, NP, M and NS vRNAs.

cRNA: By "cRNA" is meant the positive-sense RNA intermediate which is complementary to the vRNA. Once in the nucleus, the incoming negative-sense viral RNA (vRNA) is transcribed into messenger RNA (mRNA) by a primer-dependent mechanism. These mRNA products are incomplete copies of the vRNA template and are capped and polyadenylated, unlike vRNA. Replication occurs via a two-step process. A full-length, positive-sense copy of the vRNA is first made that is referred to as complementary RNA (cRNA) and is in turn used as a template to produce more vRNA.

Wild type: As is understood in the art, the phrase "wild type" generally refers to a normal form of a protein or nucleic acid, as is found in nature. For example, wild type HA polypeptides are found in natural isolates of influenza virus. A variety of different wild type HA sequences can be found in the NCBI influenza virus sequence database, available through the world wide web at ncbi.nlm.nih.gov/genomes/FLU/FLU.

DETAILED DESCRIPTION OF CERTAIN EMBODIMENTS

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

Unless stated otherwise, all technical and scientific terms and phrases used herein have the same meaning as commonly understood by one of ordinary skill in the art. Although any methods and materials similar or equivalent to those described herein can be used in the practice or testing of the present invention, the preferred methods and materials are now described. All publications mentioned herein are incorporated herein by reference.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

Generation of Optimized Nucleotide Sequences Encoding Engineered Influenza Proteins Recent advances have allowed for the production of rationally engineered influenza proteins designed to be better immunogens than native influenza proteins. Starting with an engineered influenza protein, it is possible to reverse translate the amino acid sequence of the engineered protein to generate a nucleotide sequence that encodes the engineered protein. The nucleotide sequence can be used in a reverse genetics system to facilitate the rescue of infectious influenza viruses containing modified versions of the influenza structural proteins (e.g., hemagglutinin or neuraminidase). However, it has been found that little to no infectious influenza virus can be rescued when using certain engineered influenza proteins in a reverse genetics system.

Without being bound by a particular theory, this phenomenon may be due, in part, to the nucleotide sequence encoding the engineered influenza protein lacking the optimal sequences for efficient viral packaging and/or efficient gene expression.

Disclosed herein are methods to generate an optimized nucleotide sequence encoding an engineered influenza structural protein. Optimizing the nucleotide sequence encoding the engineered influenza protein improves the likelihood of rescuing or recovering infectious influenza virus. It can also optimize virus growth and protein yield. The nucleotide sequence can be optimized through, among other things, the modification of the sequence by i) using an influenza-specific codon usage table (derived specifically for influenza structural proteins, such as hemagglutinin and neuoraminidase); and/or ii) using other influenza sequences (e.g., from wild type or previously rescued strains) as templates for reverse translations.

FIG. 1 provides a flow chart for certain embodiments of these methods. In these methods, the amino acid of the engineered structural protein is reverse translated into a nucleotide sequence, as shown in Step 1 of FIG. 1. The sequence may be reverse translated using a standard codon usage table or a codon usage table that is specific for influenza viruses. These codon usage tables are known in the art or can be prepared by comparing influenza sequences.

As shown Step 2 of FIG. 1, the first nucleotide sequence or a translation of the first nucleotide sequence is used to identify the second nucleotide sequence that encodes a corresponding influenza structural protein from a wild type virus or a previously rescued virus. That is, an initial round of comparisons to find the second sequence is performed using the first nucleotide sequence or a translated amino acid sequence thereof (e.g., against a translated nucleotide database). The nucleotide sequence of the match is then used in the downstream steps. For example, the first nucleotide sequence or a translation of the first nucleotide sequence can be used to search a database that includes influenza protein sequences or nucleotide sequences and to identify nucleotide sequences sharing a high degree of sequence identity (e.g., to identify the closest matching corresponding structural protein in a wild-type strain). The sequence similarity searching can be done using search tools, such as the NCBI Basic Local Alignment Search Tool (BLAST®) (Altschul et al., J. Mol. Biol. 215:403-410, 1990), which is available from several sources, including the National Center for Biotechnology Information (NCBI, Bethesda, Md.) and FASTA, which is available from several sources, including the EMBL-EBI website.

The first and second nucleotide sequences and/or translations thereof share a high degree of sequence identity. In certain embodiments, the second nucleotide sequence is at least 90%, 91%, 92%, 93%, 94%, 95%, 96%, 97%, 98%, or 99% identical to the first nucleotide sequence. In certain embodiments, the amino acid sequence encoded by the second nucleotide sequence is at least 90%, 91%, 92%, 93%, 94%, 95%, 96%, 97%, 98%, or 99% identical to the amino acid sequence encoded by the first nucleotide sequence. In one embodiment, the second nucleotide sequence and/or a translation thereof share the highest degree of sequence identity with the first nucleotide sequence and/or a translation thereof from among the nucleic acids or proteins in the database (e.g., the translation of the second nucleotide sequence is the closest match to the translation of the first nucleotide sequence in terms of sequence identity). In certain embodiments, the second nucleotide sequence and a translation thereof are a wild type version of the influenza structural protein. In other embodiments, the second nucleotide sequence and a translation thereof are versions of the influenza structural protein from an influenza virus that is capable of being rescued in a reverse genetics system.

Once the second nucleotide sequence is identified, the codons are compared. As shown Step 3a of FIG. 1, at every position where the codons in the first and second nucleotide sequences code for the same amino acid, the codons in the first nucleotide sequence are changed to match codons from the second nucleotide sequence. As shown in Step 3b, at every position where the codons in the first and second nucleotide sequences code for a different amino acid, the codons in the first nucleotide sequence are changed to match codons that are based on influenza protein-specific influenza codon usage preferences to generate an optimized nucleotide sequence.

In certain embodiments, the method of generating an optimized nucleotide sequence encoding an engineered influenza structural protein comprises:

a) providing an amino acid sequence of the engineered influenza structural protein;

b) reverse-translating the amino acid sequence to generate a first nucleotide sequence;

c) identifying a second nucleotide sequence that encodes a version of the influenza structural protein that shares a high degree of identity with the first nucleotide sequence (e.g., a sequence from a wild type influenza virus or an influenza virus that is capable of being rescued in a reverse genetics system);

d) at every position where the codons in the first and second nucleotide sequences code for the same amino acid, changing codons in the first nucleotide sequence to match codons from the second nucleotide sequence; and e) at every position where the codons in the first and second nucleotide sequences code for a different amino acid, changing codons in the first nucleotide sequence to match codons that are based on structural protein-specific influenza codon usage preferences, thereby generating the optimized nucleotide sequence.

In general, the amino acid sequence of the engineered influenza structural protein encoded by the optimized nucleotide sequence is the same as the amino acid sequence encoded by the first, non-optimized, nucleotide sequence. However, it is within the skill of the art to introduce minor changes in the amino acid sequence of the engineered influenza structural protein encoded by the optimized nucleotide sequence relative to the amino acid sequence encoded by the first nucleotide sequence, while retaining the ability to produce an infectious influenza virus in a reverse genetics system. Thus, in certain embodiments, the amino acid sequence of the engineered influenza structural protein encoded by the optimized nucleotide sequence has no more than 10, 9, 8, 7, 6, 5, 4, 3, 2, or 1 amino acid differences relative to the amino acid sequence encoded by the first nucleotide sequence.

Protein-specific influenza codon usage preferences can be generated by comparing influenza protein sequences. The codon usage preferences can be determined for a specific influenza structural protein (e.g., HA or NA). By way of example, exemplary protein-specific influenza codon usage preferences that have been generated by comparing influenza HA protein and nucleotide sequences are set forth below in Tables 1-5 for 1) influenza B (human), 2) influenza A H1N1 (human), 3) influenza A H1N1 (multi), 4) influenza A H3N2 (human), and 5) influenza A H3N2 (multi), where "multi" indicates that influenza sequences from multiple animal sources (e.g., human, swine, and avian) were analyzed.

TABLE 1

HA Influenza B (human) Codon Usage Preference
Coding GC 43.56%
1st letter GC 49.80%
2nd letter GC 43.52%
3rd letter GC 37.36%

| Codon | AA | Fraction | Frequency | Number |
|---|---|---|---|---|
| GCA | A | 0.462 | 31.699 | 95258 |
| GCC | A | 0.157 | 10.812 | 32492 |
| GCG | A | 0.059 | 4.041 | 12143 |
| GCT | A | 0.322 | 22.132 | 66508 |
| TGC | C | 0.789 | 20.566 | 61803 |
| TGT | C | 0.211 | 5.513 | 16566 |
| GAC | D | 0.402 | 19.190 | 57667 |
| GAT | D | 0.598 | 28.551 | 85798 |
| GAA | E | 0.797 | 44.055 | 132391 |
| GAG | E | 0.203 | 11.216 | 33705 |
| TTC | F | 0.547 | 14.288 | 42938 |
| TTT | F | 0.453 | 11.849 | 35606 |
| GGA | G | 0.526 | 51.266 | 154060 |
| GGC | G | 0.100 | 9.725 | 29226 |
| GGG | G | 0.198 | 19.282 | 57943 |
| GGT | G | 0.176 | 17.108 | 51411 |
| CAC | H | 0.390 | 11.353 | 34118 |
| CAT | H | 0.610 | 17.735 | 53295 |
| ATA | I | 0.553 | 33.601 | 100975 |
| ATC | I | 0.116 | 7.081 | 21278 |
| ATT | I | 0.331 | 20.105 | 60417 |
| AAA | K | 0.648 | 46.166 | 138734 |
| AAG | K | 0.352 | 25.100 | 75429 |
| CTA | L | 0.155 | 14.542 | 43699 |
| CTC | L | 0.231 | 21.688 | 65174 |
| CTG | L | 0.151 | 14.179 | 42610 |
| CTT | L | 0.152 | 14.215 | 42717 |
| TTA | L | 0.141 | 13.257 | 39839 |
| TTG | L | 0.169 | 15.812 | 47517 |
| ATG | M | 1.000 | 14.684 | 44126 |
| AAC | N | 0.520 | 30.638 | 92069 |
| AAT | N | 0.480 | 28.301 | 85048 |
| CCA | P | 0.387 | 19.703 | 59210 |
| CCC | P | 0.203 | 10.335 | 31057 |
| CCG | P | 0.013 | 0.678 | 2037 |
| CCT | P | 0.396 | 20.147 | 60544 |
| CAA | Q | 0.798 | 23.125 | 69494 |
| CAG | Q | 0.202 | 5.850 | 17579 |
| AGA | R | 0.642 | 21.921 | 65875 |
| AGG | R | 0.281 | 9.596 | 28837 |
| CGA | R | 0.073 | 2.478 | 7448 |
| CGC | R | 0.000 | 0.001 | 3 |
| CGG | R | 0.001 | 0.026 | 79 |
| CGT | R | 0.004 | 0.123 | 371 |
| AGC | S | 0.145 | 9.357 | 28118 |
| AGT | S | 0.144 | 9.287 | 27907 |
| TCA | S | 0.295 | 18.986 | 57056 |
| TCC | S | 0.081 | 5.186 | 15585 |
| TCG | S | 0.035 | 2.268 | 6815 |
| TCT | S | 0.300 | 19.325 | 58073 |
| ACA | T | 0.498 | 41.030 | 123299 |
| ACC | T | 0.295 | 24.274 | 72945 |
| ACG | T | 0.026 | 2.148 | 6456 |
| ACT | T | 0.181 | 14.954 | 44939 |
| GTA | V | 0.231 | 12.203 | 36671 |
| GTC | V | 0.212 | 11.192 | 33633 |
| GTG | V | 0.295 | 15.549 | 46725 |
| GTT | V | 0.262 | 13.810 | 41500 |
| TGG | W | 1.000 | 11.855 | 33613 |
| TAC | Y | 0.641 | 16.341 | 49106 |
| TAT | Y | 0.359 | 9.170 | 27557 |
| TAA | * | 0.600 | 0.001 | 3 |
| TAG | * | 0.200 | 0.000 | 1 |
| TGA | * | 0.200 | 0.000 | 1 |

TABLE 2

HA Influenza A H1N1 (human) Codon Usage Preference
Coding GC 40.67%
1st letter GC 44.58%
2nd letter GC 38.14%
3rd letter GC 39.28%

| Codon | AA | Fraction | Frequency | Number |
|---|---|---|---|---|
| GCA | A | 0.467 | 24.169 | 226427 |
| GCC | A | 0.297 | 15.363 | 143929 |
| GCG | A | 0.043 | 2.213 | 20733 |
| GCT | A | 0.194 | 10.032 | 93982 |
| TGC | C | 0.415 | 9.720 | 91067 |
| TGT | C | 0.585 | 13.721 | 128543 |
| GAC | D | 0.500 | 24.453 | 229087 |
| GAT | D | 0.500 | 24.407 | 228658 |
| GAA | E | 0.689 | 47.154 | 441772 |
| GAG | E | 0.311 | 21.288 | 199442 |
| TTC | F | 0.598 | 19.970 | 187088 |
| TTT | F | 0.402 | 13.442 | 125937 |
| GGA | G | 0.356 | 26.630 | 249488 |
| GGC | G | 0.115 | 8.604 | 80604 |
| GGG | G | 0.307 | 22.980 | 215289 |
| GGT | G | 0.223 | 16.664 | 156119 |
| CAC | H | 0.471 | 13.772 | 129023 |
| CAT | H | 0.529 | 15.471 | 144944 |
| ATA | I | 0.344 | 20.137 | 188659 |
| ATC | I | 0.141 | 8.251 | 77298 |
| ATT | I | 0.514 | 30.077 | 281779 |
| AAA | K | 0.652 | 52.096 | 488070 |
| AAG | K | 0.348 | 27.746 | 259946 |
| CTA | L | 0.275 | 20.519 | 192231 |
| CTC | L | 0.121 | 9.023 | 84533 |
| CTG | L | 0.196 | 14.616 | 136931 |
| CTT | L | 0.035 | 2.609 | 24441 |
| TTA | L | 0.152 | 11.315 | 106003 |
| TTG | L | 0.221 | 16.520 | 154767 |
| ATG | M | 1.000 | 10.255 | 96071 |
| AAC | N | 0.373 | 29.309 | 274589 |
| AAT | N | 0.627 | 49.326 | 462121 |
| CCA | P | 0.489 | 18.348 | 171892 |
| CCC | P | 0.209 | 7.858 | 73618 |
| CCG | P | 0.237 | 8.883 | 83222 |
| CCT | P | 0.065 | 2.426 | 22732 |
| CAA | Q | 0.477 | 13.241 | 124048 |
| CAG | Q | 0.523 | 14.528 | 136105 |
| AGA | R | 0.740 | 24.677 | 231194 |
| AGG | R | 0.257 | 8.561 | 80204 |
| CGA | R | 0.001 | 0.040 | 372 |
| CGC | R | 0.000 | 0.007 | 70 |
| CGG | R | 0.001 | 0.019 | 176 |
| CGT | R | 0.002 | 0.055 | 516 |
| AGC | S | 0.210 | 16.154 | 151339 |
| AGT | S | 0.128 | 9.836 | 92146 |
| TCA | S | 0.375 | 28.788 | 269704 |
| TCC | S | 0.088 | 6.763 | 63362 |
| TCG | S | 0.025 | 1.895 | 17751 |
| TCT | S | 0.175 | 13.434 | 125862 |
| ACA | T | 0.633 | 41.718 | 390845 |
| ACC | T | 0.041 | 2.724 | 25519 |
| ACG | T | 0.084 | 5.519 | 51702 |
| ACT | T | 0.242 | 15.976 | 149669 |
| GTA | V | 0.437 | 26.411 | 247437 |
| GTC | V | 0.131 | 7.925 | 74242 |
| GTG | V | 0.235 | 14.199 | 133023 |
| GTT | V | 0.197 | 11.905 | 111531 |
| TGG | W | 1.000 | 17.600 | 164889 |
| TAC | Y | 0.536 | 26.101 | 244527 |
| TAT | Y | 0.464 | 22.561 | 211362 |
| TAA | * | 0.600 | 0.001 | 6 |
| TAG | * | 0.000 | 0.000 | 0 |
| TGA | * | 0.400 | 0.000 | 4 |

TABLE 3

HA Influenza A H1N1 (multi) Codon Usage Preference
Coding GC 40.65%
1st letter GC 44.56%
2nd letter GC 38.20%
3rd letter GC 39.20%

| Codon | AA | Fraction | Frequency | Number |
|---|---|---|---|---|
| GCA | A | 0.467 | 24.211 | 252401 |
| GCC | A | 0.297 | 15.398 | 160530 |
| GCG | A | 0.041 | 2.147 | 22382 |
| GCT | A | 0.194 | 10.055 | 104821 |
| TGC | C | 0.407 | 9.531 | 99365 |
| TGT | C | 0.593 | 13.910 | 145017 |
| GAC | D | 0.496 | 24.145 | 251716 |
| GAT | D | 0.504 | 24.530 | 255736 |
| GAA | E | 0.686 | 46.936 | 489316 |
| GAG | E | 0.314 | 21.435 | 223463 |
| TTC | F | 0.589 | 19.707 | 205449 |
| TTT | F | 0.411 | 13.765 | 143505 |
| GGA | G | 0.361 | 27.066 | 282172 |
| GGC | G | 0.115 | 8.637 | 90040 |
| GGG | G | 0.302 | 22.607 | 235689 |
| GGT | G | 0.222 | 16.603 | 173089 |
| CAC | H | 0.469 | 13.712 | 142953 |
| CAT | H | 0.531 | 15.534 | 161951 |
| ATA | I | 0.346 | 20.196 | 210553 |
| ATC | I | 0.145 | 8.465 | 88247 |
| ATT | I | 0.509 | 29.734 | 309981 |
| AAA | K | 0.649 | 51.201 | 533784 |
| AAG | K | 0.351 | 27.679 | 288564 |
| CTA | L | 0.276 | 20.593 | 214690 |
| CTC | L | 0.121 | 9.003 | 93862 |
| CTG | L | 0.193 | 14.432 | 150461 |
| CTT | L | 0.037 | 2.781 | 28992 |
| TTA | L | 0.152 | 11.343 | 118255 |
| TTG | L | 0.220 | 16.445 | 171442 |
| ATG | M | 1.000 | 10.402 | 108443 |
| AAC | N | 0.373 | 29.529 | 307844 |
| AAT | N | 0.627 | 49.569 | 516765 |
| CCA | P | 0.489 | 18.306 | 190849 |
| CCC | P | 0.211 | 7.882 | 82167 |
| CCG | P | 0.226 | 8.447 | 88060 |
| CCT | P | 0.074 | 2.779 | 28971 |
| CAA | Q | 0.490 | 13.670 | 142513 |
| CAG | Q | 0.510 | 14.226 | 148315 |
| AGA | R | 0.740 | 25.010 | 260740 |
| AGG | R | 0.254 | 8.596 | 89617 |
| CGA | R | 0.003 | 0.086 | 898 |
| CGC | R | 0.001 | 0.018 | 191 |
| CGG | R | 0.002 | 0.052 | 540 |
| CGT | R | 0.002 | 0.054 | 564 |
| AGC | S | 0.211 | 16.195 | 168837 |
| AGT | S | 0.126 | 9.685 | 100965 |
| TCA | S | 0.376 | 28.927 | 301572 |
| TCC | S | 0.087 | 6.726 | 70119 |
| TCG | S | 0.024 | 1.870 | 19494 |
| TCT | S | 0.175 | 13.490 | 140633 |
| ACA | T | 0.626 | 41.367 | 431265 |
| ACC | T | 0.047 | 3.138 | 32717 |
| ACG | T | 0.085 | 5.618 | 58572 |
| ACT | T | 0.242 | 16.004 | 166842 |
| GTA | V | 0.432 | 26.042 | 271499 |
| GTC | V | 0.132 | 7.955 | 82929 |
| GTG | V | 0.238 | 14.333 | 149425 |
| GTT | V | 0.198 | 11.921 | 124277 |
| TGG | W | 1.000 | 17.632 | 183817 |
| TAC | Y | 0.535 | 26.031 | 271385 |
| TAT | Y | 0.465 | 22.638 | 236004 |
| TAA | * | 0.538 | 0.001 | 7 |
| TAG | * | 0.000 | 0.000 | 0 |
| TGA | * | 0.462 | 0.001 | 6 |

TABLE 4

HA Influenza A H3N2 (human) Codon Usage Preference
Coding GC 42.15%
1st letter GC 45.23%
2nd letter GC 39.73%
3rd letter GC 41.49%

| Codon | AA | Fraction | Frequency | Number |
|---|---|---|---|---|
| GCA | A | 0.442 | 22.845 | 155244 |
| GCC | A | 0.223 | 11.563 | 78573 |
| GCG | A | 0.070 | 3.616 | 24574 |
| GCT | A | 0.265 | 13.715 | 93200 |
| TGC | C | 0.583 | 13.614 | 92511 |
| TGT | C | 0.417 | 9.736 | 66157 |
| GAC | D | 0.499 | 28.959 | 196792 |
| GAT | D | 0.501 | 29.038 | 197325 |
| GAA | E | 0.571 | 30.883 | 209866 |
| GAG | E | 0.429 | 23.205 | 157687 |
| TTC | F | 0.650 | 23.734 | 161285 |
| TTT | F | 0.350 | 12.754 | 86666 |
| GGA | G | 0.426 | 33.349 | 226620 |
| GGC | G | 0.151 | 11.798 | 80172 |
| GGG | G | 0.225 | 17.639 | 119865 |
| GGT | G | 0.199 | 15.577 | 105853 |
| CAC | H | 0.549 | 12.081 | 82094 |
| CAT | H | 0.451 | 9.925 | 67448 |
| ATA | I | 0.397 | 30.782 | 209179 |
| ATC | I | 0.369 | 28.669 | 194821 |
| ATT | I | 0.234 | 18.160 | 123406 |
| AAA | K | 0.752 | 49.034 | 333206 |
| AAG | K | 0.248 | 16.196 | 110057 |
| CTA | L | 0.143 | 9.989 | 67881 |
| CTC | L | 0.058 | 4.019 | 27314 |
| CTG | L | 0.279 | 19.411 | 131909 |
| CTT | L | 0.244 | 17.009 | 115585 |
| TTA | L | 0.070 | 4.869 | 33088 |
| TTG | L | 0.206 | 14.328 | 97365 |
| ATG | M | 1.000 | 12.013 | 81634 |
| AAC | N | 0.405 | 33.707 | 229053 |
| AAT | N | 0.595 | 49.531 | 336587 |
| CCA | P | 0.313 | 12.110 | 82290 |
| CCC | P | 0.205 | 7.938 | 53939 |
| CCG | P | 0.190 | 7.345 | 49912 |
| CCT | P | 0.293 | 11.344 | 77090 |
| CAA | Q | 0.745 | 33.793 | 229641 |
| CAG | Q | 0.255 | 11.587 | 78739 |
| AGA | R | 0.518 | 26.434 | 179630 |
| AGG | R | 0.292 | 14.905 | 101285 |
| CGA | R | 0.143 | 7.299 | 49598 |
| CGC | R | 0.008 | 0.397 | 2701 |
| CGG | R | 0.039 | 1.985 | 13486 |
| CGT | R | 0.000 | 0.011 | 76 |
| AGC | S | 0.315 | 23.589 | 160295 |
| AGT | S | 0.147 | 11.009 | 74808 |
| TCA | S | 0.299 | 22.426 | 152395 |
| TCC | S | 0.080 | 5.983 | 40654 |
| TCG | S | 0.002 | 0.121 | 823 |
| TCT | S | 0.157 | 11.795 | 80152 |
| ACA | T | 0.378 | 23.252 | 158007 |
| ACC | T | 0.102 | 6.280 | 42678 |
| ACG | T | 0.154 | 9.500 | 64560 |
| ACT | T | 0.366 | 22.543 | 153192 |
| GTA | V | 0.329 | 14.418 | 97977 |
| GTC | V | 0.080 | 3.499 | 23779 |
| GTG | V | 0.194 | 8.527 | 57947 |
| GTT | V | 0.397 | 17.436 | 118482 |
| TGG | W | 1.000 | 17.597 | 119580 |
| TAC | Y | 0.600 | 21.091 | 143320 |
| TAT | Y | 0.400 | 14.036 | 95379 |
| TAA | * | 0.000 | 0.000 | 0 |
| TAG | * | 0.000 | 0.000 | 0 |
| TGA | * | 1.000 | 0.000 | 1 |

TABLE 5

HA Influenza A H3N2 (multi) Codon Usage Preference
Coding GC 42.18%
1st letter GC 45.27%
2nd letter GC 39.71%
3rd letter GC 41.57%

| Codon | AA | Fraction | Frequency | Number |
|---|---|---|---|---|
| GCA | A | 0.444 | 22.883 | 169211 |
| GCC | A | 0.227 | 11.694 | 86472 |
| GCG | A | 0.068 | 3.506 | 25925 |
| GCT | A | 0.261 | 13.420 | 99235 |
| TGC | C | 0.588 | 13.734 | 101558 |
| TGT | C | 0.412 | 9.616 | 71109 |
| GAC | D | 0.508 | 29.541 | 218446 |
| GAT | D | 0.492 | 28.632 | 211725 |
| GAA | E | 0.576 | 31.066 | 229724 |
| GAG | E | 0.424 | 22.871 | 169124 |
| TTC | F | 0.653 | 23.655 | 174920 |
| TTT | F | 0.347 | 12.569 | 92946 |
| GGA | G | 0.420 | 32.846 | 242891 |
| GGC | G | 0.150 | 11.724 | 86694 |
| GGG | G | 0.228 | 17.797 | 131602 |
| GGT | G | 0.203 | 15.840 | 117134 |
| CAC | H | 0.541 | 11.985 | 88629 |
| CAT | H | 0.459 | 10.153 | 75078 |
| ATA | I | 0.396 | 30.534 | 225794 |
| ATC | I | 0.367 | 28.277 | 209105 |
| ATT | I | 0.237 | 18.259 | 135020 |
| AAA | K | 0.755 | 49.021 | 362502 |
| AAG | K | 0.245 | 15.906 | 117620 |
| CTA | L | 0.147 | 10.250 | 75799 |
| CTC | L | 0.056 | 3.903 | 28861 |
| CTG | L | 0.278 | 19.345 | 143055 |
| CTT | L | 0.242 | 16.827 | 124435 |
| TTA | L | 0.072 | 4.995 | 36940 |
| TTG | L | 0.205 | 14.238 | 105284 |
| ATG | M | 1.000 | 12.163 | 89944 |
| AAC | N | 0.410 | 33.995 | 251387 |
| AAT | N | 0.590 | 48.945 | 361939 |
| CCA | P | 0.313 | 12.032 | 88973 |
| CCC | P | 0.206 | 7.941 | 58722 |
| CCG | P | 0.190 | 7.293 | 53933 |
| CCT | P | 0.292 | 11.221 | 82974 |
| CAA | Q | 0.747 | 34.087 | 252064 |
| CAG | Q | 0.253 | 11.523 | 85207 |
| AGA | R | 0.520 | 26.436 | 195491 |
| AGG | R | 0.289 | 14.695 | 108663 |
| CGA | R | 0.136 | 6.933 | 51271 |
| CGC | R | 0.008 | 0.392 | 2901 |
| CGG | R | 0.047 | 2.370 | 17528 |
| CGT | R | 0.000 | 0.019 | 139 |
| AGC | S | 0.315 | 23.616 | 174636 |
| AGT | S | 0.148 | 11.080 | 81932 |
| TCA | S | 0.297 | 22.291 | 164840 |
| TCC | S | 0.081 | 6.090 | 45033 |
| TCG | S | 0.002 | 0.151 | 1117 |
| TCT | S | 0.157 | 11.800 | 87255 |
| ACA | T | 0.376 | 23.267 | 172056 |
| ACC | T | 0.109 | 6.719 | 49687 |
| ACG | T | 0.153 | 9.466 | 69997 |
| ACT | T | 0.363 | 22.451 | 166017 |
| GTA | V | 0.330 | 14.731 | 108929 |
| GTC | V | 0.084 | 3.743 | 27682 |
| GTG | V | 0.191 | 8.524 | 63031 |
| GTT | V | 0.394 | 17.579 | 129989 |
| TGG | W | 1.000 | 17.744 | 131210 |
| TAC | Y | 0.591 | 21.055 | 155695 |
| TAT | Y | 0.409 | 14.561 | 107675 |
| TAA | * | 0.000 | 0.000 | 0 |
| TAG | * | 0.500 | 0.000 | 1 |
| TGA | * | 0.500 | 0.000 | 1 |

By way of further example, exemplary protein-specific influenza codon usage preferences that have been generated by comparing influenza NA protein and nucleotide sequences are set forth below in Tables 6-10 for 1) influenza B (human), 2) influenza A H1N1 (human), 3) influenza A H1N1 (multi), 4) influenza A H3N2 (human), and 5) influenza A H3N2 (multi), where "multi" indicates that influenza sequences from multiple animal sources (e.g., human, swine, avian) were analyzed.

TABLE 6

NA Influenza B (human) Codon Usage Preference
Coding GC 42.70%
1st letter GC 45.65%
2nd letter GC 47.02%
3rd letter GC 35.44%

| Codon | AA | Fraction | Frequency | Number |
|---|---|---|---|---|
| GCA | A | 0.497 | 32.951 | 122710 |
| GCC | A | 0.173 | 11.475 | 42731 |
| GCG | A | 0.029 | 1.928 | 7180 |
| GCT | A | 0.301 | 19.936 | 74241 |
| TGC | C | 0.549 | 21.151 | 78765 |
| TGT | C | 0.451 | 17.384 | 64737 |
| GAC | D | 0.376 | 18.458 | 68736 |
| GAT | D | 0.624 | 30.661 | 114180 |
| GAA | E | 0.785 | 42.521 | 158346 |
| GAG | E | 0.215 | 11.612 | 43242 |
| TTC | F | 0.272 | 8.577 | 31939 |
| TTT | F | 0.728 | 22.958 | 85494 |
| GGA | G | 0.473 | 45.162 | 168182 |
| GGC | G | 0.190 | 18.105 | 67424 |
| GGG | G | 0.234 | 22.381 | 83348 |
| GGT | G | 0.103 | 9.872 | 36762 |
| CAC | H | 0.310 | 7.402 | 27565 |
| CAT | H | 0.690 | 16.459 | 61293 |
| ATA | I | 0.524 | 31.908 | 118826 |
| ATC | I | 0.180 | 10.985 | 40909 |
| ATT | I | 0.295 | 17.983 | 66967 |
| AAA | K | 0.745 | 44.692 | 166434 |
| AAG | K | 0.255 | 15.260 | 56827 |
| CTA | L | 0.247 | 20.233 | 75349 |
| CTC | L | 0.104 | 8.551 | 31842 |
| CTG | L | 0.126 | 10.339 | 38501 |
| CTT | L | 0.118 | 9.712 | 36169 |
| TTA | L | 0.205 | 16.776 | 62473 |
| TTG | L | 0.200 | 16.371 | 60964 |
| ATG | M | 1.000 | 29.902 | 111356 |
| AAC | N | 0.492 | 17.205 | 64070 |
| AAT | N | 0.508 | 17.760 | 66137 |
| CCA | P | 0.435 | 21.415 | 79752 |
| CCC | P | 0.193 | 9.506 | 35401 |
| CCG | P | 0.111 | 5.490 | 20446 |
| CCT | P | 0.261 | 12.831 | 47781 |
| CAA | Q | 0.633 | 9.715 | 36178 |
| CAG | Q | 0.367 | 5.639 | 21000 |
| AGA | R | 0.549 | 24.488 | 91194 |
| AGG | R | 0.205 | 9.116 | 33948 |
| CGA | R | 0.141 | 6.281 | 23389 |
| CGC | R | 0.000 | 0.016 | 59 |
| CGG | R | 0.006 | 0.256 | 952 |
| CGT | R | 0.099 | 4.419 | 16455 |
| AGC | S | 0.109 | 8.544 | 31818 |
| AGT | S | 0.165 | 12.957 | 48250 |
| TCA | S | 0.425 | 33.319 | 124081 |
| TCC | S | 0.130 | 10.208 | 38016 |
| TCG | S | 0.027 | 2.150 | 8008 |
| TCT | S | 0.143 | 11.209 | 41741 |
| ACA | T | 0.477 | 38.419 | 143071 |
| ACC | T | 0.160 | 12.852 | 47861 |
| ACG | T | 0.076 | 6.135 | 22848 |
| ACT | T | 0.287 | 23.083 | 85959 |
| GTA | V | 0.266 | 11.492 | 42796 |
| GTC | V | 0.233 | 10.049 | 37421 |
| GTG | V | 0.223 | 9.633 | 35872 |
| GTT | V | 0.278 | 12.005 | 44706 |
| TGG | W | 1.000 | 17.130 | 63791 |
| TAC | Y | 0.419 | 17.935 | 66791 |
| TAT | Y | 0.581 | 24.903 | 92738 |
| TAA | * | 0.996 | 2.130 | 7931 |
| TAG | * | 0.001 | 0.002 | 7 |
| TGA | * | 0.003 | 0.006 | 24 |

TABLE 7

NA Influenza A H1N1 (human) Codon Usage Preference
Coding GC 41.92%
1st letter GC 39.38%
2nd letter GC 46.09%
3rd letter GC 40.30%

| Codon | AA | Fraction | Frequency | Number |
|---|---|---|---|---|
| GCA | A | 0.280 | 9.892 | 69837 |
| GCC | A | 0.189 | 6.693 | 47255 |
| GCG | A | 0.051 | 1.798 | 12694 |
| GCT | A | 0.480 | 16.973 | 119833 |
| TGC | C | 0.464 | 18.609 | 131382 |
| TGT | C | 0.536 | 21.482 | 151669 |
| GAC | D | 0.505 | 22.002 | 155343 |
| GAT | D | 0.495 | 21.599 | 152493 |
| GAA | E | 0.640 | 27.050 | 190980 |
| GAG | E | 0.360 | 15.225 | 107495 |
| TTC | F | 0.498 | 18.890 | 133367 |
| TTT | F | 0.502 | 19.063 | 134587 |
| GGA | G | 0.390 | 37.344 | 263659 |
| GGC | G | 0.162 | 15.484 | 109319 |
| GGG | G | 0.235 | 22.500 | 158857 |
| GGT | G | 0.213 | 20.363 | 143765 |
| CAC | H | 0.346 | 4.631 | 32694 |
| CAT | H | 0.654 | 8.756 | 61817 |
| ATA | I | 0.466 | 45.047 | 318045 |
| ATC | I | 0.220 | 21.316 | 150496 |
| ATT | I | 0.314 | 30.363 | 214368 |
| AAA | K | 0.510 | 21.821 | 154064 |
| AAG | K | 0.490 | 20.966 | 148022 |
| CTA | L | 0.260 | 10.196 | 71989 |
| CTC | L | 0.046 | 1.803 | 12728 |
| CTG | L | 0.111 | 4.332 | 30587 |
| CTT | L | 0.059 | 2.301 | 16248 |
| TTA | L | 0.236 | 9.252 | 65320 |
| TTG | L | 0.288 | 11.280 | 79642 |
| ATG | M | 1.000 | 15.251 | 107674 |
| AAC | N | 0.431 | 36.768 | 259591 |
| AAT | N | 0.569 | 48.628 | 343324 |
| CCA | P | 0.481 | 22.287 | 157349 |
| CCC | P | 0.133 | 6.176 | 43607 |
| CCG | P | 0.096 | 4.450 | 31415 |
| CCT | P | 0.289 | 13.393 | 94558 |
| CAA | Q | 0.584 | 17.988 | 126997 |
| CAG | Q | 0.416 | 12.817 | 90492 |
| AGA | R | 0.596 | 21.424 | 151262 |
| AGG | R | 0.184 | 6.605 | 46635 |
| CGA | R | 0.159 | 5.721 | 40389 |
| CGC | R | 0.050 | 1.781 | 12574 |
| CGG | R | 0.002 | 0.061 | 431 |
| CGT | R | 0.010 | 0.358 | 2529 |
| AGC | S | 0.180 | 20.580 | 145299 |
| AGT | S | 0.238 | 27.187 | 191950 |
| TCA | S | 0.249 | 28.412 | 200598 |
| TCC | S | 0.116 | 13.311 | 93981 |
| TCG | S | 0.051 | 5.850 | 41302 |
| TCT | S | 0.166 | 18.930 | 133651 |
| ACA | T | 0.390 | 23.049 | 162735 |
| ACC | T | 0.286 | 16.895 | 119286 |
| ACG | T | 0.002 | 0.140 | 990 |
| ACT | T | 0.322 | 19.078 | 134698 |
| GTA | V | 0.237 | 14.197 | 100232 |
| GTC | V | 0.203 | 12.153 | 85801 |
| GTG | V | 0.280 | 16.743 | 118207 |
| GTT | V | 0.279 | 16.700 | 117907 |
| TGG | W | 1.000 | 34.038 | 240319 |
| TAC | Y | 0.453 | 13.582 | 95894 |
| TAT | Y | 0.547 | 16.405 | 115827 |
| TAA | * | 0.865 | 1.740 | 12285 |
| TAG | * | 0.135 | 0.271 | 1914 |
| TGA | * | 0.000 | 0.001 | 7 |

TABLE 8

NA Influenza A H1N1 (multi) Codon Usage Preference
Coding GC 41.87%
1st letter GC 39.36%
2nd letter GC 46.11%
3rd letter GC 40.14%

| Codon | AA | Fraction | Frequency | Number |
|---|---|---|---|---|
| GCA | A | 0.287 | 10.200 | 82144 |
| GCC | A | 0.192 | 6.815 | 54887 |
| GCG | A | 0.048 | 1.707 | 13750 |
| GCT | A | 0.473 | 16.826 | 135503 |
| TGC | C | 0.472 | 18.934 | 152483 |
| TGT | C | 0.528 | 21.198 | 170719 |
| GAC | D | 0.494 | 21.688 | 174664 |
| GAT | D | 0.506 | 22.259 | 179260 |
| GAA | E | 0.642 | 26.931 | 216883 |
| GAG | E | 0.358 | 15.028 | 121026 |
| TTC | F | 0.498 | 18.791 | 151330 |
| TTT | F | 0.502 | 18.971 | 152780 |
| GGA | G | 0.391 | 37.319 | 300546 |
| GGC | G | 0.162 | 15.424 | 124218 |
| GGG | G | 0.236 | 22.496 | 181171 |
| GGT | G | 0.212 | 20.222 | 162854 |
| CAC | H | 0.344 | 4.679 | 37683 |
| CAT | H | 0.656 | 8.943 | 72018 |
| ATA | I | 0.468 | 45.150 | 363616 |
| ATC | I | 0.217 | 20.912 | 168414 |
| ATT | I | 0.316 | 30.497 | 245602 |
| AAA | K | 0.523 | 22.378 | 180218 |
| AAG | K | 0.477 | 20.421 | 164455 |
| CTA | L | 0.247 | 9.793 | 78870 |
| CTC | L | 0.043 | 1.691 | 13619 |
| CTG | L | 0.123 | 4.875 | 39264 |
| CTT | L | 0.065 | 2.577 | 20753 |
| TTA | L | 0.244 | 9.689 | 78026 |
| TTG | L | 0.279 | 11.095 | 89352 |
| ATG | M | 1.000 | 15.535 | 125108 |
| AAC | N | 0.422 | 35.632 | 286963 |
| AAT | N | 0.578 | 48.871 | 393575 |
| CCA | P | 0.484 | 22.228 | 179014 |
| CCC | P | 0.135 | 6.213 | 50035 |
| CCG | P | 0.097 | 4.450 | 35835 |
| CCT | P | 0.284 | 13.021 | 104867 |
| CAA | Q | 0.584 | 17.964 | 144671 |
| CAG | Q | 0.416 | 12.773 | 102866 |
| AGA | R | 0.595 | 21.567 | 173685 |
| AGG | R | 0.190 | 6.867 | 55305 |
| CGA | R | 0.151 | 5.467 | 44025 |
| CGC | R | 0.046 | 1.660 | 13371 |
| CGG | R | 0.005 | 0.185 | 1490 |
| CGT | R | 0.013 | 0.483 | 3890 |
| AGC | S | 0.182 | 20.844 | 167865 |
| AGT | S | 0.239 | 27.294 | 219808 |
| TCA | S | 0.246 | 28.085 | 226184 |
| TCC | S | 0.112 | 12.846 | 103451 |
| TCG | S | 0.053 | 6.002 | 48337 |
| TCT | S | 0.168 | 19.213 | 154727 |
| ACA | T | 0.389 | 23.099 | 186022 |
| ACC | T | 0.283 | 16.831 | 135545 |
| ACG | T | 0.004 | 0.227 | 1826 |
| ACT | T | 0.324 | 19.268 | 155171 |
| GTA | V | 0.240 | 14.313 | 115270 |
| GTC | V | 0.204 | 12.165 | 97967 |
| GTG | V | 0.275 | 16.414 | 132191 |
| GTT | V | 0.281 | 16.772 | 135069 |
| TGG | W | 1.000 | 34.123 | 274810 |
| TAC | Y | 0.456 | 13.719 | 110483 |
| TAT | Y | 0.544 | 16.354 | 131703 |
| TAA | * | 0.802 | 1.611 | 12977 |
| TAG | * | 0.197 | 0.396 | 3188 |
| TGA | * | 0.001 | 0.002 | 20 |

TABLE 9

NA Influenza A H3N2 (human) Codon Usage Preference
Coding GC 42.92%
1st letter GC 42.43%
2nd letter GC 44.50%
3rd letter GC 41.84%

| Codon | AA | Fraction | Frequency | Number |
|---|---|---|---|---|
| GCA | A | 0.358 | 10.743 | 59488 |
| GCC | A | 0.213 | 6.392 | 35394 |
| GCG | A | 0.073 | 2.190 | 12126 |
| GCT | A | 0.356 | 10.678 | 59132 |
| TGC | C | 0.481 | 21.541 | 119287 |
| TGT | C | 0.519 | 23.276 | 128892 |
| GAC | D | 0.400 | 20.514 | 113598 |
| GAT | D | 0.600 | 30.802 | 170566 |
| GAA | E | 0.584 | 31.840 | 176315 |
| GAG | E | 0.416 | 22.692 | 125658 |
| TTC | F | 0.561 | 17.908 | 99167 |
| TTT | F | 0.439 | 14.033 | 77711 |
| GGA | G | 0.376 | 30.885 | 171025 |
| GGC | G | 0.192 | 15.755 | 87245 |
| GGG | G | 0.197 | 16.161 | 89493 |
| GGT | G | 0.236 | 19.382 | 107328 |
| CAC | H | 0.102 | 2.182 | 12083 |
| CAT | H | 0.898 | 19.201 | 106324 |
| ATA | I | 0.472 | 38.110 | 211036 |
| ATC | I | 0.199 | 16.068 | 88976 |
| ATT | I | 0.329 | 26.514 | 146820 |
| AAA | K | 0.628 | 31.235 | 172964 |
| AAG | K | 0.372 | 18.494 | 102411 |
| CTA | L | 0.134 | 7.152 | 39602 |
| CTC | L | 0.149 | 7.993 | 44263 |
| CTG | L | 0.151 | 8.075 | 44717 |
| CTT | L | 0.160 | 8.573 | 47473 |
| TTA | L | 0.074 | 3.962 | 21938 |
| TTG | L | 0.332 | 17.749 | 98286 |
| ATG | M | 1.000 | 15.054 | 83364 |
| AAC | N | 0.477 | 30.816 | 170643 |
| AAT | N | 0.523 | 33.794 | 187134 |
| CCA | P | 0.187 | 7.746 | 42892 |
| CCC | P | 0.207 | 8.603 | 47638 |
| CCG | P | 0.053 | 2.188 | 12118 |
| CCT | P | 0.553 | 22.967 | 127181 |
| CAA | Q | 0.664 | 17.015 | 94219 |
| CAG | Q | 0.336 | 8.604 | 47646 |
| AGA | R | 0.410 | 19.188 | 106256 |
| AGG | R | 0.349 | 16.316 | 90351 |
| CGA | R | 0.048 | 2.234 | 12373 |
| CGC | R | 0.039 | 1.824 | 10101 |
| CGG | R | 0.107 | 4.997 | 27671 |
| CGT | R | 0.048 | 2.240 | 12406 |
| AGC | S | 0.178 | 17.465 | 96714 |
| AGT | S | 0.150 | 14.737 | 81609 |
| TCA | S | 0.281 | 27.573 | 152686 |
| TCC | S | 0.241 | 23.651 | 130971 |
| TCG | S | 0.023 | 2.304 | 12759 |
| TCT | S | 0.126 | 12.381 | 68560 |
| ACA | T | 0.395 | 30.801 | 170562 |
| ACC | T | 0.285 | 22.251 | 123218 |
| ACG | T | 0.085 | 6.661 | 36883 |
| ACT | T | 0.235 | 18.320 | 101450 |
| GTA | V | 0.184 | 13.713 | 75935 |
| GTC | V | 0.176 | 13.149 | 72814 |
| GTG | V | 0.305 | 22.789 | 126193 |
| GTT | V | 0.335 | 25.050 | 138713 |
| TGG | W | 1.000 | 23.518 | 130230 |
| TAC | Y | 0.149 | 4.437 | 24571 |
| TAT | Y | 0.851 | 25.405 | 140679 |
| TAA | * | 0.994 | 2.100 | 11629 |
| TAG | * | 0.005 | 0.011 | 59 |
| TGA | * | 0.001 | 0.001 | 8 |

TABLE 10

NA Influenza A H3N2 (multi) Codon Usage Preference
Coding GC 42.89%
1st letter GC 42.41%
2nd letter GC 44.53%
3rd letter GC 41.73%

| Codon | AA | Fraction | Frequency | Number |
|---|---|---|---|---|
| GCA | A | 0.357 | 10.832 | 65702 |
| GCC | A | 0.215 | 6.529 | 39601 |
| GCG | A | 0.074 | 2.242 | 13597 |
| GCT | A | 0.353 | 10.715 | 64988 |
| TGC | C | 0.486 | 21.827 | 132388 |
| TGT | C | 0.514 | 23.125 | 140264 |
| GAC | D | 0.398 | 20.438 | 123962 |
| GAT | D | 0.602 | 30.881 | 187307 |
| GAA | E | 0.581 | 31.406 | 190490 |
| GAG | E | 0.419 | 22.614 | 137160 |
| TTC | F | 0.554 | 17.602 | 106760 |
| TTT | F | 0.446 | 14.164 | 85908 |
| GGA | G | 0.374 | 30.846 | 187090 |
| GGC | G | 0.189 | 15.601 | 94624 |
| GGG | G | 0.197 | 16.272 | 98697 |
| GGT | G | 0.239 | 19.697 | 119472 |
| CAC | H | 0.103 | 2.221 | 13469 |
| CAT | H | 0.897 | 19.242 | 116710 |
| ATA | I | 0.466 | 37.598 | 228047 |
| ATC | I | 0.202 | 16.296 | 98842 |
| ATT | I | 0.332 | 26.761 | 162317 |
| AAA | K | 0.632 | 31.583 | 191559 |
| AAG | K | 0.368 | 18.366 | 111394 |
| CTA | L | 0.138 | 7.375 | 44732 |
| CTC | L | 0.146 | 7.804 | 47337 |
| CTG | L | 0.150 | 8.015 | 48615 |
| CTT | L | 0.163 | 8.716 | 52867 |
| TTA | L | 0.079 | 4.216 | 25573 |
| TTG | L | 0.323 | 17.258 | 104675 |
| ATG | M | 1.000 | 15.113 | 91668 |
| AAC | N | 0.473 | 30.661 | 185967 |
| AAT | N | 0.527 | 34.140 | 207068 |
| CCA | P | 0.192 | 7.935 | 48128 |
| CCC | P | 0.208 | 8.599 | 52156 |
| CCG | P | 0.051 | 2.099 | 12732 |
| CCT | P | 0.549 | 22.718 | 137793 |
| CAA | Q | 0.659 | 16.917 | 102607 |
| CAG | Q | 0.341 | 8.755 | 53103 |
| AGA | R | 0.410 | 19.203 | 116470 |
| AGG | R | 0.353 | 16.527 | 100239 |
| CGA | R | 0.051 | 2.414 | 14643 |
| CGC | R | 0.039 | 1.849 | 11216 |
| CGG | R | 0.103 | 4.838 | 29345 |
| CGT | R | 0.044 | 2.050 | 12433 |
| AGC | S | 0.178 | 17.426 | 105693 |
| AGT | S | 0.152 | 14.883 | 90273 |
| TCA | S | 0.278 | 27.261 | 165347 |
| TCC | S | 0.241 | 23.553 | 142859 |
| TCG | S | 0.025 | 2.466 | 14956 |
| TCT | S | 0.126 | 12.341 | 74850 |
| ACA | T | 0.395 | 30.737 | 186433 |
| ACC | T | 0.283 | 22.045 | 133712 |
| ACG | T | 0.084 | 6.501 | 39428 |
| ACT | T | 0.238 | 18.495 | 112178 |
| GTA | V | 0.191 | 14.196 | 86104 |
| GTC | V | 0.176 | 13.096 | 79434 |
| GTG | V | 0.300 | 22.375 | 135712 |
| GTT | V | 0.333 | 24.837 | 150648 |
| TGG | W | 1.000 | 23.690 | 143689 |
| TAC | Y | 0.154 | 4.620 | 28023 |
| TAT | Y | 0.846 | 25.306 | 153489 |
| TAA | * | 0.994 | 2.099 | 12729 |
| TAG | * | 0.005 | 0.011 | 65 |
| TGA | * | 0.001 | 0.002 | 11 |

Thus, in certain embodiments of the methods described herein, the optimized nucleotide sequence encoding for an engineered HA influenza protein is generated using the HA-specific influenza codon usage preferences set forth in one of Tables 1-5. In some embodiments of the methods described herein, the optimized nucleotide sequence encoding for an engineered NA influenza protein is generated using the NA-specific influenza codon usage preferences set forth in one of Tables 6-10.

Further Optimization by Modifying Other Regions of Structural Influenza Protein

In addition to changing codons, the optimized nucleotide sequences encoding the engineered influenza structural protein can optionally be further optimized through the modification of the sequence by i) using 5'- and/or 3' non-coding sequences from the structural proteins of wild type or other recovered viruses, such as a high titer, recovered virus; and/or ii) using 5' and 3' terminal coding sequences, encoding signal peptide, transmembrane domains, and/or cytoplasmic tails from wild type or other recovered viruses, such as high titer, recovered virus. See e.g., Harvey et al. (2011), J. Virol. 85(12):6086-6090; Gomila et al. (2013), Vaccine (310:4736-4743. By way of example, these additional modifications are depicted in Steps 4 and 5 of FIG. 1. Each of the modifications may be applied to the optimized nucleotide sequences independently or in combination and does not modify the ectodomain (extracellular) coding portion of the protein.

Identifying the 5' and/or 3' non-coding regions, signal peptides, transmembrane domains, cytoplasmic domains, and/or ectodomains of proteins, such as structural influenza proteins, is routine in the art and can be carried out using known methods and techniques.

For example, the location of the signal peptide and ectodomain sequences of structural influenza proteins, such as HA, can be determined based on sequence alignments and reference to influenza A subtype H1N1 and H3N2 structural models in RCSB PDB, which are available through the world wide web at rcsb.org. The signal peptide can also be determined through the use of software for prediction the signal peptides, such as SignalP (Thomas Nordahl Petersen et al., Nature Methods, 8:785-86, 2011).

Figure 3:
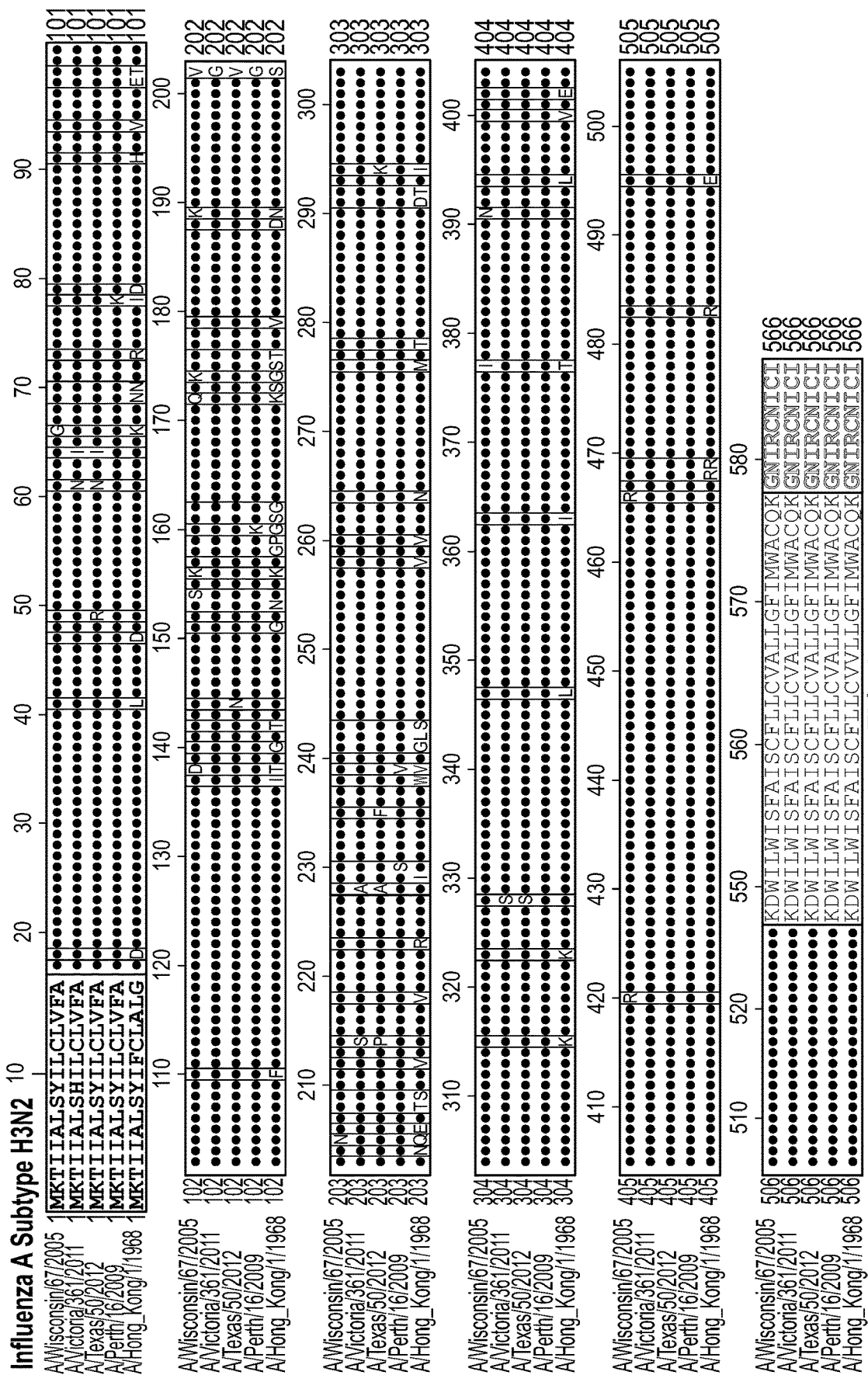
FIG. 3 shows the annotated alignment of HA protein sequences of several influenza A subtype H3N2 strains (SEQ ID NOS 43-47, respectively, in order of appearance). The full length sequences of the HA proteins of the strains exemplified in FIG. 3 are provided in the sequence listing as follows: A/Wisconsin/67/2005 (SEQ ID NO: 70); A/Victoria/361/2011 (SEQ ID NO: 71); A/Texas/50/2012 (SEQ ID NO: 72); A/Perth/16/2009 (SEQ ID NO: 73); and A/Hong_Kong/1/1968 (SEQ ID NO: 74).

The signal peptide of influenza A subtype H1N1 encompasses residues 1-17 of the H1N1 polypeptide. The ectodomain starts with the residue D at position 18. An annotated alignment of H1N1 HA protein sequences is shown in FIG. 2. Commonly, the ectodomain sequence begins with DTIC (SEQ ID NO: 19) for seasonal-like sequences or DTLC (SEQ ID NO: 20) for pandemic like sequences. H. M. Berman et al., The Protein Data Bank. Nucleic Acids Research, 28: 235-242, 2000. The signal peptide of influenza A subtype H3N2 encompasses residues 1-16 of the H3N2 polypeptide. The ectodomain starts with the residue Q at position 17. An annotated alignment of H3N2 HA protein sequences is shown in FIG. 3. Commonly, the ectodomain sequence begins with QKLP (SEQ ID NO: 21) or QDLP (SEQ ID NO: 22). H. M. Berman et al., The Protein Data Bank. Nucleic Acids Research, 28: 235-242, 2000.

Similarly, the location of the transmembrane and cytoplasmic domain sequences of structural influenza proteins, such as HA, can be determined based on sequence alignments. The sequence alignment of the HA transmembrane domain of various representative influenza A strains is shown in FIG. 4. See also, Secondary Structure, Orientation, Oligomerization, and Lipid Interactions of the Transmembrane Domain of Influenza Hemagglutinin. Suren A. Tatulian and Lukas K. Tamm. Biochemistry, 2000, 39 (3), pp 496-507. Software is also available for the skilled artisan to identify transmembrane and cytoplasmic domains, including, for example, TMPred (K. Hofmann & W. Stoffel, 1993, TMbase—A database of membrane spanning proteins segments. Biol. Chem. Hoppe-Seyler 374,166); InterProScan (Zdobnov E. M. and Apweiler R., 2001, Bioinformatics, 17(9): 847-48); and TMHMM (Krogh, B. et al., Journal of Molecular Biology, 2001, 305(3):567-580).

Thus, in certain embodiments, the methods of generating an optimized nucleotide sequence encoding an engineered influenza structural protein, further comprises one or more of the following steps:

a) adding 5' and 3' non-coding sequences from another influenza strain, such as a high titer rescued strain;

b) exchanging the sequence encoding the signal peptide in the optimized nucleotide sequence with a nucleotide sequence encoding the signal peptide from another influenza strain, such as a high titer rescued strain;

c) exchanging the sequence encoding the transmembrane domain in the optimized nucleotide sequence with a nucleotide sequence encoding the transmembrane from another influenza strain, such as a high titer rescued strain; and/or d) exchanging the sequence encoding the cytoplasmic domain in the optimized nucleotide sequence with a nucleotide sequence encoding the cytoplasmic domain from another influenza strain, such as a high titer rescued strain.

In certain embodiments, the methods described herein further comprise step a); step b); step c); step d); steps a) and b); steps a) and c); steps a) and d); steps a), b), and c); steps a), b), and d); steps a), c), and d); steps a), b), c), and d); steps b) and c); steps b) and d); steps b), c), and d); or steps c) and d).

The 5' and 3' non-coding sequences from another influenza strain can further comprise coding sequence without disrupting the amino acid sequence. Thus, the 5' and 3' terminal nucleotide sequences can include non-coding and coding sequences. In some embodiments, the 5' and 3' terminal sequences are predominantly coding sequence, including the signal peptide and extending into the stem region at the 5' end; and including the stem, transmembrane region and cytoplasmic tail at the 3' end.

Optimized Nucleotide Sequence Encoding an Engineered Influenza Structural Protein Another aspect is directed to an optimized nucleotide sequence encoding the engineered influenza structural protein that is obtained by the methods described herein, wherein at every position where the codons in the reverse translated nucleotide sequence (i.e., the first nucleotide sequence) and a second nucleotide sequences (that encodes a corresponding influenza structural protein from a wild type virus or a previously rescued virus) code for the same amino acid, the codons in the optimized nucleotide sequence have been changed to match the codons from the second nucleotide sequence; and wherein at every position where the codons in the first and second nucleotide sequences code for a different amino acid, the codons in the optimized nucleotide sequence have been changed to match codons that are based on influenza protein-specific influenza codon usage preferences.

In certain embodiments, the optimized nucleotide sequence further comprises one or more of the following modifications:

a) 5' and 3' non-coding nucleotide sequences (e.g., non-coding sequences) from another influenza strain, such as a high titer rescued strain;

b) a nucleotide sequence encoding the signal peptide from another influenza strain, such as a high titer rescued strain;

c) a nucleotide sequence encoding the transmembrane from another influenza strain, such as a high titer rescued strain; and/or d) a nucleotide sequence encoding the cytoplasmic domain from another influenza strain, such as a high titer rescued strain.

In certain embodiments, the optimized nucleotide sequence further comprises modification a); modification b); modification c); modification d); modifications a) and b); modifications a) and c); modifications a) and d); steps a), b), and c); modifications a), b), and d); modifications a), c), and d); modifications a), b), c), and d); modifications b) and c); modifications b) and d); modifications b), c), and d); or modifications c) and d).

Engineered Influenza Proteins

The methods described herein for optimizing nucleotide sequences are preferably performed on engineered influenza structural proteins, including, but not limited to, HA and NA. The methods described herein can be performed on any engineered influenza structural protein.

For example, to induce more broadly reactive immune responses, computationally optimized broadly reactive antigens (COBRAs) have been developed for influenza HA proteins through a series of HA protein alignments and subsequent consensus sequences based on selected H5N1 and H1N1 influenza virus isolates, as described in WO2013/122827 and US Publication Nos. 2015/0044247, 2015/0017196, 2014/0147459, 2014/0127248, and 2013/0183342, all of which are hereby incorporated by reference in their entirety.

These recombinantly engineered COBRAs have a uniquely designed amino acid sequence for eliciting a broadly reactive immune response against a broad range of influenza isolates, such as most or all influenza viruses within s specific subtype, such as H1N1 or H5N1. The amino acid sequence of the COBRAs does not occur in nature. In addition to the specific COBRAs described in WO2013/122827 and US Publication Nos. 2015/0044247, 2015/0017196, 2014/0147459, 2014/0127248, and 2013/0183342, it is also possible to generate other recombinantly engineered COBRAs using the methods disclosed in these published applications.

The amino acid sequences of certain exemplary H5N1 COBRAs are set forth in Table 11.

TABLE 11

Exemplary H5N1 COBRA Amino Acid Sequences

All H5N1 COBRA
MEKIVLLLAIVSLVKSDQICIGYHANNSTEQVDTIMEKNVTVTHAQDIL
EKTHNGKLCDLDGVKPLILRDCSVAGWLLGNPMCDEFINVPEWSYIVEK
ASPANDLCYPGDFNDYEELKHLLSRINHFEKIQIIPKSSWSNHEASSGV
SSACPYQGKSSFFRNVVWLIKKNSAYPTIKRSYNNTNQEDLLVLWGIHH
PNDAAEQTKLYQNPTTYISVGTSTLNQRLVPKIATRSKVNGQSGRMEFF
WTILKPNDAINFESNGNFIAPEYAYKIVKKGDSAIMKSELEYGNCNTKC
QTPMGAINSSMPFHNIHPLTIGECPKYVKSNRLVLATGLRNSPQRERRR
KKRGLFGAIAGFIEGGWQGMVDGWYGYHHSNEQGSGYAADKESTQKAID
GVTNKVNSIIDKMNTQFEAVGREFNNLERRIENLNKKMEDGFLDVWTYN
AELLVLMENERTLDFHDSNVKNLYDKVRLQLRDNAKELGNGCFEFYHKC
DNECMESVRNGTYDYPQYSEEARLKREEISGVKLESIGTYQILSIYSTV
ASSLALAIMVAGLSLWMCSNGSLQCRICI
(SEQ ID NO: 1)

Human/Avian COBRA-2
MEKIVLLLAIVSLVKSDQICIGYHANNSTEQVDTIMEKNVTVTHAQDIL
EKTHNGKLCDLDGVKPLILRDCSVAGWLLGNPMCDEFINVPEWSYIVEK
ANPANDLCYPGNFNDYEELKHLLSRINHFEKIQIIPKSSWSDHEASSGV
SSACPYQGKSSFFRNVVWLIKKNSAYPTIKRSYNNTNQEDLLVLWGIEM
PNDAAEQTRLYQNPTTYISVGTSTLNQRLVPKIATRSKVNGQSGRMEFF
WTILKPNDAINFESNGNFIAPEYAYKIVKKGDSAIMKSELEYGNCNTKC
QTPMGAINSSMPFHNIHPLTIGECPKYVKSNRLVLATGLRNSPQRERRR
KRGLFGAIAGFIEGGWQGMVDGWYGYHHSNEQGSGYAADKESTQKAIDG
VTNKVNSIIDKMNTQFEAVGREFNNLERRIENLNKKMEDGFLDVWTYNA TABLE 11-continued Exemplary H5N1 COBRA Amino Acid Sequences ELLVLMENERTLDFHDSNVKNLYDKVRLQLRDNAKELGNGCFEFYHKCD
NECMESVRNGTYDYPQYSEEARLKREEISGVKLESIGTYQILSIYSTVA
SSLALAIMVAGLSLWMCSNGSLQCRICI
(SEQ ID NO: 2)

Human COBRA-2
MEKIVLLLAIVSLVKSDQICIGYHANNSTEQVDTIMEKNVTVTHAQDIL
EKTHNGKLCDLDGVKPLILRDCSVAGWLLGNPMCDEFINVPEWSYIVEK
ANPANDLCYPGNFNDYEELKHLLSRINHFEKIQIIPKSSWSDHEASSGV
SSACPYQGSPSFFRNVVWLIKKNNTYPTIKRSYNNTNQEDLLVLWGIHH
PNDAAEQTRLYQNPTTYISVGTSTLNQRLVPKIATRSKVNGQSGRMEFF
WTILKPNDAINFESNGNFIAPEYAYKIVKKGDSAIMKSELEYGNCNTKC
QTPIGAINSSMPFHNIHPLTIGECPKYVKSNRLVLATGLRNSPQRESRR
KKRGLFGAIAGFIEGGWQGMVDGWYGYHHSNEQGSGYAADKESTQKAID
GVTNKVNSIIDKMNTQFEAVGREENNLERRIENLNKKMEDGFLDVWTYN
AELLVLMENERTLDFHDSNVKNLYDKVRLQLRDNAKELGNGCFEFYHKC
DNECMESVRNGTYDYPQYSEEARLKREEISGVKLESIGTYQILSIYSTV
ASSLALAIMVAGLSLWMCSNGSLQCRICI
(SEQ ID NO: 3)

The amino acid sequences of certain exemplary H1N1 COBRAs are set forth in Table 12.

TABLE 12

Exemplary H1N1 COBRA Amino Acid Sequences

Pandemic H1N1 COBRA (Human and Swine 1933-2011): P1
MKARLLVLLCALAATDADTICIGYHANNSTDTVDTVLEKNVTVTHSVNL
LEDSHNGKLCKLKGIAPLQLGKCNIAGWLLGNPECESLLSARSWSYIVE
TPNSENGTCYPGDFIDYEELREQLSSVSSFERFEIFPKESSWPNHNTTK
GVTAACSHAGKSSFYRNLLWLTKKGGSYPKLSKSYVNNKGKEVLVLWGV
HHPSTSTDQQSLYQNENAYVSVVSSNYNRRFTPEIAERPKVRGQAGRMN
YYWTLLEPGDTIIFEATGNLIAPWYAFALSRGSGSGIITSNASMHECNT
KCQTPQGAINSSLPFQNIHPVTIGECPKYVRSTKLRMVTGLRNIPSIQS
RGLFGAIAGFIEGGWTGMIDGWYGYHHQNEQGSGYAADQKSTQNAINGI
TNKVNSVIEKMNTQFTAVGKEFNNLEKRMENLNKKVDDGFLDIWTYNAE
LLVLLENERTLDFHDSNVKNLYEKVKSQLRNNAKEIGNGCFEFYHKCDN
ECMESVKNGTYDYPKYSEESKLNREKIDGVKLESMGVYQILAIYSTVAS
SLVLLVSLGAISFWMCSNGSLQCRICI
(SEQ ID NO: 4)

Seasonal H1N1 COBRA (Human 1999-2012): X6
MEARLLVLLCAFAATNADTICIGYHANNSTDTVDTVLEKNVTVTHSVNL
LEDSHNGKLCLLKGIAPLQLGNCSVAGWILGNPECELLISKESWSYIVE
TPNPENGTCYPGYFADYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRKFTPEIAKRPKVRDQEGRINY
YWTLLEPGDTIIFEANGNLIAPRYAFALSRGFGSGIITSNAPMDECDAK
CQTPQGAINSSLPFQNVHPVTIGECPKYVRSAKLRMVTGLRNIPSIQSR
GLFGAIAGFIEGGWTGMVDGWYGYHHQNEQGSGYAADQKSTQNAINGIT
NKVNSVIEKMNTQFTAVGKEFNKLERRMENLNKKVDDGFLDIWTYNAEL
LVLLENERTLDFHDSNVKNLYEKVKSQLKNNAKEIGNGCFEFYHKCNNE
CMESVKNGTYDYPKYSEESKLNREKIDGVKLESMGVYQILAIYSTVASS
LVLLVSLGAISFWMCSNGSLQCRICI
(SEQ ID NO: 5)

Seasonal H1N1 COBRA (Human 1978-2008): X3
MEARLLVLLCAFAATNADTICIGYHANNSTDTVDTVLEKNVTVTHSVNL
LEDSHNGKLCRLKGIAPLQLGNCSVAGWILGNPECESLFSKESWSYIAE
TPNPENGTCYPGYFADYEELREQLSSVSSFERFEIFPKESSWPNHTVTK
GVTASCSHNGKSSFYRNLLWLTEKNGLYPNLSKSYVNNKEKEVLVLWGV
HHPSNIGDQRAIYHTENAYVSVVSSHYSRRFTPEIAKRPKVRDQEGRIN
YYWTLLEPGDTIIFEANGNLIAPWYAFALSRGFGSGIITSNASMDECDA
KCQTPQGAINSSLPFQNVHPVTIGECPKYVRSTKLRMVTGLRNIPSIQS
RGLFGAIAGFIEGGWTGMIDGWYGYHHQNEQGSGYAADQKSTQNAINGI
TNKVNSVIEKMNTQFTAVGKEFNKLERRMENLNKKVDDGFLDIWTYNAE
LLVLLENERTLDFHDSNVKNLYEKVKSQLKNNAKEIGNGCFEFYHKCNN
ECMESVKNGTYDYPKYSEESKLNREKIDGVKLESMGVYQILAIYSTVAS
SLVLLVSLGAISFWMCSNGSLQCRICI
(SEQ ID NO: 6)

Seasonal H1N1 COBRA (Human 1918-2012): X1
MEARLLVLLCAFAATNADTICIGYHANNSTDTVDTVLEKNVTVTHSVNL
LEDSHNGKLCKLKGIAPLQLGKCNIAGWILGNPECESLLSKRSWSYIVE
TPNSENGTCYPGDFIDYEELREQLSSVSSFERFEIFPKESSWPNHNTTK TABLE 12-continued Exemplary H1N1 COBRA Amino Acid Sequences GVTAACSHAGKSSFYRNLLWLTKKNGSYPNLSKSYVNNKGKEVLVLWGV
HHPSNIEDQQSLYQNENAYVSVVSSNYNRRFTPEIAKRPKVRDQEGRMN
YYWTLLEPGDTIIFEANGNLIAPWYAFALSRGFGSGIITSNASMHECDT
KCQTPQGAINSSLPFQNIHPVTIGECPKYVRSTKLRMVTGLRNIPSIQS
RGLFGAIAGFIEGGWTGMIDGWYGYHHQNEQGSGYAADQKSTQNAINGI
TNKVNSVIEKMNTQFTAVGKEFNNLEKRMENLNKKVDDGFLDIWTYNAE
LLVLLENERTLDFHDSNVKNLYEKVKSQLKNNAKEIGNGCFEFYHKCNN
ECMESVKNGTYDYPKYSEESKLNREKIDGVKLESMGVYQILAIYSTVAS
SLVLLVSLGAISFWMCSNGSLQCRICI
(SEQ ID NO: 7)

H1N1 COBRA (1918-2011): A1
MKAKLLVLLCAFTATYADTICIGYHANNSTDTVDTVLEKNVTVTHSVNL
LEDSHNGKLCRLKGIAPLQLGNCSIAGWILGNPECESLFSKESWSYIVE
TPNSENGTCYPGYFADYEELREQLSSVSSFERFEIFPKESSWPNHTVTK
GVTASCSHNGKSSFYRNLLWLTEKNGSYPNLSKSYVNNKEKEVLVLWGV
HHPSNIGDQRAIYHTENAYVSVVSSHYSRRFTPEIAKRPKVRDQEGRIN
YYWTLLEPGDTIIFEANGNLIAPWYAFALSRGFGSGIITSNASMDECDA
KCQTPQGAINSSLPFQNVHPVTIGECPKYVRSTKLRMVTGLRNIPSIQS
RGLFGAIAGFIEGGWTGMIDGWYGYHHQNEQGSGYAADQKSTQNAINGI
TNKVNSVIEKMNTQFTAVGKEFNKLERRMENLNKKVDDGFLDIWTYNAE
LLVLLENERTLDFHDSNVKNLYEKVKSQLKNNAKEIGNGCFEFYHKCNN
ECMESVKNGTYDYPKYSEESKLNREKIDGVKLESMGVYQILAIYSTVAS
SLVLLVSLGAISFWMCSNGSLQCRICI
(SEQ ID NO: 8)

In some embodiments, an engineered COBRA has a sequence at least about 90% (e.g., at least about 91%, 92%, 93%, 94%, 95%, 96%, 97%, 98% or 99%) identical to a sequence that appears in Table 11 or 12. In some embodiments, an engineered HA COBRA has a sequence that is substantially identical to a sequence that appears in Table 11 or 12. In some embodiments, an engineered HA COBRA has a sequence that is identical to a sequence that appears in Table 11 or 12.

By way of further example, engineered HA sequences have been developed using a rational design approach to include epitopes from multiple viral isolates in a polyvalent vaccine, as described in PCT/US2016/035594 (claiming priority to U.S. Provisional Application No. 62/169,814), which is hereby incorporated by reference in its entirety. In certain embodiments, the designs are based on combinations of multiple B cell epitopes and antigenic regions from different HA sequences (subtype H1) into mosaic antigens. These mosaic epitope antigens, in some embodiments, are predicted to confer cross-protection against multiple subtype H1 strains by maximizing sequence homology for at least one neutralizing epitope. The best mosaic sequence templates are selected by evaluating overall alignment coverage by geographic regions, viral isolate years, sequence clusters or other scoring methods. The selected set of mosaic template sequences are combined with target backbone sequences to generate a set of full-length mosaic protein sequences. Structure refinement of these mosaic sequences yields the final set of vaccination proteins. The amino acid sequences of these engineered HA proteins do not match the amino acid sequences of any naturally occurring strains. The amino acid sequences of certain exemplary engineered HA proteins are set forth in Table 13.

TABLE 13

Exemplary H1N1 Mosaic HA Proteins

SP1
MKAKLLVLLCTFTATYADTICIGYHANNSTDTVDTVLEKNVTVTHSVNL
LEDSHNGKLCKLKGIAPLQLGKCSVAGWILGNPECESLSTASSWSYIVE
TSNPENGTCYPGYFADYEELREQLSSVSSFERFEIFPKESSWPNHTVTG

TABLE 13-continued

Exemplary H1N1 Mosaic HA Proteins

VTASCSHAGKSSFYRNLLWLTGKNGSYPNLSKSYVNNKEKEVLVLWGVH
HPSNIGDQQTLYQTENAYVSVVSSRYSRRFTPEIAKRPKVRDQEGRMNY
YWTLVEPGDTIIFEANGNLIAPWYAFALSRGFGSGIITSNAPVHDCNTK
CQTPQGAINSSLPFQNVHPVTIGECPKYVRSAKLRMATGLRNIPSIQSR
GLFGAIAGFIEGGWTGMVDGWYGYHHQNEQGSGYAADQKSTQNAIDGIT
NKVNSVIEKMNTQFTAVGKEFNKLERRMENLNKKVDDGFLDIWTYNAEL
LVLLENERTLDFHDSNVKNLYEKVKSQLKNNAKEIGNGCFEFYHKCNNT
CMESVKNGTYDYPKYSEESKLNREKIDGVKLESMGVYQILAIYSTVASS
LVLLVSLGAISFWMCSNGSLQCRICI
(SEQ ID NO: 9)

SP2
MKAKLLVLLCTFTATYADTICIGYHANNSTDTVDTVLEKNVTVTHSVNL
LEDSHNGKLCLLKGIAPLQLGNCSVAGWILGNPECELLSTKSSWSYIVE
TPNPENGTCYPGYFADYEELREQLSSVSSFERFEIFPKESSWPNHDVTG
VSASCSHNGASSFYRNLLWLTKKNNLYPNLSKSYANNKGKEVLVLWGVH
HPSTIADQQTLYHTENAYVSVVSSHYSRRFTPEIAIRPKVRDQEGRINY
YWTLLEPGDTIIFEANGNLIAPWYAFALSRGFGSGIITSNAPMDECNTT
CQTPQGAINSSLPFQNVHPVTIGECPKYVRSAKLRMVTGLRNIPSIQSR
GLFGAIAGFIEGGWTGMVDGWYGYHHQNEQGSGYAADLKSTQNAINGIT
NKVNSVIEKMNTQFTAVGKEFNKLERRMENLNKKVDDGFLDIWTYNAEL
LVLLENERTLDFHDSNVKNLYEKVKSQLKNNAKEIGNGCFEFYHKCNNE
CMESVKNGTYDYPKYSEESKLNREKIDGVKLESMGVYQILAIYSTVASS
LVLLVSLGAISFWMCSNGSLQCRICI
(SEQ ID NO: 10)

SP3
MKAKLLVLLCTFTATYADTICIGYHANNSTDTVDTVLEKNVTVTHSVNL
LEDSHNGKLCLKLKGIAPLQLGKCSVAGWILGNPECESLSTASSWSYIVE
TSSPDNGTCYPGYFADYEELREQLSSVSSFERFEIFPKTSSWPNHDSNG
VTASCPHAGAKSFYRNLLWLVKKGNSYPKLSKSYINDKGKEVLVLWGVH
HPSTSADQQSLYQNANAYVSVVTSRYSRRFTPEIAIRPKVRDQEGRMNY
YWTLVEPGDTIIFEATGNLIAPWYAFALSRGFGSGIITSDTPVHDCNTT
CQTPQGAINSSLPFQNVHPVTIGECPKYVRSAKLRMATGLRNIPSIQSR
GLFGAIAGFIEGGWTGMVDGWYGYHHQNEQGSGYAADLKSTQNAIDGIT
NKVNSVIEKMNTQFTAVGKEFNKLERRMENLNKKVDDGFLDIWTYNAEL
LVLLENERTLDFHDSNVKNLYEKVKSQLKNNAKEIGNGCFEFYHKCNNT
CMESVKNGTYDYPKYSEESKLNREKIDGVKLESMGVYQILAIYSTVASS
LVLLVSLGAISFWMCSNGSLQCRICI
(SEQ ID NO: 11)

SP4
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALSRGFGSGIITSNAPMDKCDAK
CQTPQGAINSSLPFQNVHPVTIGECPKYVRSAKLRMVTGLRNIPFIQSR
GLFGAIAGFIEGGWTGMVDGWYGYHHQNEQGSGYAADQKSTQNAINGIT
NKVNSVIEKMNTQFTAVGKEFNKLERRMENLNKKVDDGFLDIWTYNAEL
LVLLENERTLDFHDSNVKNLYEKVKSQLKNNAKEIGNGCFEFYHKCNDE
CMESVKNGTYDYPKYSEESKLNREKIDGVKLESMGVYQILAIYSTVASS
LVLLVSLGAISFWMCSNGSLQCRICI
(SEQ ID NO: 12)

SP5
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKESSWPNHTVTG
VSASCPHNGESSSFYRNLLWLTGKNGLYPNLSKSYANNKEKEVLVLWGVH
HPPNIGDQKTLYHTENAYVSVVSSHYSRRFTPEIAKRPKVRDQEGRINY
YWTLLEPGDTIIFEANGNLIAPWYAFALSRGFGSGIITSNAPMDKCDAK
CQTPQGAINSSLPFQNVHPVTIGECPKYVRSAKLRMATGLRNIQSIQSR
GLFGAIAGFIEGGWTGMVDGWYGYHHQNEQGSGYAADLKSTQNAINGIT
NKVNSVIEKMNTQFTAVGKEFNKLERRMENLNKKVDDGFLDIWTYNAEL
LVLLENERTLDFHDSNVKNLYEKVKSQLKNNAKEIGNGCFEFYHKCNNT
CMESVKNGTYDYPKYSEESKLNREKIDGVKLESMGVYQILAIYSTVASS
LVLLVSLGAISFWMCSNGSLQCRICI
(SEQ ID NO: 13)

SP6
MKAILVVLLYTFATANADTLCIGYHANNSTDTVDTVLEKNVTVTHSVNL
LEDKHNGKLCKLRGVAPLHLGKCNIAGWILGNPECESLSTASSWSYIVE
TSNSENGTCYPGDFIDYEELREQLSSVSSFERFEIFPKESSWPNHTVTK
GVTAACSHAGKSSFYKNLIWLTGKNGSYPNLSKSYVNNKEKEVLVLWGI
HHPSNIGDQQTLYQTEDTYVFVGSSRYSKKFKPEIAKRPKVRDQEGRMN
YYWTLVEPGDKITFEANGNLVVPRYAFAMERNAGSGIIISNAPVHDCNT

TABLE 13-continued

Exemplary H1N1 Mosaic HA Proteins

KCQTPKGAINTSLPFQNIHPITIGKCPKYVKSTKLRLATGLRNIPSIQS
RGLFGAIAGFIEGGWTGMVDGWYGYHHQNEQGSGYAADQKSTQNAIDEI
TNKVNSVIEKMNTQFTAVGKEFNHLEKRIENLNKKVDDGFLDIWTYNAE
LLVLLENERTLDYHDSNVKNLYEKVRSQLKNNAKEIGNGCFEFYHKCDN
TCMESVKNGTYDYPKYSEEAKLNREEIDGVKLESTRIYQILAIYSTVAS
SLVLVVSLGAISFWMCSNGSLQCRICI
(SEQ ID NO: 14)

SP7
MKAILVVLLYTFATANADTLCIGYHANNSTDTVDTVLEKNVTVTHSVNL
LEDKHNGKLCLLRGVAPLHLGNCNIAGWILGNPECELLSTKSSWSYIVE
TPNSENGTCYPGDFIDYEELREQLSSVSSFERFEIFPKESSWPNHDVTK
GVSAACSHNGASSFYKNLIWLTKKNNLYPNLSKSYANNKGKEVLVLWGI
HHPSTIADQQTLYHTEDTYVFVGSSHYSKKFKPEIAIRPKVRDQEGRIN
YYWTLLEPGDKITFEANGNLVVPRYAFAMERNAGSGIIISNAPMDECNT
TCQTPKGAINTSLPFQNIHPITIGKCPKYVKSTKLRLVTGLRNIPSIQS
RGLFGAIAGFIEGGWTGMVDGWYGYHHQNEQGSGYAADLKSTQNAINEI
TNKVNSVIEKMNTQFTAVGKEFNHLEKRIENLNKKVDDGFLDIWTYNAE
LLVLLENERTLDYHDSNVKNLYEKVRSQLKNNAKEIGNGCFEFYHKCDN
ECMESVKNGTYDYPKYSEEAKLNREEIDGVKLESTRIYQILAIYSTVAS
SLVLVVSLGAISFWMCSNGSLQCRICI
(SEQ ID NO: 15)

SP8
MKAILVVLLYTFATANADTLCIGYHANNSTDTVDTVLEKNVTVTHSVNL
LEDKHNGKLCKLRGVAPLHLGKCNIAGWILGNPECESLSTASSWSYIVE
TSSSDNGTCYPGDFIDYEELREQLSSVSSFERFEIFPKESSWPNHDSNK
GVTAACPHAGAKSFYKNLIWLVKKGNSYPKLSKSYINDKGKEVLVLWGI
HHPSTSADQQSLYQNADTYVFVGTSRYSKKFKPEIAIRPKVRDQEGRMN
YYWTLVEPGDKITFEATGNLVVPRYAFAMERNAGSGIIISDTPVHDCNT
TCQTPKGAINTSLPFQNIHPITIGKCPKYVKSTKLRLATGLRNIPSIQS
RGLFGAIAGFIEGGWTGMVDGWYGYHHQNEQGSGYAADLKSTQNAIDEI
TNKVNSVIEKMNTQFTAVGKEFNHLEKRIENLNKKVDDGFLDIWTYNAE
LLVLLENERTLDYHDSNVKNLYEKVRSQLKNNAKEIGNGCFEFYHKCDN
TCMESVKNGTYDYPKYSEEAKLNREEIDGVKLESTRIYQILAIYSTVAS
SLVLVVSLGAISFWMCSNGSLQCRICI
(SEQ ID NO: 16)

SP9
MKAILVVLLYTFATANADTLCIGYHANNSTDTVDTVLEKNVTVTHSVNI
LEDKHNGKLCLLRGVAPLHLGNCNIAGWILGNPECELLISKESWSYIVE
KPNSENGTCYPGDFIDYEELREQLSSVSSFERFEIFPKESSWPNHTVTK
GVSAACSHNGKSSFYKNLIWLTGKNGLYPNLSKSYANNKEKEVLVLWGI
HHPPNIGDQRALYHTEDTYVFVGSSHYSKKFKPEIAKRPKVRDQEGRIN
YYWTLLEPGDKITFEANGNLVVPRYAFAMERNAGSGIIISNAPMDKCDA
KCQTPKGAINTSLPFQNIHPITIGKCPKYVKSTKLRLVTGLRNIPFIQS
RGLFGAIAGFIEGGWTGMVDGWYGYHHQNEQGSGYAADQKSTQNAINEI
TNKVNSVIEKMNTQFTAVGKEFNHLEKRIENLNKKVDDGFLDIWTYNAE
LLVLLENERTLDYHDSNVKNLYEKVRSQLKNNAKEIGNGCFEFYHKCDD
ECMESVKNGTYDYPKYSEEAKLNREEIDGVKLESTRIYQILAIYSTVAS
SLVLVVSLGAISFWMCSNGSLQCRICI
(SEQ ID NO: 17)

SP10
MKAILVVLLYTFATANADTLCIGYHANNSTDTVDTVLEKNVTVTHSVNI
LEDKHNGKLCLLRGVAPLHLGNCNIAGWILGNPECELLISKESWSYIVE
KPNSENGTCYPGDFIDYEELREQLSSVSSFERFEIFPKESSWPNHTVTK
GVSAACPHNGESSFYKNLIWLTGKNGLYPNLSKSYANNKEKEVLVLWGI
HHPPNIGDQKTLYHTEDTYVFVGSSHYSKKFKPEIAKRPKVRDQEGRIN
YYWTLLEPGDKITFEANGNLVVPRYAFAMERNAGSGIIISNAPMDKCDA
KCQTPKGAINTSLPFQNIHPITIGKCPKYVKSTKLRLATGLRNIQSIQS
RGLFGAIAGFIEGGWTGMVDGWYGYHHQNEQGSGYAADLKSTQNAINEI
TNKVNSVIEKMNTQFTAVGKEENHLEKRIENLNKKVDDGELDIWTYNAE
LLVLLENERTLDYHDSNVKNLYEKVRSQLKNNAKEIGNGCFEFYHKCDN
TCMESVKNGTYDYPKYSEEAKLNREEIDGVKLESTRIYQILAIYSTVAS
SLVLVVSLGAISFWMCSNGSLQCRICI
(SEQ ID NO: 18)

By way of further example, engineered HA sequences from influenza B have been developed using a rational design approach, as described in U.S. Provisional Application No. 62/344,862), which is hereby incorporated by reference in its entirety. The amino acid sequences of these engineered HA proteins do not match the amino acid sequences of any naturally occurring strains. The amino acid sequences of certain exemplary engineered influenza B HA proteins are set forth in Table 14.

TABLE 14

Exemplary Influenza B SMARt HA Proteins br08_C01
MKAIIVLLMVVTSNADRICTGITSSNSPHVVKTATQGEVNVTGVIPLTT
TPTKSHFANLKGTETRGKLCPKCLNCTDLDVALGRPKCTGKIPSARVSI
LHEVRPVTSGCFPIMHDRTKIRQLPNLLRGYEHIRLSTQNVINAENAPG
GPYKIGTSGSCPNATNKSGFFATMAWAVPKNDNNKTATNPLTIEVPYIC
TEGEDQITVWGFHSDNKTQMKKLYGDSKPQKFTSSANGVTTHYVSQIGG
FPNQTEDGGLPQSGRIVVDYMVQKPGKTGTIVYQRGILLPQKVWCASGR
SKVIKGSLPLIGEADCLHEKYGGLNKSKPYYTGEHAKAIGNCPIWVKTP
LKLANGTKYRPPAKLLKERGFFGAIAGFLEGGWEGMIAGWHGYTSHGAH
GVAVAADLKSTQEAINKITKNLNSLSELEVKNLQRLSGAMDELHNEILE
LDEKVDDLRADTISSQIELAVLLSNEGIINSEDEHLLALERKLKKMLGP
SAVEIGNGCFETKHKCNQTCLDRIAAGTFDAGEFSLPTFDSLNITAASL
NDDGLDNHTILLYYSTAASSLAVTLMIAIFVVYMVSRDNVSCSICL
(SEQ ID NO: 75)

br08_D02
MKAIIVLLMVVTSNADRICTGITSSNSPHVVKTATQGEVNVTGVIPLTT
TPTKSYFANLKGTETRGKLCPKCLNCTDLDVALGRPKCTGKIPSAKVSI
LHEVRPVTSGCFPIMHDRTKIRQLPNLLRGYEHIRLSTQNVIDAENAPG
GPYKIGTSGSCPNATNKSGFFATMAWAVPKNDNNKTATNPLTIEVPYIC
TEGEDQITVWGFHSDNKTQMKKLYGDSKPQKFTSSANGVTTHYVSQIGG
FPDQTEDGGLPQSGRIVVDYMVQKPGKTGTIVYQRGILLPQKVWCASGR
SKVIKGSLPLIGEADCLHEKYGGLNKSKPYYTGEHAKAIGNCPIWVKTP
LKLANGTKYRPPAKLLKERGFFGAIAGFLEGGWEGMVAGWHGYTSHGAH
GVAVAADLKSTQEAINKITKNLNSLSELEIKNLQRLSGAMDELHNEILE
LDEKVDDLRADTISSQIELAVLLSNEGIINSEDEHLLALERKLKKMLGP
SAVEIGNGCFETKHKCNQTCLDRIAAGTFDAGEFSLPTFDSLNITAASL
NDDGLDNHTILLYYSTAASSLAVTLMIAIFVVYMVSRDNVSCSICL
(SEQ ID NO: 76)

br08_D03
MKAIIVLLMVVTSNADRICTGITSSNSPHVVKTATQGEVNVTGVISLTT
TPTKSHFANLKGTKTRGKLCPKCPNCTDLDVALGRPMCTGTIPSAKVSI
LHEVRPVTSGCFPIMHDRTKIRQLPNLLRGYEHIRLSTHNVINAENAPG
GPYKIGTSGSCPNATNKIGFFATMAWAVPKNDNNKTATNPLTIEVPYIC
AEGEDQITVWGFHSDDKTQMKKLYGDSKPQKFTSSANGVTTHYVSQIGD
FPNQTEDGGLPQSGRIVVDYMVQKPGKTGTITYQRGILLPQKVWCASGR
SKVIKGSLPLIGEADCLHEKYGGLNKSKPYYTGEHAKAIGNCPIWVKTP
LKLANGTKYRPPTKLLKERGFFGAIAGFLEGGWEGMIAGWHGYTSHGAH
GVAVAADLKSTQEAINKITKNLNSLSELEVKNLQRLSGAMDELHNEILE
LDEKVDDLRADTISSQIELAVLLSNEGIINSEDEHLLALERKLKKMLGP
SAVEIGNGCFETKHKCNQTCLNRIAAGTFDAGEFSLPTFDSLNITAASL
NDDGLDNHTILLYYSTAASSLAVTLMIAIFVVYMVSRDNVSCSICL
(SEQ ID NO: 77)

pan90_D02
MKAIIVLLMVVTSNADRICTGITSSNSPHVVKTATQGEVNVTGVIPLTT
TPTKSYFANLKGTETRGKLCPNCLNCTDLDVALGRPKCVGKIPSAKASI
LHEVRPVTSGCFPIMHDRTKIRQLPNLLRGYEHIRLSTQNVIDAERAPG
GPYRLGTSGSCPNATSKSGFFATMAWAVPKDDNNKTATNPLTVEVPYIC
TEGEDQITVWGFHSDNKTQMKNLYGDSNPQKFTSSANGVTTHYVSQIGG
FPDQTEDGGLPQSGRIVVDYMVQKPGKTGTIVYQRGVLLPQKVWCASGR
SKVIKGSLPLIGEADCLHEKYGGLNKSKPYYTGEHAKAIGNCPIWVKTP
LKLANGTKYRPPAKLLKERGFFGAIAGFLEGGWEGMVAGWHGYTSHGAH
GVAVAADLKSTQEAINKITKNLNSLSELEIKNLQRLSGAMDELHNEILE
LDEKVDDLRADTISSQIELAVLLSNEGIINSEDEHLLALERKLKKMLGP
SAVDIGNGCFETKHKCNQTCLDRIAAGTFNAGEFSLPTFDSLNITAASL
NDDGLDNHTILLYYSTAASSLAVTLMIAIFIVYMVSRDNVSCSICL
(SEQ ID NO: 78)

mal2_RA82
MKAIIVLLMVVTSNADRICTGITSSKSPHVVKTATQGEVNVTGVIPLTT
TPTKSHFANLRGTKTRGKLCPDCLNCTDLDVALGRPKCVGNTPSAKASI
LHEVRPVTSGCFPIMHDRTKIRQLANLLRGYEHIRLSNYNVIDAEKAPG
GPYRLGTSRSCPNVTSRSGFFATMAWAVPKDDSNKNATNPLTVEVPYIC
TEGEDQITVWGFHSDNKTQMVNLYGDSNPQKFTSSANGVTTHYVSQIGD
FPDQTEDGGLPQSGRIVVDYMMQKSGKTGTITYQRGVLLPQKVWCASGR
SKVIKGTLPLIGEADCLHEKYGGLNKSKPYYTGEHAKAIGNCPIWVKTP
LKLANGTKYRPPAKLLKERGFFGAIAGFLEGGWEGMIAGWHGYTSHGAH
GVAVAADLKSTQEAINKITKNLNSLSELEVKNLQRLSGAMDELHNEILE
LDEKVDDLRADTISSQIELAVLLSNEGIINSEDEHLLALERKLKKMLGP
SAVDIGNGCFETKHKCNQTCLDRIAAGTFNAGEFSLPTFDSLNITAASL
NDDGLDNHTILLYYSTAASSLAVTLMLAIFIVYMVSRDNVSCSICL
(SEQ ID NO: 79)

TABLE 14-continued

Exemplary Influenza B SMARt HA Proteins sing79_RA103
MKAIIVLLMVVTSNADRICTGITSSNSPHVVKTATQGEVNVTGVIPLTT
TPTKSYFANLKGTKTRGKLCPNCLNCTDLDVALGRPMCMGTIPSAKASI
LHEVRPVTSGCFPIMHDRTKIRQLPNLLRGYENIRLSTHNVINAERAPG
GPYIIGTSGSCPNATNKNGFFATMAWAVPKDDNNKTATNPLTVEVPYIC
TEGEDQITVWGFHSDNKTQMKKLYGDSKPQKFTSSANGVTTHYVSQIGG
FPDQTEDGGLPQSGRIVVDYMVQKSGKTGTITYQRGVLLPQKVWCASGR
SKVIKGSLPLIGEADCLHEKYGGLNKSKPYYTGEHAKAIGNCPIWVKTP
LKLANGTKYRPPAKLLKERGFFGAIAGFLEGGWEGMIAGWHGYTSHGAH
GVAVAADLKSTQEAINKITKNLNSLSELEVKNLQRLSGAMDELHNEILE
LDEKVDDLRADTISSQIELAVLLSNEGIINSEDEHLLALERKLKKMLGP
SAVDIGNGCFETKHKCNQTCLDRIAAGTFNAGEFSLPTFDSLNITAASL
NDDGLDNHTILLYYSTAASSLAVTLMIAIFIVYMVSRDNVSCSICL
(SEQ ID NO: 80)

By way of further example, engineered HA sequences have been developed to extend a seasonal response profile to cover pandemic strains, or vice versa as described in U.S. Provisional Application No. 62/354,502, which is hereby incorporated by reference in its entirety. These strategies extend the immune profile across clusters of sequences (or clades) of antigenically distinct strains; they can be applied to an engineered recombinant HA molecule over time so that it continues to elicit an immune response against antigenically drifted circulating seasonal strains. The strategy is designed to generally preserve specific residues of the receptor binding site (RBS) of a host HA polypeptide with modifications engineered in the region near the RBS. Similar strategies may be used to extend a pandemic response profile to cover seasonal strains. The modifications described in U.S. Provisional Application No. 62/354,502, can be used to further tailor or optimize the immunogenic profile so that an engineered HA polypeptide is re-engineered to elicit antibodies against more or less seasonal strains (or demonstrate an improved or more anti-seasonal antibody response) or more or less pandemic strains (or demonstrate an improved or more anti-pandemic antibody response). The amino acid sequences of these modified, engineered HA proteins do not match the amino acid sequences of any naturally occurring strains. The amino acid sequences of certain exemplary modified, engineered HA proteins are set forth in Table 15.

TABLE 15

Exemplary Modified Influenza HA Proteins

D02a
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALSRGFGSGIITSNAPMDKCDAK
CQTPQGAINSSLPFQNVHPVTIGECPKYVRSAKLRMVTGLRNIPFIQSR
GLFGAIAGFIEGGWTGMVDGWYGYHHQNEQGSGYAADLKSTQNAINGIT
NKVNSVIEKMNTQFTAVGKEFNKLERRMENLNKKVDDGFLDIWTYNAEL
LVLLENERTLDFHDSNVKNLYEKVKSQLKNNAKEIGNGCFEFYHKCNDE
CMESVKNGTYDYPKYSEESKLNREKIDGVKLESMGVYQILAIYSTVASS
LVLLVSLGAISFWMCSNGSLQCRICI
(SEQ ID NO: 81)

D02aRBStrunc00_resG63_G278_graftedontoD01a
MKAKLLVLLCTFTATYADTICIGYHANNSTDTVDTVLEKNVTVTHSVNL
LEDSHNGKLCKLKGIAPLQLGNCSVAGWILGNPECELLISKESWSYIVE
KPNPENGTCYPGYFADYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALSRGFGSGIITSDTPVHDCNTT
CQTPQGAINSSLPFQNVHPVTIGECPKYVRSAKLRMATGLRNIPSIQSR
GLFGAIAGFIEGGWTGMVDGWYGYHHQNEQGSGYAADLKSTQNAIDGIT
NKVNSVIEKMNTQFTAVGKEFNKLERRMENLNKKVDDGFLDIWTYNAEL
LVLLENERTLDFHDSNVKNLYEKVKSQLKNNAKEIGNGCFEFYHKCNNT
CMESVKNGTYDYPKYSEESKLNREKIDGVKLESMGVYQILAIYSTVASS
LVLLVSLGAISFWMCSNGSLQCRICI
(SEQ ID NO: 82)

D02aRBStrunc00_resG63_G277_graftedontoCal2009
MKAKLLVLLCTFTATYADTLCIGYHANNSTDTVDTVLEKNVTHSVNL
LEDKHNGKLCKLRGIAPLQLGNCSVAGWILGNPECELLISKESWSYIVE
KPNPENGTCYPGYFADYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALSRGAGSGIIISDTPVHDCNTT
CQTPKGAINTSLPFQNIHPITIGKCPKYVKSTKLRLATGLRNIPSIQSR
GLFGAIAGFIEGGWTGMVDGWYGYHHQNEQGSGYAADLKSTQNAIDEIT
NKVNSVIEKMNTQFTAVGKEFNHLEKRIENLNKKVDDGFLDIWTYNAEL
LVLLENERTLDYHDSNVKNLYEKVRSQLKNNAKEIGNGCFEFYHKCDNT
CMESVKNGTYDYPKYSEEAKLNREEIDGVKLESTRIYQILAIYSTVASS
LVLVVSLGAISFWMCSNGSLQCRICI
(SEQ ID NO: 83)

D02aRBStrunc00_resG63_G277_graftedontoSC1918
MKAKLLVLLCTFTATYADTICIGYHANNSTDTVDTVLEKNVTVTHSVNL
LEDSHNGKLCKLKGIAPLQLGNCSVAGWILGNPECELLISKESWSYIVE
KPNPENGTCYPGYFADYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALSRGSGSGIITSDAPVHDCNTK
CQTPHGAINSSLPFQNVHPVTIGECPKYVRSTKLRMATGLRNIPSIQSR
GLFGAIAGFIEGGWTGMIDGWYGYHHQNEQGSGYAADQKSTQNAIDGIT
NKVNSVIEKMNTQFTAVGKEFNNLERRIENLNKKVDDGFLDIWTYNAEL
LVLLENERTLDFHDSNVRNLYEKVKSQLKNNAKEIGNGCFEFYHKCDDA
CMESVRNGTYDYPKYSEESKLNREEIDGVKLESMGVYQILAIYSTVASS
LVLLVSLGAISFWMCSNGSLQCRICI
(SEQ ID NO: 84)

D02aRBStrunc00_resG63_G277_graftedontoNJ1976
MKAKLLVLLCTFTATYADTLCIGYHANNSTDTVDTVLEKNVTVTHSVNL
LEDRHNGKLCKLGGIAPLQLGNCSVAGWILGNPECELLISKESWSYIVE
KPNPENGTCYPGYFADYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALSRGSGSGIIISDAPVHDCNTK
CQTPKGAINTSLPFQNIHPVTIGECPKYVKSTKLRMATGLRNIPSIQSR
GLFGAIAGFIEGGWTGMIDGWYGYHHQNEQGSGYAADQRSTQNAIDGIT
NKVNSVIEKMNTQFTAVGKEFNHLEKRIENLNKKVDDGFLDIWTYNAEL
LVLLENERTLDFHDSNVKNLYEKVRSQLRNNAKEIGNGCFEFYHKCDDT
CMESVKNGTYDYPKYSEESKLNREEIDGVKLESTRIYQILAIYSTVASS
LVLLVSLGAISFWMCSNGSLQCRICI
(SEQ ID NO: 85)

D02aRBStrunc01_resV125_G277_graftedontoD01a
MKAKLLVLLCTFTATYADTICIGYHANNSTDTVDTVLEKNVTVTHSVNL
LEDSHNGKLCKLKGIAPLQLGKCSVAGWILGNPECESLSTASSWSYIVE
TSSPDNGTCYPGYFADYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALSRGFGSGIITSDTPVHDCNTT
CQTPQGAINSSLPFQNVHPVTIGECPKYVRSAKLRMATGLRNIPSIQSR
GLFGAIAGFIEGGWTGMVDGWYGYHHQNEQGSGYAADLKSTQNAIDGIT
NKVNSVIEKMNTQFTAVGKEFNKLERRMENLNKKVDDGFLDIWTYNAEL
LVLLENERTLDFHDSNVKNLYEKVKSQLKNNAKEIGNGCFEFYHKCNNT
CMESVKNGTYDYPKYSEESKLNREKIDGVKLESMGVYQILAIYSTVASS
LVLLVSLGAISFWMCSNGSLQCRICI
(SEQ ID NO: 86)

D02aRBStrunc01_resV125_G277_graftedontoCal2009
MKAKLLVLLCTFTATYADTLCIGYHANNSTDTVDTVLEKNVTVTHSVNL
LEDKHNGKLCKLRGVAPLHLGKCNIAGWILGNPECESLSTASSWSYIVE
TPSSDNGTCYPGDFIDYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALSRGAGSGIIISDTPVHDCNTT
CQTPKGAINTSLPFQNIHPITIGKCPKYVKSTKLRLATGLRNIPSIQSR
GLFGAIAGFIEGGWTGMVDGWYGYHHQNEQGSGYAADLKSTQNAIDEIT
NKVNSVIEKMNTQFTAVGKEFNHLEKRIENLNKKVDDGFLDIWTYNAEL TABLE 15-continued Exemplary Modified Influenza HA Proteins LVLLENERTLDYHDSNVKNLYEKVRSQLKNNAKEIGNGCFEFYHKCDNT
CMESVKNGTYDYPKYSEEAKLNREEIDGVKLESTRIYQILAIYSTVASS
LVLVVSLGAISFWMCSNGSLQCRICI
(SEQ ID NO: 87)

DO2aRBStrunc01_resV125_G277_graftedontoSC1918
MKAKLLVLLCTFTATYADTICIGYHANNSTDTVDTVLEKNVTVTHSVNL
LEDSHNGKLCKLKGIAPLQLGKCNIAGWLLGNPECDLLLTASSWSYIVE
TSNSENGTCYPGDFIDYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALSRGSGSGIITSDAPVHDCNTK
CQTPHGAINSSLPFQNIHPVTIGECPKYVRSTKLRMATGLRNIPSIQSR
GLFGAIAGFIEGGWTGMIDGWYGYHHQNEQGSGYAADQKSTQNAIDGIT
NKVNSVIEKMNTQFTAVGKEFNNLERRIENLNKKVDDGFLDIWTYNAEL
LVLLENERTLDFHDSNVRNLYEKVKSQLKNNAKEIGNGCFEFYHKCDDA
CMESVRNGTYDYPKYSEESKLNREEIDGVKLESMGVYQILAIYSTVASS
LVLLVSLGAISFWMCSNGSLQCRICI
(SEQ ID NO: 88)

DO2aRBStrunc01_resV125_G277_graftedontoNJ1976
MKAKLLVLLCTFTATYADTLCIGYHANNSTDTVDTVLEKNVTVTHSVNL
LEDRHNGKLCKLGGIAPLHLGKCNIAGWLLGNPECELLLTVSSWSYIVE
TSNSDNGTCYPGDFINYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALSRGSGSGIITSDAPVHDCNTK
CQTPKGAINTSLPFQNIHPVTIGECPKYVKSTKLRMATGLRNIPSIQSR
GLFGAIAGFIEGGWTGMIDGWYGYHHQNEQGSGYAADQRSTQNAIDGIT
NKVNSVIEKMNTQFTAVGKEFNHLEKRIENLNKKVDDGFLDIWTYNAEL
LVLLENERTLDFHDSNVKNLYEKVRSQLRNNAKEIGNGCFEFYHKCDDT
CMESVKNGTYDYPKYSEESKLNREEIDGVKLESTRIYQILAIYSTVASS
LVLLVSLGAISFWMCSNGSLQCRICI
(SEQ ID NO: 89)

DO2aRBStrunc02_resP135_P269_graftedontoDO1A
MKAKLLVLLCTFTATYADTICIGYHANNSTDTVDTVLEKNVTVTHSVNL
LEDSHNGKLCKLKGIAPLQLGKCSVAGWILGNPECESLSTASSWSYIVE
TSSPDNGTCYPGYFADYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALSRGFGSGIITSDTPVHDCNTT
CQTPQGAINSSLPFQNVHPVTIGECPKYVRSAKLRMTGLRNIPSIQSR
GLFGAIAGFIEGGWTGMVDGWYGYHHQNEQGSGYAADLKSTQNAIDGIT
NKVNSVIEKMNTQFTAVGKEFNKLERRMENLNKKVDDGFLDIWTYNAEL
LVLLENERTLDFHDSNVKNLYEKVKSQLKNNAKEIGNGCFEFYHKCNNT
CMESVKNGTYDYPKYSEESKLNREKIDGVKLESMGVYQILAIYSTVASS
LVLLVSLGAISFWMCSNGSLQCRICI
(SEQ ID NO: 90)

DO2aRBStrunc02_resP135_P269_graftedontoCal2009
MKAKLLVLLCTFTATYADTLCIGYHANNSTDTVDTVLEKNVTVTHSVNL
LEDKHNGKLCKLRGVAPLHLGKCNIAGWILGNPECESLSTASSWSYIVE
TPSSDNGTCYPGDFIDYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPRYAFAMERNAGSGIIISDTPVHDCNTT
CQTPKGAINTSLPFQNIHPITIGKCPKYVKSTKLRLATGLRNIPSIQSR
GLFGAIAGFIEGGWTGMVDGWYGYHHQNEQGSGYAADLKSTQNAIDEIT
NKVNSVIEKMNTQFTAVGKEFNHLEKRIENLNKKVDDGFLDIWTYNAEL
LVLLENERTLDYHDSNVKNLYEKVRSQLKNNAKEIGNGCFEFYHKCDNT
CMESVKNGTYDYPKYSEEAKLNREEIDGVKLESTRIYQILAIYSTVASS
LVLVVSLGAISFWMCSNGSLQCRICI
(SEQ ID NO: 91)

DO2aRBStrunc02_resP135_P269_graftedontoSC1918
MKAKLLVLLCTFTATYADTICIGYHANNSTDTVDTVLEKNVTVTHSVNL
LEDSHNGKLCKLKGIAPLQLGKCNIAGWLLGNPECDLLLTASSWSYIVE
TSNSENGTCYPGDFIDYEELREQLSSVSSFEKFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPWYAFALNRGSGSGIITSDAPVHDCNTK
CQTPHGAINSSLPFQNIHPVTIGECPKYVRSTKLRMATGLRNIPSIQSR
GLFGAIAGFIEGGWTGMIDGWYGYHHQNEQGSGYAADQKSTQNAIDGIT
NKVNSVIEKMNTQFTAVGKEFNNLERRIENLNKKVDDGFLDIWTYNAEL
LVLLENERTLDFHDSNVRNLYEKVKSQLKNNAKEIGNGCFEFYHKCDDA
CMESVRNGTYDYPKYSEESKLNREEIDGVKLESMGVYQILAIYSTVASS
LVLLVSLGAISFWMCSNGSLQCRICI
(SEQ ID NO: 92)

DO2aRBStrunc02_resP135_P269_graftedontoNJ1976
MKAKLLVLLCTFTATYADTLCIGYHANNSTDTVDTVLEKNVTVTHSVNL
LEDRHNGKLCKLGGIAPLHLGKCNIAGWLLGNPECELLLTVSSWSYIVE
TSNSDNGTCYPGDFINYEELREQLSSVSSFERFEIFPKESSWPNHTVTG
VSASCSHNGKSSFYRNLLWLTGKNGLYPNLSKSYANNKEKEVLVLWGVH
HPPNIGDQRALYHTENAYVSVVSSHYSRRFTPEIAKRPKVRDQEGRINY
YWTLLEPGDTIIFEANGNLIAPRYAFAMNRGSGSGIIISDAPVHDCNTK
CQTPKGAINTSLPFQNIHPVTIGECPKYVKSTKLRMATGLRNIPSIQSR
GLFGAIAGFIEGGWTGMIDGWYGYHHQNEQGSGYAADQRSTQNAIDGIT
NKVNSVIEKMNTQFTAVGKEFNHLEKRIENLNKKVDDGFLDIWTYNAEL
LVLLENERTLDFHDSNVKNLYEKVRSQLRNNAKEIGNGCFEFYHKCDDT
CMESVKNGTYDYPKYSEESKLNREEIDGVKLESTRIYQILAIYSTVASS
LVLLVSLGAISFWMCSNGSLQCRICI
(SEQ ID NO: 93)

SMARt_NC_DO2a_NGlyMod
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKESSWPNHDSN-
GVSASCSHNGKSSFYRNLLWLTGKNGLYPKLSKSYANNKEKEVLVLWGV
HHPPNIGDQRALYHTENAYVSVVSSHYSRRFTPEIAKRPKVRDQEGRIN
YYWTLLEPGDTIIFEANGNLIAPYAFALSRGFGSGIITSNAPMDKCAKCQTPQGAINSSLPFQNVHPVTIGECPKYVRSAKLRMVTGLRNIPFIQS
RGLFGAIAGFIEGGWTGMVDGWYGYHHQNEQGSGYAADQKSTQNAINGI
TNKVNSVIEKMNTQFTAVGKEFNKLERRMENLNKKVDDGFLDIWTYNAE
LLVLLENERTLDFHDSNVKNLYEKVKSQLKNNAKEIGNGCFEFYHKCND
ECMESVKNGTYDYPKYSEESKLNREKIDGVKLESMGVYQILAIYSTVAS
SLVLLVSLGAISFWMCSNGSLQCRICI
(SEQ ID NO: 94)

SMARt_NC_DO2a_NGlyMod+loopInsertion(CA09)
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKESSWPNHDSNK
GVSASCSHNGKSSFYRNLLWLTGKNGLYPKLSKSYANNKEKEVLVLWGV
HHPPNIGDQRALYHTENAYVSVVSSHYSRRFTPEIAKRPKVRDQEGRIN
YYWTLLEPGDTIIFEANGNLIAPYAFALSRGFGSGIITSNAPMDKCDA
KCQTPQGAINSSLPFQNVHPVTIGECPKYVRSAKLRMVTGLRNIPFIQS
RGLFGAIAGFIEGGWTGMVDGWYGYHHQNEQGSGYAADQKSTQNAINGI
TNKVNSVIEKMNTQFTAVGKEFNKLERRMENLNKKVDDGFLDIWTYNAE
LLVLLENERTLDFHDSNVKNLYEKVKSQLKNNAKEIGNGCFEFYHKCND
ECMESVKNGTYDYPKYSEESKLNREKIDGVKLESMGVYQILAIYSTVAS
SLVLLVSLGAISFWMCSNGSLQCRICI
(SEQ ID NO: 95)

SMART_NC_DO2A_NGLYMOD+LOOPINSERTION(SC18)
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKESSWPNHETTK
GVSASCSHNGKSSFYRNLLWLTGKNGLYPKLSKSYANNKEKEVLVLWGV
HHPPNIGDQRALYHTENAYVSVVSSHYSRRFTPEIAKRPKVRDQEGRIN
YYWTLLEPGDTIIFEANGNLIAPYAFALSRGFGSGIITSNAPMDKCDA
KCQTPQGAINSSLPFQNVHPVTIGECPKYVRSAKLRMVTGLRNIPFIQS
RGLFGAIAGFIEGGWTGMVDGWYGYHHQNEQGSGYAADQKSTQNAINGI
TNKVNSVIEKMNTQFTAVGKEFNKLERRMENLNKKVDDGFLDIWTYNAE
LLVLLENERTLDFHDSNVKNLYEKVKSQLKNNAKEIGNGCFEFYHKCND
ECMESVKNGTYDYPKYSEESKLNREKIDGVKLESMGVYQILAIYSTVAS
SLVLLVSLGAISFWMCSNGSLQCRICI
(SEQ ID NO: 96)

SMARt_NC_DO2a_mods_outstide_ch65_eptiope1
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKTSSWPNHTVT-
GVSASCPHAGAKSFYRNLLWLTGKNGLYPNLSKSYANNKEKEVLVLWGV
HHPPNIGDQRALYQNADAYVSVVSSHYSRRFTPEIAKRPKVRDQEGRIN
YYWTLLEPGDTIIFEATGNLIAPWYAFALSRGFGSGIITSNAPMDKCDA
KCQTPQGAINSSLPFQNVHPVTIGECPKYVRSAKLRMTGLRNIPSIQS
RGLFGAIAGFIEGGWTGMVDGWYGYHHQNEQGSGYAADQKSTQNAINGI
TNKVNSVIEKMNTQFTAVGKEFNKLERRMENLNKKVDDGFLDIWTYNAE
LLVLLENERTLDFHDSNVKNLYEKVKSQLKNNAKEIGNGCFEFYHKCND
ECMESVKNGTYDYPKYSEESKLNREKIDGVKLESMGVYQILAIYSTVAS
SLVLLVSLGAISFWMCSNGSLQCRICI
(SEQ ID NO: 97)

TABLE 15-continued

Exemplary Modified Influenza HA Proteins

SMARt_NC_DO2a_mods_outstide_ch65_eptiope2
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKESSWPNHTVT-
GVSASCPHAGAKSFYRNLLWLTGKNGLYPNLSKSYANNKEKEVLVLWGV
HHPPNIGDQRALYHTENAYVSVVSSHYSRRFTPEIAKRPKVRDQEGRIN
YYWTLLEPGDTIIFEANGNLIAPWYAFALSRGFGSGIITSNAPMDKCDA
KCQTPQGAINSSLPFQNVHPVTIGECPKYVRSAKLRMVTGLRNIPFIQS
RGLFGAIAGFIEGGWTGMVDGWYGYHHQNEQGSGYAADQKSTQNAINGI
TNKVNSVIEKMNTQFTAVGKEFNKLERRMENLNKKVDDGFLDIWTYNAE
LLVLLENERTLDFHDSNVKNLYEKVKSQLKNNAKEIGNGCFEFYHKCND
ECMESVKNGTYDYPKYSEESKLNREKIDGVKLESMGVYQILAIYSTVAS
SLVLLVSLGAISFWMCSNGSLQCRICI
(SEQ ID NO: 98)

SMARt_NC_DO2a_mods_outstide_ch65_eptiope3
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKESSWPNHTVT-
GVSASCSHNGKSSFYRNLLWLTGKNGLYPNLSKSYANNKEKEVLVLWGV
HHPPNIGDQRALYQNADAYVSVVSSHYSRRFTPEIAKRPKVRDQEGRIN
YYWTLLEPGDTIIFEANGNLIAPWYAFALSRGFGSGIITSNAPMDKCDA
KCQTPQGAINSSLPFQNVHPVTIGECPKYVRSAKLRMVTGLRNIPFIQS
RGLFGAIAGFIEGGWTGMVDGWYGYHHQNEQGSGYAADQKSTQNAINGI
TNKVNSVIEKMNTQFTAVGKEFNKLERRMENLNKKVDDGFLDIWTYNAE
LLVLLENERTLDFHDSNVKNLYEKVKSQLKNNAKEIGNGCFEFYHKCND
ECMESVKNGTYDYPKYSEESKLNREKIDGVKLESMGVYQILAIYSTVAS
SLVLLVSLGAISFWMCSNGSLQCRICI
(SEQ ID NO: 99)

SMARt_NC_DO2a_mods_outside_ch65_eptiope1-noGly
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKTSSWPNHNTT-
GVSASCPHAGAKSFYRNLLWLTGKNGLYPKLSKSYANNKEKEVLVLWGV
HHPPNIGDQRALYQNADAYVSVVSSHYSRRFTPEIAKRPKVRDQEGRIN
YYWTLLEPGDTIIFEATGNLIAPWYAFALSRGFGSGIITSNAPMDKCDA
KCQTPQGAINSSLPFQNVHPVTIGECPKYVRSAKLRMVTGLRNIPFIQS
RGLFGAIAGFIEGGWTGMVDGWYGYHHQNEQGSGYAADQKSTQNAINGI
TNKVNSVIEKMNTQFTAVGKEFNKLERRMENLNKKVDDGFLDIWTYNAE
LLVLLENERTLDFHDSNVKNLYEKVKSQLKNNAKEIGNGCFEFYHKCND
ECMESVKNGTYDYPKYSEESKLNREKIDGVKLESMGVYQILAIYSTVAS
SLVLLVSLGAISFWMCSNGSLQCRICI
(SEQ ID NO: 100)

SMARt_NC_DO2a_mods_outstide_ch65_eptiope2-noGly
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKESSWPNHTVT-
GVSASCPHAGAKSFYRNLLWLTGKNGLYPKLSKSYANNKEKEVLVLWGV
HHPPNIGDQRALYHTENAYVSVVSSHYSRRFTPEIAKRPKVRDQEGRIN
YYWTLLEPGDTIIFEANGNLIAPWYAFALSRGFGSGIITSNAPMDKCDA
KCQTPQGAINSSLPFQNVHPVTIGECPKYVRSAKLRMVTGLRNIPFIQS
RGLFGAIAGFIEGGWTGMVDGWYGYHHQNEQGSGYAADQKSTQNAINGI
TNKVNSVIEKMNTQFTAVGKEFNKLERRMENLNKKVDDGFLDIWTYNAE
LLVLLENERTLDFHDSNVKNLYEKVKSQLKNNAKEIGNGCFEFYHKCND
ECMESVKNGTYDYPKYSEESKLNREKIDGVKLESMGVYQILAIYSTVAS
SLVLLVSLGAISFWMCSNGSLQCRICI
(SEQ ID NO: 101)

SMARt_NC_DO2a_mods_outstide_ch65_eptiope3-noGly
MKAKLLVLLCTFTATYADTICIGYHANNSTDTVDTVLEKNVTVTHSVNI
LEDSHNGKLCLLKGIAPLQLGNCSVAGWILGNPECELLISKESWSYIVE
KPNPENGTCYPGYFADYEELREQLSSVSSFERFEIFPKESSWPNHTT-
GVSASCSHNGKSSFYRNLLWLTGKNGLYPKLSKSYANNKEKEVLVLWGV
HHPPNIGDQRALYQNADAYVSVVSSHYSRRFTPEIAKRPKVRDQEGRIN
YYWTLLEPGDTIIFEANGNLIAPWYAFALSRGFGSGIITSNAPMDKCDA
KCQTPQGAINSSLPFQNVHPVTIGECPKYVRSAKLRMVTGLRNIPFIQS
RGLFGAIAGFIEGGWTGMVDGWYGYHHQNEQGSGYAADQKSTQNAINGI
TNKVNSVIEKMNTQFTAVGKEFNKLERRMENLNKKVDDGFLDIWTYNAE
LLVLLENERTLDFHDSNVKNLYEKVKSQLKNNAKEIGNGCFEFYHKCND
ECMESVKNGTYDYPKYSEESKLNREKIDGVKLESMGVYQILAIYSTVAS
SLVLLVSLGAISFWMCSNGSLQCRICI
(SEQ ID NO: 102)

In various embodiments, engineered HA mosaic polypeptides as described herein comprise combinations of epitope patterns on a particular viral backbone sequence. Multiple epitopes can be assembled on to any viral backbone as desired. Exemplary viral backbone sequences include A/New Caledonia/20/1999, A/California/07/2009, and a consensus (e.g., 1918-2011) sequence. In some embodiments, engineered HA mosaic polypeptides as described herein comprise a New Caledonia 99 or California 09 backbone sequence.

In some embodiments, an engineered HA polypeptide has a sequence at least about 90% (e.g., at least about 91%, 92%, 93%, 94%, 95%, 96%, 97%, 98% or 99%) identical to a sequence that appears in Table 13, 14, or 15. In some embodiments, an engineered HA polypeptide has a sequence that is substantially identical to a sequence that appears in Table 13, 14, or 15. In some embodiments, an engineered HA polypeptide has a sequence that is identical to a sequence that appears in Table 13, 14, or 15.

Expression of Engineered Structural Influenza Proteins

Optimized nucleotide sequences obtained by the methods described herein may be expressed in in a cell-free system or in a host cell using known methods. Expression of optimized nucleotide sequences of the present invention may be regulated by a second nucleic acid sequence so that the molecule is expressed in a host transformed with the recombinant DNA molecule. For example, expression of the optimized nucleotide sequence of the invention may be controlled by a promoter and/or enhancer element, which are known in the art.

Nucleic acid constructs of the present invention are inserted into an expression vector or viral vector by methods known to the art, and nucleic acid molecules are operatively linked to an expression control sequence.

An expression vector containing a nucleic acid molecule is transformed into a suitable host cell to allow for production of the protein encoded by the nucleic acid constructs. Exemplary host cells include prokaryotes (e.g., E. coli) and eukaryotes (e.g., a COS, 293 or CHO cell). Host cells transformed with an expression vector are grown under conditions permitting production of an engineered structural influenza protein followed by recovery of the engineered protein.

Vectors comprising the nucleic acid molecules encoding recombinant structural influenza proteins are also provided. The vector can be any suitable vector for expression of the engineered structural influenza protein, such as a mammalian expression vector. In particular examples, the vector is the pTR600 expression vector (U.S. Patent Application Publication No. 2002/0106798, herein incorporated by reference; Ross et ah, Nat Immunol. 1(2): 102-103, 2000; Green et al., Vaccine 20:242-248, 2001). In some examples, the vector includes a promoter operably linked to the optimized nucleotide sequence encoding the engineered structural influenza protein. In particular examples, the promoter is a CMV promoter.

Engineered structural influenza polypeptides may be purified by any technique known in the art. For example, not wishing to be bound by theory, engineered structural influenza polypeptides may be recovered from cells either as soluble polypeptides or as inclusion bodies, from which they may be extracted quantitatively by 8M guanidinium hydrochloride and dialysis. In order to further purify engineered structural influenza polypeptides, conventional ion exchange chromatography, hydrophobic interaction chromatography, reverse phase chromatography or gel filtration may be used. Engineered structural influenza polypeptides of the present invention may also be recovered from conditioned media following secretion from eukaryotic or prokaryotic cells.

Reverse Genetics Methods

The optimized nucleotide sequences obtained by the methods described herein can be combined with one or more donor viruses and used in a reverse genetics system to produce an infectious reassortant influenza virus. As discussed above, reverse genetics systems can be used produce infectious, reassortant viruses, or attenuated viruses from their cDNAs. The reverse genetics methods are well-known by the one skilled in the art and include, but are not limited to, the methods using the plasmids described in Neuman et al, 1999, Proc Natl Acad Sci USA, 96(16):9345-9350; Neumann et al, 2005, Proc Natl Acad Sci USA, 102(46): 16825-16829; Zhang et al, 2009, J Virol, 83(18):9296-9303; Massin et al, 2005, J Virol, 79(21):13811-13816; Murakami et al, 2008, 82(3):1605-1609; and/or the cells described in Neuman et al, 1999, Proc Natl Acad Sci USA, 96(16):9345-9350; Neumann et al, 2005, Proc Natl Acad Sci USA, 102(46): 16825-16829; Zhang et al, 2009, J Virol, 83(18): 9296-9303; Massin et al, 2005, J Virol, 79(21):13811-13816; Murakami et al, 2008, 82(3):1605-1609; Koudstaal et al, 2009, Vaccine, 27(19):2588-2593; Schickli et al, 2001, Philos Trans R Soc Lond Biol Sci, 356(1416):1965-1973; Nicolson et al, 2005, Vaccine, 23(22):2943-2952; Legastelois et al, 2007, Influenza Other Respi Viruses, 1 (3):95-104; Whiteley et al, 2007, Influenza Other Respi Viruses, 1 (4): 157-166.

In certain embodiments, the reverse genetics method may be:

(i) the 16 plasmid method, such as the method described by Neuman et al, 1999, Proc Natl Acad Sci USA, 96(16): 9345-9350, and in US 2009/0246830 or US 2011/0143424 (each of which is hereby incorporated by reference in its entirety), in which the influenza virus is produced by transfecting cells, using a polyamine derivative (Trans IT-LT1), with 8 plasmids each containing a cDNA complementary to one influenza vRNA under the control of an RNA polymerase I promoter and an RNA polymerase I terminator, and 8 plasmids each containing a cDNA complementary to one of the PA, PB1, PB2, NP, HA, NA, M and NS mRNAs under the control of RNA polymerase II promoter. In particular, the cells are human kidney embryonic adherent cells (293T cell line);

(ii) the 12 plasmid method, such as the method described by Fodor et al, 1999, J Virol, 73(11):9679-9682, and in US 2004/0142003, US 2012/0058538 (each of which is hereby incorporated by reference in its entirety) in which the influenza virus is produced by transfecting a first cell type with 8 plasmids each containing a cDNA complementary to one influenza vRNA under the control of an RNA polymerase I promoter and an RNA polymerase I terminator (hepatitis delta ribozyme), and 4 plasmids each containing a cDNA complementary to one of the NP, PA, PB1 and PB2 mRNAs under the control of RNA polymerase II promoter, and by further amplifying the virus on a second cell type. In particular, said first cell type is Vero cells and said second cell type is MDBK;

(iii) the 13 plasmid method, such as the method described by De Wit et al, 2007, Journal of General Virology, 88:1281-1287 (which is hereby incorporated by reference in its entirety) in which the influenza virus is produced by transfecting cells with 8 plasmids each containing a cDNA complementary to one influenza vRNA under the control of an T7 RNA polymerase promoter and an T7 RNA polymerase terminator, 4 plasmids each containing a cDNA complementary to one of the NP, PA, PB1 and PB2 mRNAs under the control of RNA polymerase II, and one plasmid containing the cDNA complementary to the mRNA encoding the T7 RNA polymerase and a nuclear localization signal under the control of RNA polymerase II. In particular, the transfected cells are Vero, 293T, or QT6 (fibrosarcoma cell line from Japanese quail) cells.

(iv) the 8 plasmid method, such as the method described by Hoffmann et al, 2000, PNAS, 97(11):6108-6113 and in WO 01/83794 (each of which is hereby incorporated by reference in its entirety) in which each plasmid is capable of expressing both mRNA and vRNA(s). Thus each plasmid contains cDNA complementary to one influenza vRNA and two transcription cassettes instead of one as in the preceding case. The cDNA complementary of each of the eight influenza virus vRNAs is inserted between the polymerase I terminator and the polymerase I promoter. This polymerase I transcription unit is flanked by the polymerase II promoter and a polyadenylation signal. The first transcription cassette allows the transcription of cDNA in the form of a vRNA. The second transcription cassette allows the transcription of cDNA in the form of mRNA which is then translated into viral protein(s) using the cellular machinery. With the aid of this double cassette system for transcription, also called Pol 1-Pol II system, the cDNA of the same plasmid is transcribed both in the form of vRNA and in the form of mRNA. This manifests itself at the level of the transfected cell by the expression of a vRNA and of one or more viral proteins. In particular, a co-culture of adherent MDCK cells and of 293T cells and, as transfection agent, a polyamine derivative (Trans IT-LT1) are used.

(v) the 3 plasmid method, such as the method described by Neumann et al, 2005, PNAS, 102(46): 16825-16829 (which is hereby incorporated by reference in its entirety), in which the influenza virus is produced by transfecting cells with one plasmid containing the 8 cDNAs complementary to PB2, PB1, PA, HA, NP, NA, M and NS vRNAs each under the control of an RNA polymerase I promoter and a polymerase I terminator and 2 plasmids, the first one containing the 3 cDNA complementary to one of the PB2, PB1 and PA mRNAs and the second one containing the cDNA complementary to the NP mRNA, under the control of a RNA polymerase II promoter. In particular, the transfected cells are 293T or Vero.

(vi) the 1 plasmid method, such as the method described by Zhang et al, J. Virol., 83(18): 9296-9303 (which is hereby incorporated by reference in its entirety), in which the influenza virus is produced by transfecting cells with one plasmid containing the 8 cDNAs complementary to PB2, PB1, PA, HA, NP, NA, M and NS vRNA under the control of murine polymerase I terminator and a chicken RNA polymerase I promoter and with a polymerase II promoter and a polyadenylation signal between PB2, PB1, PA and NP cDNAs. In particular, the transfected cells are CEF cells.

(vii) the method described in WO 2005/062820 (which is hereby incorporated by reference in its entirety) using two different cellular systems: in a first step, cells are transfected with 8 bidirectional plasmids with the PolI-PolII system (Pol/PolI) and then in a second step, the transfected cells are cultured with cells from another cell line that is very permissive for the influenza virus in order to amplify the production of the influenza virus. In particular, said transfected cells in the first step are Vero cells, and said other cell line in the second step are CEK or CEF cell lines which are lines derived from chicken embryo cells.

Thus, certain embodiments are directed to a method of producing an infectious reassortant influenza virus ("reverse genetics" method), the method comprising transfecting cells with an expression vector comprising an optimized nucleotide sequence encoding a structural influenza protein and one or more donor vectors, and producing the infectious reassortant influenza virus (or seed virus). In certain embodiments, the cells are mammalian cells, including, but not limited to, Vero cells, HEK-293 cells, MDCK cells, or Chinese Hamster Ovary (CHO) cells and combinations thereof. In some embodiments, the methods described herein and the optimized nucleotide sequences thereof are used with the vectors, recombination cassettes and overall system described in WO2014/019990 and U.S. application Ser. No. 14/419,235, (U.S. Publication No. 2015-0191703 A1), which are incorporated herein by reference in their entirety.

The supernatant of the transfected cells contains infectious reassortant influenza virus, which can be harvested and/or isolated and used as an infectious seed virus to infect a separate population of cells or eggs. Alternatively, after the transfection step, cells or eggs can be added in situ to the transfected cells to allow the proliferation of infectious influenza virus. In certain embodiments, the cells are mammalian cells, including, but not limited to, Vero cells or Chinese Hamster Ovary (CHO) cells.

It is well understood that the infection of cells with the seed virus is made under culture conditions well known by the skilled in the art that allow the proliferation of infectious influenza virus. The proliferation of the infectious influenza virus can be further amplified by successive infections of the cell populations or any other highly permissive cell populations, or by infecting the allantoic cavity of embryonated hen's eggs.

The transfected mammalian cells are preferably adapted for culture in serum-free medium and/or animal component free conditions. Cell adaptation to culture in serum free medium may readily achieved by the one skilled in the art by progressively passaging cells on media containing decreasing serum amounts, until the cells can successfully survive and proliferate in a serum-free medium.

Cells can be transfected by any method known by the one skilled in the art. For example, transfection may be performed by membrane electroporation, nuclear electroporation. In certain embodiments, transfection is performed by nuclear electroporation. The expression "nuclear electroporation" is understood to mean a method of transfection of nucleic acids by means of one or more electric shocks whose intensity is sufficient to increase the number of nuclear pores and/or the permeability thereof.

In certain embodiments, the recombinant virus comprises an HA influenza polypeptide encoded by an optimized nucleotide sequence as described herein, a wild-type NA polypeptide from an influenza strain and a backbone of internal protein genes from a donor virus (e.g., influenza A/Puerto Rico/8/34 (PR8)) that confers a high yield in eggs. For example, six plasmids encoding the internal proteins of the high-growth influenza A/Puerto Rico/8/34 (PR8) donor virus can be co-transfected with a plasmid encoding an engineered influenza structural polypeptide as described herein and a wild-type neuraminidase (NA) glycoprotein into qualified mammalian cells (e.g., Vero cells), followed by isolation of the recombinant virus. Recombinant viruses containing internal protein genes from the PR8 virus may be used to prepare inactivated influenza virus vaccines (see, e.g., Fodor, E. et al. *Rescue of influenza A virus from Recombinant DNA*. J. Virol., 1999, 73, 9679-9682; incorporated by reference herein).

Influenza Virus-Like Particles (VLPs)

In some embodiments, the present invention provides for influenza virus-like particles (VLPs) and combinations thereof comprising one or more of the engineered structural influenza proteins encoded by an optimized nucleotide sequence as described herein. The influenza VLPs are, in some embodiments, generally made up of HA, NA and virus structural (e.g., HIV gag) proteins. Production of influenza VLPs is known in the art and will be readily apparent to persons of skill upon reading the present disclosure. For example, influenza VLPs may be produced by transfection of host cells with plasmids encoding the HA, NA and HIV gag proteins. To give but one example, a suitable host cell includes a human cell (e.g., HEK293T). After incubation of the transfected cells for an appropriate time to allow for protein expression (such as for approximately 72 hours), VLPs may be isolated from cell culture supernatants. In some embodiments, influenza VLPs as disclosed herein may be used as influenza vaccines to elicit a broadly neutralizing immune response against influenza viruses.

Whole Influenza Viruses

Also provided are whole recombinant influenza viruses comprising one or more of the engineered influenza structural proteins described herein. The recombinant influenza viruses can be produced by plasmid-based reverse genetics, as described herein, and cell-based or egg-based technologies. Recombinant viruses containing internal protein genes from a donor virus may be used to prepare inactivated influenza virus vaccines (see, e.g., Fodor, E. et al. *Rescue of influenza A virus from Recombinant DNA*. J. Virol., 1999, 73, 9679-9682; incorporated by reference herein). Distinct recombinant influenza viruses, each comprising a different recombinant, structural influenza polypeptide, can also be separately produced and then combined into combinations/cocktails. The recombinant influenza virus combinations/cocktails can be used as influenza vaccines to elicit a protective immune response against influenza viruses; for example, they can be administered as components of a live-attenuated or split-inactivated vaccine.

Thus, in some embodiments, the present invention provides inactivated influenza vaccines comprising a structural influenza polypeptide (or combinations or cocktails thereof) encoded by an optimized nucleotide sequence, wherein the vaccines comprise one of three types of antigen preparation: inactivated whole virus, sub-virions where purified virus particles are disrupted with detergents or other reagents to solubilize the lipid envelope ("split" vaccine) or purified structural influenza polypeptide ("subunit" vaccine). In some embodiments, virus can be inactivated by treatment with formaldehyde, beta-propiolactone, ether, ether with detergent (such as TWEEN-80®), cetyl trimethyl ammonium bromide (CTAB) and Triton N101, sodium deoxycholate and tri(n-butyl) phosphate. Inactivation can occur after or prior to clarification of allantoic fluid (from virus produced in eggs); the virions are isolated and purified by centrifugation (Nicholson et al., eds., 1998, *Textbook of Influenza*, Blackwell Science, Malden, Mass.; incorporated herein by reference). To assess the potency of the vaccine, the single radial immunodiffusion (SRD) test can be used (Schild et al., 1975, *Bull. World Health Organ.*, 52:43-50 & 223-31; Mostow et al., 1975, *J. Clin. Microbiol.*, 2:531; both of which are incorporated herein by reference).

In some embodiments, influenza virus for use in vaccines is grown in eggs, for example, in embryonated hen eggs, in which case the harvested material is allantoic fluid. Alternatively or additionally, influenza virus or an influenza structural polypeptide encoded by an optimized nucleotide sequence may be produced from any method using tissue culture to grow the virus. Suitable cell substrates for growing the virus or otherwise recombinantly producing the engineered, structural influenza polypeptides include, for example, CHO cells, dog kidney cells such as MDCK or cells from a clone of MDCK, MDCK-like cells, monkey kidney cells such as AGMK cells including Vero cells, cultured epithelial cells as continuous cell lines, 293T cells, BK-21 cells, CV-1 cells, or any other mammalian cell type suitable for the production of influenza virus (including upper airway epithelial cells) for vaccine purposes, readily available from commercial sources (e.g., ATCC, Rockville, Md.). Suitable cell substrates also include human cells such as MRC-5 cells. Suitable cell substrates are not limited to cell lines; for example primary cells such as chicken embryo fibroblasts are also included.

Methods for Preparing Pharmaceutical Compositions

Also provided herein are methods for preparing an influenza vaccine composition, the method comprising:

a) generating a seed virus by transfecting mammalian cells with a set of expression vectors, one or more of which comprises an optimized nucleotide sequence encoding an engineered influenza structural protein;
b) harvesting the seed virus;
c) infecting eggs or mammalian cells with the seed virus to produce an infectious influenza virus;
d) harvesting the infectious influenza virus after multiplication in the eggs of mammalian cells;
e) purifying the harvested infectious influenza virus,
d) optionally inactivating the purified virus, and
e) mixing the purified virus with a pharmaceutically acceptable carrier.

In some embodiments, the expression vectors are those described in WO2014/019990 and U.S. application Ser. No. 14/419,235, (U.S. Publication No. 2015-0191703 A1), which are incorporated herein by reference in their entirety; in some embodiments, the vectors comprise the recombination cassettes described in WO2014/019990.

In some embodiments, said set of expression vectors comprises: expression vectors allowing the expression of mRNAs encoding at least influenza PB, PB2, PA and NP proteins, and expression vectors allowing the expression of at least influenza PB1, PB2, PA, NP, M, NS, HA and NA vRNAs, or the corresponding cRNAs. Expression of said set of expression vectors allows (i) the formation of the ribonucleoprotein complex (RNP) containing the influenza vRNA(s), and (ii) the generation of infectious influenza viruses in said transfected cells. In particular embodiments, the expression vectors allowing the expression of mRNAs encoding influenza PB1, PB2, PA and NP proteins comprise four different uni-directional plasmids, each plasmid containing a cDNA complementary to a mRNA encoding one of the four distinct proteins selected from PB1, PB2, PA and NP influenza proteins under the control of a promoter that binds to RNA polymerase II, and the expression vectors allowing the expression of influenza PB1, PB2, PA, NP, M, NS, HA and NA vRNAs, or the corresponding cRNAs, comprise eight different uni-directional plasmids, each plasmid containing a cDNA complementary to one of the eight distinct vRNAs selected from said PB1, PB2, PA, NP, M, NS, HA and NA influenza vRNAs, or to the corresponding cRNAs, under the control of a promoter that binds to RNA polymerase I. In some embodiments, each plasmid containing a cDNA complementary to one of said influenza PB1, PB2, PA, NP, M, NS, HA and NA vRNAs (e.g., a cDNA comprising an optimized nucleotide sequence as described herein), or the corresponding cRNAs, under the control of a promoter that binds to RNA polymerase I has been obtained by cloning said cDNA sequence into a vector comprising, in the 5' to 3' sense:

a) a promoter that binds to RNA polymerase I, or a T7 RNA polymerase; b) a recombination cassette comprising, in the 5' to 3' sense:

- an inverted complementary recognition sequence for a first restriction enzyme which has its cutting site outside of its recognition sequence and produces sticky ends;
- a restriction site for a second restriction enzyme which has its cutting site inside of its recognition sequence;
- a restriction site for a third restriction enzyme which has its cutting site inside of its recognition sequence; and
- a recognition sequence for said first restriction enzyme which has its cutting site outside of its recognition sequence and produces sticky ends; wherein said second and third restriction enzymes are different; and c) a terminator sequence. In particular embodiments, when the promoter binds to RNA polymerase I, said terminator sequence is hepatitis delta ribozyme sequence, and when the promoter binds to T7 RNA polymerase, said terminator sequence is T7 polymerase terminator sequence.

The purification may be brief and may be limited to a step of concentrating the virus by centrifugation after having generally clarified the harvested infectious virus. The purification may be supplemented with centrifugation step carried out for example by means of sucrose density gradients (EP 0 7760362). Chromatographic methods may also be carried out in order to purify the virus. A suspension of purified whole viruses is thus obtained which can be further processed to get the final vaccine composition. The purified virus suspension may also undergo subsequent treatments. Flu virus-derived products are thus obtained. The viral suspension may be fragmented using detergents or lipid solvents according to methods well known to those skilled in the art, in order to manufacture, for example, vaccines based on fragmented or split viruses, virosomes, or subunit vaccines containing the engineered influenza virus structural protein. The fragmented or split viruses, the virosomes containing the engineered influenza structural protein and the subunit vaccines containing the engineered influenza structural protein which are obtained from the purified virus are considered to be flu virus-derived products.

The final vaccine composition can be made up of whole inactivated influenza virus or attenuated influenza virus. The inactivation of the viral suspension is carried out by conventional means, using β-propiolactone (E. Budowsky et al. 1991, Vaccine, 9: 319-325; 1991, Vaccine, 9: 398-402; 1993, Vaccine, 11: 343-348), ethyleneimine or derivatives (D. King 1991, Avian Dis. 35: 505-514) or formol (EP 0 776 0362). The inactivation of the virus can be carried out before or after the purification step.

The final vaccine composition is generally formulated with a pharmaceutically acceptable carrier. The vaccine composition may also comprise one or more adjuvants. For example, alum, aluminum salts (Baylor et al., 2002*, Vaccine,* 20:S18; incorporated herein by reference) and monophosphoryl lipid A (MPL; Ribi et al., 1986*, Immunology and Immunopharmacology of Bacterial Endotoxins*, Plenum Publ. Corp., NY, p. 407; incorporated herein by reference) can be used as adjuvants in human vaccines. Alternatively or additionally, new compounds are currently being tested as adjuvants in human vaccines, such as MF59 (See, e.g., Ott et al., "*MF59—Design and Evaluation of a Safe and Potent Adjuvant for Human Vaccines*" in *Vaccine Design: The Subunit and Adjuvant Approach* (Powell, M. F. and Newman, M. J. eds.) Plenum Press, New York, 1995, pp. 277-296; incorporated herein by reference); CpG oligodeoxynudeotide (ODN) adjuvants such as CPG 7909 (Cooper et al., 2004, *Vaccine*, 22:3136; incorporated herein by reference); Monophosphoryl lipid A (MPL) adjuvants and lipid A mimetis including AS04 (Didierlaurent, A. M. et al, *J. Immunol.*, 2009, 183: 6186-6197; incorporated by reference herein), monophosphoryl lipid A (MPL, GSK) and glucopyranosyl lipid A GLA (Immune Design Corporation, IDC); AF03 (Klucker, M. F. et al, *J. Pharm Sci.*, 2012, 101: 4490-4500; incorporated herein by reference); the TLR-3 ligand polyinosinic:polycytidylic acid [poly(I:C)]; TLR9 adjuvants such as IC31 (Riedl, K. et al., *Vaccine*, 2008, 26: 3461-3468; incorporated herein by reference); imidazoquinolines (double cyclic organic molecules that act as TLR-7/8 agonists) such as imiquimod (R837) or resiquimod (R848); saponins such as QS21 (Ghochikyan et al., 2006, *Vaccine*, 24:2275; incorporated herein by reference), ISCOMATRIX adjuvant (Duewell, P., et al., *J. Immunol*, 2011, 187: 55-63; incorporated herein by reference), and Matrix-M™ (Novavax).

Additionally, some adjuvants are known in the art to enhance the immunogenicity of influenza vaccines, such as poly[di(carboxylatophenoxy)phosphazene] (PCCP; Payne et al., 1998, *Vaccine*, 16:92; incorporated herein by reference), interferon-γ (Cao et al., 1992, *Vaccine*, 10:238; incorporated herein by reference), block copolymer P1205 (CRL1005; Katz et al., 2000, *Vaccine.*, 18:2177; incorporated herein by reference), interleukin-2 (IL-2; Mbwuike et al., 1990, *Vaccine*, 8:347; incorporated herein by reference), and polymethyl methacrylate (PMMA; Kreuter et al., 1981, *J. Pharm. Sci.*, 70:367; incorporated herein by reference).

The present invention will be more fully understood by reference to the following Examples. All literature citations are incorporated by reference.

EXAMPLES

Example 1—Nucleotide Sequence Optimization of P1, X6, and X1 COBRAs

Methods of generating an optimized nucleotide sequence encoding an engineered influenza structural protein were implemented using the P1 (SEQ ID NO: 4), X6 (SEQ ID NO: 5), and X1 (SEQ ID NO: 7) COBRAs. Without optimizing the nucleotide sequences encoding the COBRAs, little to no viral rescue was possible in a reverse genetics system. For each COBRA, two optimized nucleotide sequences were produced: one that was obtained following steps 1-4 in FIG. 1 and one that was obtained following steps 1-5 in FIG. 1.

More specifically, for each of the P1, X6, and X1 COBRAs, an optimized nucleotide sequence was obtained by reverse translating the COBRA amino acid sequence, comparing the reverse translated nucleotide sequence to a database of influenza sequences, and optimizing the reverse translated nucleotide sequence according to the rules set forth in Steps 3a and 3b of FIG. 1. The optimized nucleotide sequences were also modified by adding the 5' and 3' non-coding regions from the high-titer rescued strain A/PuertoRico/8/34 ("PR8"). These optimized nucleotide sequences are referred to as "codon bias" in FIG. 5.

In the case of PR8, the following 5'- and 3'-terminal nucleotide sequences were used:

PR8 5' terminal sequence
(SEQ ID NO: 23)
AGCAAAAGCAGGGGAAAATAAAAACAACCAAAATGAAGGCAAACCTACT PR8 3' terminal sequence
(SEQ ID NO: 24)
CAGATTCTGGCGATCTACTCAACTGTCGCCAGTTCACTGGTGCTTTTGG

TCTCCCTGGGGGCAATCAGTTTCTGGATGTGTTCTAATGGATCTTTGCA

GTGCAGAATATGCATCTGAGATTAGAATTTCAGAGATATGAGGAAAAAC

ACCCTTGTTTCT

The "codon bias" optimized sequences were also further modified by exchanging certain coding regions with other influenza HA proteins. The optimized X6 COBRA sequence was further modified by exchanging the signal peptide at the 5' terminus with a signal peptide from either the COBRA X3 sequence (see Table 12) or a wild type influenza virus (A/Wellington/24/2000). More specifically, the sequence encoding the signal peptide of the X6 COBRA was exchanged with the following nucleotide sequences encoding the signal peptide from the A/Wellington/24/2000 strain (SEQ ID NO: 25) or the X3 COBRA (SEQ ID NO: 26). The coding sequences are italicized.

5' A/Wellington/24/2000 terminal sequence:
(SEQ ID NO: 25)
*ATGAAAGTAAAACTACTGGTCCTGTTATGTACATTTACAGCTACATATG*

*C*

5' X3 COBRA terminal sequence:
(SEQ ID NO: 26)
*ATGGAAGCAAGACTACTAGTCCTGTTATGTGCATTTGCAGCTACAAATG*

*CAGACACAATATGTATAGGCTACCATGCG*

The optimized X1 COBRA sequence was further modified by swapping 5' and 3' termini with the 5' and 3' termini of COBRA A1 or PR8. More specifically, the 5' nucleotide sequence encoding the signal peptide and into an initial part of the ectodomain were swapped with the corresponding COBRA A1 sequence. This exchange introduced changes in the signal peptide but not the ectodomain region (i.e., only codon changes were made in the ectodomain). The 3' terminal region, encoding the transmembrane domain and cytoplasmic tail, was also swapped with the corresponding sequence from COBRA A1. The 5' and 3' COBRA A1 terminal sequences that were exchanged correspond to SEQ ID NO: 27 and SEQ ID NO: 28, respectively. The coding sequences are italicized.

5' COBRA A1 terminal sequence:
(SEQ ID NO: 27)
*ATGAAAGCAAAACTACTAGTTCTGTTATGTGCATTTACAGCTACATATG*

*CAGACACAATATGTATAGGCTACCATGCGAACAACTCAACCGACACTGT*

*TGACACAGTACTTGAAAAGAACGTGACAGTGACACACTCTGTCAACCTA*

*CTTGAGGACAGTCACAACGGAAAACTATGTCGACTAAAAGGAATAGCCC*

*CACTACAATTGGGT*

3' COBRA A1 terminal sequence:
(SEQ ID NO: 28)
*AAGAACAATGCCAAAGAAATAGGAAACGGGTGTTTTGAATTCTACCACA*

-continued

```
AGTGTAACAATGAATGCATGGAAAGTGTGAAAAATGGAACTTATGACTA

TCCAAAATATTCCGAGGAATCAAAGTTAAACAGGGAAAAAATTGATGGA

GTGAAATTGGAATCAATGGGAGTCTATCAGATTCTGGCGATCTACTCAA

CTGTCGCCAGTTCACTGGTGCTTTTGGTCTCCCTGGGGGCAATCAGCTT

CTGGATGTGTTCTAATGGGTCTTTGCAGTGTAGAATATGCATCTGAGAT

TAGAATTTCAGAGATATGAGGAAAAACACCCTTGTTTCT
```

The 5' nucleotide sequence encoding the signal peptide (but not including any portion of the ectodomain) of COBRA X1 was also swapped with the corresponding PR8 sequence. This exchange did not introduce any change in the amino acid sequence. The 3' terminal region of PR8, encoding the transmembrane domain and cytoplasmic tail, was also swapped with the corresponding 3' sequence from COBRA X1. The 5' and 3' PR8 terminal sequences that were exchanged correspond to SEQ ID NO: 29 and SEQ ID NO: 30, respectively. The coding sequences are italicized.

```
5' PR8 terminal sequence:
                                    (SEQ ID NO: 29)
AGCAAAAGCAGGGGAAAATAAAAACAACCAAAATGAAGGCAAACCTACT

GGTCCTGTTATGTGCACTTGCAGCTGCAGATGC

3' PR8 terminal sequence:
                                    (SEQ ID NO: 30)
ACAGATTCTGGCGATCTACTCAACTGTCGCCAGTTCACTGGTGCTTTTG

GTCTCCCTGGGGGCAATCAGTTTCTGGATGTGTTCTAATGGATCTTTGC

AGTGCAGAATATGCATCTGAGATTAGAATTTCAGAGATATGAGGAAAAA

CACCCTTGTTTCT
```

The optimized P1 COBRA sequence was further modified by swapping 5' and 3' termini with the COBRA A1 sequence (see Table 12). More specifically, the 5' nucleotide sequence encoding the signal peptide of COBRA P1 was swapped with the corresponding COBRA A1 sequence, resulting in amino acid changes in the signal peptide. The 3' nucleotide sequence from COBRA P1 was also exchanged with the corresponding sequence from COBRA A1, including the sequence encoding the transmembrane region. However, this exchange did not introduce any amino acid changes in the 3' terminus. The 5' and 3' COBRA A1 terminal sequences that were exchanged correspond to SEQ ID NO: 31 and SEQ ID NO: 32, respectively. The coding sequences are italicized.

```
5' COBRA A1 terminal sequence:
                                    (SEQ ID NO: 31)
ATGAAAGCAAAACTACTAGTTCTGTTATGTGCATTTACAGCTACATATG

CAGACACAATATGTATAGGCTACCATGCGAACAACTCAACCGACACTGT

TGACACAGTACTTGAAAAGAACGTGACAGTGACACACTCTGTCAACCTA

CTTGAGGACAGTCACAACGGAAAACTA

3' COBRA A1 terminal sequence:
                                    (SEQ ID NO: 32)
GTGAAAAATGGAACTTATGACTATCCAAAATATTCCGAGGAATCAAAGT

TAAACAGGGAAAAAATTGATGGAGTGAAATTGGAATCAATGGGAGTCTA

TCAGATTCTGGCGATCTACTCAACTGTCGCCAGTTCACTGGTGCTTTTG

GTCTCCCTGGGGGCAATCAGCTTCTGGATGTGTTCTAATGGGTCTTTGC

AGTGTAGAATATGCATCTGAGATTAGAATTTCAGAGATATGAGGAAAAA

CACCCTTGTTTCT
```

These additional optimized X6, X1, and P1 sequences are identified in Table 16 below as "codon bias+swap (termini or signal peptide)." All optimized nucleotide sequences were cloned by homologous recombination into a reverse genetics plasmid ("optimized HA plasmid"). The X6 codon bias sequence could not be cloned into the reverse genetics plasmid due to instability in E. coli. Viral rescue or recovery was tested in a reverse genetics system by co-transfecting into a mixed 293FT/1VDCK cell culture the optimized HA plasmid with an NA plasmid (encoding various NA proteins as indicated in Table 16 below) and a PR8 backbone plasmid. Virus recovery was monitored for up to 10 days by measuring HA activity of the cell culture supernatant. HA titer was determined using turkey red blood cells and was calculated as the reciprocal of the highest viral suspension dilution with HA activity. Recovered virus was harvested from the cell culture and used to inoculate 10-day old hen embryonated eggs and viral growth was determined 72 hours post-inoculation.

All vaccine candidates were successfully recovered as viruses with at least one of the optimized nucleotide sequences generated with this new methodology, as summarized below in Table 16. In most cases, viruses recovered from cell culture were also able to grow in eggs at high titers (>1×10$^6$ pfu/ml), thereby showing promise as seeds for vaccine manufacturing in eggs. The COBRA P1 codon bias sequence (without additional 5' or 3' termini swap) was able to support viral rescue in cell culture and eggs with some, but not all NAs tested. Thus, in certain instances, the codon bias sequence was sufficient to support viral rescue. Swapping the termini of the optimized P1 sequence resulted in viral rescue for all NAs tested. For the X1 and X6 optimized sequences, codon bias alone was not sufficient to support viral rescue. However, exchanging the 5' and 3' coding sequences (e.g., signal peptide, transmembrane and/or cytoplasmic domain) of the codon bias sequences, permitted viral recovery both in cell culture and in eggs.

TABLE 16

| Hemagglutinin (HA) candidate | HA Nucleotide sequence generation | Neuraminidase | Virus recovery in 293FT/MDCK cells HA titer | Virus passage in hen embryonated eggs HA titer | Virus passage in hen embryonated eggs Plaque assay |
|---|---|---|---|---|---|
| COBRA P1 | Codon bias | N3SB-DB06 | ND | | |
| | | N3TK-IT02 | ND | | |
| | | N1_FortMontmouth47 | ND | | |

TABLE 16-continued

| Hemagglutinin (HA) candidate | HA Nucleotide sequence generation | Neuraminidase | Virus recovery in 293FT/MDCK cells HA titer | Virus passage in hen embryonated eggs HA titer | Plaque assay |
|---|---|---|---|---|---|
| | | N1_Singapore86 | 16 | 512 | $23 \times 10^6$ pfu/ml |
| | | N1_NewCaledonia99 | 8 | 512 | $13 \times 10^6$ pfu/ml |
| | | N1_California09 | ND | | |
| | | N3SB-DB06 | 16 | 256 | $66 \times 10^6$ pfu/ml |
| | | N3TK-IT02 | 16 | 256 | $520 \times 10^6$ pfu/ml |
| | Codon bias + termini swap with COBRA A1 virus | N1_FortMontmouth47 | 32 | 512 | $35 \times 10^6$ pfu/ml |
| | | N1_Singapore86 | 32 | 256 | $2.7 \times 10^6$ pfu/ml |
| | | N1_NewCaledonia99 | 32 | 256 | $1.1 \times 10^6$ pfu/ml |
| | | N1_California09 | 32 | 1024 | $3.7 \times 10^6$ pfu/ml |
| COBRA X6 | Codon bias | | | | |
| | Codon bias + signal peptide swap with COBRA X3 virus | N3TK-IT02 | 32 | 512 | $1.3 \times 10^7$ pfu/ml |
| | | N1_California09 | 2 | | |
| | Codon bias + signal peptide swap with wild-type virus | N3SB-DB06 | 32 | 512 | $1.13 \times 10^7$ pfu/ml |
| | | N3TK-IT02 | 32 | 512 | $4.95 \times 10^7$ pfu/ml |
| | | N1_Singapore86 | 16 | 1024 | $1.98 \times 10^7$ pfu/ml |
| | | N1_NewCaledonia99 | 16 | 512 | $5.0 \times 10^6$ pfu/ml |
| | | N1_California09 | 8 | 256 | $1.20 \times 10^7$ pfu/ml |
| COBRA X1 | Codon bias | N3SB-DB06 | ND | | |
| | | N3TK-IT02 | ND | | |
| | | N1_PuertoRico34 | ND | | |
| | | N1_New Jersey76 | ND | | |
| | | N1_Fort Monmouth47 | ND | | |
| | | N1_Boston | ND | | |
| | | N1_Singapore86 | ND | | |
| | | N1_NewCaledonia99 | ND | | |
| | | N1_California09 | ND | | |
| | Codon bias + termini swap with COBRA A1 virus | N3TK-IT02 | 1 | 256 | $>1.0 \times 10^5$ pfu/ml |
| | | N1_California09 | ND | ND | |
| | | N1_Singapore86 | ND | 512 | $>1.0 \times 10^6$ pfu/ml |
| | Codon bias + termini swap with PR8 virus | N3TK-IT02 | 8 | 512 | $1.25 \times 10^6$ pfu/ml |
| | | N1_California09 | ND | 512 | $3.5 \times 10^4$ pfu/ml |
| | | N1_Singapore86 | 2 | 128 | $1.5 \times 10^6$ pfu/ml |

Example 2—Nucleotide Sequence Optimization of Influenza B SMARt HAs

Methods of generating an optimized nucleotide sequence encoding an engineered influenza structural protein were implemented using the following influenza B SMARt HA polypeptides: br08_CO1 (SEQ ID NO: 75), br08_DO2 (SEQ ID NO: 76), br08_DO3 (SEQ ID NO: 77), pan90_DO2 (SEQ ID NO: 78), and ma12_RA82 (SEQ ID NO: 79). For each SMARt HA, two optimized nucleotide sequences were produced: one that was obtained following steps 1-3b in FIG. 1 and one that was obtained following steps 1-5 in FIG. 1.

More specifically, for each of the br08_CO1, br08_DO2, br08_DO3, pan90_DO2 and ma12_RA82 SMARt HAs, an optimized nucleotide sequence was obtained by reverse translating the SMARt HA amino acid sequence, comparing the reverse translated nucleotide sequence to a database of influenza sequences, and optimizing the reverse translated nucleotide sequence according to the rules set forth in Steps 3a and 3b of FIG. 1. The optimized nucleotide sequences were also modified by adding the 5' and 3' non-coding regions from successfully rescued strain B/Memphis/12/1997.

In the case of B/Memphis/12/1997, the following 5'- and 3'-terminal nucleotide sequences were used:

5' B/Memphis/12/1997 terminal sequence
(SEQ ID NO: 103)
AGCAGAAGCAGAGCATTTTCTAATATCCACAAAATG 3' B/Memphis/12/1997 terminal sequence
(SEQ ID NO: 104)
TAAGGAAAATTAAGCCCTGTATTTTCCTTTATTGTAGTGCTTGTTTGCT

TGTTATCATTACAAAGAAACGTTATTGAAAAATGCTCTTGTTACTACT

The optimized br08_CO1 SMARt HA sequence was further modified by swapping 5' and 3' termini with the 5' and 3' termini of B/Brisbane/60/2008. More specifically, the 5' nucleotide sequence encoding the signal peptide and into an initial part of the ectodomain were swapped with the corresponding B/Brisbane/60/2008 sequence. This exchange did not introduce changes in the signal peptide or the ectodomain region (i.e., only codon changes were made). The 3' terminal region, encoding a portion of the ectodomain, transmembrane domain and cytoplasmic tail, was also swapped with the corresponding sequence from B/Brisbane/60/2008 without introducing changes in the protein coding sequence. In the case of conflicts the original codon was used. The 5' and 3' B/Brisbane/60/2008 terminal sequences that were exchanged correspond to SEQ ID NO: 105 and SEQ ID NO: 106, respectively:

5' B/Brisbane/60/2008 terminal sequence:
(SEQ ID NO: 105)
ATGAAGGCAATAATTGTACTACTCATGGTAGTAACATCCAATGCAGATC

GAATCTGCACTGGGATAACATCGTCA

-continued

3' B/Brisbane/60/2008 terminal sequence:
(SEQ ID NO: 106)
GCAGGAGAATTTTCTCTCCCCACCTTTGATTCACTGAATATTACTGCTG

CATCTTTAAATGACGATGGATTGGATAATCATACTATACTGCTTTACTA

CTCAACTGCTGCCTCCAGTTTGGCTGTAACACTGATGATAGCTATCTTT

GTTGTTTATATGGTCTCCAGAGACAATGTTTCTTGCTCCATCTGTCTAT

AA

The optimized br08_D02 SMARt HA sequence was further modified by swapping 5' and 3' termini with the 5' and 3' termini of B/Brisbane/60/2008. More specifically, the 5' nucleotide sequence encoding the signal peptide and into an initial part of the ectodomain were swapped with the corresponding B/Brisbane/60/2008 sequence. This exchange did not introduce changes in the signal peptide or the ectodomain region (i.e., only codon changes were made). The 3' terminal region, encoding a portion of the ectodomain, transmembrane domain and cytoplasmic tail, was also swapped with the corresponding sequence from B/Brisbane/60/2008 without introducing changes in the protein coding sequence. In the case of conflicts the original codon was used. The 5' and 3' B/Brisbane/60/2008 terminal sequences that were exchanged correspond to SEQ ID NO: 105 and SEQ ID NO: 106, respectively.

The optimized br08_DO3 SMARt HA sequence was further modified by swapping 5' and 3' termini with the 5' and 3' termini of B/Brisbane/60/2008. More specifically, the 5' nucleotide sequence encoding the signal peptide and into an initial part of the ectodomain were swapped with the corresponding B/Brisbane/60/2008 sequence. This exchange did not introduce changes in the signal peptide or the ectodomain region (i.e., only codon changes were made). The 3' terminal region, encoding a portion of the ectodomain, transmembrane domain and cytoplasmic tail, was also swapped with the corresponding sequence from B/Brisbane/60/2008 without introducing changes in the protein coding sequence. In the case of conflicts the original codon was used. The 5' and 3' B/Brisbane/60/2008 terminal sequences that were exchanged correspond to SEQ ID NO: 105 and SEQ ID NO: 106, respectively.

The optimized pan90_DO2 SMARt HA sequence was further modified by swapping 5' and 3' termini with the 5' and 3' termini of B/Brisbane/60/2008. More specifically, the 5' nucleotide sequence encoding the signal peptide and into an initial part of the ectodomain were swapped with the corresponding B/Brisbane/60/2008 sequence. This exchange did not introduce changes in the signal peptide or the ectodomain region (i.e., only codon changes were made). The 3' terminal region, encoding a portion of the ectodomain, transmembrane domain and cytoplasmic tail, was also swapped with the corresponding sequence from B/Brisbane/60/2008 without introducing changes in the protein coding sequence. In the case of conflicts the original codon was used. The 5' and 3' B/Brisbane/60/2008 terminal sequences that were exchanged correspond to SEQ ID NO: 105 and SEQ ID NO: 106, respectively.

The optimized ma12_RA82 SMARt HA sequence was further modified by swapping 5' and 3' termini with the 5' and 3' termini of B/Brisbane/60/2008. More specifically, the 5' nucleotide sequence encoding the signal peptide and into an initial part of the ectodomain were swapped with the corresponding B/Brisbane/60/2008 sequence. This exchange did not introduce changes in the signal peptide or the ectodomain region (i.e., only codon changes were made). The 3' terminal region, encoding a portion of the ectodomain, transmembrane domain and cytoplasmic tail, was also swapped with the corresponding sequence from B/Brisbane/60/2008 without introducing changes in the protein coding sequence. In the case of conflicts the original codon was used. The 5' and 3' B/Brisbane/60/2008 terminal sequences that were exchanged correspond to SEQ ID NO: 105 and SEQ ID NO: 106, respectively.

Viral recovery experiments with the optimized nucleic acids derived from the influenza B SMARt HAs have not yet been tested.

Example 3—Nucleotide Sequence Optimization of H3 COBRAs

Methods of generating an optimized nucleotide sequence encoding an engineered influenza structural protein were implemented using 6 different H3 COBRAs. For each H3 COBRA HA polypeptide, an optimized nucleotide sequence was obtained by following steps 1-3b in FIG. 1. The optional steps 4 and 5 were not carried out for these polypeptides.

More specifically, for each of the H3 COBRAs, an optimized nucleotide sequence was obtained by reverse translating the H3 COBRA amino acid sequence, comparing the reverse translated nucleotide sequence to a database of influenza sequences, and optimizing the reverse translated nucleotide sequence according to the rules set forth in Steps 3a and 3b of FIG. 1.

The optimized H3 COBRA nucleotide sequences were cloned by homologous recombination into a reverse genetics plasmid ("optimized HA plasmid"). Viral rescue or recovery was tested in a reverse genetics system by co-transfecting into a mixed 293FT/MDCK cell culture the optimized HA plasmid with an NA plasmid and a PR8 backbone plasmid. Virus recovery was monitored for up to 10 days by measuring HA activity of the cell culture supernatant. HA titer was determined using turkey red blood cells and was calculated as the reciprocal of the highest viral suspension dilution with HA activity. Recovered virus was harvested from the cell culture and used to inoculate 10-day old hen embryonated eggs and viral growth was determined 72 hours post-inoculation.

All of the optimized nucleotide sequences derived from the H3 COBRA polypeptides were successfully recovered as viruses with at least one of the optimized nucleotide sequences generated with this new methodology.

EQUIVALENTS

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

---

We claim:

1. A method of preparing an influenza vaccine composition, the method comprising:
   generating a seed virus by transfecting mammalian cells with a set of expression vectors, one or more of which comprises an optimized nucleotide sequence encoding an engineered influenza structural protein generated by the method of:
   a) providing an amino acid sequence of the engineered influenza structural protein;
   b) reverse-translating the amino acid sequence to generate a first nucleotide sequence;
   c) identifying a second nucleotide sequence that encodes an influenza structural protein that shares a high degree of sequence identity with the engineered influenza structural protein;
   d) at every position where the codons in the first and second nucleotide sequences code for the same amino acid, changing codons in the first nucleotide sequence to match codons from the second nucleotide sequence; and
   e) at every position where the codons in the first and second nucleotide sequences code for a different amino acid, changing codons in the first nucleotide sequence to match codons that are based on structural protein-specific influenza codon usage preferences, thereby generating the optimized nucleotide sequence;
   harvesting the seed virus;
   producing infectious influenza virus by infecting eggs or mammalian cells with the seed virus;
   harvesting the infectious influenza virus after multiplication in the eggs or mammalian cells;
   purifying the harvested infectious influenza virus;
   optionally inactivating the purified virus; and
   mixing the purified virus with a pharmaceutically acceptable carrier.

2. A method of inducing an immune response to one or more influenza polypeptides in a subject, the method comprising administering the influenza vaccine composition generated by the method of claim 1.

3. The method of claim 1, wherein the influenza structural protein that shares a high degree of sequence identity with the engineered influenza structural protein is a wild-type influenza structural protein.

4. The method of claim 1, further comprising adding the 5' and 3' non-coding sequences from a high titer rescued strain to the optimized nucleotide sequence.

5. The method of claim 4, wherein in the high titer rescued strain is A/PuertoRico/8/34 (PR8).

6. The method of claim 1, wherein the amino acid sequence of the engineered influenza structural protein encoded by the optimized nucleotide sequence is the same as the amino acid sequence encoded by the first nucleotide sequence.

7. The method of claim 1, wherein the optimized nucleotide sequence further comprises a nucleotide sequence encoding a signal peptide, a nucleotide sequence coding for a transmembrane domain, and/or a nucleotide sequence coding for a cytoplasmic domain.

8. The method of claim 7, further comprising exchanging the nucleotide sequence encoding the signal peptide in the optimized nucleotide sequence with a nucleotide sequence encoding the signal peptide from a high titer rescued strain.

9. The method of claim 7, further comprising exchanging the nucleotide sequence encoding the transmembrane domain with a nucleotide sequence encoding the transmembrane domain from a high titer rescued strain.

10. The method of claim 7, further comprising exchanging the nucleotide sequence encoding the cytoplasmic domain with a nucleotide sequence encoding the cytoplasmic domain from a high titer rescued strain.

11. The method of claim 8, wherein the high titer rescued strain is A/PuertoRico/8/34 (PR8).

12. The method of claim 1, wherein the engineered influenza structural protein is an influenza type A hemagglutinin protein.

13. The method of claim 12, wherein the hemagglutinin protein is a subtype selected from the group consisting of H1, H2, H3, H4, H5, H6, H7, H8, H9, H10, H11, H12, H13, H14, H15, H16, and H17.

14. The method of claim 1, wherein the structural protein-specific influenza codon usage preferences are set forth in Tables 1-10.

15. The method of claim 1, wherein reverse translating the amino acid sequence to generate a first nucleotide sequence comprises use of a codon usage table specific for influenza viruses.

16. The method of claim 1, wherein the second nucleotide sequence encodes a wild type version of the influenza structural protein and is identified from a publicly available database comprising influenza nucleotide sequences.

17. The method of claim 4, wherein the 5' non-coding sequence comprises the nucleotide sequence of SEQ ID NO: 23 and/or the 3' non-coding sequence comprises the nucleotide sequence of SEQ ID NO: 24 or wherein the 5' non-coding sequence comprises the nucleotide sequence of SEQ ID NO: 103 and/or the 3' non-coding sequence comprises the nucleotide sequence of SEQ ID NO: 104.

18. The method of claim 1, wherein the engineered influenza structural protein comprises an amino acid sequence selected from the group consisting of SEQ ID NO: 4, SEQ ID NO: 5, SEQ ID NO: 6, and SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83 SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, and SEQ ID NO: 102.

\* \* \* \* \*